United States Patent
Chu et al.

(10) Patent No.: US 8,088,760 B2
(45) Date of Patent: Jan. 3, 2012

(54) BENZOXAZOLE CARBOXAMIDE INHIBITORS OF POLY(ADP-RIBOSE)POLYMERASE (PARP)

(75) Inventors: Daniel Chu, Santa Clara, CA (US); Bing Wang, San Jose, CA (US)

(73) Assignee: BioMarin Pharmaceutical Inc., Novato, CA (US)

( * ) Notice: Subject to any disclaimer, the term of this patent is extended or adjusted under 35 U.S.C. 154(b) by 217 days.

(21) Appl. No.: 12/355,692

(22) Filed: Jan. 16, 2009

(65) Prior Publication Data

US 2009/0197863 A1 Aug. 6, 2009

Related U.S. Application Data

(60) Provisional application No. 61/026,690, filed on Feb. 6, 2008.

(51) Int. Cl.
*A61K 31/422* (2006.01)
*A61K 31/423* (2006.01)
*A61K 31/496* (2006.01)
*C07D 263/54* (2006.01)
*C07D 413/02* (2006.01)
*A61P 35/00* (2006.01)

(52) U.S. Cl. ............... 514/210.21; 514/254.02; 514/375; 544/368; 548/217

(58) Field of Classification Search .................. None
See application file for complete search history.

(56) References Cited

U.S. PATENT DOCUMENTS

| 4,690,926 | A | | 9/1987 | Saitoh et al. | |
|---|---|---|---|---|---|
| 6,015,827 | A | * | 1/2000 | Griffin et al. | 514/394 |
| 6,316,455 | B1 | | 11/2001 | Griffin et al. | |
| 7,045,539 | B2 | * | 5/2006 | Barlaam et al. | 514/367 |
| 7,220,769 | B2 | | 5/2007 | Farina et al. | |
| 2004/0082542 | A1 | | 4/2004 | Mjalli et al. | |
| 2004/0102435 | A1 | | 5/2004 | Barlaam et al. | |

FOREIGN PATENT DOCUMENTS

| WO | WO 01/58896 A1 | 8/2001 |
|---|---|---|
| WO | WO 2004/098494 | 11/2004 |
| WO | WO 2006/089100 A1 | 8/2006 |
| WO | WO 2006/124780 | 11/2006 |
| WO | WO 2007/041357 | 4/2007 |

OTHER PUBLICATIONS

Science IP Search dated Feb. 6, 2008.
ISA/KR PCT International Search Report dated Aug. 18, 2009, for International Application No. PCT/US2009/031163, filed Jan. 15, 2009.
ISA/KR PCT International Written Opinion dated Aug. 18, 2009, for International Application No. PCT/US2009/031163, filed Jan. 15, 2009.
ISA/KR PCT International Preliminary Report on Patentability dated Aug. 10, 2010, for International Application No. PCT/US2009/031163, filed Jan. 15, 2009.

EPO Extended European Search Report dated Aug. 17, 2011, for European Patent Application No. EP 09708325.7-2117, filed Jan. 15, 2009.
Denny, W. A., at al., 1990, "Structure-activity relationships for the mutagenic activity of tricyclic intercalating agents in *Salmonella typhimurium*," *Mutation Research* 232(2): 233-241.
Bahner, I., at al., 1997, "Bis(trifluoromethylated) 4-(2'benzoxazolyl)actinocin derivatives," *Eur. J. Org. Chem.* No. 5: 999-1003.
Mazzitelli, C. L., et al., 2008, "Evaluation of metal-mediated DNA binding of benzoxazole ligands by electrospray ionization mass spectrometry," *J. Am. Soc. Mass Spectrom.* 19(2): 209-218.
Suto, M. J., et ah, 1995, "Synthesis of boxazomycin B and related analogs," *Tetrahedron Letters* 36(4): 7213-7216.
Griffin, R. J., et al, 1995, "Novel potent inhibitors of the DNA repair enzyme poly(ADP-ribose)polymerase (PARP)," *Anti-Cancer Drug Design* 10(6): 507-514.
Kusumi, K., et al., 1988, "Structure of the novel antibiotics boxazomycins A, B, and C," *J. Am. Chem. Soc.* 110: 2954-2958.
Chen, K. X., et al., 2008, "Potent and selective small molecule NS3 serine protease inhibitors of Hepatitis C virus with dichlorocyclopropylproline as P2 residue," *Bioorg. Med. Chem.* 16(4): 1874-1883.

* cited by examiner

*Primary Examiner* — Kamal Saeed
(74) *Attorney, Agent, or Firm* — Jones Day

(57) ABSTRACT

A compound having the structure set forth in Formula (I) or Formula (II):

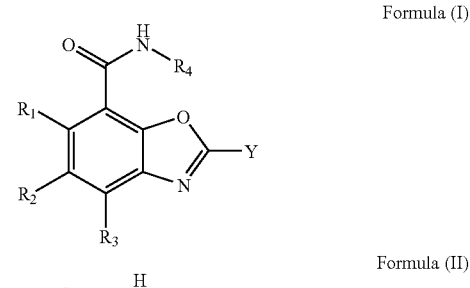

Formula (I)

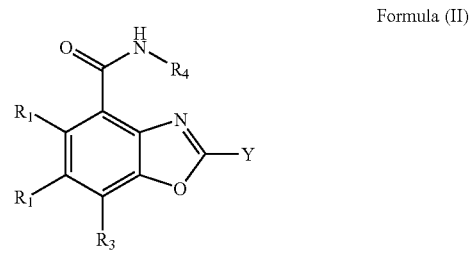

Formula (II)

wherein the variables Y, $R_1$, $R_2$, $R_3$, and $R_4$ are as defined herein. Provided herein are inhibitors of poly(ADP-ribose) polymerase activity. Also described herein are pharmaceutical compositions that include at least one compound described herein and the use of a compound or pharmaceutical composition described herein to treat diseases, disorders and conditions that are ameliorated by the inhibition of PARP activity.

25 Claims, No Drawings

BENZOXAZOLE CARBOXAMIDE INHIBITORS OF POLY(ADP-RIBOSE)POLYMERASE (PARP)

CROSS REFERENCE TO RELATED APPLICATIONS

This application claims the benefit of U.S. Provisional Application No. 61/026,690, entitled, "Benzoxazole Carboxamide Inhibitors of Poly(ADP-Ribose)Polymerase (PARP), filed Feb. 6, 2008, which application is incorporated herein by reference in its entirety.

FIELD OF THE INVENTION

Described herein are compounds, methods of making such compounds, pharmaceutical compositions and medicaments containing such compounds, and methods of using such compounds to treat or prevent diseases or conditions associated with the enzyme poly(ADP-ribose)polymerase (PARP).

BACKGROUND OF THE INVENTION

The family of poly(ADP-ribose)polymerases (PARP) includes approximately 18 proteins, which all display a certain level of homology in their catalytic domain but differ in their cellular functions (Ame et al., *BioEssays.*, 26 (8), 882-893 (2004)). PARP-1 and PARP-2 are unique members of the family, in that their catalytic activities are stimulated by the occurrence of DNA strand breaks.

PARP has been implicated in the signaling of DNA damage through its ability to recognize and rapidly bind to DNA single or double strand breaks (D'Amours, et al., *Biochem. J.*, 342, 249-268 (1999)). It participates in a variety of DNA-related functions including gene amplification, cell division, differentiation, apoptosis, DNA base excision repair as well as effects on telomere length and chromosome stability (d'Adda di Fagagna, et al., *Nature Gen.*, 23 (1), 76-80 (1999)).

SUMMARY OF THE INVENTION

In certain embodiments, provided herein are compounds, compositions and methods for modulating the activity of PARP. Among the compounds that are provided herein, are compounds that are inhibitors of PARP. Also described herein is the use of such compounds, compositions and methods for the treatment of diseases, disorders or conditions associated with the activity of PARP.

In some embodiments, compounds provided herein have the structure of Formula (I) or Formula (II) and pharmaceutically acceptable salts, solvates, esters, acids and prodrugs thereof. In certain embodiments, provided herein are compounds having the structure of Formula (I) or Formula (II) that are inhibitors of the enzyme poly(ADP-ribose)polymerase (PARP).

In certain embodiments, isomers and chemically protected forms of compounds having a structure represented by Formula (I) or Formula (II) are also provided.

Formula (I) or Formula (II) are as follows:

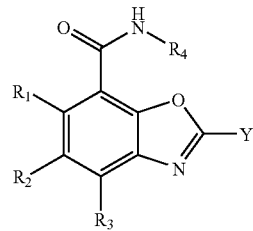

Formula (I)

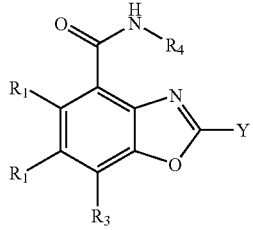

Formula (II)

wherein:
Y is selected from the group consisting of
a) an aryl group optionally substituted with 1, 2, or 3 $R_5$; wherein each $R_5$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl, wherein when aryl is phenyl, the phenyl is substituted with at least one substituent selected independently from the group consisting of alkoxyalkyl, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $(NR_AR_B)$alkyl;
b) a heteroaryl group optionally substituted with 1, 2, or 3 $R_5$; wherein each $R_5$ is previously as defined;
c) a L-T group where L is selected from the group consisting of alkenylene, alkylene, alkynylene, cycloalkylene and spiroheterocycle and T is selected from the group consisting of heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$;
d) a non-aromatic 4, 5, 6, 7, 8, 9, 10, 11, or 12-membered monocyclic or bicyclic heterocycle ring having 1 or 2 nitrogen atoms and, optionally, one sulfur or oxygen atom, wherein the heterocycle is optionally substituted with 1, 2, or 3 $R_6$; wherein each $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and (NR$_A$R$_B$)sulfonyl and wherein when the heterocycle is bicyclic, the optional substituent(s) are attached to either one or both of the cyclic rings;

R$_1$, R$_2$, and R$_3$, are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkyl, nitro, NR$_C$R$_D$, and (NR$_C$R$_D$)carbonyl;

each R$_A$, R$_B$, R$_C$, and R$_D$ are independently selected from the group consisting of hydrogen, alkyl, cycloalkyl, and alkylcarbonyl;

R$_4$, is selected from the group consisting of hydrogen, alkyl, cycloalkyl, alkoxyalkyl, haloalkyl, hydroxyalkyl, and (NR$_A$R$_B$)alkyl; or isomers, salts, solvates, chemically protected forms, and prodrugs thereof.

DETAILED DESCRIPTION OF THE INVENTION

PARP has an essential role in facilitating DNA repair, controlling RNA transcription, mediating cell death, and regulating immune response. PARP inhibitors demonstrate efficacy in numerous models of disease particularly in models of ischemia reperfusion injury, inflammatory disease, degenerative diseases, protection from above adverse effects of cytotoxic compounds, and potentiation of cytotoxic cancer therapy. They are efficacious in the prevention of ischemia reperfusion injury in models of myocardial infarction, stoke, other neural trauma, organ transplantation, as well as reperfusion of the eye, kidney, gut and skeletal muscle. Inhibitors are efficacious in inflammatory diseases such as arthritis, gout, inflammatory bowel disease, CNS inflammation such as MS and allergic encephalitis, sepsis, septic shock, hemorrhagic shock, pulmonary fibrosis, and uveitis. PARP inhibitors also show benefit in several models of degenerative disease including diabetes and Parkinsons disease. PARP inhibitors ameliorate the liver toxicity following acetaminophen overdose, cardiac and kidney toxicities from doxorubicin and platinum based antineoplastic agents, as well as skin damage secondary to sulfur mustards. In various cancer models, PARP inhibitors are shown to potentiate radiation and chemotherapy by increasing apoptosis of cancer cells, limiting tumor growth, decreasing metastasis, and prolonging the survival of tumor-bearing animals.

In certain embodiments are provided compounds of Formula (I) or Formula (II)

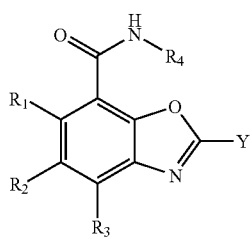

Formula (I)

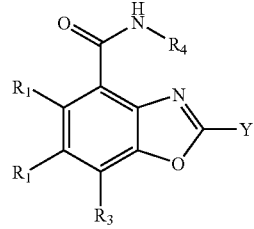

Formula (II)

or a therapeutically acceptable salt thereof wherein R$_1$, R$_2$, and R$_3$, are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkyl, nitro, NR$_C$R$_D$, and (NR$_C$R$_D$)carbonyl; R$_C$, and R$_D$ are each independently selected from the group consisting of hydrogen, alkyl, cycloalkyl, and alkylcarbonyl; R$_4$, is selected from the group consisting of hydrogen, alkyl, cycloalkyl, alkoxyalkyl, haloalkyl, hydroxyalkyl, and (NR$_A$R$_B$)alkyl;

Y is selected from the group consisting of a) an aryl group optionally substituted with 1, 2, or 3 R$_5$; wherein each R$_5$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, NR$_A$R$_B$, (NR$_A$R$_B$)alkyl, (NR$_A$R$_B$)carbonyl, (NR$_A$R$_B$)carbonylalkyl, and (NR$_A$R$_B$)sulfonyl, wherein when aryl is phenyl, the phenyl is substituted with at least one substituent selected independently from the group consisting of alkoxyalkyl, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, (NR$_A$R$_B$)alkyl;

b) a heteroaryl group optionally substituted with 1, 2, or 3 R$_5$; wherein each R$_5$ is previously as defined;

c) a L-T group where L is selected from the group consisting of alkenylene, alkylene, alkynylene, cycloalkylene and spiroheterocycle and T is selected from the group consisting of heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, NR$_A$R$_B$;

d) a non-aromatic 4, 5, 6, 7, 8, 9, 10, 11, or 12-membered monocyclic or bicyclic heterocycle ring having 1 or 2 nitrogen atoms and, optionally, one sulfur or oxygen atom; selected from the group consisting of

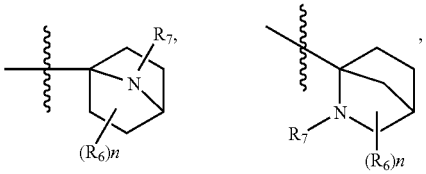

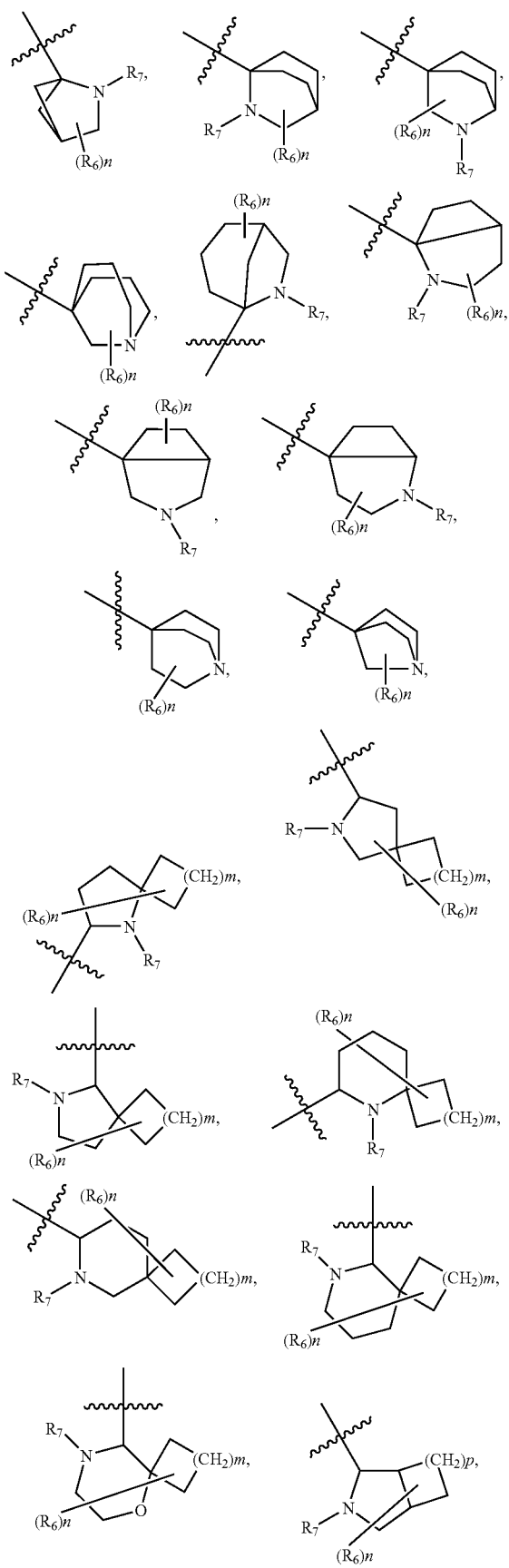
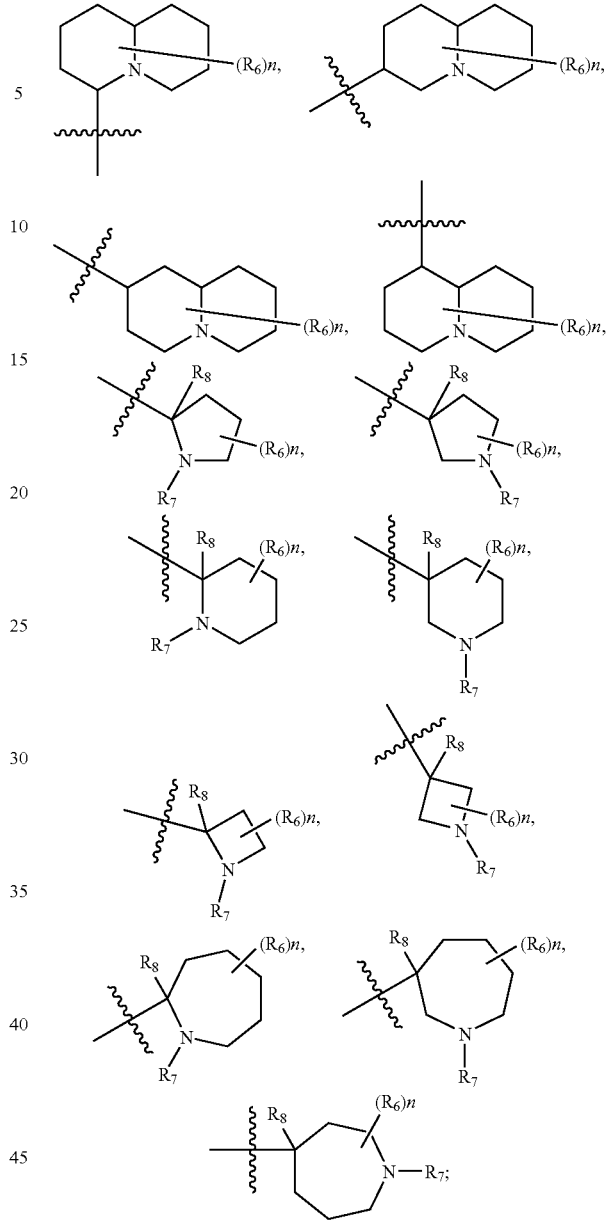

wherein
n is 0, 1, 2 or 3; m is 0, 1, 2 or 3; p is 0, 1, 2 or 3; each $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl and wherein when the heterocycle is bicyclic, the optional substituent(s) are attached to either one or both of the cyclic rings; $R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl; $R_8$ is selected from the group consisting of hydrogen, alkyl, alkynyl, alkenyl, alkoxyalkyl, cycloalkyl, haloalkyl, hydroxyl-$C_2$-$C_6$ alkyl; and $R_A$, and $R_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein $R_1$, $R_2$, and $R_3$, are hydrogen; $R_4$, is selected from the group consisting of hydrogen, alkyl, cycloalkyl, alkoxyalkyl, haloalkyl, hydroxyalkyl, and $(NR_AR_B)$alkyl;

Y is selected from the group consisting of a) an aryl group optionally substituted with 1, 2, or 3 $R_5$; wherein each $R_5$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$ alkyl, $(NR_AR_B)$carbonyl, $(NR_AR_B)$carbonylalkyl, and $(NR_AR_B)$sulfonyl, wherein when aryl is phenyl, the phenyl is substituted with at least one substituent selected independently from the group consisting of alkoxyalkyl, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $(NR_AR_B)$alkyl;

b) a heteroaryl group optionally substituted with 1, 2, or 3 $R_5$; wherein each $R_5$ is previously as defined;

c) a L-T group where L is selected from the group consisting of alkenylene, alkylene, alkynylene, cycloalkylene and spiroheterocycle and T is selected from the group consisting of heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$;

d) a non-aromatic 4, 5, 6, 7, 8, 9, 10, 11, or 12-membered monocyclic or bicyclic heterocycle ring having 1 or 2 nitrogen atoms and, optionally, one sulfur or oxygen atom; selected from the group consisting of

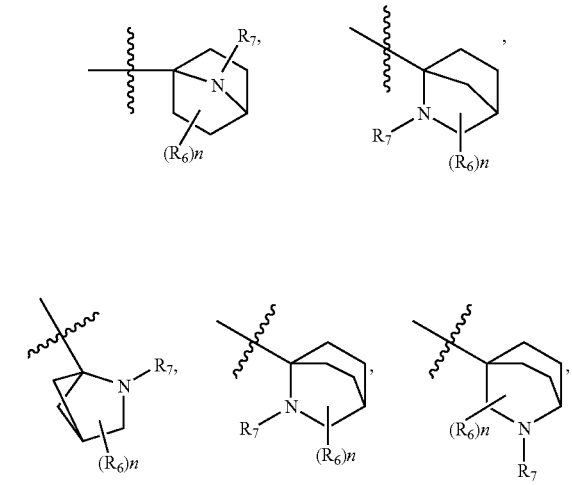

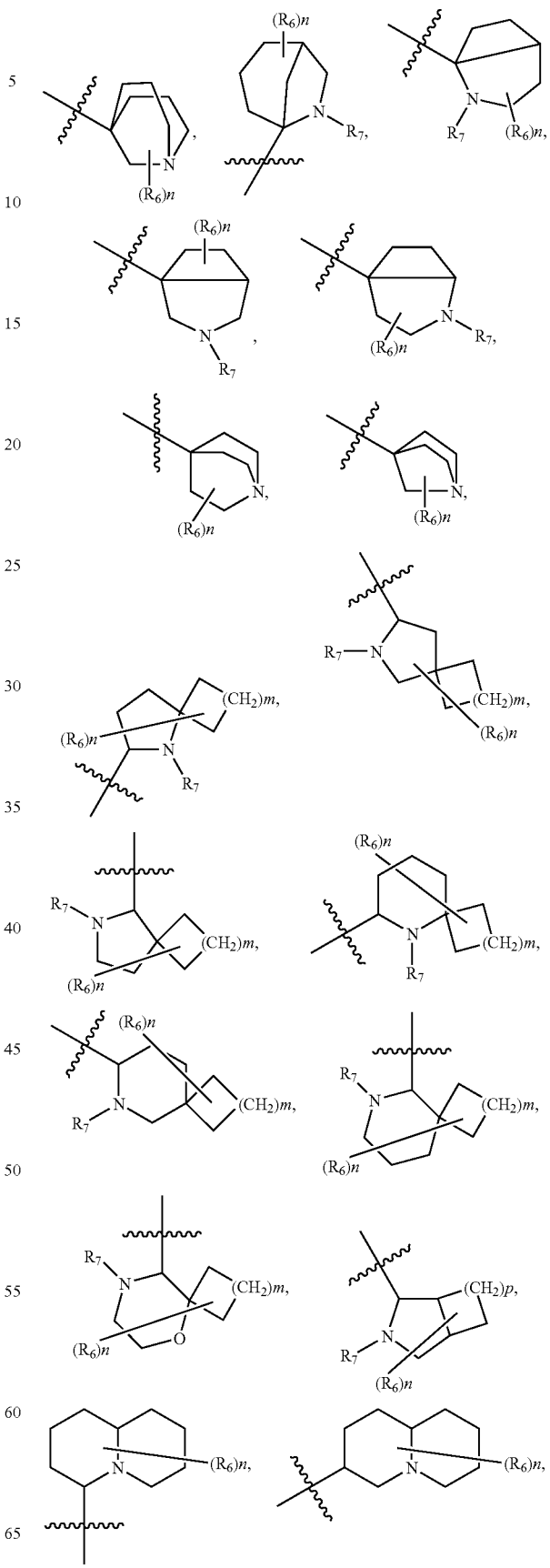

-continued

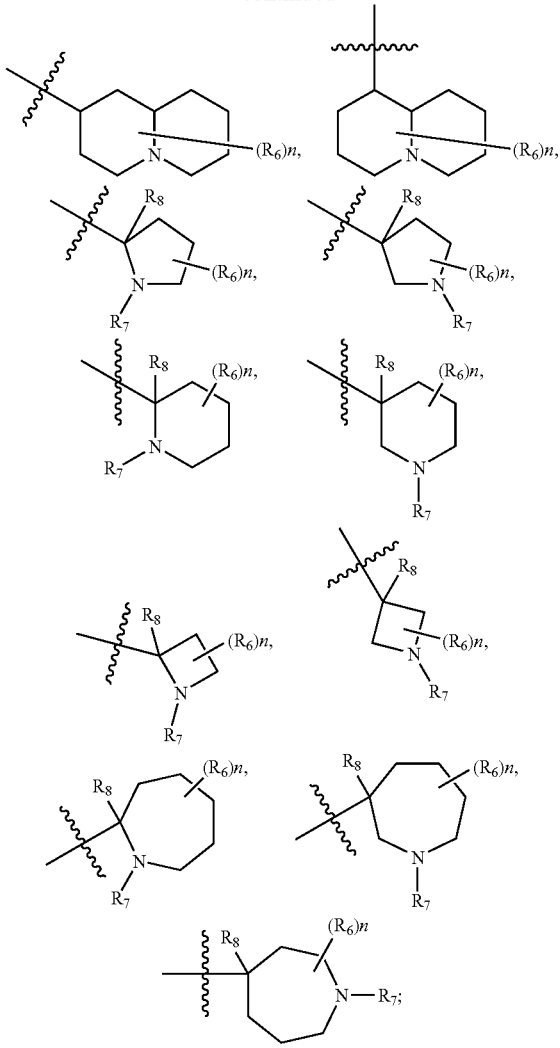

wherein
n is 0, 1, 2 or 3; m is 0, 1, 2 or 3; p is 0, 1, 2 or 3; each $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl and wherein when the heterocycle is bicyclic, the optional substituent(s) are attached to either one or both of the cyclic rings; $R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl; $R_8$ is selected from the group consisting of hydrogen, alkyl, alkynyl, alkenyl, alkoxyalkyl, cycloalkyl, haloalkyl, hydroxyl-$C_2$-$C_6$ alkyl; and $R_A$, and $R_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein $R_1$, $R_2$, $R_3$, and $R_4$ are hydrogen and $R_8$ is hydrogen or alkyl; Y is selected from the group consisting of a) an aryl group optionally substituted with 1, 2, or 3 $R_5$; wherein each $R_5$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl, wherein when aryl is phenyl, the phenyl is substituted with at least one substituent selected independently from the group consisting of alkoxyalkyl, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $(NR_AR_B)$alkyl;

b) a heteroaryl group optionally substituted with 1, 2, or 3 $R_5$; wherein each $R_5$ is previously as defined;

c) a L-T group where L is selected from the group consisting of alkenylene, alkylene, alkynylene, cycloalkylene and spiroheterocycle and T is selected from the group consisting of heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$;

d) a non-aromatic 4, 5, 6, 7, 8, 9, 10, 11, or 12-membered monocyclic or bicyclic heterocycle ring having 1 or 2 nitrogen atoms and, optionally, one sulfur or oxygen atom; selected from the group consisting of

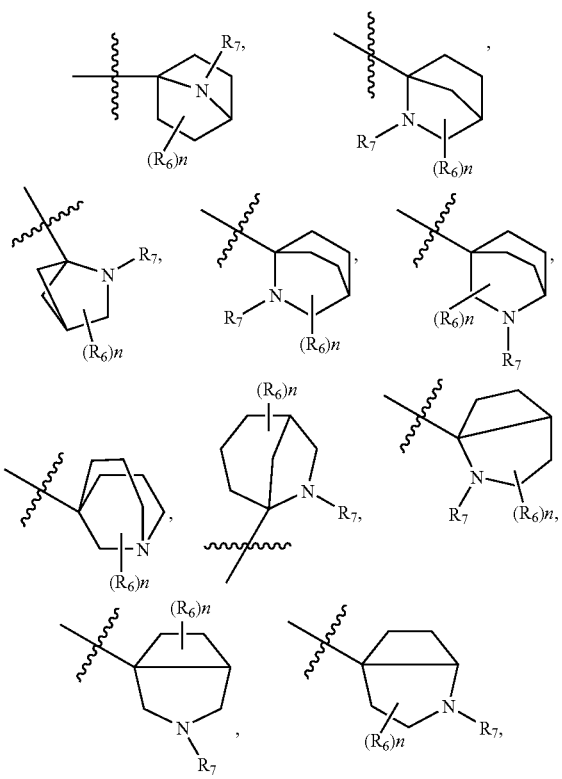

-continued

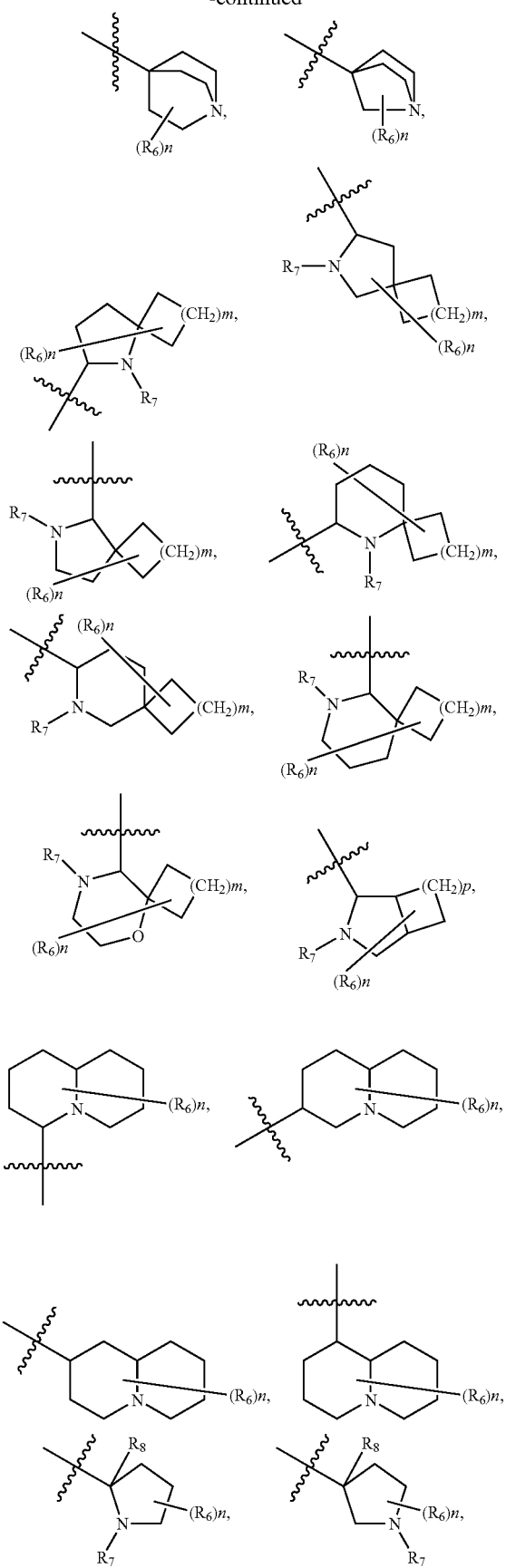

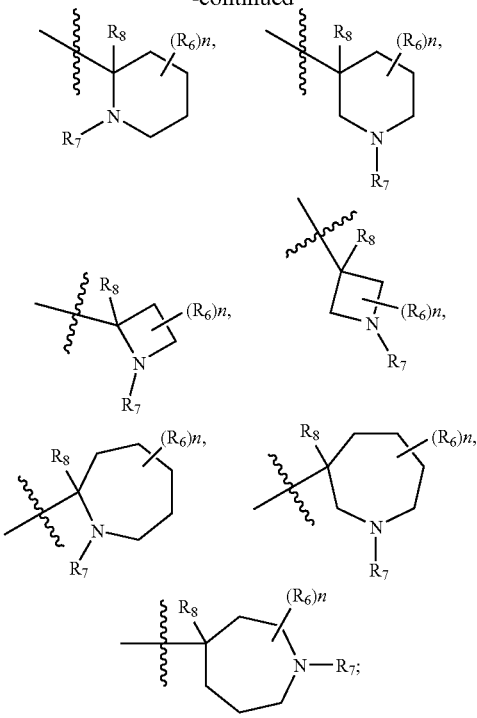

wherein n is 0, 1, 2 or 3; m is 0, 1, 2 or 3; p is 0, 1, 2 or 3; each $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl and when the heterocycle is bicyclic, the optional substituent(s) are attached to either one or both of the cyclic rings; $R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl; and $R_A$ and $R_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein $R_1$, $R_2$, $R_3$, and $R_4$ are hydrogen and $R_8$ is methyl; Y is selected from the group consisting of
a) an aryl group optionally substituted with 1, 2, or 3 $R_5$; wherein each $R_5$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl, wherein when aryl is phenyl, the phenyl is substituted with at least one substituent selected independently from the group consisting of alkoxyalkyl, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, (NR$_A$R$_B$)alkyl;

b) a heteroaryl group optionally substituted with 1, 2, or 3 R$_5$; wherein each R$_5$ is previously as defined;

c) a L-T group where L is selected from the group consisting of alkenylene, alkylene, alkynylene, cycloalkylene and spiroheterocycle and T is selected from the group consisting of heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, NR$_A$R$_B$;

d) a non-aromatic 4, 5, 6, 7, 8, 9, 10, 11, or 12-membered monocyclic or bicyclic heterocycle ring having 1 or 2 nitrogen atoms and, optionally, one sulfur or oxygen atom; selected from the group consisting of

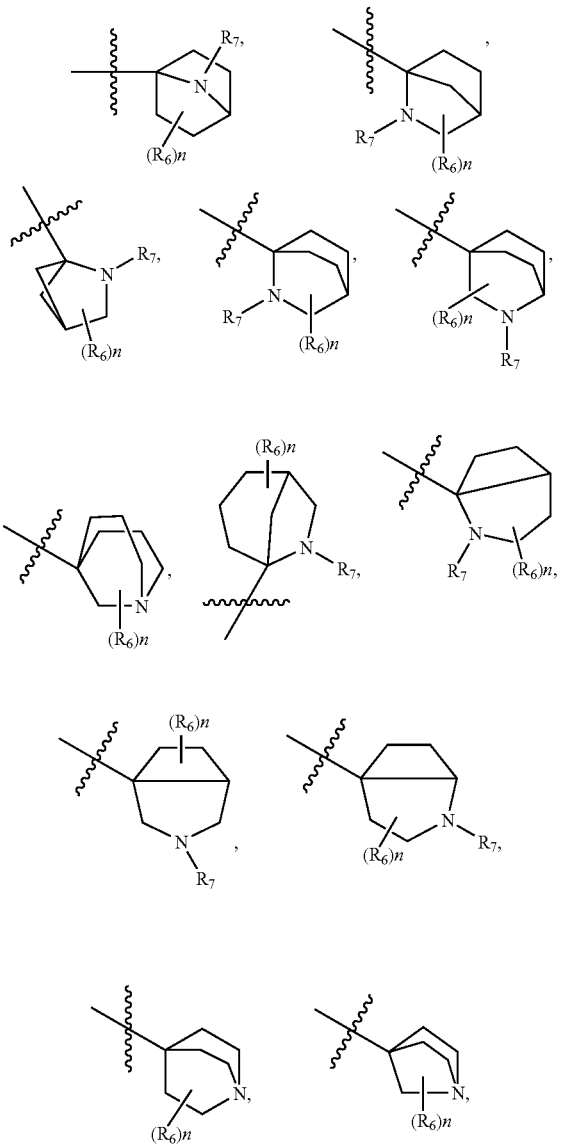

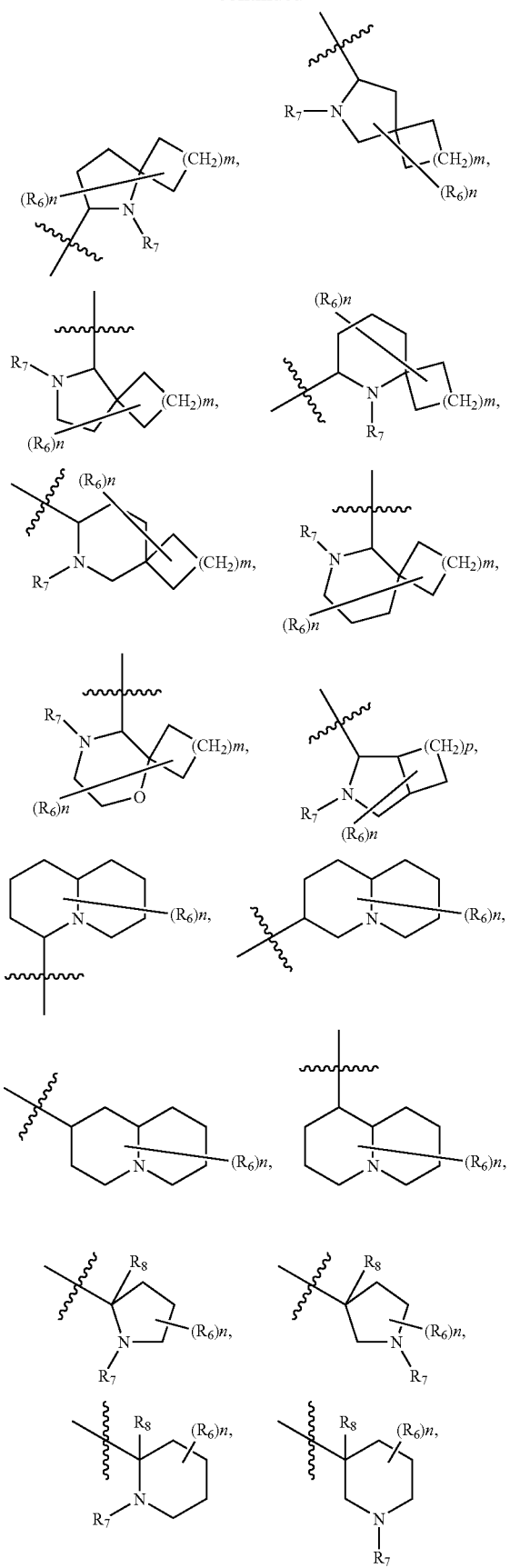

-continued

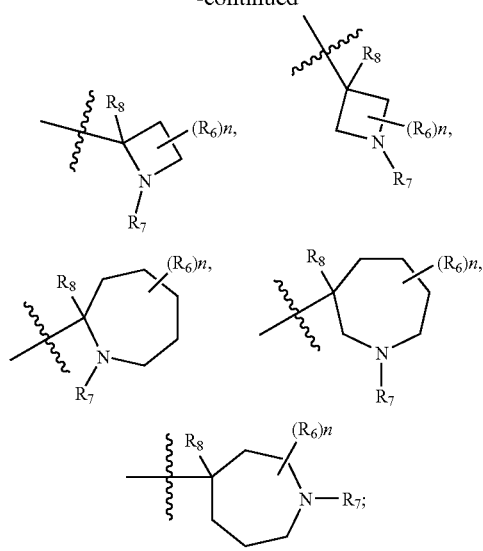

wherein
n is 0, 1, 2 or 3; m is 0, 1, 2 or 3; p is 0, 1, 2 or 3; each $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl and when the heterocycle is bicyclic, the optional substituent(s) are attached to either one or both of the cyclic rings; $R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl; and $R_A$, and $R_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein $R_1$, $R_2$, $R_3$ and $R_4$ are hydrogen; $R_8$, is hydrogen or alkyl; Y is selected from the group consisting of

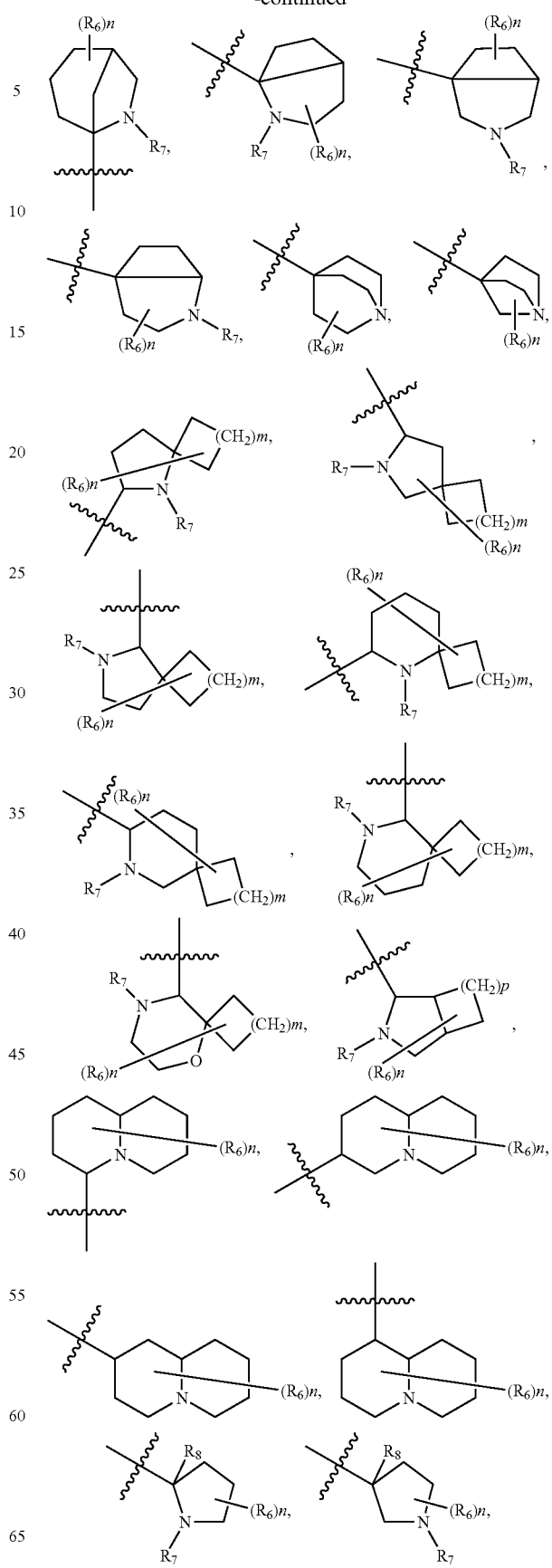

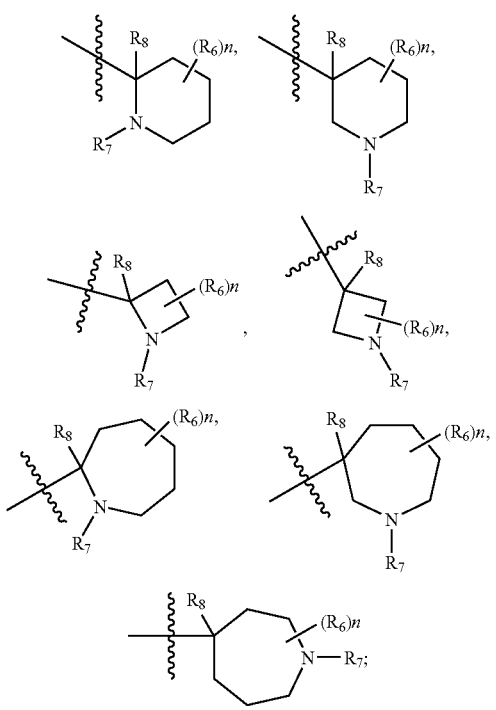

n is 0, 1, 2 or 3; m is 0, 1, 2 or 3; p is 0, 1, 2 or 3; each $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl and when the heterocycle is bicyclic, the optional substituent(s) are attached to either one or both of the cyclic rings; $R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl; and $R_A$ and $R_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein $R_1$, $R_2$, $R_3$, and $R_4$, are hydrogen and $R_8$ is hydrogen or methyl; Y is selected from the group consisting of

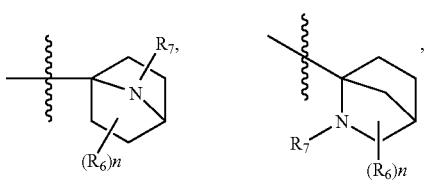

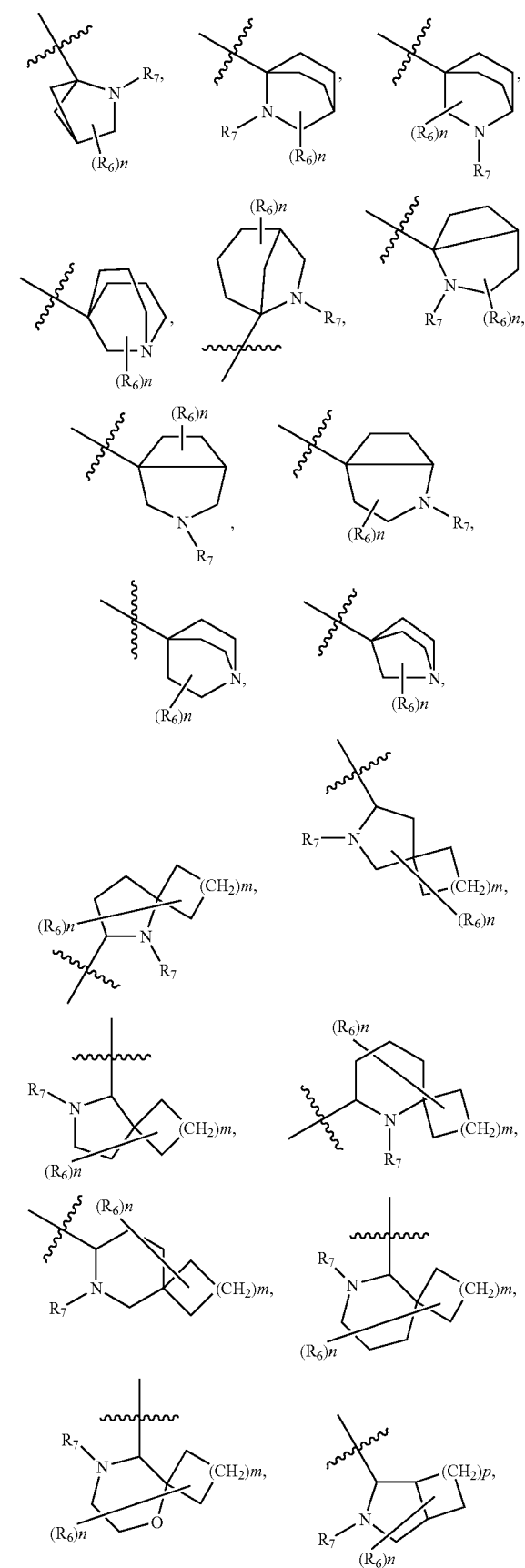

-continued

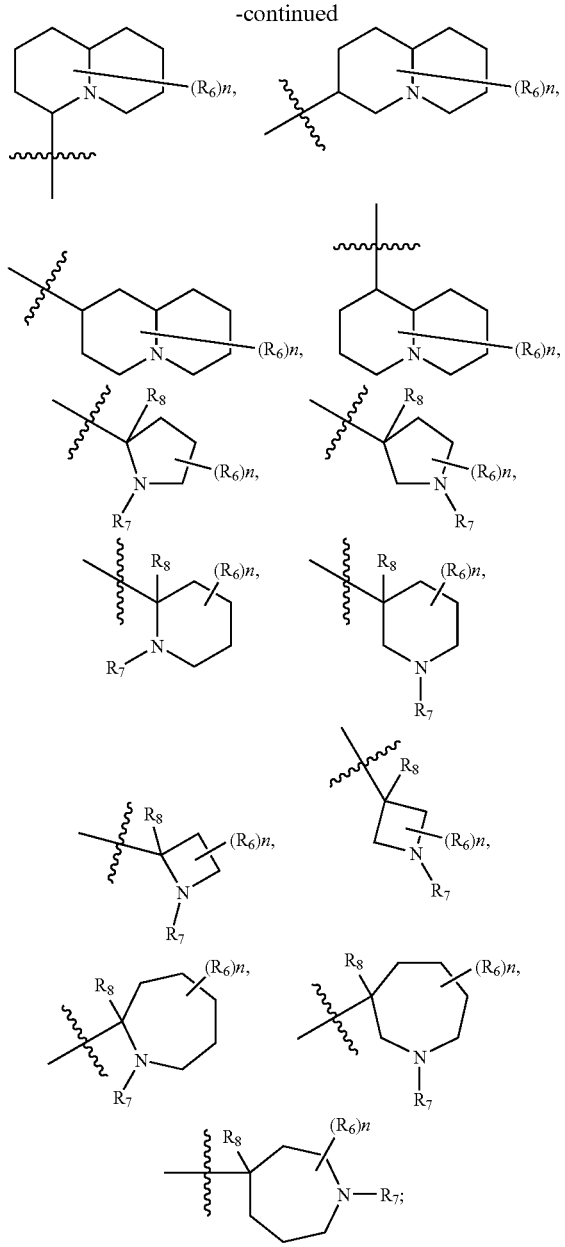

n is 0, 1, 2 or 3; m is 0, 1, 2 or 3; p is 0, 1, 2 or 3; each $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl and when the heterocycle is bicyclic, the optional substituent(s) are attached to either one or both of the cyclic rings; $R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl; and $R_A$ and $R_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein $R_1$, $R_2$, $R_3$, and $R_4$ are hydrogen, $R_8$, is hydrogen or methyl and $R_6$, is hydrogen;

Y is selected from the group consisting of

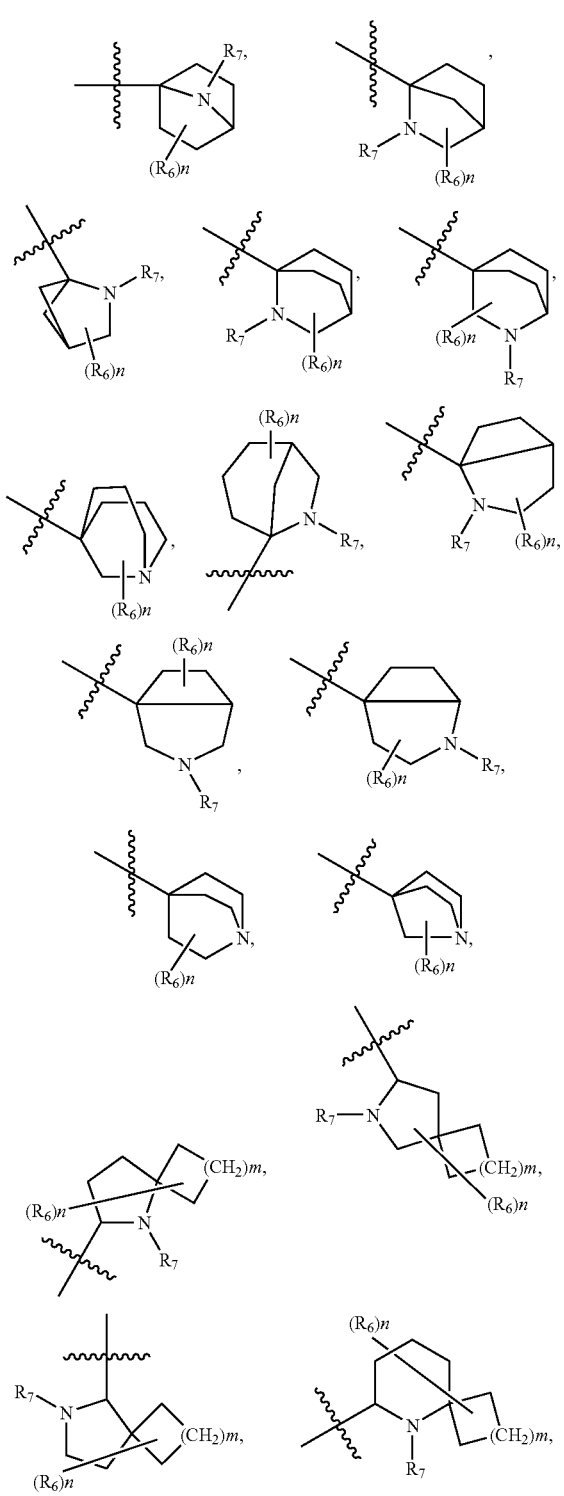

-continued

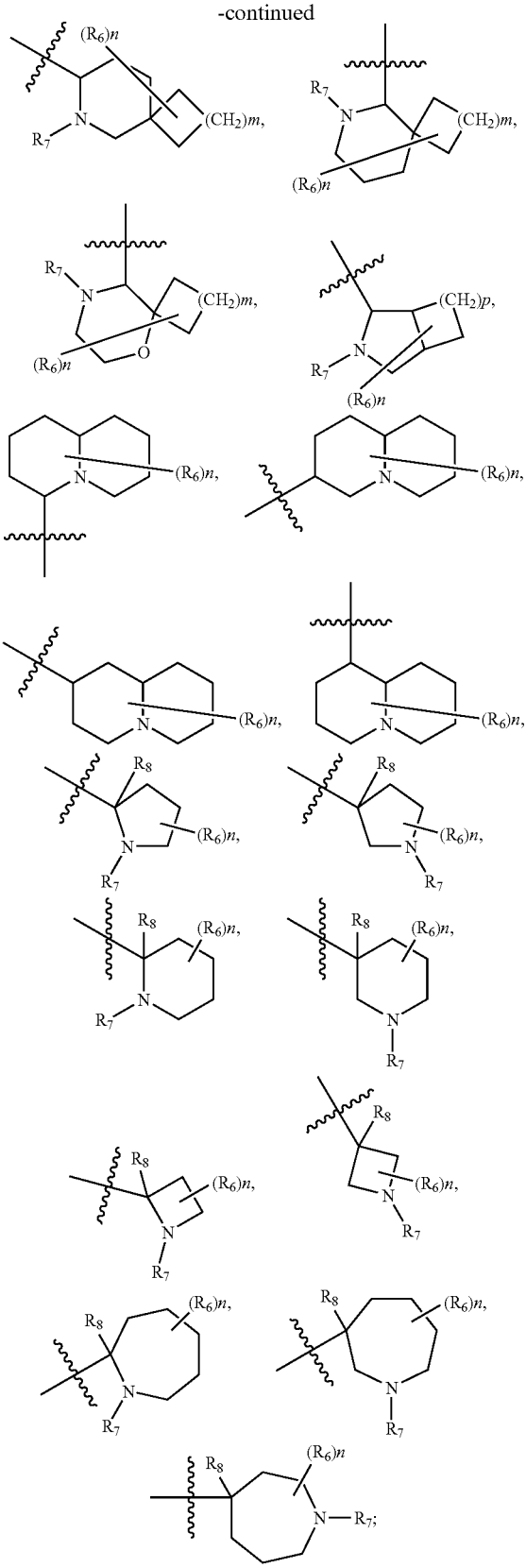

n is 0; m is 0, 1, 2 or 3; p is 0, 1, 2 or 3; R$_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, (NR$_A$R$_B$)alkyl, (NR$_A$R$_B$)carbonyl, (NR$_A$R$_B$)carbonylalkyl, and (NR$_A$R$_B$)sulfonyl; and R$_A$, and R$_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein Y is selected from the group consisting of

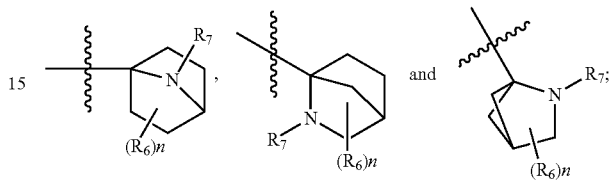

and n, R$_1$, R$_2$, R$_3$, R$_4$, R$_6$, and R$_7$ are as defined in Formula (I) or Formula (II).

In certain embodiments are provided compounds of Formula (I) or a therapeutically acceptable salt thereof wherein Y is selected from the group consisting of

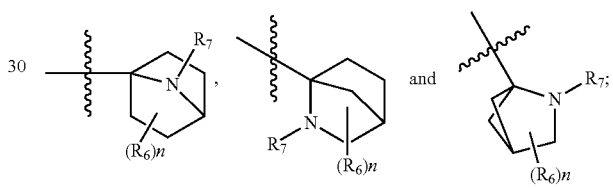

and n is 0; R$_1$, R$_2$, R$_3$, and R$_4$, are hydrogen; R$_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, (NR$_A$R$_B$)alkyl, (NR$_A$R$_B$)carbonyl, (NR$_A$R$_B$)carbonylalkyl, and (NR$_A$R$_B$)sulfonyl; and R$_A$, and R$_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein Y is selected from the group consisting of

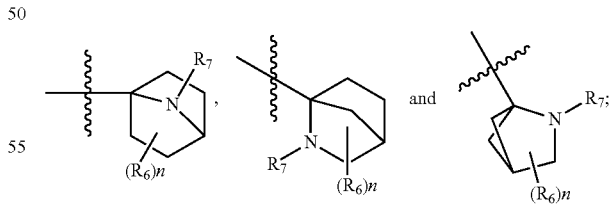

and n is 0; R$_1$, R$_2$, R$_3$, and R$_4$, are hydrogen; R$_7$ is selected from the group consisting of hydrogen, alkyl, cycloalkyl, arylalkyl, and (NR$_A$R$_B$)sulfonyl; and R$_A$, and R$_B$ are each independently selected from the group consisting of hydrogen, alkyl, and cycloalkyl.

In certain embodiments are provided compounds of Formula (I) or Formula (II) or a therapeutically acceptable salt thereof wherein Y is selected from the group consisting of

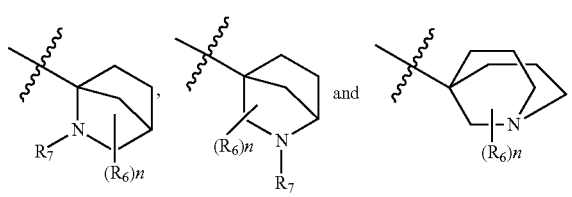

and n, R$_1$, R$_2$, R$_3$, R$_4$, R$_6$, and R$_7$ are as defined in Formula (I) or Formula (II).

In certain embodiments are provided compounds of Formula (I) or Formula (II) or a therapeutically acceptable salt thereof wherein Y is selected from the group consisting of

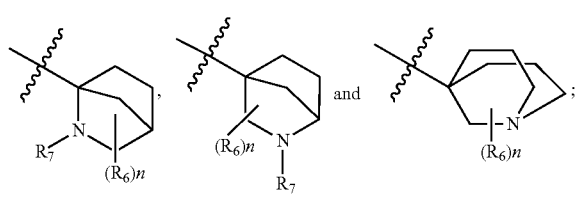

and n is 0; R$_1$, R$_2$, R$_3$, and R$_4$, are hydrogen; R$_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, (NR$_A$R$_B$)alkyl, (NR$_A$R$_B$)carbonyl, (NR$_A$R$_B$)carbonylalkyl, and (NR$_A$R$_B$)sulfonyl; and R$_A$, and R$_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein Y is selected from the group consisting of

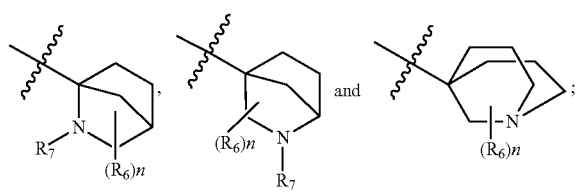

and n is 0; R$_1$, R$_2$, R$_3$, and R$_4$, are hydrogen; R$_7$ is selected from the group consisting of hydrogen, alkyl, cycloalkyl, arylalkyl, and (NR$_A$R$_B$)sulfonyl; and R$_A$, and R$_B$ are each independently selected from the group consisting of hydrogen, alkyl, and cycloalkyl.

In certain embodiments are provided compounds of Formula (I) or Formula (II) or a therapeutically acceptable salt thereof wherein Y is selected from the group consisting of

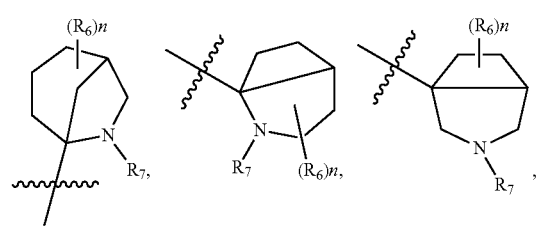

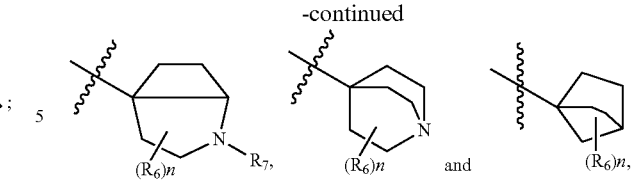

and n, R$_1$, R$_2$, R$_3$, R$_4$, R$_6$, and R$_7$ are as defined in Formula (I) or Formula (II).

In certain embodiments are provided compounds of Formula (I) or Formula (II) or a therapeutically acceptable salt thereof wherein Y is selected from the group consisting of

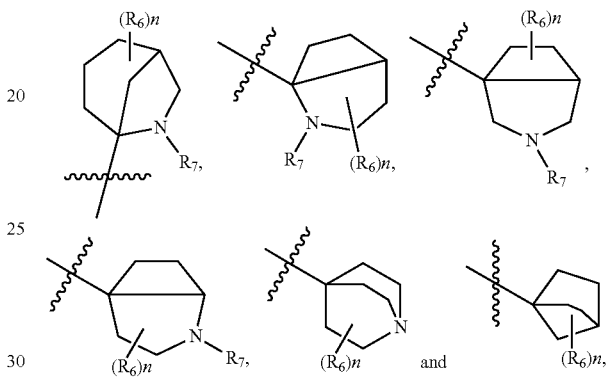

and n is 0; R$_1$, R$_2$, R$_3$, and R$_4$, are hydrogen; R$_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, (NR$_A$R$_B$)alkyl, (NR$_A$R$_B$)carbonyl, (NR$_A$R$_B$)carbonylalkyl, and (NR$_A$R$_B$)sulfonyl; and R$_A$, and R$_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein Y is selected from the group consisting of

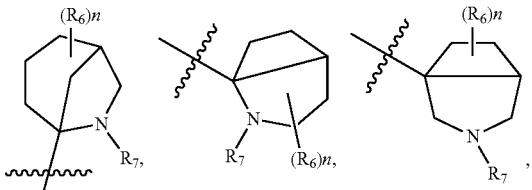

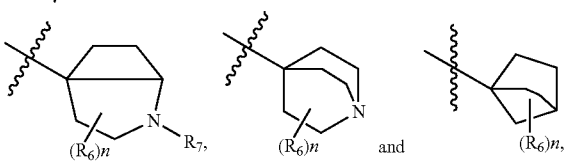

and n is 0; R$_1$, R$_2$, R$_3$, and R$_4$, are hydrogen; R$_7$ is selected from the group consisting of hydrogen, alkyl, cycloalkyl, arylalkyl, and (NR$_A$R$_B$)sulfonyl; and R$_A$, and R$_B$ are each independently selected from the group consisting of hydrogen, alkyl, and cycloalkyl.

In certain embodiments are provided compounds of Formula (I) or Formula (II) or a therapeutically acceptable salt thereof wherein Y is selected from the group consisting of

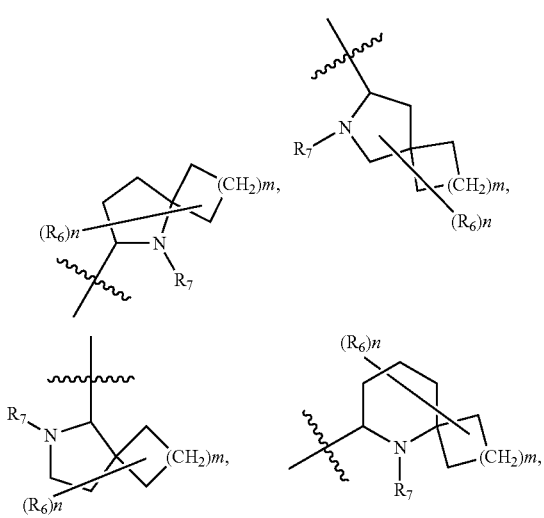

and n, m, $R_1$, $R_2$, $R_3$, $R_4$, $R_6$, and $R_7$ are as defined in Formula (I) or Formula (II).

In certain embodiments are provided compounds of Formula (I) or Formula (II) or a therapeutically acceptable salt thereof wherein Y is selected from the group consisting of

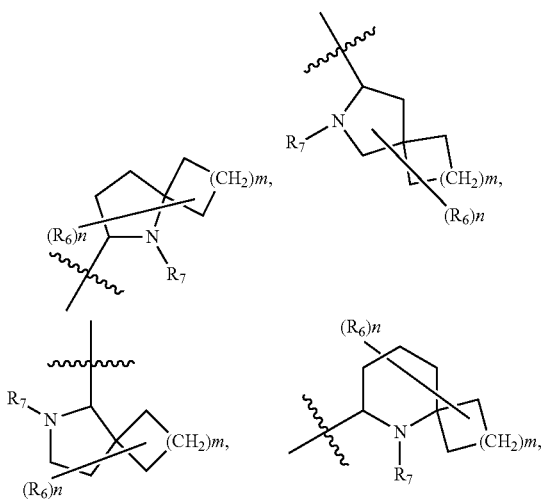

and n is 0; m is 0, 1, 2 or 3; $R_1$, $R_2$, $R_3$, and $R_4$, are hydrogen; $R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl; and $R_A$, and $R_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein Y is selected from the group consisting of

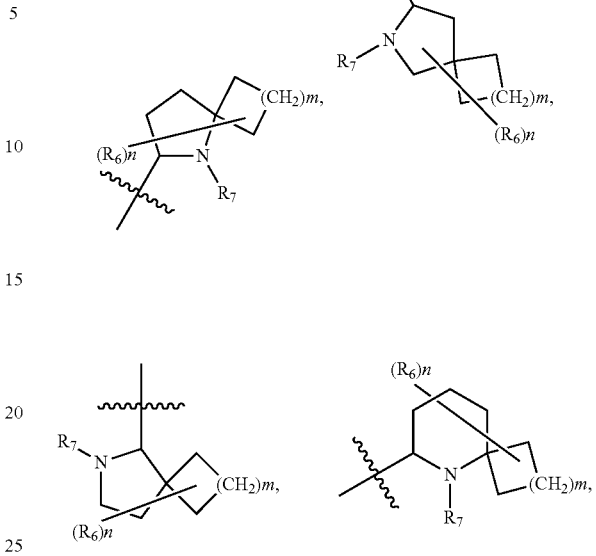

and n is 0; m is 0, 1, 2, or 3; $R_1$, $R_2$, $R_3$, and $R_4$, are hydrogen; $R_7$ is selected from the group consisting of hydrogen, alkyl, cycloalkyl, arylalkyl, and $(NR_AR_B)$sulfonyl; and $R_A$, and $R_B$ are each independently selected from the group consisting of hydrogen, and alkyl.

In certain embodiments are provided compounds of Formula (I) or Formula (II) or a therapeutically acceptable salt thereof wherein Y is selected from the group consisting of

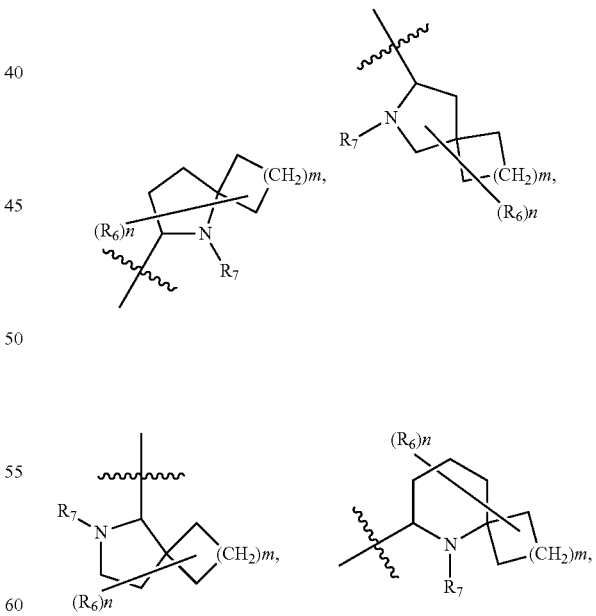

and n is 0; m is 0 or 1; $R_1$, $R_2$, $R_3$, and $R_4$, are hydrogen; $R_7$ is selected from the group consisting of hydrogen, alkyl, cycloalkyl, arylalkyl, and $(NR_AR_B)$sulfonyl; and $R_A$, and $R_B$ are each independently selected from the group consisting of hydrogen, alkyl, and cycloalkyl.

In certain embodiments are provided compounds of Formula (I) or Formula (II) or a therapeutically acceptable salt thereof wherein Y is selected from the group consisting of and n, m, $R_1$, $R_2$, $R_3$, $R_4$, $R_6$, and $R_7$ are as defined in Formula (I) or Formula (II).

In certain embodiments are provided compounds of Formula (I) or Formula (II) or a therapeutically acceptable salt thereof wherein Y is selected from the group consisting of and n is 0; m is 0, 1, 2 or 3; $R_1$, $R_2$, $R_3$, and $R_4$, are hydrogen; $R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl; and $R_A$, and $R_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein Y is selected from the group consisting of and n is 0; m is 0, 1, 2, or 3; $R_1$, $R_2$, $R_3$, and $R_4$, are hydrogen; $R_7$ is selected from the group consisting of hydrogen, alkyl, cycloalkyl, arylalkyl, and $(NR_AR_B)$sulfonyl; and $R_A$, and $R_B$ are each independently selected from the group consisting of hydrogen, alkyl, and cycloalkyl.

In certain embodiments are provided compounds of Formula (I) or Formula (II) or a therapeutically acceptable salt thereof wherein Y is selected from the group consisting of and n is 0; m is 0 or 1; $R_1$, $R_2$, $R_3$, and $R_4$, are hydrogen; $R_7$ is selected from the group consisting of hydrogen, alkyl, cycloalkyl, arylalkyl, and $(NR_AR_B)$sulfonyl; and $R_A$, and $R_B$ are each independently selected from the group consisting of hydrogen, alkyl, and cycloalkyl.

In certain embodiments are provided compounds of Formula (I) or Formula (II) or a therapeutically acceptable salt thereof wherein Y is selected from the group consisting of and n, p, $R_1$, $R_2$, $R_3$, $R_4$, $R_6$, and $R_7$ are as defined in Formula (I) or Formula (II).

In certain embodiments are provided compounds of Formula (I) or Formula (II) or a therapeutically acceptable salt thereof wherein Y is selected from the group consisting of

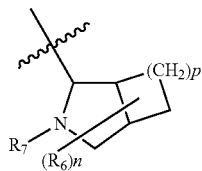

and n is 0; p is 0, 1, 2 or 3; $R_1$, $R_2$, $R_3$, and $R_4$, are hydrogen; $R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl; and $R_A$, and $R_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein Y is selected from the group consisting of

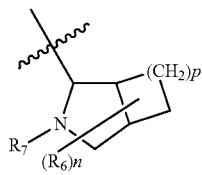

and n is 0; p is 0, 1, 2, or 3; $R_1$, $R_2$, $R_3$, and $R_4$, are hydrogen; $R_7$ is selected from the group consisting of hydrogen, alkyl, cycloalkyl, arylalkyl, and $(NR_AR_B)$sulfonyl; and $R_A$, and $R_B$ are each independently selected from the group consisting of hydrogen, alkyl, and cycloalkyl.

In certain embodiments are provided compounds of Formula (I) or Formula (II) or a therapeutically acceptable salt thereof wherein Y is selected from the group consisting of

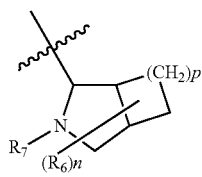

and n is 0; p is 0 or 1; $R_1$, $R_2$, $R_3$, and $R_4$, are hydrogen; $R_7$ is selected from the group consisting of hydrogen, alkyl, cycloalkyl, arylalkyl, and $(NR_AR_B)$sulfonyl; and $R_A$, and $R_B$ are each independently selected from the group consisting of hydrogen, alkyl, and cycloalkyl.

In certain embodiments are provided compounds of Formula (I) or Formula (II) or a therapeutically acceptable salt thereof wherein Y is selected from the group consisting of

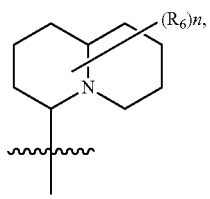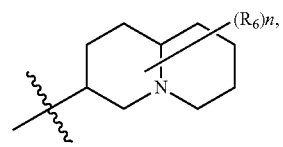

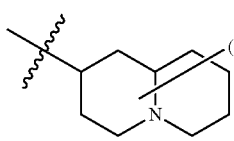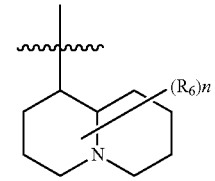

and n, $R_1$, $R_2$, $R_3$, $R_4$, and $R_6$ are as defined in Formula (I) or Formula (II).

In certain embodiments are provided compounds of Formula (I) or Formula (II) or a therapeutically acceptable salt thereof wherein Y is selected from the group consisting of

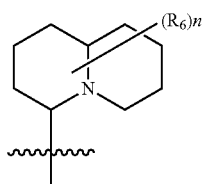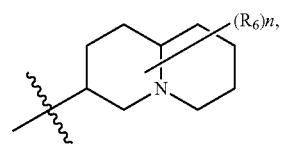

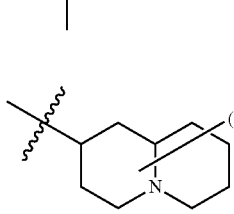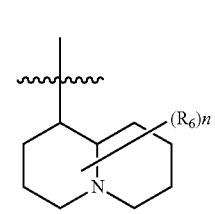

and n is 0, 1, 2 or 3; $R_1$, $R_2$, $R_3$, and $R_4$, are hydrogen; each $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl and can be attached to either one or both of the cyclic rings; and $R_A$, and $R_B$ are each independently selected from the group consisting of hydrogen, alkyl, cycloalkyl, and alkylcarbonyl.

In certain embodiments are provided compounds of Formula (I) or Formula (II) or a therapeutically acceptable salt thereof wherein Y is selected from the group consisting of

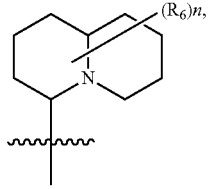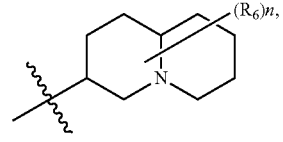

-continued

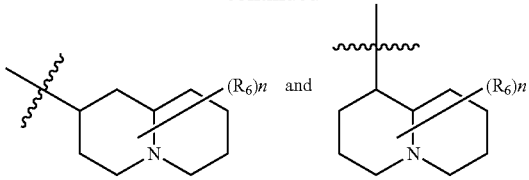

and n is 0; $R_1$, $R_2$, $R_3$, and $R_4$, are hydrogen.

In certain embodiments are provided compounds of Formula (I) or Formula (II) or a therapeutically acceptable salt thereof wherein Y is selected from the group consisting of

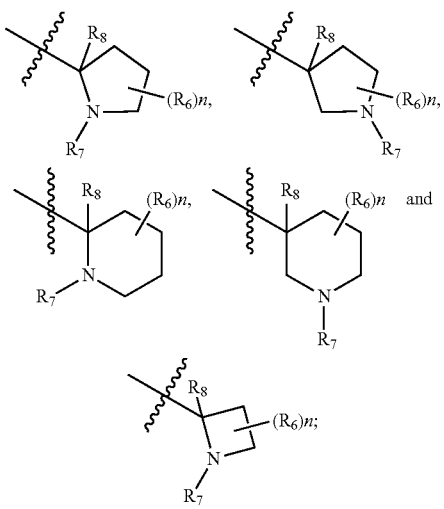

and n, $R_1$, $R_2$, $R_3$, $R_4$, $R_6$, $R_7$ and $R_8$ are as defined in Formula (I) or Formula (II).

In certain embodiments are provided compounds of Formula (I) or a therapeutically acceptable salt thereof wherein Y is selected from the group consisting of

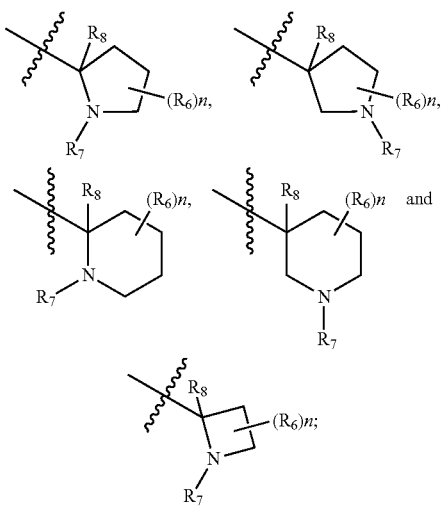

and n is 0; $R_1$, $R_2$, $R_3$, and $R_4$, are hydrogen; $R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl; and $R_A$ and $R_B$ are each independently selected from the group consisting of hydrogen, alkyl, cycloalkyl, and alkylcarbonyl; $R_8$ is hydrogen or alkyl.

In certain embodiments are provided compounds of Formula (I) or Formula (II) or a therapeutically acceptable salt thereof wherein Y is selected from the group consisting of

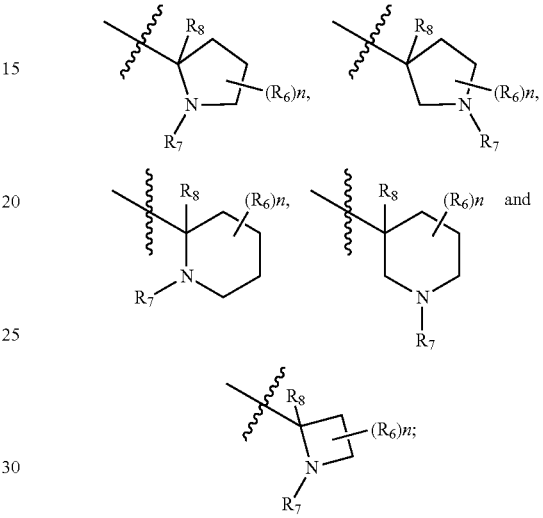

and n is 0; $R_1$, $R_2$, $R_3$, and $R_4$, are hydrogen; $R_7$ is selected from the group consisting of hydrogen, alkyl, cycloalkyl, arylalkyl, and $(NR_AR_B)$sulfonyl; and $R_A$ and $R_B$ are each independently selected from the group consisting of hydrogen, alkyl, and cycloalkyl; $R_8$ is hydrogen or methyl.

In certain embodiments are provided compounds of Formula (I) or Formula (II) or a therapeutically acceptable salt thereof wherein Y is selected from the group consisting of

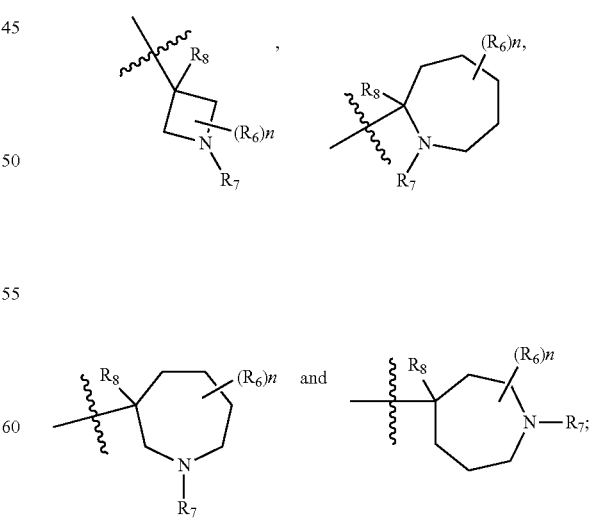

and n, $R_1$, $R_2$, $R_3$, $R_4$, $R_6$, $R_7$ and $R_8$ are as defined in Formula (I) or Formula (II).

In certain embodiments are provided compounds of Formula (I) or Formula (II) or a therapeutically acceptable salt thereof wherein Y is selected from the group consisting of

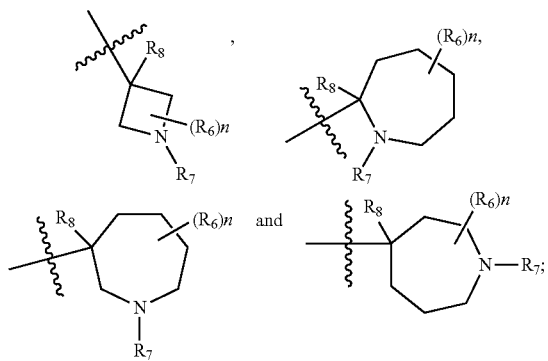

and n is 0; $R_1$, $R_2$, $R_3$, and $R_4$, are hydrogen; $R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl; and $R_A$ and $R_B$ are each independently selected from the group consisting of hydrogen, alkyl, cycloalkyl, and alkylcarbonyl; $R_8$ is hydrogen or alkyl.

In certain embodiments are provided compounds of Formula (I) or Formula (II) or a therapeutically acceptable salt thereof wherein Y is selected from the group consisting of

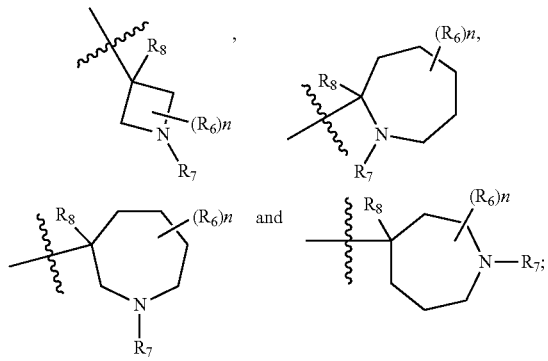

and n is 0; $R_1$, $R_2$, $R_3$, and $R_4$, are hydrogen; $R_7$ is selected from the group consisting of hydrogen, alkyl, cycloalkyl, arylalkyl, and $(NR_AR_B)$sulfonyl; and $R_A$ and $R_B$ are each independently selected from the group consisting of hydrogen, alkyl, and cycloalkyl; $R_8$ is hydrogen or methyl.

In certain embodiments are provided compounds of Formula (I) or Formula (II) or a therapeutically acceptable salt thereof wherein Y is an aryl group optionally substituted with 1, 2, or 3 $R_5$; wherein each $R_5$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl, wherein when aryl is phenyl, the phenyl is substituted with 1, 2, or 3 substituents selected independently from the group consisting of alkoxyalkyl, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $(NR_AR_B)$alkyl; and $R_1$, $R_2$, $R_3$, and $R_4$, are hydrogen.

In certain embodiments are provided compounds of Formula (I) or Formula (II) or a therapeutically acceptable salt thereof wherein Y is an heteroaryl group optionally substituted with 1, 2, or 3 $R_5$; wherein each $R_5$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $NR_AR_B)$sulfonyl; and $R_1$, $R_2$, $R_3$, and $R_4$, are hydrogen.

In certain embodiments are provided compounds of Formula (I) or Formula (II) or a therapeutically acceptable salt thereof wherein Y is a L-T group where L is selected from the group consisting of alkenylene, alkylene, alkynylene, cycloalkylene and spiroheterocycle and T is selected from the group consisting of heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, and $NR_AR_B$; and $R_1$, $R_2$, $R_3$, and $R_4$, are hydrogen.

Described herein are compounds, such as by way of example only:

2-(4-((Methylamino)methyl)phenyl)benzo[d]oxazole-4-carboxamide;
2-(2-Methylpyrrolidin-2-yl)benzo[d]oxazole-4-carboxamide;
2-(4-((Methylamino)methyl)phenyl)benzo[d]oxazole-7-carboxamide;
2-(2-Methylpyrrolidin-2-yl)benzo[d]oxazole-7-carboxamide;
2-(Pyrrolidin-2-yl)benzo[d]oxazole-4-carboxamide;
2-(Pyrrolidin-2-yl)benzo[d]oxazole-7-carboxamide;
2-(7-Azabicyclo[2.2.1]heptan-1-yl)benzo[d]oxazole-4-carboxamide;
2-(7-Azabicyclo[2.2.1]heptan-1-yl)benzo[d]oxazole-7-carboxamide;
2-(2-Methyl-7-azabicyclo[2.2.1]heptan-1-yl)benzo[d]oxazole-4-carboxamide;
2-(2-Methyl-7-azabicyclo[2.2.1]heptan-1-yl)benzo[d]oxazole-7-carboxamide;
2-(2-Azabicyclo[2.1.1]hexan-1-yl)benzo[d]oxazole-4-carboxamide;
2-(2-Azabicyclo[2.1.1]hexan-1-yl)benzo[d]oxazole-7-carboxamide;
2-(6-Azabicyclo[3.2.1]octan-5-yl)benzo[d]oxazole-4-carboxamide;
2-(6-Azabicyclo[3.2.1]octan-5-yl)benzo[d]oxazole-7-carboxamide;
2-((1S,5R)-6-Azabicyclo[3.2.1]octan-5-yl)benzo[d]oxazole-4-carboxamide;
2-((1S,5R)-6-Azabicyclo[3.2.1]octan-5-yl)benzo[d]oxazole-7-carboxamide;
2-((1R,5S)-6-Azabicyclo[3.2.1]octan-5-yl)benzo[d]oxazole-4-carboxamide;
2-((1R,5S)-6-Azabicyclo[3.2.1]octan-5-yl)benzo[d]oxazole-7-carboxamide;

2-(2-Benzyl-2-azabicyclo[2.2.2]octan-1-yl)benzo[d]oxazole-4-carboxamide;
2-(2-Benzyl-2-azabicyclo[2.2.2]octan-1-yl)benzo[d]oxazole-7-carboxamide;
2-(2-Azabicyclo[2.2.2]octan-1-yl)benzo[d]oxazole-4-carboxamide;
2-(2-Azabicyclo[2.2.2]octan-1-yl)benzo[d]oxazole-7-carboxamide;
2-(4-Azaspiro[2.4]heptan-5-yl)benzo[d]oxazole-4-carboxamide;
2-(4-Azaspiro[2.4]heptan-5-yl)benzo[d]oxazole-7-carboxamide;
2-((1R,4S)-2-Methyl-2-azabicyclo[2.2.1]heptan-1-yl)benzo[d]oxazole-4-carboxamide;
2-((1R,4S)-2-Methyl-2-azabicyclo[2.2.1]heptan-1-yl)benzo[d]oxazole-7-carboxamide;
2-((1R,4S)-2-Ethyl-2-azabicyclo[2.2.1]heptan-1-yl)benzo[d]oxazole-4-carboxamide;
2-((1R,4S)-2-Ethyl-2-azabicyclo[2.2.1]heptan-1-yl)benzo[d]oxazole-7-carboxamide;
2-((1R,4S)-2-Cyclopropyl-2-azabicyclo[2.2.1]heptan-1-yl)benzo[d]oxazole-4-carboxamide;
2-((1R,4S)-2-Cyclopropyl-2-azabicyclo[2.2.1]heptan-1-yl)benzo[d]oxazole-7-carboxamide;
2-(2-Azabicyclo[2.2.1]heptan-1-yl)benzo[d]oxazole-4-carboxamide;
2-(2-Azabicyclo[2.2.1]heptan-1-yl)benzo[d]oxazole-7-carboxamide;
2-(7-Azabicyclo[2.2.1]heptan-1-yl)-5-chlorobenzo[d]oxazole-4-carboxamide;
2-(7-Azabicyclo[2.2.1]heptan-1-yl)-5-chlorobenzo[d]oxazole-7-carboxamide;
2-(2-Azabicyclo[2.2.1]heptan-1-yl)-5-chlorobenzo[d]oxazole-4-carboxamide;
2-(2-Azabicyclo[2.2.1]heptan-1-yl)-5-chlorobenzo[d]oxazole-7-carboxamide;
2-(1-Azabicyclo[2.2.1]heptan-4-yl)benzo[d]oxazole-4-carboxamide;
2-(1-Azabicyclo[2.2.1]heptan-4-yl)benzo[d]oxazole-7-carboxamide;
2-(Quinuclidin-4-yl)benzo[d]oxazole-4-carboxamide;
2-(Quinuclidin-4-yl)benzo[d]oxazole-7-carboxamide;
2-(1-Azabicyclo[3.3.1]nonan-5-yl)benzo[d]oxazole-4-carboxamide;
2-(1-Azabicyclo[3.3.1]nonan-5-yl)benzo[d]oxazole-7-carboxamide;
2-(Octahydro-1H-quinolizin-2-yl)benzo[d]oxazole-4-carboxamide;
2-(Octahydro-1H-quinolizin-2-yl)benzo[d]oxazole-7-carboxamide;
2-(Octahydro-1H-quinolizin-1-yl)benzo[d]oxazole-4-carboxamide;
2-(Octahydro-1H-quinolizin-1-yl)benzo[d]oxazole-7-carboxamide;
2-(Octahydro-1H-quinolizin-4-yl)benzo[d]oxazole-4-carboxamide;
2-(Octahydro-1H-quinolizin-4-yl)benzo[d]oxazole-7-carboxamide;
2-(Octahydro-1H-quinolizin-3-yl)benzo[d]oxazole-4-carboxamide;
2-(Octahydro-1H-quinolizin-3-yl)benzo[d]oxazole-7-carboxamide;
2-(Octahydrocyclopenta[c]pyrrol-1-yl)benzo[d]oxazole-4-carboxamide;
2-(Octahydrocyclopenta[c]pyrrol-1-yl)benzo[d]oxazole-7-carboxamide;
2-(2-Azabicyclo[2.2.1]heptan-4-yl)benzo[d]oxazole-4-carboxamide;
2-(2-Azabicyclo[2.2.1]heptan-4-yl)benzo[d]oxazole-7-carboxamide;
2-(2-Oxa-5-Azabicyclo[2.2.1]heptan-4-yl)benzo[d]oxazole-4-carboxamide;
2-(2-Oxa-5-Azabicyclo[2.2.1]heptan-4-yl)benzo[d]oxazole-7-carboxamide;
2-(2-Azabicyclo[2.2.2]octan-4-yl)benzo[d]oxazole-4-carboxamide;
2-(2-Azabicyclo[2.2.2]octan-4-yl)benzo[d]oxazole-7-carboxamide;
2-(3-Azabicyclo[3.2.0]heptan-1-yl)benzo[d]oxazole-4-carboxamide;
2-(3-Azabicyclo[3.2.0]heptan-1-yl)benzo[d]oxazole-7-carboxamide;
2-(2-Azabicyclo[3.2.0]heptan-1-yl)benzo[d]oxazole-4-carboxamide;
2-(2-Azabicyclo[3.2.0]heptan-1-yl)benzo[d]oxazole-7-carboxamide;
2-(2-Azabicyclo[3.2.0]heptan-4-yl)benzo[d]oxazole-4-carboxamide;
2-(2-Azabicyclo[3.2.0]heptan-4-yl)benzo[d]oxazole-7-carboxamide;
2-(2-Azabicyclo[3.2.0]heptan-3-yl)benzo[d]oxazole-4-carboxamide;
2-(2-Azabicyclo[3.2.0]heptan-3-yl)benzo[d]oxazole-7-carboxamide;
2-(5-Azaspiro[2.4]heptan-6-yl)benzo[d]oxazole-4-carboxamide;
2-(5-Azaspiro[2.4]heptan-6-yl)benzo[d]oxazole-7-carboxamide;
2-(4-Azaspiro[2.4]heptan-6-yl)benzo[d]oxazole-4-carboxamide;
2-(4-Azaspiro[2.4]heptan-6-yl)benzo[d]oxazole-7-carboxamide;
2-(6-Azaspiro[3.4]octan-7-yl)benzo[d]oxazole-4-carboxamide;
2-(6-Azaspiro[3.4]octan-7-yl)benzo[d]oxazole-7-carboxamide;
2-(5-Azaspiro[3.4]octan-6-yl)benzo[d]oxazole-4-carboxamide;
2-(5-Azaspiro[3.4]octan-6-yl)benzo[d]oxazole-7-carboxamide;
2-(5-Azaspiro[3.4]octan-7-yl)benzo[d]oxazole-4-carboxamide;
2-(5-Azaspiro[3.4]octan-7-yl)benzo[d]oxazole-7-carboxamide;
2-(6-Azaspiro[2.5]octan-5-yl)benzo[d]oxazole-4-carboxamide;
2-(6-Azaspiro[2.5]octan-5-yl)benzo[d]oxazole-7-carboxamide;
2-(4-Azaspiro[2.5]octan-5-yl)benzo[d]oxazole-4-carboxamide;
2-(4-Azaspiro[2.5]octan-5-yl)benzo[d]oxazole-7-carboxamide;
2-(5-Azaspiro[2.5]octan-7-yl)benzo[d]oxazole-4-carboxamide;
2-(5-Azaspiro[2.5]octan-7-yl)benzo[d]oxazole-7-carboxamide;
2-(4-Oxa-7-azaspiro[2.5]octan-5-yl)benzo[d]oxazole-4-carboxamide;
2-(4-Oxa-7-azaspiro[2.5]octan-5-yl)benzo[d]oxazole-7-carboxamide;
2-(4-Azaspiro[2.5]octan-7-yl)benzo[d]oxazole-4-carboxamide;

2-(4-Azaspiro[2.5]octan-7-yl)benzo[d]oxazole-7-carboxamide;
2-(5-Azaspiro[3.5]nonan-6-yl)benzo[d]oxazole-4-carboxamide;
2-(5-Azaspiro[3.5]nonan-6-yl)benzo[d]oxazole-7-carboxamide;
2-(6-Azaspiro[3.5]nonan-8-yl)benzo[d]oxazole-4-carboxamide;
2-(6-Azaspiro[3.5]nonan-8-yl)benzo[d]oxazole-7-carboxamide;
2-(7-Azaspiro[3.5]nonan-6-yl)benzo[d]oxazole-4-carboxamide;
2-(7-Azaspiro[3.5]nonan-6-yl)benzo[d]oxazole-7-carboxamide;
2-(5-Azaspiro[3.5]nonan-8-yl)benzo[d]oxazole-4-carboxamide;
2-(5-Azaspiro[3.5]nonan-8-yl)benzo[d]oxazole-7-carboxamide;
2-(8-Oxa-5-azaspiro[3.5]nonan-6-yl)benzo[d]oxazole-4-carboxamide;
2-(8-Oxa-5-azaspiro[3.5]nonan-6-yl)benzo[d]oxazole-7-carboxamide;
2-(5-Oxa-5-azaspiro[3.5]nonan-6-yl)benzo[d]oxazole-4-carboxamide;
2-(5-Oxa-5-azaspiro[3.5]nonan-6-yl)benzo[d]oxazole-7-carboxamide;
2-(2,3,4,6,7,9a-Hexahydro-1H-quinolizin-2-yl)benzo[d]oxazole-4-carboxamide;
2-(2,3,4,6,7,9a-Hexahydro-1H-quinolizin-2-yl)benzo[d]oxazole-7-carboxamide;
2-(Decahydropyrido[1,2-a]azepin-4-yl)benzo[d]oxazole-4-carboxamide;
2-(Decahydropyrido[1,2-a]azepin-4-yl)benzo[d]oxazole-7-carboxamide;
2-(2-fluoro-4-(pyridine-2-yl)phenyl)benzo[d]oxazole-7-carboxamide;
2-(2-fluoro-4-(piperidin-2-yl)phenyl)benzo[d]oxazole-7-carboxamide;
2-(2-fluoro-4-(1-propylpiperidin-2-yl)phenyl)benzo[d]oxazole-7-carboxamide;
2-(2-fluoro-4-(pyrrolidin-2-yl)phenyl)benzo[d]oxazole-7-carboxamide;
2-(4-((methylamino)methyl)phenyl)benzo[d]oxazole-4-carboxamide;
2-(pyridin-4-yl)benzo[d]oxazole-4-carboxamide;
2-(pyridin-3-yl)benzo[d]oxazole-4-carboxamide;
2-(4-((methylamino)methyl)phenyl)benzo[d]oxazole-7-carboxamide;
5-fluoro-2-(4-((methylamino)methyl)phenyl)benzo[d]oxazole-7-carboxamide;
2-(4-((dimethylamino)methyl)phenyl)benzo[d]oxazole-7-carboxamide;
2-(4-(piperazin-1-ylmethyl)phenyl)benzo[d]oxazole-7-carboxamide;
2-(3-((methylamino)methyl)phenyl)benzo[d]oxazole-7-carboxamide;
2-(3-((dimethylamino)methyl)phenyl)benzo[d]oxazole-7-carboxamide;
2-(3-(pyrrolidin-1-ylmethyl)phenyl)benzo[d]oxazole-7-carboxamide;
2-(3-(piperazin-1-ylmethyl)phenyl)benzo[d]oxazole-7-carboxamide;
2-(3-(2-(dimethylamino)ethylamino)methyl)phenyl)benzo[d]oxazole-7-carboxamide;
2-(pyridin-4-yl)benzo[d]oxazole-7-carboxamide;
2-(pyridin-3-yl)benzo[d]oxazole-7-carboxamide;
2-(1H-indol-2-yl)benzo[d]oxazole-7-carboxamide;
2-(4-methoxyphenylbenzo[d]oxazole-4-carboxamide;
2-(4-methoxyphenylbenzo[d]oxazole-7-carboxamide;
2-(4-((dimethylamino)methyl)phenyl)benzo[d]oxazole-4-carboxamide;
2-(4-((dimethylamino)methyl)phenyl)-5-fluorobenzo[d]oxazole-7-carboxamide;
2-(4-((methoxyamino)methyl)phenyl)benzo[d]oxazole-7-carboxamide;
2-(4-((methoxy(methyl)amino)methyl)phenyl)benzo[d]oxazole-7-carboxamide;
5-fluoro-2-(4-((methoxyamino)methyl)phenyl)benzo[d]oxazole-7-carboxamide;
5-fluoro-2-(4-((methoxy(methyl)amino)methyl)phenyl)benzo[d]oxazole-7-carboxamide;
2-(pyrrolidin-2-yl)benzo[d]oxazole-7-carboxamide;
2-(piperidin-4-yl)benzo[d]oxazole-7-carboxamide;
2-(azetidin-3-yl)benzo[d]oxazole-7-carboxamide;
2-(piperidin-3-yl)benzo[d]oxazole-7-carboxamide;
2-(2-methylpyrrolidin-2-yl)benzo[d]oxazole-7-carboxamide;
2-(4-(pyridin-2-yl)phenyl)benzo[d]oxazole-7-carboxamide;
2-(4-(piperidin-2-yl)phenyl)benzo[d]oxazole-7-carboxamide;
2-(4-(pyridin-3-yl)phenyl)benzo[d]oxazole-7-carboxamide;
2-(4-(piperidin-3-yl)phenyl)benzo[d]oxazole-7-carboxamide;
2-(4-(pyridin-4-yl)phenyl)benzo[d]oxazole-7-carboxamide;
2-(4-(piperidin-4-yl)phenyl)benzo[d]oxazole-7-carboxamide;
2-(3-(pyridin-2-yl)phenyl)benzo[d]oxazole-7-carboxamide;
2-(3-(piperidin-2-yl)phenyl)benzo[d]oxazole-7-carboxamide;
2-(3-(pyridin-3-yl)phenyl)benzo[d]oxazole-7-carboxamide;
2-(3-(piperidin-3-yl)phenyl)benzo[d]oxazole-7-carboxamide;
2-(3-(pyridin-4-yl)phenyl)benzo[d]oxazole-7-carboxamide;
2-(3-(piperidin-4-yl)phenyl)benzo[d]oxazole-7-carboxamide;
2-((1-(2-dimethylamino)acetyl)piperidin-3-yl)benzo[d]oxazole-7-carboxamide;
2-(3-(4-isobutyrylpiperazine-1-carbonyl)phenyl)benzo[d]oxazole-7-carboxamide;
2-(3-(4-(cyclopropanecarbonyl)piperazine-1-carbonyl)phenyl)benzo[d]oxazole-7-carboxamide;
2-(4-(Piperidin-3-yl)phenyl)benzo[d]oxazole-7-carboxamide;
2-(1-azabicyclo[3.2.1]octan-5-yl)benzo[d]oxazole-7-carboxamide;
2-(4-(2-(methylamino)ethyl)phenyl)benzo[d]oxazole-7-carboxamide;
2-(4-(2-(dimethylamino)ethyl)phenyl)benzo[d]oxazole-7-carboxamide;
2-(1-propylpiperidin-3-yl)benzo[d]oxazole-7-carboxamide;
2-(1-propylpiperidin-4-yl)benzo[d]oxazole-7-carboxamide;
2-(2-fluoro-4-(pyridin-4-yl)phenyl)benzo[d]oxazole-7-carboxamide;
2-(2-fluoro-4-(piperidin-4-yl)phenyl)benzo[d]oxazole-7-carboxamide;
2-(2-fluoro-4-(1-propylpiperidin-4-yl)phenyl)benzo[d]oxazole-7-carboxamide;
2-(1-pentylpiperidin-4-yl)benzo[d]oxazol-7-carboxamide;
2-(1-butylpiperidin-4-yl)benzo[d]oxazol-7-carboxamide;
2-(4-(1-propylpiperidin-3-yl)phenyl)benzo[d]oxazole-7-carboxamide;
2-(4-(1-propylpiperidin-4-yl)phenyl)benzo[d]oxazole-7-carboxamide; and 2-(4-(1-(2-(dimethylamino)acetyl)piperidin-4-yl)phenyl)benzo[d]oxazole-7-carboxamide.

In some embodiments, provided herein is a pharmaceutical composition comprising of a compound of Formula (I) or Formula (II), or a pharmaceutically acceptable salt, a pharmaceutically acceptable solvate, pharmaceutically acceptable prodrug thereof in combination with a pharmaceutically acceptable carrier, excipient, binder or diluent.

Certain embodiments provide a method of inhibiting PARP in a subject in recognized need of such treatment comprising administering to the subject a therapeutically acceptable amount of a compound of Formula (I) or Formula (II) or a therapeutically acceptable salt thereof.

In one embodiment, provided herein is a method of treatment of disease ameliorated by the inhibition of PARP that includes administering to a subject in need of treatment a therapeutically-effective amount of a compound of Formula (I) or Formula (II). In some embodiments, the disease is selected from the group consisting of: vascular disease; septic shock; ischemic injury; reperfusion injury; neurotoxicity; hemorrhagic shock; inflammatory diseases; multiple sclerosis; secondary effects of diabetes; and acute treatment of cytotoxicity following cardiovascular surgery.

In certain embodiments, provided herein is a method for the treatment of cancer, which includes administering to a subject in need of treatment a therapeutically-effective amount of a compound of Formula (I) or (II).

Certain embodiments provide a method of potentiation of cytotoxic cancer therapy in a subject in recognized need of such treatment comprising administering to the subject a therapeutically acceptable amount of a compound of Formula (I) or Formula (II) or a therapeutically acceptable salt thereof.

In some embodiments, provided herein is a method for the treatment of cancer, which includes administering to a subject in need of treatment a therapeutically-effective amount of a compound of Formula (I) or (II) in combination with ionizing radiation or one or more chemotherapeutic agents. In some embodiments, the compound described herein is administered simultaneously with ionizing radiation or one or more chemotherapeutic agents. In other embodiments, the compound described herein is administered sequentially with ionizing radiation or one or more chemotherapeutic agents.

In certain embodiments, provided herein is a method for the treatment of cancer, which includes administering to a subject in need of treatment a therapeutically-effective amount of a compound of Formula (I) or Formula (II) in combination with ionizing radiation and one or more chemotherapeutic agents. In some embodiments, the compound described herein is administered simultaneously with ionizing radiation and one or more chemotherapeutic agents. In other embodiments, the compound described herein is administered sequentially with ionizing radiation and one or more chemotherapeutic agents.

Certain embodiments provide a method of treating leukemia, colon cancer, glioblastomas, lymphomas, melanomas, carcinomas of breast, or cervical carcinomas in a subject in recognized need of such treatment comprising administering to the subject a therapeutically acceptable amount of a compound of Formula (I) or Formula (II) or therapeutically acceptable salt thereof.

In some embodiments, provided herein is a method of treatment of a cancer deficient in Homologous Recombination (HR) dependent DNA double strand break (DSB) repair pathway, which includes administering to a subject in need of treatment a therapeutically-effective amount of a compound of Formula (I) or Formula (II). In certain embodiments, the cancer includes one or more cancer cells having a reduced or abrogated ability to repair DNA DSB by HR relative to normal cells. In some embodiments, the cancer cells have a BRCA1 or BRCA2 deficient phenotype. In some embodiments, the cancer cells are deficient in BRCA1 or BRCA2. In some embodiments, the methods provided herein involve treatment of an individual who is heterozygous for a mutation in a gene encoding a component of the HR dependent DNA DSB repair pathway. In certain embodiment, the individual is heterozygous for a mutation in BRCA1 and/or BRCA2. In some embodiments, the method of treatment of a cancer includes treatment of breast, ovary, pancreas and/or prostate cancer. In some embodiments, the method of treatment of a cancer further includes administration of ionizing radiation or a chemotherapeutic agent.

Certain embodiments provide a method of treating ischemia reperfusion injury associated with, but not limited to, myocardial infarction, stroke, other neural trauma, and organ transplantation, in a subject in recognized need of such treatment comprising administering to the subject a therapeutically acceptable amount of a compound of Formula (I) or Formula (II) or a therapeutically acceptable salt thereof.

Certain embodiments provide a method of treating reperfusion including, but not limited to, reperfusion of the eye, kidney, gut, and skeletal muscle, in a subject in recognized need of such treatment comprising administering to the subject a therapeutically acceptable amount of a compound of Formula (I) or Formula (II) or a therapeutically acceptable salt thereof.

Certain embodiments provide a method of treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a subject in recognized need of such treatment comprising administering to the subject a therapeutically acceptable amount of a compound of Formula (I) or Formula (II) or a therapeutically acceptable salt thereof.

Certain embodiments provide a method of treating immunological diseases or disorders such a rheumatoid arthritis and septic shock in a subject in recognized need of such treatment comprising administering to the subject a therapeutically acceptable amount of a compound of Formula (I) or Formula (II) or a therapeutically acceptable salt thereof.

Certain embodiments provide a method of treating degenerative diseases including, but not limited to, diabetes and Parkinsons disease in a subject in recognized need of such treatment comprising administering to the subject a therapeutically acceptable amount of a compound of Formula (I) or Formula (II) or a therapeutically acceptable salt thereof.

Certain embodiments provide a method of treating hypoglycemia in a subject in recognized need of such treatment comprising administering to the subject a therapeutically acceptable amount of a compound of Formula (I) or Formula (II) or a therapeutically acceptable salt thereof.

Certain embodiments provide a method of treating retroviral infection in a subject in recognized need of such treatment comprising administering to the subject a therapeutically acceptable amount of a compound of Formula (I) or Formula (II) or a therapeutically acceptable salt thereof.

Certain embodiments provide a method of treating liver toxicity following acetaminophen overdose in a subject in recognized need of such treatment comprising administering to the subject a therapeutically acceptable amount of a compound of Formula (I) or Formula (II) or a therapeutically acceptable salt thereof.

Certain embodiments provide a method of treating cardiac and kidney toxicities from doxorubicin and platinum based antineoplastic agents in a subject in recognized need of such treatment comprising administering to the subject a therapeutically acceptable amount of a compound of Formula (I) or Formula (II) or a therapeutically acceptable salt thereof.

Certain embodiments provide a method of treating skin damage secondary to sulfur mustards in a subject in recognized need of such treatment comprising administering to the subject a therapeutically acceptable amount of a compound of Formula (I) or Formula (II) or a therapeutically acceptable salt thereof.

Certain embodiments provide a use of a compound of Formula (I) or Formula (II) or a therapeutically acceptable salt thereof, to prepare a medicament for inhibiting the PARP enzyme in a subject in recognized need of such treatment.

Certain embodiments provide a use of a compound of Formula (I) or Formula (II) or a therapeutically acceptable salt thereof, to prepare a medicament for inhibiting tumor growth in a subject in recognized need of such treatment.

Certain embodiments provide a use of a compound of Formula (I) or Formula (II) or a therapeutically acceptable salt thereof, to prepare a medicament for treating cancer in a subject in recognized need of such treatment.

Certain embodiments provide a use of a compound of Formula (I) or Formula (II) or a therapeutically acceptable salt thereof, to prepare a medicament for treating leukemia, colon cancer, glioblastomas, lymphomas in a subject in recognized need of such treatment.

Certain embodiments provide a method of treating degenerative diseases including, but not limited to, diabetes and Parkinsons disease in a subject in recognized need of such treatment comprising administering to the subject a therapeutically acceptable amount of a compound of Formula (I) or Formula (II) or a therapeutically acceptable salt thereof.

Certain embodiments provide a use of a compound of Formula (I) or Formula (II) or a therapeutically acceptable salt thereof, to prepare a medicament for potentiation of cytotoxic cancer therapy in a subject in recognized need of such treatment comprising administering to the subject a therapeutically acceptable amount of a compound of Formula (I) or Formula (II) or a therapeutically acceptable salt thereof.

Certain embodiments provide a use of a compound of Formula (I) or Formula (II) or a therapeutically acceptable salt thereof, to prepare a medicament for treating ischemia reperfusion injury associated with, but not limited to, myocardial infarction, stroke, other neural trauma, and organ transplantation, in a subject in recognized need of such treatment comprising administering to the subject a therapeutically acceptable amount of a compound of Formula (I) or Formula (II) or a therapeutically acceptable salt thereof.

Certain embodiments provide a use of a compound of Formula (I) or Formula (II) or a therapeutically acceptable salt thereof, to prepare a medicament for treating reperfusion including, but not limited to, reperfusion of the eye, kidney, gut and skeletal muscle, in a subject in recognized need of such treatment comprising administering to the subject a therapeutically acceptable amount of a compound of Formula (I) or Formula (II) or a therapeutically acceptable salt thereof.

Certain embodiments provide a use of a compound of Formula (I) or Formula (II) or a therapeutically acceptable salt thereof, to prepare a medicament for treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a subject in recognized need of such treatment comprising administering to the subject a therapeutically acceptable amount of a compound of Formula (I) or Formula (II) or a therapeutically acceptable salt thereof.

Certain embodiments provide a use of a compound of Formula (I) or Formula (II) or a therapeutically acceptable salt thereof, to prepare a medicament for treating immunological diseases or disorders such as rheumatoid arthritis and septic shock in a mammal in recognized need of such treatment comprising administering to the subject a therapeutically acceptable amount of a compound of Formula (I) or Formula (II) or a therapeutically acceptable salt thereof.

Certain embodiments provide a use of a compound of Formula (I) or Formula (II) or a therapeutically acceptable salt thereof, to prepare a medicament for treating hypoglycemia in a subject in recognized need of such treatment comprising administering to the subject a therapeutically acceptable amount of a compound of Formula (I) or Formula (II) or a therapeutically acceptable salt thereof.

Certain embodiments provide a use of a compound of Formula (I) or Formula (II) or a therapeutically acceptable salt thereof, to prepare a medicament for treating retroviral infection in a subject in recognized need of such treatment comprising administering to the subject a therapeutically acceptable amount of a compound of Formula (I) or Formula (II) or a therapeutically acceptable salt thereof.

Certain embodiments provide a use of a compound of Formula (I) or Formula (II) or a therapeutically acceptable salt thereof, to prepare a medicament for treating liver toxicity following acetaminophen overdose in a subject in recognized need of such treatment comprising administering to the subject a therapeutically acceptable amount of a compound of Formula (I) or Formula (II) or a therapeutically acceptable salt thereof.

Certain embodiments provide a use of a compound of Formula (I) or Formula (II) or a therapeutically acceptable salt thereof, to prepare a medicament for treating cardiac and kidney toxicities from doxorubicin and platinum based antineoplastic agents in a subject in recognized need of such treatment comprising administering to the mammal a therapeutically acceptable amount of a compound of Formula (I) or Formula (II) or a therapeutically acceptable salt thereof.

Certain embodiments provide a use of a compound of Formula (I) or Formula (II) or a therapeutically acceptable salt thereof, to prepare a medicament for treating skin damage secondary to sulfur mustards in a subject in recognized need of such treatment comprising administering to the mammal a therapeutically acceptable amount of a compound of Formula (I) or Formula (II) or a therapeutically acceptable salt thereof.

Articles of manufacture, which include packaging material, a compound provided herein that is effective for modulating the activity of the enzyme poly(ADP-ribose)polymerase, or for treatment, prevention or amelioration of one or more symptoms of a poly(ADP-ribose)polymerase-dependent or poly(ADP-ribose)polymerase-mediated disease or condition, within the packaging material, and a label that indicates that the compound or composition, or pharmaceutically acceptable salt, pharmaceutically acceptable N-oxide, pharmaceutically active metabolite, pharmaceutically acceptable prodrug, or pharmaceutically acceptable solvate thereof, is used for modulating the activity of poly(ADP-ribose)polymerase, or for treatment, prevention or amelioration of one or more symptoms of a poly(ADP-ribose)polymerase-dependent or poly(ADP-ribose)polymerase-mediated disease or condition, are provided.

Any combination of the groups described above for the various variables is contemplated herein.

In one embodiment, disclosed herein is a pharmaceutical composition that includes a compound, pharmaceutically acceptable salt, pharmaceutically acceptable N-oxide, pharmaceutically active metabolite, pharmaceutically acceptable prodrug, or pharmaceutically acceptable solvate of any of the compounds disclosed herein. In some embodiments, the pharmaceutical compositions further include a pharmaceutically acceptable diluent, excipient or binder. In certain embodiments, the pharmaceutical composition further includes a second pharmaceutically active ingredient.

In one embodiment, the PARP mediated disease or condition in a patient, or the PARP dependent disease or condition in a patient is cancer or a non-cancerous disorder. In some embodiments, the disease or condition is iatrogenic.

In some embodiments are methods for reducing/inhibiting the activity of PARP in a subject that include administering to the subject at least once an effective amount of a compound described herein.

Certain embodiments provided herein are methods for modulating, including reducing and/or inhibiting the activity of PARP, directly or indirectly, in a subject that include administering to the subject at least once an effective amount of at least one compound described herein.

In further embodiments are methods for treating PARP mediated conditions or diseases, that include administering to the subject at least once an effective amount of at least one compound described herein.

Some embodiments include the use of a compound described herein in the manufacture of a medicament for treating a disease or condition in a subject in which the activity of at least one PARP-protein contributes to the pathology and/or symptoms of the disease or condition.

In any of the aforementioned embodiments are further embodiments in which administration is enteral, parenteral, or both, and wherein:

(a) the effective amount of the compound is systemically administered to the subject;

(b) the effective amount of the compound is administered orally to the subject;

(c) the effective amount of the compound is intravenously administered to the subject;

(d) the effective amount of the compound administered by inhalation;

(e) the effective amount of the compound is administered by nasal administration;

(f) the effective amount of the compound is administered by injection to the subject;

(g) the effective amount of the compound is administered topically (dermal) to the subject;

(h) the effective amount of the compound is administered by ophthalmic administration; and/or (i) the effective amount of the compound is administered rectally to the subject.

In any of the aforementioned embodiments are further embodiments that include single administrations of the effective amount of the compound, including further embodiments in which the compound is administered to the subject (i) once;

(ii) multiple times over the span of one day;

(iii) continually; or (iv) continuously.

In any of the aforementioned embodiments are further embodiments that include multiple administrations of the effective amount of the compound, including further embodiments wherein:

(i) the compound is administered in a single dose;

(ii) the time between multiple administrations is every 6 hours;

(iii) the compound is administered to the subject every 8 hours.

In further or alternative embodiments, the method includes a drug holiday, wherein the administration of the compound is temporarily suspended or the dose of the compound being administered is temporarily reduced; at the end of the drug holiday, dosing of the compound is resumed. The length of the drug holiday can vary from 2 days to 1 year.

In any of the aforementioned embodiments involving the treatment of proliferative disorders, including cancer, are further embodiments that include administering at least one additional agent selected from among alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, paclitaxel, Taxol®, temozolomide, thioguanine, and classes of drugs including hormones (an antiestrogen, an antiandrogen, or gonadotropin releasing hormone analogues, interferons such as, for example, alpha interferon, nitrogen mustards such as, for example, busulfan, melphalan or mechlorethamine, retinoids such as, for example, tretinoin, topoisomerase inhibitors such as, for example, irinotecan or topotecan, tyrosine kinase inhibitors such as, for example, gefinitinib or imatinib, and agents to treat signs or symptoms induced by such therapy including allopurinol, filgrastim, granisetron/ondansetron/palonosetron, and dronabinol.

Other objects, features and advantages of the compounds, methods and compositions described herein will become apparent from the following description. It should be understood, however, that the description and the specific examples, while indicating specific embodiments, are given by way of illustration only, since various changes and modifications within the spirit and scope of the present description will become apparent from this detailed description.

Described herein are compounds, methods of making such compounds, pharmaceutical compositions and medicaments that include such compounds, and methods of using such compounds to treat or prevent diseases or conditions associated with PARP activity.

Described herein are compounds having activity in inhibiting the enzyme poly(ADP-ribose)polymerase (PARP). In some embodiments, the compounds have the structure set forth in Formula (I) or Formula (II).

The mammalian enzyme PARP-1 is a multidomain protein. PARP-1 is implicated in the signaling of DNA damage through its ability to recognize and rapidly bind to DNA single or double strand breaks. D'Amours, et al., *Biochem. J.*, 342, 249-268 (1999); and Virag et al. *Pharmacological Reviews*, vol. 54, no. 3, 375-429 (2002) are hereby incorporated by reference for such disclosure.

The family of poly(ADP-ribose)polymerases includes approximately 18 proteins, which all display a certain level of homology in their catalytic domain but differ in their cellular functions. PARP-1 and PARP-2 are unique members of the family, in that their catalytic activities are stimulated by the occurrence of DNA strand breaks. Ame et al., *BioEssays,* 26 (8), 882-893 (2004) is hereby incorporated by reference for such disclosure.

PARP-1 participates in a variety of DNA-related functions including gene amplification, cell division, differentiation, apoptosis, DNA base excision repair as well as effects on telomere length and chromosome stability. d'Adda di Fagagna, et al., *Nature Gen.*, 23 (1), 76-80 (1999) is hereby incorporated by reference for such disclosure.

Studies on the mechanism by which PARP-1 modulates DNA repair and other processes identifies its importance in the formation of poly(ADP-ribose) chains within the cellular nucleus. The DNA-bound, activated PARP-1 utilizes NAD+ to synthesize poly(ADP-ribose) on a variety of nuclear target proteins, including topoisomerases, histones and PARP itself. Althaus, F. R. and Richter, C., ADP-Ribosylation of Proteins: Enzymology and Biological Significance, Springer-Verlag, Berlin (1987); and Rhun, et al., *Biochem. Biophys. Res. Commun.*, 245, 1-10 (1998) are hereby incorporated by reference for such disclosure.

Poly(ADP-ribosyl)ation is also associated with malignant transformation. For example, PARP-1 activity is higher in the isolated nuclei of SV40-transformed fibroblasts, while both leukemic cells and colon cancer cells show higher enzyme activity than the equivalent normal leukocytes and colon mucosa. Furthermore, malignant prostate tumors have increased levels of active PARP as compared to benign prostate cells, which is associated with higher levels of genetic instability. Miwa, et al., *Arch. Biochem. Biophys.*, 181, 313-321 (1977); Burzio, et al., *Proc. Soc. Exp. Biol. Med.*, 149, 933-938 (1975); Hirai, et al., *Cancer Res.*, 43, 3441-3446 (1983); and Mcnealy, et al., *Anticancer Res.*, 23, 1473-1478 (2003) are hereby incorporated by reference for such disclosure.

In cells treated with alkylating agents, the inhibition of PARP leads to a marked increase in DNA-strand breakage and cell killing. PARP-1 inhibitors also enhance the effects of radiation response by suppressing the repair of potentially lethal damage. PARP inhibitors are also effective in radiosensitizing hypoxic tumor cells. In certain tumor cell lines, chemical inhibition of PARP activity is also associated with marked sensitization to very low doses of radiation.

Furthermore, PARP-1 knockout (PARP −/−) animals exhibit genomic instability in response to alkylating agents and γ-irradiation. Data indicates that PARP-1 and PARP-2 possess both overlapping and non-redundant functions in the maintenance of genomic stability, making them both interesting targets. Wang, et al., *Genes Dev.*, 9, 509-520 (1995); Menissier de Murcia, et al., *Proc. Natl. Acad. Sci. USA*, 94, 7303-7307 (1997); and Menissier de Murcia, et al., *EMBO. J.*, 22 (9), 2255-2263 (2003) are hereby incorporated by reference for such disclosure.

There is also a role for PARP-1 in certain vascular diseases, such as, for example, septic shock, ischaemic injury and neurotoxicity. Oxygen radical DNA damage that leads to strand breaks in DNA, which are subsequently recognized by PARP-1, is a major contributing factor to such disease states as shown by PARP-1 inhibitor studies. PARP also plays a role in the pathogenesis of haemorrhagic shock. Cantoni, et al., *Biochim. Biophys. Acta*, 1014, 1-7 (1989); Szabo, et al., *J. Clin. Invest.*, 100, 723-735 (1997); Cosi, et al., *J. Neurosci. Res.*, 39, 3846 (1994); Said, et al., *Proc. Natl. Acad. Sci. U.S.A.*, 93, 4688-4692 (1996); and Liaudet, et al., *Proc. Natl. Acad. Sci. U.S.A.*, 97(3), 10203-10208 (2000) are hereby incorporated by reference for such disclosure.

Furthermore, efficient retroviral infection of mammalian cells is blocked by the inhibition of PARP-1 activity. Such inhibition of recombinant retroviral vector infections occurs in various different cell types. In some embodiments, inhibitors of PARP-1 are used in anti-viral therapies and in cancer treatment. Gaken, et al., i *J. Virology*, 70 (6), 3992-4000 (1996) is hereby incorporated by reference for such disclosure.

Moreover, in certain embodiments, PARP-1 inhibition delays the onset of aging characteristics in human fibroblasts. While not intending to bound by any theory, this may be related to the role that PARP plays in controlling telomere function. Rattan and Clark, *Biochem. Biophys. Res. Comm.*, 201 (2), 665-672 (1994); and d'Adda di Fagagna, et al., *Nature Gen.*, 23 (1), 76-80 (1999) are hereby incorporated by reference for such disclosure.

In some embodiments, PARP inhibitors are relevant to the treatment of inflammatory bowel disease, ulcerative colitis and Crohn's disease. Szabo C., Role of Poly(ADP-Ribose) Polymerase Activation in the Pathogenesis of Shock and Inflammation, In PARP as a Therapeutic Target; Ed J. Zhang, 2002 by CRC Press; 169-204; Zingarelli, B, et al., *Immunology*, 113 (4), 509-517 (2004); and Jijon, H. B., et al., *Am. J. Physiol. Gastrointest. Liver Physiol.*, 279, G641-G651 (2000) are hereby incorporated by reference for such disclosure.

In certain embodiments, PARP inhibitors, such as those of Formula (I) and Formula (II), have utility in: (a) preventing or inhibiting poly(ADP-ribose) chain formation by, e.g., inhibiting the activity of cellular PARP (PARP-1 and/or PARP-2); (b) treating vascular disease; septic shock; ischaemic injury, both cerebral and cardiovascular; reperfusion injury, both cerebral and cardiovascular; neurotoxicity, including acute and chronic treatments for stroke and Parkinsons disease; haemorraghic shock; inflammatory diseases, such as arthritis, inflammatory bowel disease, ulcerative colitis and Crohn's disease; multiple sclerosis; secondary effects of diabetes; as well as the acute treatment of cytotoxicity following cardiovascular surgery or diseases ameliorated by the inhibition of the activity of PARP; (c) use as an adjunct in cancer therapy or for potentiating tumor cells for treatment with ionizing radiation and/or chemotherapeutic agents.

In specific embodiments, compounds provided herein, such as, for example, Formula (I) or Formula (II), are used in anti-cancer combination therapies (or as adjuncts) along with alkylating agents, such as methyl methanesulfonate (MMS), temozolomide and dacarbazine (DTIC), also with topoisomerase-1 inhibitors like Topotecan, Irinotecan, Rubitecan, Exatecan, Lurtotecan, Gimetecan, Diflomotecan (homocamptothecins); as well as 7-substituted non-silatecans; the 7-silyl camptothecins, BNP 1350; and non-camptothecin topoisomerase-I inhibitors such as indolocarbazoles also dual topoisomerase-I and II inhibitors like the benzophenazines, XR 11576/MLN 576 and benzopyridoindoles. In certain embodiments, such combinations are given, for example, as intravenous preparations or by oral administration as dependent on the method of administration for the particular agent.

In some embodiments, PARP inhibitors, such as, for example, compounds of Formula (I) or Formula (II), are used in the treatment of disease ameliorated by the inhibition of PARP, which includes administering to a subject in need of treatment a therapeutically-effective amount of a compound provided herein, and in one embodiment in the form of a pharmaceutical composition. In certain embodiments, PARP inhibitors, such as, for example, compounds of Formula (I) or Formula (II), are used in the treatment of cancer, which includes administering to a subject in need of treatment a therapeutically-effective amount of a compound provided herein in combination, and in one embodiment in the form of a pharmaceutical composition, simultaneously or sequentially with radiotherapy (ionizing radiation) or chemotherapeutic agents.

In certain embodiments, PARP inhibitors, such as, for example, compounds of Formula (I) or Formula (II), are used in the preparation of a medicament for the treatment of cancer which is deficient in Homologous Recombination (HR) dependent DNA double strand break (DSB) repair activity, or in the treatment of a patient with a cancer which is deficient in HR dependent DNA DSB repair activity, which includes administering to said patient a therapeutically-effective amount of the compound.

The HR dependent DNA DSB repair pathway repairs double-strand breaks (DSBs) in DNA via homologous mechanisms to reform a continuous DNA helix. The components of the HR dependent DNA DSB repair pathway include, but are not limited to, ATM (NM_000051), RAD51 (NM_002875), RAD51L1 (NM_002877), RAD51C (NM_002876), RAD51L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY. HR components are also described in Wood, et al., *Science,* 291, 1284-1289 (2001), which is hereby incorporated by reference for such disclosure. K. K. Khanna and S. P. Jackson, *Nat. Genet.* 27(3): 247-254 (2001); and Hughes-Davies, et al., *Cell,* 115, pp 523-535 are also incorporated herein by reference for such disclosure.

In some embodiments, a cancer which is deficient in HR dependent DNA DSB repair includes one or more cancer cells which have a reduced or abrogated ability to repair DNA DSBs through that pathway, relative to normal cells, i.e. the activity of the HR dependent DNA DSB repair pathway are reduced or abolished in the one or more cancer cells.

In certain embodiments, the activity of one or more components of the HR dependent DNA DSB repair pathway is abolished in the one or more cancer cells of an individual having a cancer which is deficient in HR dependent DNA DSB repair. Components of the HR dependent DNA DSB repair pathway include the components listed above.

In some embodiments, the cancer cells have a BRCA1 and/or a BRCA2 deficient phenotype, i.e., BRCA1 and/or BRCA2 activity is reduced or abolished in the cancer cells. In certain embodiments, cancer cells with this phenotype are deficient in BRCA1 and/or BRCA2, i.e., expression and/or activity of BRCA1 and/or BRCA2 is reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor or by an epigenetic mechanism such as gene promoter methylation.

BRCA1 and BRCA2 are tumor suppressors whose wild-type alleles are frequently lost in tumors of heterozygous carriers. BRCA1 and/or BRCA2 mutations are associated with breast cancer. Amplification of the EMSY gene, which encodes a BRCA2 binding factor, is associated with breast and ovarian cancer. Jasin M., *Oncogene,* 21 (58), 8981-93 (2002); Tutt, et al., *Trends Mol Med.,* 8 (12), 571-6, (2002); and Radice, P. J., *Exp Clin Cancer Res.,* 21 (3 Suppl), 9-12 (2002) are hereby incorporated by reference for such disclosure.

Carriers of mutations in BRCA1 and/or BRCA2 are also at elevated risk of cancer of the ovary, prostate and pancreas.

In some embodiments, the individual is heterozygous for one or more variations, such as mutations and polymorphisms, in BRCA1 and/or BRCA2 or a regulator thereof. The detection of variation in BRCA1 and BRCA2 is described, for example in EP 699 754, EP 705 903, Neuhausen, S. L. and Ostrander, E. A., *Genet. Test,* 1, 75-83 (1992); Janatova M., et al., *Neoplasma,* 50 (4), 246-50 (2003), which is hereby incorporated by reference for such disclosure. Determination of amplification of the BRCA2 binding factor EMSY is described in Hughes-Davies, et al., *Cell,* 115, 523-535).

In certain instances, mutations and polymorphisms associated with cancer are detected at the nucleic acid level by detecting the presence of a variant nucleic acid sequence or at the protein level by detecting the presence of a variant (i.e. a mutant or allelic variant) polypeptide.

DEFINITIONS

Unless defined otherwise, all technical and scientific terms used herein have the standard meaning pertaining to the claimed subject matter belongs. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless otherwise indicated, conventional methods of mass spectroscopy, NMR, HPLC, protein chemistry, biochemistry, recombinant DNA techniques and pharmacology are employed. Unless specific definitions are provided, the standard nomenclature employed in connection with, and the standard laboratory procedures and techniques of, analytical chemistry, synthetic organic chemistry, and medicinal and pharmaceutical chemistry are employed. In certain instances, standard techniques are used for chemical syntheses, chemical analyses, pharmaceutical preparation, formulation, and delivery, and treatment of patients. In certain embodiments, standard techniques are used for recombinant DNA, oligonucleotide synthesis, and tissue culture and transformation (e.g., electroporation, lipofection). In some embodiments, reactions and purification techniques are performed e.g., using kits of manufacturer's specifications or as commonly accomplished or as described herein.

As used throughout this application and the appended claims, the following terms have the following meanings:

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. Depending on the structure, an alkenyl group includes a monoradical or a diradical (i.e., an alkenylene group). Alkenyl groups include optionally substituted groups. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-cecenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight, branched chain, or cyclic (in this case, it would also be known as "cycloalkyl") hydrocarbon containing from 1-10 carbon atoms. Representative examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

The term substituted alkyl as used herein refers to alkyl substituted by one, two or three groups consisting of halogen, alkoxy, amino, alkylamino, dialkylamino, hydroxy, aryl, heteroaryl, alkenyl or alkynyl group.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

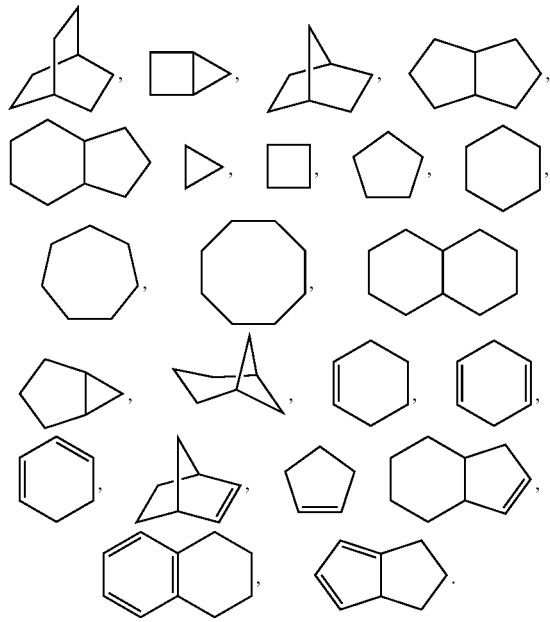

Depending on the structure, a cycloalkyl group includes a monoradical or a diradical (e.g., a cycloalkylene group).

The term "cycloalkyl groups" as used herein refers to groups which are optionally substituted with 1, 2, 3, or 4 substituents selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxyl, hydroxyalkyl, mercapto, oxo, —$NR_AR_A$, and $(NR_AR_B)$carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "carbocyclic" as used herein, refers to a compound which contains one or more covalently closed ring structures, and that the atoms forming the backbone of the ring are all carbon atoms The term "carbocycle" as used herein, refers to a ring, wherein each of the atoms forming the ring is a carbon atom. Carbocyclic rings include those formed by three, four, five, six, seven, eight, nine, or more than nine carbon atoms. Carbocycles are optionally substituted.

The term "alkoxyalkyl" as used herein, means at least one alkoxy group, as defined herein, appended to the parent molecular moiety through an alkyl group, as defined herein. Representative examples of alkoxyalkyl include, but are not limited to, 2-methoxyethyl, 2-ethoxyethyl, tert-butoxyethyl and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylthio" or "thioalkoxy" as used herein, means an alkyl group, as defined herein, appended to the parent molecular moiety through a sulfur atom. Representative examples of alkylthio include, but are not limited to, methylthio, ethylthio, butylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited to, methylthiomethyl, 2-(ethylthio)ethyl, butylthiomethyl, and hexylthioethyl.

The term "alkynyl" as used herein, means a straight, branched chain hydrocarbon containing from 2-10 carbons and containing at least one carbon-carbon triple bond. Alkynyl groups are optionally substituted. Representative examples of alkynyl include, but are not limited to, acetylenyl, 1-propynyl, 2-propynyl, 3-butynyl, 2-pentynyl, and 1-butynyl.

The term "aromatic" as used herein, refers to a planar ring having a delocalized π-electron system containing 4n+2π electrons, where n is an integer. Aromatic rings include those formed by five, six, seven, eight, nine, or more than nine atoms. Aromatics are be optionally substituted. The term includes monocyclic or fused-ring polycyclic (i.e., rings which share adjacent pairs of carbon atoms) groups.

The term "aryl" as used herein, refers to an aromatic ring wherein each of the atoms forming the ring is a carbon atom. Aryl rings include those formed by five, six, seven, eight, nine, or more than nine carbon atoms. Examples of aryl groups include, but are not limited to phenyl, naphthalenyl, phenanthrenyl, anthracenyl, fluorenyl, and indenyl.

The term "aryl" as used herein means an aryl group that are optionally substituted with one, two, three, four or five substituents independently selected from the group consisting of alkenyl, alkoxy, alkoxyalkyl, alkoxycarbonyl, alkyl, alkylcarbonyl, alkylcarbonyloxy, alkylthio, alkylthioalkyl, alkynyl, carbonyl, cyano, formyl, haloalkoxy, haloalkyl, halogen, hydroxyl, hydroxyalkyl, mercapto, nitro, —NR$_A$R$_A$, and (NR$_A$R$_B$)carbonyl.

The term "arylalkyl" as used herein, means an aryl group, as defined herein, appended to the parent molecular moiety through an alkyl group, as defined herein. Representative examples of arylalkyl include, but are not limited to benzyl, 2-phenylethyl, -phenylpropyl, 1-methyl-3-phenylpropyl, and 2-naphth-2-ylethyl.

The term "carbonyl" as used herein, means a —C(O)— group.

The term "carboxy" as used herein, means a —COOH group.

The term "cyano" as used herein, means a —CN group.

The term "formyl" as used herein, means a —C(O)H group.

The term "halo" or "halogen" as used herein, means a —Cl, —Br, —I or —F.

The term "mercapto" as used herein, means a —SH group.
The term "nitro" as used herein, means a —NO$_2$ group.
The term "hydroxy" as used herein, means a —OH group.
The term "oxo" as used herein, means a =O group.
The term "bond" or "single bond" as used herein, refers to a chemical bond between two atoms, or two moieties when the atoms joined by the bond are considered to be part of larger substructure.

The terms "haloalkyl," "haloalkenyl," "haloalkynyl" and "haloalkoxy" as used herein, include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In certain embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

The term "alkylamine" refers to the —N(alkyl)$_x$H$_y$ group, where x and y are selected from among x=1, y=1 and x=2, y=0. When x=2, the alkyl groups, taken together with the N atom to which they are attached, optionally form a cyclic ring system.

The term "amide" as used herein, is a chemical moiety with the formula —C(O)NHR or —NHC(O)R, where R is selected from among hydrogen, alkyl, cycloalkyl, aryl, heteroaryl (bonded through a ring carbon) and heteroalicyclic (bonded through a ring carbon). An amide moiety includes a linkage between an amino acid or a peptide molecule and a compound described herein, e.g., in a prodrug. Any amine, or carboxyl side chain on the compounds described herein is optionally amidified.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein is optionally esterified.

The terms "heteroalkyl" "heteroalkenyl" and "heteroalkynyl" as used herein, include optionally substituted alkyl, alkenyl and alkynyl radicals in which one or more skeletal chain atoms are selected from an atom other than carbon, e.g., oxygen, nitrogen, sulfur, silicon, phosphorus or combinations thereof The term "heteroatom" as used herein refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms are the same as one another, or some or all of the two or more heteroatoms are different from the other or others.

The term "ring" as used herein, refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings are optionally substituted. In some instances, rings form part of a ring system.

As used herein, the term "ring system" refers to two or more rings, wherein two or more of the rings are fused. The term "fused" refers to structures in which two or more rings share one or more bonds.

The terms "heteroaryl" or, alternatively, "heteroaromatic" refers to an aromatic group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. The polycyclic heteroaryl group include both fused and non-fused groups. Representative of heteroaryl groups include, but are not limited to, the following moieties:

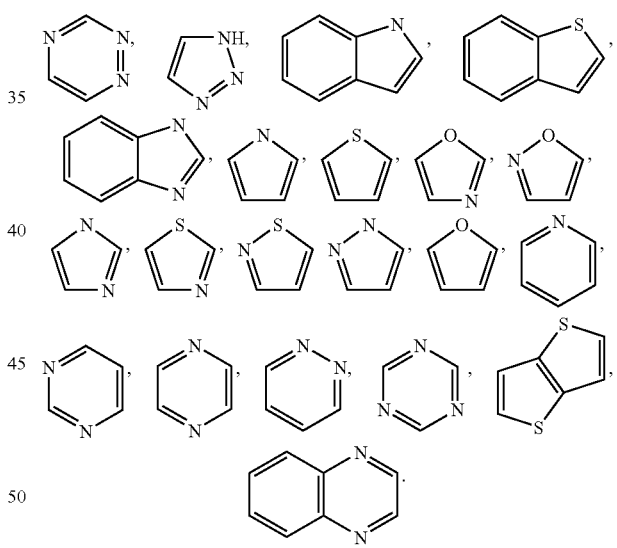

Depending on the structure, a heteroaryl group includes a monoradical or a diradical (i.e., a heteroarylene group).

The term "substituted heteroaryl" (or its equivalent) means heteroaryl groups that are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alynyl, carboxy, cyano, formyl, haloalkoxy, haloalkyl, halogen, hydroxyl, hydroxyalkyl, mercapto, nitro, —NR$_A$R$_B$, and —(NR$_A$R$_B$)carbonyl.

The term "heteroarylalkyl" as used herein, means a heteroaryl, as defined herein, appended to the parent molecular moiety through an alkyl group, as defined herein. Representative examples of heteroarylalkyl include, but are not limited to, pyridinylmethyl.

The term "non-aromatic heterocycle", "non-aromatic heterocyclic", "heterocycloalkyl" or "heteroalicyclic" as used herein, refers to a non-aromatic ring wherein one or more atoms forming the ring is a heteroatom. A "non-aromatic heterocycle" or "non-aromatic heterocyclic", "heterocycloalkyl" or "heteroalicyclic" group refers to a cycloalkyl group that includes at least one heteroatom selected from nitrogen, oxygen and sulfur. The radicals include those fused with an aryl or heteroaryl. Non-aromatic heterocycle rings include those formed by three, four, five, six, seven, eight, nine, or more than nine atoms. Heterocycloalkyl rings are optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Representative examples of heterocycloalkyl groups, also referred to as non-aromatic heterocycles, include, but are not limited to

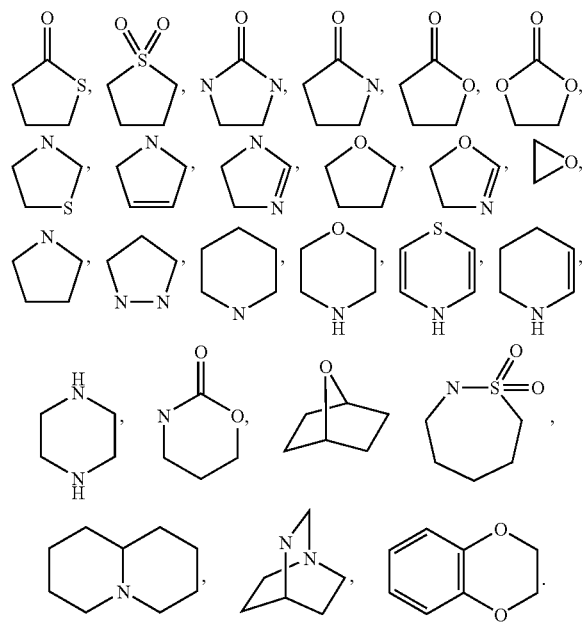

The term heteroalicyclic also includes all ring forms of the carbohydrates, including but not limited to the monosaccharides, the disaccharides and the oligosaccharides.

The term "heterocycle" refers to heteroaromatic and heteroalicyclic used herein, refers to groups containing one to four heteroatoms each selected from O, S and N, wherein each heterocyclic group has from 4 to 10 atoms in its ring system, and wherein the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocyclic ring optionally has additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms are the same or different from one another. Heterocycles are optionally substituted. Binding to a heterocycle is at a heteroatom or at a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, include those that are C-attached or N-attached where such is possible. For instance, a group derived from pyrrole includes pyrrol-1-yl groups (N-attached) or pyrrol-3-yl groups (C-attached). Further, a group derived from imidazole includes imidazol-1-yl or imidazol-3-yl (both N-attached) or imidazol-2-yl, imidazol-4-yl or imidazol-5-yl (all C-attached) groups. The heterocyclic groups include benzo-fused ring systems and ring systems substituted with one or two oxo (=O) moieties such as pyrrolidin-2-one. Depending on the structure, a heterocycle group includes a monoradical or a diradical (i.e., a heterocyclene group).

The heterocycles described herein are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alynyl, carboxy, cyano, formyl, haloalkoxy, haloalkyl, halogen, hydroxyl, hydroxyalkyl, mercapto, nitro, —$NR_AR_B$, and —$(NR_AR_B)$carbonyl.

The term "heterocycloalkyl" as used herein, means a heterocycle, as defined herein, appended to the parent molecular moiety through an alkyl group, as defined herein.

The term "membered ring" embraces any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "non-aromatic 5, 6, 7, 8, 9, 10, 11 or 12-bicyclic heterocycle" as used herein, means a non-aromatic heterocycle, as defined herein, consisting of two carbocyclic rings, fused together at the same carbon atom (forming a spiro structure) or different carbon atoms (in which two rings share one or more bonds), having 5 to 12 atoms in its overall ring system, wherein one or more atoms forming the ring is a heteroatom. Representative examples of non-aromatic 5, 6, 7, 8, 9, 10, 11, or 12-bicyclic heterocycle ring include, but are not limited to, 2-azabicyclo[2.2.1]heptanyl, 7-azabicyclo[2.2.1]heptanyl, 2-azabicyclo[3.2.0]heptanyl, 3-azabicyclo[3.2.0]heptanyl, 4-azaspiro[2.4]heptanyl, 5-azaspiro[2.4]heptanyl, 2-oxa-5-azabicyclo[2.2.1]heptanyl, 4-azaspiro[2.5]octanyl, 5-azaspiro[2.5]octanyl, 5-azaspiro[3.4]octanyl, 6-azaspiro[3.4]octanyl, 4-oxa-7-azaspiro[2.5]octanyl, 2-azabicyclo[2.2.2]octanyl, 1,3-diazabicyclo[2.2.2]octanyl, 5-azaspiro[3.5]nonanyl, 6-azaspiro[3.5]nonanyl, 5-oxo-8-azaspiro[3.5]nonanyl, octahydrocyclopenta[c]pyrrolyl, octahydro-1H-quinolizinyl, 2,3,4,6,7,9a-hexahydro-1H-quinolizinyl, decahydropyrido[1,2-a]azepinyl, decahydro-1H-pyrido[1,2-a]azocinyl, 1-azabicyclo[2.2.1]heptanyl, 1-azabicyclo[3.3.1]nonanyl, quinuclidinyl, and 1-azabicyclo[4.4.0]decanyl.

The term hydroxylalkyl" as used herein, means at least one hydroxyl group, as defined herein, is appended to the parent molecular moiety through an alkyl group, as defined herein. Representative examples of hydroxyalkyl include, but not limited to hydroxymethyl, 2-hydroxy-ethyl, 3-hydroxypropyl and 4-hydroxyheptyl.

The term "$NR_A NR_B$" as used herein, means two group, $R_A$ and $R_B$, which are appended to the parent molecular moiety through a nitrogen atom. $R_A$ and $R_B$ are each independently hydrogen, alkyl, and alkylcarbonyl. Representative examples of $NR_A R_B$ include, but are not limited to, amino, methylamino, acetylamino, and acetylmethylamino.

The term "($NR_A NR_B$)carbonyl" as used herein, means a $R_A R_B$, group, as defined herein, appended to the parent molecular moiety through a carbonyl group, as defined herein. Representative examples of ($NR_A R_B$)carbonyl include, but are not limited to, aminocarbonyl, (methylamino)carbonyl, (dimethylamino)carbonyl, and (ethylmethylamino)carbonyl.

The term "$NR_C NR_D$" as used herein, means two group, $R_C$ and $R_D$, which are appended to the parent molecular moiety through a nitrogen atom. $R_C$ and $R_D$ are each independently hydrogen, alkyl, and alkylcarbonyl. Representative examples of $NR_C R_D$ include, but are not limited to, amino, methylamino, acetylamino, and acetylmethylamino.

The term "($NR_C NR_D$)carbonyl" as used herein, means a $R_C R_D$, group, as defined herein, appended to the parent molecular moiety through a carbonyl group, as defined herein. Representative examples of ($NR_C R_D$)carbonyl include, but are not limited to, aminocarbonyl, (methylamino)carbonyl, (dimethylamino)carbonyl, and (ethylmethylamino)carbonyl.

As used herein, the term "mercaptyl" refers to a (alkyl)S— group.

As used herein, the term "moiety" refers to a specific segment or functional group of a molecule. Chemical moieties are often recognized chemical entities embedded in or appended to a molecule.

As used herein, the term "sulfinyl" refers to a —S(=O)—R, where R is selected from the group consisting of alkyl, cycloalkyl, aryl, heteroaryl (bonded through a ring carbon) and heteroalicyclic (bonded through a ring carbon).

As used herein, the term "sulfonyl" refers to a —S(=O)$_2$—R, where R is selected from the group consisting of alkyl, cycloalkyl, aryl, heteroaryl (bonded through a ring carbon) and heteroalicyclic (bonded through a ring carbon).

As used herein, the term "O carboxy" refers to a group of formula RC(=O)O—.

As used herein, the term "C carboxy" refers to a group of formula —C(=O)OR.

As used herein, the term "acetyl" refers to a group of formula —C(=O)CH$_3$.

As used herein, the term "trihalomethanesulfonyl" refers to a group of formula X$_3$CS(=O)$_2$— where X is a halogen.

As used herein, the term "isocyanato" refers to a group of formula —NCO.

As used herein, the term "thiocyanato" refers to a group of formula —CNS.

As used herein, the term "isothiocyanato" refers to a group of formula —NCS.

As used herein, the term "S sulfonamido" refers to a group of formula —S(=O)$_2$NR$_2$.

As used herein, the term "N sulfonamido" refers to a group of formula RS(=O)$_2$NH—.

As used herein, the term "trihalomethanesulfonamido" refers to a group of formula X$_3$CS(=O)$_2$NR—.

As used herein, the term "O carbamyl" refers to a group of formula —OC(=O)NR$_2$.

As used herein, the term "N carbamyl" refers to a group of formula ROC(=O)NH—.

As used herein, the term "O thiocarbamyl" refers to a group of formula —OC(=S)NR$_2$.

As used herein, the term "N thiocarbamyl" refers to a group of formula ROC(=S)NH—.

As used herein, the term "C amido" refers to a group of formula —C(=O)NR$_2$.

As used herein, the term "N amido" refers to a group of formula RC(=O)NH—.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

The term "substituted" means that the referenced group is optionally substituted (substituted or unsubstituted) with one or more additional group(s) individually and independently selected from alkyl, cycloalkyl, aryl, heteroaryl, heteroalicyclic, hydroxy, alkoxy, aryloxy, mercapto, alkylthio, arylthio, alkylsulfoxide, arylsulfoxide, alkylsulfone, arylsulfone, cyano, halo, carbonyl, thiocarbonyl, isocyanato, thiocyanato, isothiocyanato, nitro, perhaloalkyl, perfluoroalkyl, silyl, and amino, including mono- and di-substituted amino groups, and the protected derivatives thereof By way of example an optional substituents is $L_s R_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted C$_1$-C$_6$ alkyl), or -(substituted or unsubstituted C$_2$-C$_6$ alkenyl); and each $R_s$ is independently selected from H, (substituted or unsubstituted lower alkyl), (substituted or unsubstituted lower cycloalkyl), heteroaryl, or heteroalkyl.

The term "protecting group" refers to a removable group which modifies the reactivity of a functional group, for example, a hydroxyl, ketone or amine, against undesirable reaction during synthetic procedures and to be later removed. Examples of hydroxy-protecting groups include, but not limited to, methylthiomethyl, tert-dimethylsilyl, tert-butyldiphenylsilyl, ethers such as methoxymethyl, and esters including acetyl, benzoyl, and the like. Examples of ketone protecting groups include, but not limited to, ketals, oximes, O-substituted oximes for example O-benzyl oxime, O-phenylthiomethyl oxime, 1-isopropoxycyclohexyl oxime, and the like. Examples of amine protecting groups include, but are not limited to, tert-butoxycarbonyl (Boc) and carbobenzyloxy (Cbz).

The term "optionally substituted" as defined herein, means the referenced group is substituted with zero, one or more substituents as defined herein.

The term "protected-hydroxy" refers to a hydroxy group protected with a hydroxy protecting group, as defined above.

In some embodiments, compounds of the described herein exist as stereoisomers, wherein asymmetric or chiral centers are present. Stereoisomers are designated (R) or (S) depending on the configuration of substituents around the chiral carbon atom. The term (R) and (S) used herein are configurations as defined in IUPAC 1974 Recommendations for Section E, Fundamental Stereochemistry, Pure Appl. Chem., (1976), 45:13-30, hereby incorporated by reference. The embodiments described herein specifically includes the various stereoisomers and mixtures thereof. Stereoisomers include enantiomers, diastereomers, and mixtures of enantiomers or diastereomers. In some embodiments, individual stereoisomers of compounds are prepared synthetically from commercially available starting materials which contain asymmetric or chiral centers or by preparation of racemic mixtures followed by resolution. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic column.

The methods and formulations described herein include the use of N-oxides, crystalline forms (also known as polymorphs), or pharmaceutically acceptable salts of compounds described herein, as well as active metabolites of these compounds having the same type of activity. In some situations, compounds exist as tautomers. All tautomers are included within the scope of the compounds presented herein. In some embodiments, the compounds described herein exist in unsolvated as well as solvated forms with pharmaceutically acceptable solvents such as water, ethanol, and the like. The solvated forms of the compounds presented herein are also considered to be disclosed herein.

Throughout the specification, groups and substituents thereof are chosen, in certain embodiments, to provide stable moieties and compounds.

Preparation of Compounds Described Herein

In certain embodiments, the compounds described herein are synthesized using any synthetic techniques including standard synthetic techniques and the synthetic processes described herein. In specific embodiments, the following synthetic processes are utilized.

Formation of Covalent Linkages by Reaction of an Electrophile with a Nucleophile Selected examples of covalent linkages and precursor functional groups which yield them are given in the Table entitled "Examples of Covalent Linkages and Precursors Thereof." Precursor functional groups are shown as electrophilic groups and nucleophilic groups. In certain embodiments, a functional group on an organic substance is attached directly, or attached via any useful spacer or linker as defined below.

TABLE 1

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In general, carbon electrophiles are susceptible to attack by complementary nucleophiles, including carbon nucleophiles, wherein an attacking nucleophile brings an electron pair to the carbon electrophile in order to form a new bond between the nucleophile and the carbon electrophile.

Suitable carbon nucleophiles include, but are not limited to alkyl, alkenyl, aryl and alkynyl Grignard, organolithium, organozinc, alkyl-, alkenyl, aryl- and alkynyl-tin reagents (organostannanes), alkyl-, alkenyl-, aryl- and alkynyl-borane reagents (organoboranes and organoboronates); these carbon nucleophiles have the advantage of being kinetically stable in water or polar organic solvents. Other carbon nucleophiles include phosphorus ylids, enol and enolate reagents; these carbon nucleophiles have the advantage of being relatively easy to generate from precursors. Carbon nucleophiles, when used in conjunction with carbon electrophiles, engender new carbon-carbon bonds between the carbon nucleophile and carbon electrophile.

Non-carbon nucleophiles suitable for coupling to carbon electrophiles include but are not limited to primary and secondary amines, thiols, thiolates, and thioethers, alcohols, alkoxides, azides, semicarbazides, and the like. These non-carbon nucleophiles, when used in conjunction with carbon electrophiles, typically generate heteroatom linkages (C—X—C), wherein X is a heteroatom, e. g, oxygen or nitrogen.

Use of Protecting Groups

The term "protecting group" refers to chemical moieties that block some or all reactive moieties and prevent such groups from participating in chemical reactions until the protective group is removed. In specific embodiments, more than one protecting group is utilized. In more specific embodiments, each protective group is removable by a different process. Protective groups that are cleaved under totally disparate reaction conditions fulfill the requirement of differential removal. In various embodiments, protective groups are removed by acid, base, or hydrogenolysis. Groups such as trityl, dimethoxytrityl, acetal and t-butyldimethylsilyl are acid labile and are, in some embodiments, used to protect carboxy and hydroxy reactive moieties in the presence of amino groups protected with Cbz groups, which are removable by hydrogenolysis, and Fmoc groups, which are base labile. In some embodiments, carboxylic acid and hydroxy reactive moieties are blocked with base labile groups such as, without limitation, methyl, ethyl, and acetyl in the presence of amines blocked with acid labile groups such as t-butyl carbamate or with carbamates that are both acid and base stable but hydrolytically removable.

In certain embodiments, carboxylic acid and hydroxy reactive moieties are blocked with hydrolytically removable protective groups such as the benzyl group, while, in some embodiments, amine groups capable of hydrogen bonding with acids are blocked with base labile groups such as Fmoc. In various embodiments, carboxylic acid reactive moieties are protected by conversion to simple ester derivatives as exemplified herein, or they are blocked with oxidatively-removable protective groups such as 2,4-dimethoxybenzyl, while, in some embodiments, co-existing amino groups are blocked with fluoride labile silyl carbamates.

In certain instances, allyl blocking groups are useful in the presence of acid- and base-protecting groups since the former are stable. In some embodiments, such groups are subsequently removed by metal or pi-acid catalysts. For example, in some embodiments, an allyl-blocked carboxylic acid is deprotected with a Pd⁰-catalyzed reaction in the presence of acid labile t-butyl carbamate or base-labile acetate amine protecting groups. In some embodiments, a protecting group is a resin to which a compound or intermediate is attached. As long as the residue is attached to the resin, that functional group is blocked and cannot react. Once released from the resin, the functional group is available to react.

In some embodiments, blocking/protecting groups are selected from, by way of non-limiting example:

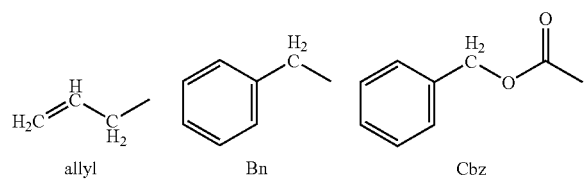

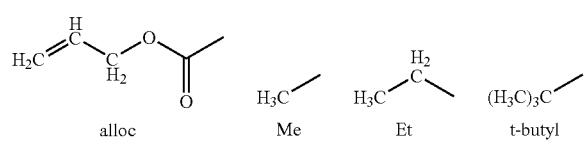

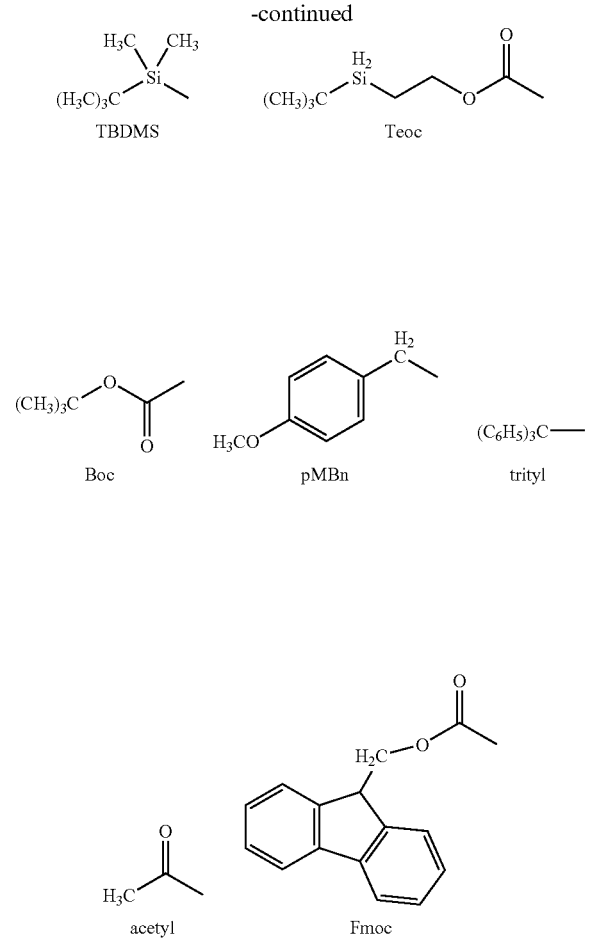

Other protecting groups are described in Greene and Wuts, Protective Groups in Organic Synthesis, 3rd Ed., John Wiley & Sons, New York, N.Y., 1999.

Compounds of Formula (I) or Formula (II)

In certain embodiments, compounds of Formula (I) or Formula (II) are prepared in various ways, as outlined in Synthetic Scheme 1-2. In each scheme, the variables (e.g., $R_1$, $R_2$, $R_3$, $R_4$, and Y) correspond to the same definitions as those recited above. In some embodiments, compounds are synthesized using methodologies analogous to those described below by the use of appropriate alternative starting materials.

In certain embodiments, compounds of Formula (I) are synthesized according to Synthetic Scheme 1 by condensation of the acyl chloride 2 with 2-hydroxy-3-aminobenzoic acid 1 in preferably non-polar solvents such as toluene or xylene and the like in the presence of pyridine to yield benzo [d]-7-carboxylic acid 3. In some embodiments, conversion of the carboxylic acid 3 to the acyl chloride is achieved with the use of thionyl chloride or oxalyl chloride. In certain embodiments, amination of the acyl chloride with the use of ammonium hydroxide in dimethylformamide will produce the benzo[d]-7-carboxyamide I where $R_4$ is hydrogen. In some embodiments, replacement of ammonium hydroxide with an appropriate $R_4NH_2$ yields the benzo[d]-7-carboyxamide I where $R_4$ is not hydrogen. In alternative embodiments, the benzo[d]-7-carboyylic acid 3 is produced by reaction of the 2-hydroxy-3-aminobenzoic acid 1 with the trimethoxymethyl derivative 4 in the presence of pyridinium p-toluenesulfonate.

Synthetic Scheme 1

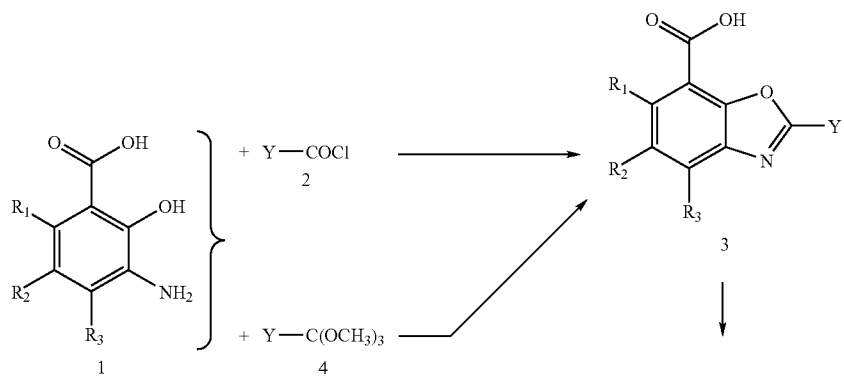

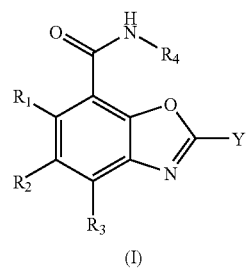

In certain embodiments, compounds of Formula (II) are synthesized according to Synthetic Scheme 2 by condensation of the acyl chloride 2 with 3-hydroxy-2-aminobenzoic acid 5 in preferably non-polar solvents such as toluene or xylene and the like in the presence of pyridine to yield benzo[d]-4-carboxylic acid 6. In some embodiments, conversion of the carboxylic acid 6 to the acyl chloride is achieved with the use of thionyl chloride or oxalyl chloride. In some embodiments, amination of the acyl chloride with the use of ammonium hydroxide in dimethylformamide produces the benzo[d]-4-carboxyamide I where $R_4$ is hydrogen. In certain embodiments, replacement of ammonium hydroxide with an appropriate $R_4NH_2$ yields the benzo[d]-4-carboyxamide I where $R_4$ is not hydrogen. In alternative embodiments, the benzo[d]-4-carboyylic acid 3 is produced by reaction of the 3-hydroxy-2-aminobenzoic acid 5 with the trimethoxymethyl derivative 4 in the presence of pyridinium p-toluenesulfonate.

Synthetic Scheme 2

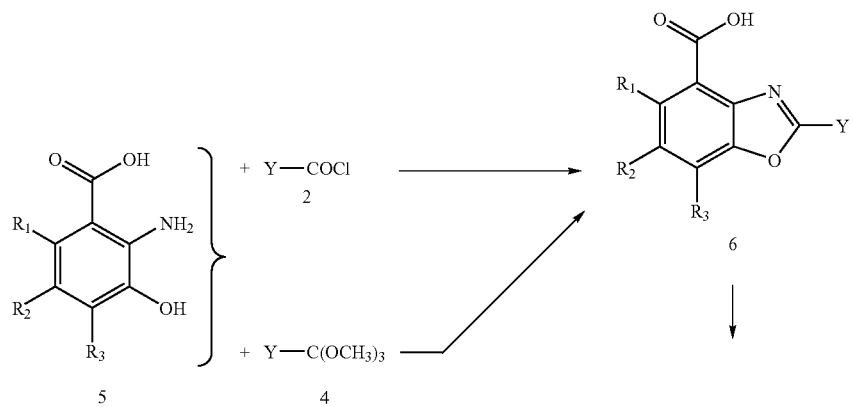

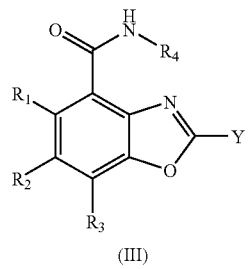

(III)

Certain Pharmaceutical Terminology

The term "acceptable" with respect to a formulation, composition or ingredient, as used herein, means having no persistent detrimental effect on the general health of the subject being treated.

As used herein, the term "selective binding compound" refers to a compound that selectively binds to any portion of one or more target proteins.

As used herein, the term "selectively binds" refers to the ability of a selective binding compound to bind to a target protein, such as, for example, PARP, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "target protein" refers to a molecule or a portion of a protein capable of being bound by a selective binding compound. In certain embodiments, a target protein is the enzyme poly(ADP-ribose)polymerase (PARP).

As used herein, the terms "treating" or "treatment" encompass either or both responsive and prophylaxis measures, e.g., designed to inhibit, slow or delay the onset of a symptom of a disease or disorder, achieve a full or partial reduction of a symptom or disease state, and/or to alleviate, ameliorate, lessen, or cure a disease or disorder and/or its symptoms.

As used herein, amelioration of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

As used herein, the term "modulator" refers to a compound that alters an activity of a molecule. For example, a modulator includes a compound that causes an increase or a decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

As used herein, the term "selective modulator" refers to a compound that selectively modulates a target activity.

As used herein, the term "PARP" refers to the family of the enzyme poly(ADP-ribose)polymerase which includes approximately 18 proteins, particularly poly(ADP-ribose)polymerase-1 (PARP-1) and poly(ADP-ribose)polymerase-2 (PARP-2).

As used herein, the term "selective PARP modulator" refers to a compound that selectively modulates at least one activity associated with the enzyme poly(ADP-ribose)polymerase (PARP). In various embodiments, the selective modulator selectively modulates the activity of PARP-1, PARP-2, both PARP-1 and PARP-2 or several members of the family of the enzyme poly(ADP-ribose)polymerase (PARP).

As used herein, the term "method of inhibiting PARP" refers to a method of inhibiting the activity of either one or more of the family of enzyme poly(ADP-ribose)polymerase (PARP). As used herein, the term "inhibition of PARP" refers to inhibition of the activity of either one or more of the family of enzyme poly(ADP-ribose)polymerase (PARP).

As used herein, the term "modulating the activity of the enzyme poly(ADP-ribose)polymerase" refers to a modulating the activity of either one or more of the family of enzyme poly(ADP-ribose)polymerase (PARP).

As used herein, the term "selectively modulates" refers to the ability of a selective modulator to modulate a target activity to a greater extent than it modulates a non-target activity. In certain embodiments the target activity is selectively modulated by, for example about 2 fold up to more that about 500 fold, in some embodiments, about 2, 5, 10, 50, 100, 150, 200, 250, 300, 350, 400, 450 or more than 500 fold.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "agonist" refers to a compound, the presence of which results in a biological activity of a protein that is the same as the biological activity resulting from the presence of a naturally occurring ligand for the protein, such as, for example, PARP.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" or "inhibitor" refers to a compound, the presence of which results in a decrease in the magnitude of a biological activity of a protein. In certain embodiments, the presence of an antagonist results in complete inhibition of a biological activity of a protein, such as, for example, the enzyme poly(ADP-ribose)polymerase (PARP).

As used herein, the $IC_{50}$ refers to an amount, concentration or dosage of a particular test compound that achieves a 50% inhibition of a maximal response, such as modulation of PARP, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

The term "cancer", as used herein refers to an abnormal growth of cells which tend to proliferate in an uncontrolled way and, in some cases, to metastasize (spread). The types of cancer include, but are not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to relatively non-toxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents include chemicals used to stabilize compounds because they provide a more stable environment. Salts dissolved in buffered solutions (which also can provide pH control or maintenance) are utilized as diluents in certain embodiments, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result include reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "enzymatically cleavable linker," as used herein refers to unstable or degradable linkages which are degraded by one or more enzymes.

The term "inflammatory disorders" refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal., chronic, cirrhotic, diffuse, disseminated, exudative, fibrinous, fibrosing, focal., granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arteritis); joints (arthritis: crystalline, osteo-, psoriatic, reactive, rheumatoid, Reiter's); gastrointestinal tract (Chrohn's Disease, ulcerative colitis); skin (dermatitis); or multiple organs and tissues (systemic lupus erythematosus).

The term "PARP-mediated", as used herein, refers to conditions or disorders that are ameliorated by the one or more of the family of enzyme poly(ADP-ribose)polymerase (PARP).

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, in certain instances, enzymes produce specific structural alterations to a compound. In some embodiments, metabolites of the compounds disclosed herein are identified either by administration of compounds to a host and analysis of tissue samples from the host, or by incubation of compounds with hepatic cells in vitro and analysis of the resulting compounds.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

By "pharmaceutically acceptable" or "therapeutically acceptable", as used herein, refers a material, such as a carrier or diluent, which does not abrogate the biological activity or properties of the compound, and is relatively nontoxic. In certain instances, nontoxic and non-abrogative materials includes materials that when administered to an individual do not cause substantial, undesirable biological effects and/or do not interact in a deleterious manner with any of the components of the composition in which it is contained.

The term "pharmaceutically acceptable salt" or "therapeutically acceptable salt", refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

A "prodrug" refers to an agent that is converted into the parent drug in vivo. Prodrugs are often useful because, in some situations, they are easier to administer than the parent drug. In certain instances, a prodrug is bioavailable by oral administration whereas the parent is not. In some instances, a prodrug has improved solubility in pharmaceutical compositions over the parent drug. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid or amino group where the peptide is metabolized to reveal the active moiety. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In some embodiments, the prodrug is designed to alter the metabolic stability or the transport characteristics of a drug, to mask side effects or toxicity, to improve the flavor of a drug or to alter other characteristics or properties of a drug.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Composition/Formulation

In certain embodiments, pharmaceutical compositions are formulated in any manner, including using one or more physiologically acceptable carriers comprising excipients and/or auxiliaries which facilitate processing of the active compounds into pharmaceutical preparations. In some embodiments, proper formulation is dependent upon the route of administration chosen. In various embodiments, any techniques, carriers, and excipients are used as suitable.

Provided herein are pharmaceutical compositions that include a compound described herein and a pharmaceutically acceptable diluent(s), excipient(s), and/or carrier(s). In addition, in some embodiments, the compounds described herein are administered as pharmaceutical compositions in which compounds described herein are mixed with other active ingredients, as in combination therapy.

A pharmaceutical composition, as used herein, refers to a mixture of a compound described herein with other chemical components, such as carriers, stabilizers, diluents, dispersing agents, suspending agents, thickening agents, and/or excipients. In certain embodiments, a pharmaceutical composition facilitates administration of the compound to an organism. In some embodiments, practicing the methods of treatment or use provided herein, includes administering or using a pharmaceutical composition comprising a therapeutically effective amount of a compound provided herein. In specific embodiments, the methods of treatment provided for herein include administering such a pharmaceutical composition to a mammal having a disease or condition to be treated. In one embodiment, the mammal is a human. In some embodiments, the therapeutically effective amount varies widely depending on the severity of the disease, the age and relative health of the subject, the potency of the compound used and other factors. In various embodiments, the compounds described herein are used singly or in combination with one or more therapeutic agents as components of mixtures.

In certain embodiments, the pharmaceutical compositions provided herein are formulated for intravenous injections. In certain aspects, the intravenous injection formulations provided herein are formulated as aqueous solutions, and, in some embodiments, in physiologically compatible buffers such as Hank's solution, Ringer's solution, or physiological saline buffer. In certain embodiments, the pharmaceutical compositions provided herein are formulated for transmucosal administration. In some aspects, transmucosal formulations include penetrants appropriate to the barrier to be permeated. In certain embodiments, the pharmaceutical compositions provided herein are formulated for other parenteral injections, appropriate formulations include aqueous or non-aqueous solutions, and in one embodiment, with physiologically compatible buffers or excipients.

In certain embodiments, the pharmaceutical compositions provided herein are formulated for oral administration. In certain aspects, the oral formulations provided herein comprise compounds described herein that are formulated with pharmaceutically acceptable carriers or excipients. Such carriers enable the compounds described herein to be formulated as tablets, powders, pills, dragees, capsules, liquids, gels, syrups, elixirs, slurries, suspensions and the like, for oral ingestion by a patient to be treated.

In some embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are optionally added, such as the cross-linked croscarmellose sodium, polyvinylpyrrolidone, agar, or alginic acid or a salt thereof such as sodium alginate.

In certain embodiments, provided herein is a pharmaceutical composition formulated as dragee cores with suitable coatings. In certain embodiments, concentrated sugar solutions are used in forming the suitable coating, and optionally contain gum arabic, talc, polyvinylpyrrolidone, carbopol gel, polyethylene glycol, and/or titanium dioxide, lacquer solutions, and suitable organic solvents or solvent mixtures. In some embodiments, dyestuffs and/or pigments are added to tablets, dragees and/or the coatings thereof for, e.g., identification or to characterize different combinations of active compound doses.

In certain embodiments, pharmaceutical preparations which are used include orally include push-fit capsules made of gelatin, as well as soft, sealed capsules made of gelatin and a plasticizer, such as glycerol or sorbitol. In some embodiments, the push-fit capsules contain the active ingredients in admixture with filler such as lactose, binders such as starches, and/or lubricants such as talc or magnesium stearate and, optionally, stabilizers. In certain embodiments, in soft capsules, the active compounds are dissolved or suspended in suitable liquids, such as fatty oils, liquid paraffin, or liquid polyethylene glycols. In addition, stabilizers are optionally added. In certain embodiments, the formulations for oral administration are in dosages suitable for such administration.

In certain embodiments, the pharmaceutical compositions provided herein are formulated for buccal or sublingual administration. In certain embodiments, buccal or sublingual compositions take the form of tablets, lozenges, or gels formulated in a conventional manner. In certain embodiments, parenteral injections involve bolus injection or continuous infusion. In some embodiments, formulations for injection are presented in unit dosage form, e.g., in ampoules or in multi-dose containers, with an added preservative. In some embodiments, the pharmaceutical composition described herein is in a form suitable for parenteral injection as a sterile suspensions, solutions or emulsions in oily or aqueous vehicles, and optionally contains formulatory agents such as suspending, stabilizing and/or dispersing agents. Pharmaceutical formulations for parenteral administration include aqueous solutions of the active compounds in water-soluble form. In some embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. In certain embodiments, aqueous injection suspensions contain substances which increase the viscosity of the suspension, such as sodium carboxymethyl cellulose, sorbitol, or dextran. Optionally, the suspensions also contain suitable stabilizers or agents which increase the solubility of the compounds to allow for the preparation of highly concentrated solutions. In alternative embodiments, the active ingredient is in powder form for constitution with a suitable vehicle, e.g., sterile pyrogen-free water, before use.

In some embodiments, the compounds described herein are administered topically. In specific embodiments, the compounds described herein are formulated into a variety of topically administrable compositions, such as solutions, suspensions, lotions, gels, pastes, medicated sticks, balms, creams or ointments. Such pharmaceutical compounds optionally contain solubilizers, stabilizers, tonicity enhancing agents, buffers and/or preservatives.

In certain embodiments, the pharmaceutical compositions provided herein are formulated for transdermal administration of compounds described herein. In some embodiments, administration of such compositions employs transdermal delivery devices and transdermal delivery patches. In certain embodiments, the compositions are lipophilic emulsions or buffered, aqueous solutions, dissolved and/or dispersed in a polymer or an adhesive. Such patches include those constructed for continuous, pulsatile, or on demand delivery of pharmaceutical agents. In some embodiments, transdermal delivery of the compounds described herein is accomplished by use of iontophoretic patches and the like. In certain embodiments, transdermal patches provide controlled delivery of the compounds provided herein, such as, for example, compounds of Formula (I) or Formula (II). In certain embodiments, the rate of absorption is slowed by using rate-controlling membranes or by trapping the compound within a polymer matrix or gel. Conversely, absorption enhancers are optionally used to increase absorption. Absorption enhancer and carrier include absorbable pharmaceutically acceptable solvents that assist in passage of the compound through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In certain embodiments, the pharmaceutical compositions provided herein are formulated for administration by inhalation. In certain embodiments, in such pharmaceutical compositions formulated for inhalation, the compounds described herein are in a form as an aerosol, a mist or a powder. In some embodiments, pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In certain aspects of a pressurized aerosol, the dosage unit is determined by providing a valve to deliver a metered amount. In certain embodiments, capsules and cartridges of, such as, by way of example only, gelatin for use in an inhaler or insufflator is formulated containing a powder mix of the compound described herein and a suitable powder base such as lactose or starch.

In some embodiments, the compounds described herein are formulated in rectal compositions such as enemas, rectal gels, rectal foams, rectal aerosols, suppositories, jelly suppositories, or retention enemas. In certain embodiments, rectal compositions optionally contain conventional suppository bases such as cocoa butter or other glycerides, as well as synthetic polymers such as polyvinylpyrrolidone, PEG, and the like. In certain suppository forms of the compositions, a low-melting wax such as, but not limited to, a mixture of fatty acid glycerides, optionally in combination with cocoa butter is first melted.

In various embodiments provided herein, the pharmaceutical compositions are formulated in a conventional manner using one or more physiologically acceptable carriers comprising excipients and auxiliaries which facilitate processing of the active compounds into pharmaceutically acceptable preparations. In certain embodiments, proper formulation is dependent upon the route of administration chosen. In various embodiments, any of the techniques, carriers, and excipients is used as suitable. In some embodiments, pharmaceutical compositions comprising a compound described herein are manufactured in a conventional manner, such as, by way of example only, by means of conventional mixing, dissolving, granulating, dragee-making, levigating, emulsifying, encapsulating, entrapping or compression processes.

In certain embodiments, the pharmaceutical compositions include at least one pharmaceutically acceptable carrier, diluent or excipient and a compound described herein described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds described herein exist as tautomers. All tautomers are included within the scope of the compounds presented herein. Additionally, included herein are the solvated and unsolvated forms of the compounds described herein. Solvated compounds include those that are solvated with pharmaceutically acceptable solvents such as water, ethanol, and the like. The solvated forms of the compounds presented herein are also considered to be disclosed herein. In some embodiments, the pharmaceutical compositions described herein include other medicinal or pharmaceutical agents, carriers, adjuvants, such as preserving, stabilizing, wetting or emulsifying agents, solution promoters, salts for regulating the osmotic pressure, and/or buffers. In additional embodiments, the pharmaceutical compositions described herein also contain other therapeutically valuable substances.

Methods for the preparation of compositions containing the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. In various embodiments, the compositions are in liquid solutions or suspensions, solid forms suitable for solution or suspension in a liquid prior to use, or as emulsions. These compositions optionally contain minor amounts of nontoxic, auxiliary substances, such as wetting or emulsifying agents, pH buffering agents, and so forth.

In some embodiments, a composition comprising a compound described herein takes the form of a liquid where the agents are present in solution, in suspension or both. In some embodiments, when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

Useful aqueous suspension optionally contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

Useful compositions optionally comprise an mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful compositions optionally include solubilizing agents to aid in the solubility of a compound described herein. The term "solubilizing agent" generally includes agents that result in formation of a micellar solution or a true solution of the agent. Solubilizing agents include certain acceptable nonionic surfactants, for example polysorbate 80, and ophthalmically acceptable glycols, polyglycols, e.g., polyethylene glycol 400, and glycol ethers.

Useful compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Useful compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Certain useful compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Some useful compositions optionally include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Certain useful compositions optionally one or more antioxidants to enhance chemical stability where required. Suitable antioxidants include, by way of example only, ascorbic acid and sodium metabisulfite.

In some embodiments, aqueous suspension compositions are packaged in single-dose non-reclosable containers. In alternative embodiments, multiple-dose reclosable containers are used, in which case it is typical to include a preservative in the composition.

In various embodiments, any delivery system for hydrophobic pharmaceutical compounds is employed. Liposomes and emulsions are examples of delivery vehicles or carriers for hydrophobic drugs. In certain embodiments, certain organic solvents such as N-methylpyrrolidone are employed. In some embodiments, the compounds are delivered using a sustained-release system, such as semipermeable matrices of solid hydrophobic polymers containing the therapeutic agent. Various sustained-release materials are utilized in the embodiments herein. In certain embodiments, sustained-release capsules release the compounds for a few weeks up to over 100 days. In some embodiments, depending on the chemical nature and the biological stability of the therapeutic reagent, additional strategies for protein stabilization are employed.

In certain embodiments, the formulations or compositions described herein benefit from and/or optionally comprise antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Methods of Dosing and Treatment Regimens

In certain embodiments, the compounds described herein are used in the preparation or manufacture of medicaments for the treatment of diseases or conditions that are mediated by the enzyme poly(ADP-ribose)polymerase (PARP) or in which inhibition of the enzyme poly(ADP-ribose)polymerase (PARP) ameliorates the disease or condition. In some embodiments, a method for treating any of the diseases or conditions described herein in a subject in need of such treatment, involves administration of pharmaceutical compositions containing at least one compound described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. In some embodiments, amounts effective for this use will depend on the severity and course of the disease or condition, previous therapy, the patient's health status, weight, and response to the drugs, and the judgment of the treating physician. In certain instances, it is considered appropriate for the caregiver to determine such therapeutically effective amounts by routine experimentation (including, but not limited to, a dose escalation clinical trial).

In certain prophylactic applications, compositions containing the compounds described herein are administered to a patient susceptible to or otherwise at risk of a particular disease, disorder or condition. In some embodiments, the amount administers is defined to be a "prophylactically effective amount or dose." In certain embodiments of this use, the precise amounts of compound administered depend on the patient's state of health, weight, and the like. In some embodiments, it is considered appropriate for the caregiver to determine such prophylactically effective amounts by routine experimentation (e.g., a dose escalation clinical trial). In certain embodiments, when used in a patient, effective amounts for this use will depend on the severity and course of the disease, disorder or condition, previous therapy, the patient's health status and response to the drugs, and the judgment of the treating physician.

In certain instances, a patient's condition does not improve or does not significantly improve following administration of a compound or composition described herein and, upon the doctor's discretion the administration of the compounds is optionally administered chronically, that is, for an extended period of time, including throughout the duration of the patient's life in order to ameliorate or otherwise control or limit the symptoms of the patient's disease or condition.

In certain cases wherein the patient's status does improve or does not substantially improve, upon the doctor's discretion the administration of the compounds are optionally given continuously; alternatively, the dose of drug being administered is optionally temporarily reduced or temporarily suspended for a certain length of time (i.e., a "drug holiday"). In certain embodiments, the length of the drug holiday varies between 2 days and 1 year, including by way of example only, about 2 days, about 3 days, about 4 days, about 5 days, about 6 days, about 7 days, about 10 days, about 12 days, about 15 days, about 20 days, about 28 days, about 35 days, about 50 days, about 70 days, about 100 days, about 120 days, about 150 days, about 180 days, about 200 days, about 250 days, about 280 days, about 300 days, about 320 days, about 350 days, or about 365 days. The dose reduction during a drug holiday includes a reduction from 10%-100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In certain embodiments, once improvement of the patient's conditions has occurred, a maintenance dose is administered if necessary. In some embodiments, the dosage, e.g., of the maintenance dose, or the frequency of administration, or both, are reduced, as a function of the symptoms, to a level at which the improved disease, disorder or condition is retained. In certain embodiments, however, patients are optionally given intermittent treatment on a long-term basis upon any recurrence of symptoms.

In certain embodiments, the amount of a given agent that corresponds to an effective amount varies depending upon factors such as the particular compound, disease or condition and its severity, the identity (e.g., weight) of the subject or host in need of treatment. In some embodiments, the effective amount is, nevertheless, determined according to the particular circumstances surrounding the case, including, e.g., the specific agent that is administered, the route of administration, the condition being treated, and the subject or host being treated. In certain embodiments, however, doses employed for adult human treatment is in the range of about 0.02—about 5000 mg per day, in a specific embodiment about 1—about 1500 mg per day. In various embodiments, the desired dose is conveniently presented in a single dose or as divided doses administered simultaneously (or over a short period of time) or at appropriate intervals, for example as two, three, four or more sub-doses per day.

In some embodiments, the pharmaceutical compositions described herein are in a unit dosage form suitable for single administration of precise dosages. In some instances, in unit dosage form, the formulation is divided into unit doses containing appropriate quantities of one or more compound. In certain embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. In alternative embodiments, multiple-dose reclosable containers are used, in which case it is typical to include a preservative in the composition. By way of example only, formulations for parenteral injection are, in some embodiments, presented in unit dosage form, which include, but are not limited to ampoules, or in multi-dose containers, with an added preservative.

In certain embodiments, the daily dosages appropriate for the compounds described herein described herein are from about 0.01 to about 2.5 mg/kg per body weight. In some embodiments, an indicated daily dosage in the larger subject, including, but not limited to, humans, is in the range from about 0.5 mg to about 100 mg, conveniently administered in divided doses, including, but not limited to, up to four times a day or in extended release form. In certain embodiments, suitable unit dosage forms for oral administration comprise from about 1 to 50 mg active ingredient. The foregoing ranges are merely suggestive, as the number of variables in regard to an individual treatment regime is large, and considerable excursions from these recommended values are not uncommon. In certain embodiments, the dosages are altered depending on a number of variables, not limited to the activity of the compound used, the disease or condition to be treated, the mode of administration, the requirements of the individual subject, the severity of the disease or condition being treated, and the judgment of the practitioner.

In certain embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. In certain embodiments, compounds exhibiting high therapeutic indices are preferred. In some embodiments, the data obtained from cell culture assays and animal studies is used in formulating a range of dosage for use in human. In specific embodiments, the dosage of such compounds lies within a range of circulating concentrations that include the $ED_{50}$ with minimal toxicity. In certain embodiments, the dosage varies within this range depending upon the dosage form employed and the route of administration utilized.

Combination Treatments

In certain instances, it is appropriate to administer at least one compound described herein in combination with another therapeutic agent. By way of example only, if one of the side effects experienced by a patient upon receiving one of the compounds herein is inflammation, then, in some embodiments, it is appropriate to administer an anti-inflammatory agent in combination with the initial therapeutic agent. In some embodiments, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). In certain embodiments, the benefit experienced by a patient is increased by administering one of the compounds described herein with another therapeutic agent (which also includes a therapeutic regimen) that also has therapeutic benefit. In some embodiments, regardless of the disease, disorder or condition being treated, the overall benefit experienced by the patient as a result of a combination treatment is additive or synergistic.

In certain embodiments, therapeutically-effective dosages vary when the drugs are used in treatment combinations. In some embodiments, therapeutically-effective dosages of drugs and other agents for use in combination treatment regimens is determined in any suitable manner, e.g., through the use of metronomic dosing, i.e., providing more frequent, lower doses in order to minimize toxic side effects. In some embodiments, combination treatment regimen described herein encompass treatment regimens in which administration of a PARP inhibitor described herein is initiated prior to, during, or after treatment with a second agent described above, and continues until any time during treatment with the second agent or after termination of treatment with the second agent. It also includes treatments in which a PARP inhibitor described herein and the second agent being used in combination are administered simultaneously or at different times and/or at decreasing or increasing intervals during the treatment period. Combination treatment further includes periodic treatments that start and stop at various times to assist with the clinical management of the patient. For example, in some embodiments, a PARP inhibitor described herein in the combination treatment is administered weekly at the onset of treatment, decreasing to biweekly, and decreasing further as appropriate.

In certain embodiments, compositions and methods for combination therapy are provided herein. In accordance with one aspect, the pharmaceutical compositions disclosed herein are used to in a method of treating a PARP mediated disease or condition or a disease or condition that is ameliorated by inhibition of PARP. In accordance with certain aspects, the pharmaceutical compositions disclosed herein are used to treat vascular disease; septic shock; ischaemic injury; reperfusion injury; neurotoxicity; haemorraghic shock; inflammatory diseases; multiple sclerosis; secondary effects of diabetes; and acute treatment of cytotoxicity following cardiovascular surgery. In a certain aspect, the pharmaceutical compositions disclosed herein are used in combination, either simultaneously or sequentially, with ionizing radiation or one or more chemotherapeutic agents.

In certain embodiments, combination therapies described herein are used as part of a specific treatment regimen intended to provide a beneficial effect from the co-action of a PARP inhibitor described herein and a concurrent treatment. It is understood that the dosage regimen to treat, prevent, or ameliorate the condition(s) for which relief is sought, is optionally modified in accordance with a variety of factors.

In certain combination therapies described herein, dosages of the co-administered compounds vary depending on the type of co-drug employed, on the specific drug employed, on the disease or condition being treated and so forth. In some embodiments, when co-administered with one or more biologically active agents, the compound provided herein is administered either simultaneously with the biologically active agent(s), or sequentially. In certain aspects wherein the agents are administered sequentially, the attending physician will decide on the appropriate sequence of administering protein in combination with the biologically active agent(s).

In various embodiments, the multiple therapeutic agents (one of which is one of the compounds described herein) are administered in any order or even simultaneously. In certain instances, administration is simultaneous and the multiple therapeutic agents are, optionally, provided in a single, unified form, or in multiple forms (by way of example only, either as a single pill or as two separate pills). In some embodiments, one of the therapeutic agents is given in multiple doses, or both are given as multiple doses. In some instances, administration is not simultaneous and the timing between the multiple doses varies, by way of non-limiting example, from more than zero weeks to less than four weeks. In addition, the combination methods, compositions and formulations are not to be limited to the use of only two agents; the use of multiple therapeutic combinations are also envisioned.

In additional embodiments, the compounds described herein are used in combination with procedures that provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

In certain embodiments, the compounds described herein and combination therapies are administered before, during or after the occurrence of a disease or condition. In certain embodiments, the timing of administering the composition containing a compound varies. Thus, for example, in some embodiments, the compounds are used as a prophylactic and are administered continuously to subjects with a propensity to develop conditions or diseases in order to prevent the occurrence of the disease or condition. In some embodiments, the compounds and compositions are administered to a subject during or as soon as possible after the onset of the symptoms. In certain embodiments, the administration of the compounds is initiated within the first 48 hours of the onset of the symptoms, within the first 6 hours of the onset of the symptoms, or within 3 hours of the onset of the symptoms. The initial administration is achieved via any route practical, such as, for example, an intravenous injection, a bolus injection, infusion over 5 minutes to about 5 hours, a pill, a capsule, transdermal patch, buccal delivery, and the like, or combination thereof. In some embodiments, a compound is administered as soon as is practicable after the onset of a disease or condition is detected or suspected, and for a length of time necessary for the treatment of the disease, such as, from about 1 month to about 3 months. In certain embodiments, the length of treatment varies for each subject, and the length is determined using any criteria. In exemplary embodiments, a compound or a formulation containing the compound is administered for at least 2 weeks, for about 1 month to about 5 years, or for about 1 month to about 3 years.

Other Combination Therapies

In certain embodiments described herein, methods for treatment of PARP mediated conditions or diseases, such as proliferative disorders, including cancer, include administration to a patient compounds, pharmaceutical compositions, or medicaments described herein in combination with at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, and dronabinol.

Kits/Articles of Manufacture

For use in the therapeutic applications described herein, kits and articles of manufacture are also described herein. In various embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In some embodiments, the containers are formed from a variety of materials such as glass or plastic.

In some embodiments, the articles of manufacture provided herein contain packaging materials. Packaging materials for use in packaging pharmaceutical products include, but are not limited to, blister packs, bottles, tubes, inhalers, pumps, bags, vials, containers, syringes, bottles, and any packaging material suitable for a selected formulation and intended mode of administration and treatment.

In some embodiments, the container(s) described herein comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound with an identifying description or label or instructions relating to its use in the methods described herein.

In some embodiments, a kit will comprises one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions is optionally included.

In certain embodiments, a label is on or associated with the container. In some embodiments, a label is on a container when letters, numbers or other characters forming the label are attached, molded or etched into the container itself; a label can be associated with a container when it is present within a receptacle or carrier that also holds the container, e.g., as a package insert. In certain embodiments, a label indicates that the contents are to be used for a specific therapeutic application. In some embodiments, the label indicates directions for use of the contents, such as in the methods described herein.

In certain embodiments, the pharmaceutical compositions are presented in a pack or dispenser device which contains one or more unit dosage forms containing a compound provided herein. In some embodiments, the pack contains a metal or plastic foil, such as a blister pack. The pack or dispenser device is optionally accompanied by instructions for administration. In some embodiments, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. In certain embodiments, such notice is, for example, the labeling approved by the U.S. Food and Drug Administration for prescription drugs, or the approved product insert. In some embodiments, compositions containing a compound provided herein are formulated in a compatible pharmaceutical carrier and are placed in an appropriate container labeled for treatment of an indicated condition.

EXAMPLES

In order to assess the inhibitory action of the compounds, the following assay was used to determine $IC_{50}$ values (Dillon et al., *JBS.*, 8 (3), 347-352 (2003)).

Mammalian PARP, isolated from Hela cell nuclear extract, was incubated with Z-buffer (25 mM Hepes (Sigma); 12.5 mM MgCl$_2$ (Sigma); 50 mM KCl (Sigma); 1 mM DTT (Sigma); 10% Glycerol (Sigma) 0.001% NP-40 (Sigma); pH 7.4) in 96 well FlashPlates™ (NEN, UK) and varying concentrations of said inhibitors added. All compounds were diluted in DMSO and gave final assay concentrations of between 10 and 0.01 μM, with the DMSO being at a final concentration of 1% per well. The total assay volume per well was 40 μL.

After 10 minutes incubation at 30° C., the reactions were initiated by the addition of a 10 μL reaction mixture, containing NAD (5 μM), $^3$H-NAD and 30 mer double stranded DNA-oligos. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 μL 30% acetic acid to each well. The plates were then shaken for 1 hour at room temperature.

The plates were transferred to a TopCount NXT™ (Packard, UK) for scintillation counting. Values recorded are counts per minute (cpm) following a 30 second counting of each well.

The % enzyme activity for each compound is then calculated using the following equation:

$$\% \text{ Inhibition} = 100 - \left\{ 100 \times \frac{(\text{cpm of unknown} - \text{mean negative cpm})}{(\text{mean positive cpm} - \text{mean negative cpm})} \right\}$$

IC$_{50}$ values (the concentration at which 50% of the enzyme activity is inhibited) were calculated, which are determined over a range of different concentrations, normally from about 10 μM down to about 0.001 μM. Such IC$_{50}$ values are used as comparative values to identify increased compound potencies.

In some embodiments, the compounds tested had an IC$_{50}$ of less than 50 nM.

Chemosensitization assay determines the extent by which a PARP inhibitor enhances the tumor cell-killing effect of cytotoxic drugs expressed as PF50 (potentiation factor at GI50)]. 8000 LoVo cells were seeded into each well of a flat-bottomed 96-well microtiter plate in a volume of 50 μl and incubated in F12K containing 10% (v/v) FBS (medium) overnight at 37° C. Cells were added with 50 μl medium alone, medium containing 1 μM PARP inhibitor, medium containing increasing concentration of Temozolomide (0-1000 μM), and medium containing 1 μM PARP inhibitor and increasing concentration of Temozolomide (0-1000 μM). Final concentration range for Temozolomide was 0-1000 μM where applicable, final concentration of PARP inhibitor was 1 μM where applicable. Final concentration of DMSO was 1% in each well. Cells were allowed to grow for 5 days before cell survival was determined by CellTiter Glo staining (Promega, Madison, Wis., USA). Cell growth, determined after subtraction of time 0 values, was expressed as a percentage of the control well that contained medium with 1% DMSO. GI50 (concentration of drug that inhibited growth by 50%) values were calculated from the computer generated curves (Graph-Pad Software, Inc. San Diego Calif.). The potentiation factor [PF50 (potentiation factor at GI50)] was calculated as GI50 of Temozolomide alone/GI50 of Temozolomide+PARP inhibitor. Reference: Thomas H. D. et al. (2007). Preclinical selection of a novel poly(ADP-ribose) polymerase inhibitor for clinical trial. *Molecular Cancer Therapy* 6, 945-956.

In other embodiments, the compounds tested had a PF50 of more than 2×.

Xenograft Studies
Homologous Recombination DNA Repair Deficient Cells

Capab-1 or MDA-MB-468 cells are implanted intramuscularly into the thigh of 40 CD-1 nude mice. Treatments are initiated when tumors are of measurable size (approximate leg diameter of 11 mm). Animals receive either a compound of Formula (I) (two doses of 25 or 50 mg/kg in saline) or saline (10 mg/ml) intraperitoneally administered daily on days 1-28, and are monitored on a daily basis during treatment (tumor measurements, body weights and clinical evidence are recorded); and as required after the last treatment.

The in vitro assays disclosed herein, along with other in vitro assays (Farmer et al, *Nature* 2005; 434:913-7: clonogenic survival assay finding that a BRCA2-deficient cell line V-C8, compared with the BRCA2 wild type control exhibited sensitivity to AG14361, a PARP-1 inhibitor, (Ki=5 nm) and NU1025, a moderately potent PARP-1 inhibitor (Ki=50 nM); & Mcabe et al., Cancer Biology & Therapy 2005; 4:9, 934-36; clonogenic survival assay using CAPAN-1 cells maintained in DMEM supplemented with FCS (20% v/v), glutamine and antibiotics showing sensitivity to PARP inhibition using KU0058684) demonstrate the activity of PARP-inhibitors in a static test situation. Additionally, animal models have been used to analyze the relationship between in vitro tests and parameters of in vivo efficacy. By way of example only, Farmer et al., has shown in vivo efficacy in blocking the growth of BRCA2-deficient tumors using KU0058684, a PARP-1 inhibitor. Nature 2005; 434:913-7. This indicates that PARP-1 inhibition is a viable cancer treatment for BRCA1/2 mutation carriers. Furthermore, KU0059436, a PARP-1 inhibitor is currently in Phase I clinical trials for patients with advanced solid tumors. Given this information, compounds of Formula (I) which have shown in vitro inhibitory action are likely to show analogous in vivo (mouse and human) efficacy.

Phase II Clinical Trial of the Safety and Efficacy of Compounds of Formula (I) or (II)

The purpose of this phase II trial is to study the side effects and best dose of a compound of Formula (I) or (II) and to determine how well it works in treating patients with locally advanced or metastatic breast cancer or advanced ovarian cancer.

Objectives:
  Primary:
    A. To determine the response rate to a compound of Formula (I) or (II) in patients with locally advanced or metastatic breast or advanced ovarian cancer shown to express the BRCA 1 or 2 mutations
    B. To evaluate the toxicity of a compound of Formula (I) or (II) in these patients
  Secondary:
    A. To evaluate the time to progression and overall survival in patients treated with a compound of Formula (I) or (II)
    B. To study pharmacokinetics of a compound of Formula (I) or (II) in these patients
    C. To evaluate the Poly(ADP-ribose) polymerase (PARP) activity in peripheral blood lymphocytes from BRCA 1 and 2 heterozygotic patients
  Tertiary:
    A. To evaluate PARP expression using quantitative western blotting immuno-assays
    B. To investigate pharmacogenomics, including CYP2D6 and CYP3A5, drug transport proteins, as well as polymorphisms in the genes coding for the PARP enzymes themselves C. To analyze tumor biopsy samples (when possible) for BRCA mutation status, PARP activity, and PARP expression D. To analyze paraffin sections from original diagnostic biopsies/operative procedures (when available) for DNA repair enzyme status using immunohistochemical techniques E. To analyze cells obtained from ascitic or pleural fluid (where available) for primary cell culture for DNA double strand break repair pathway function Patients: Eligible Subjects will be Men and Women 18 Years and Older Criteria:
Disease Characteristics:
Histologically confirmed locally advanced or metastatic breast cancer or advanced ovarian cancer
Must meet 1 of the following criteria:
Proven a carrier of a known mutation of BRCA 1 or BRCA 2
Considered highly likely a carrier of BRCA 1 or 2 mutation (score of $\geq$20 per Manchester criteria)
No more than 3 prior chemotherapy regimens for patients with breast or ovarian cancer
More than 2 months since prior carboplatin- or cisplatin-containing chemotherapy for ovarian cancer
Measurable disease, as defined by RECIST criteria and measured by x-ray, CT scan, or MRI
Patients with bone disease must have other measurable disease for evaluation
Previously irradiated lesions cannot be used for measurable disease
No known brain metastases
Hormone receptor status not specified
Patient Characteristics:
WHO performance status 0-1
Life expectancy$\geq$12 weeks
Menopausal status not specified
Hemoglobin$\geq$9.0 g/dL
Absolute neutrophils$\geq$1,500/mm$^3$
Platelets$\geq$100,000/mm$^3$
Serum bilirubin$\leq$1.5 times upper limit of normal (ULN)
ALT or AST$\leq$2.5 times ULN ($\leq$5 times ULN if due to tumor)
Glomerular filtration rate (GFR) $\geq$50 mL/min
Not pregnant or nursing
Negative pregnancy test
Fertile patients must use two highly effective forms of contraception (i.e., oral, injected, or implanted hormonal contraception, intrauterine device, barrier method of condom plus spermicide, or are surgically sterile) 4 weeks prior to (females), during, and for 6 months after (males and females) completion of study therapy
Able to cooperate with treatment and follow-up
No non-malignant systemic disease, including active uncontrolled infection
No other concurrent malignancy, except adequately treated cone-biopsied carcinoma in situ of the uterine cervix, basal cell or squamous cell carcinoma of the skin, or breast and ovarian carcinoma
Cancer survivors who have undergone potentially curative therapy for a prior malignancy, have no evidence of that disease for 5 years, and are deemed at low risk for recurrence are eligible
No active or unstable cardiac disease or history of myocardial infarction within the past 6 months
Patients with cardiovascular signs or symptoms should have a MUGA scan or echocardiogram, and those with a left ventricular ejection fraction (LVEF) below the institutional limit of normal should be excluded
No other condition which, in the investigator's opinion, would not make the patient a good candidate for this study Prior Concurrent Therapy:
At least 4 weeks since prior radiotherapy (except for palliative reasons), endocrine therapy, immunotherapy or chemotherapy (6 weeks for nitrosoureas and mitomycin C)
At least 4 weeks since prior major thoracic and/or abdominal surgery and recovered
Concurrent radiotherapy for the control of bone pain or skin lesions allowed, but not within 5 days of the last dose of study drug
Concurrent bisphosphonates allowed provided the dose is stable and treatment was started at least 2 weeks prior to recruitment
No unresolved toxicities (CTCAE$\geq$grade 1) from prior treatments (except for alopecia)
No concurrent anticancer therapy or investigational drugs
No concurrent tetracycline antibiotic therapy for prolonged periods (short courses [5-7 days] for treatment of infection are allowed)

Study Design: This is a dose-escalation study followed by an open label multicenter study. Patients will be stratified according to tumor type (breast vs ovarian) and mutation status (BRCA 1 vs BRCA 2). Patients will receive a compound of Formula (I) or (II) (at one of several possible dosages) over 30 minutes once daily on days 1-5. Treatment repeats every 21 days for 12 courses in the absence of disease progression or unacceptable toxicity. Patients who achieve stable or responding disease may receive additional courses of treatment at the discretion of the chief investigator or Drug Development Office (DDO). Patients will undergo blood sample collection periodically for pharmacokinetic and pharmacodynamic studies. Samples will be analyzed for tumor marker (CA 125 or CA 15.3) measurements, plasma levels of a compound of Formula (I) or (II) via liquid chromatography/mass spectrometry/mass spectrometry, PARP activity, and PARP protein expression via western blotting immunoassays. Paraffin embedded sections from original diagnostic biopsy are also collected and analyzed for PARP protein expression via immunohistochemical technique. Pleural and ascitic fluid may be collected and analyzed for DNA DS break repair proficiency via immunohistochemical technique. Some patients will also undergo biopsy of tumors and samples will be analyzed for BRCA 2 mutation as well as PARP activity via validated PARP immunoblotting assay. After completion of the study treatment, patients will be followed for 28 days.

Primary Outcome Measures:
Assessment of antitumor activity according to RECIST using tumor size measured clinically or radiologically with CT scan, MRI, plain x-ray, or other imaging techniques
Safety profile Secondary Outcome Measures:
Time to progression and overall survival
Plasma levels by Liquid Chromatography/Mass Spectrometry/Mass Spectrometry
Poly(ADP-ribose) polymerase (PARP) activity measured ex vivo using validated assays
PARP expression using quantitative Western blotting immuno-assays
Pharmacogenomics including CYP2D6 and CYP3A5, drug transport proteins, as well as polymorphisms in the genes coding for the PARP enzymes themselves
BRCA mutation status, PARP activity, and PARP expression in tumor biopsy samples (when possible)
DNA repair enzyme status using immunohistochemical techniques in paraffin sections from original diagnostic biopsies/operative procedures (where available)

DNA double strand break repair pathway function in cells obtained from ascitic or pleural fluid (where available) for primary cell culture Abbreviations Abbreviations which may have been used in the descriptions of the schemes and the examples that follow are: AcOH for acetic acid; AIBN for azobisisobutyronitrile; BPO for benzoyl peroxide; nBu for normal butyl; (Boc)2O for di-tert-butyl dicarbonate, $Bu_3SnH$ for tributyltin hydride; CDI for carbonyldiimidazole; DBU for 1,8-diazabicyclo[5.4.0]undec-7-ene; DCC for dicyclohexyl carbodiimide; DCM for dichloromethane; DEAD for diethylazodicarboxylate; DMF for dimethylformamide; EDCl for 1-(3-dimethylaminopropyl)-3-ethylcarbodiimide hydrochloride; DIEA or DIPEA for N,N-diisopropylethylamine; DMP for 2,2-dimethoxypropane; DMSO for dimethylsulfoxide (or methylsulfoxide); DPPA for diphenylphosphoryl azide; $Et_3N$ for triethylamine; EtOAc for ethyl acetate; $Et_2O$ for diethyl ether; EtOH for ethanol; HOAc for acetic acid; HOBT for 1-hydroxybenzotriazole; HOSu for N-hydroxysuccinimide; LiHMDS or LiN$(TMS)_2$ for lithium bis(trimethylsilyl)amide; MCPBA for meta-chloroperbenzoic acid; MeOH for methanol; MsCl for methanesulfonyl chloride; NaHMDS or NaN$(TMS)_2$ for sodium bis(trimethylsilyl)amide; NMO for N-methylmorpholine N-oxide; $SOCl_2$ for thionyl chloride; PPA for polyphosphoric acid; PPTS for pyridium p-toluene sulfonate; Pd(OAc)$_2$ for palladium (II) acetate; $PPh_3$ for triphenylphosphine; Py for pyridine; TFA for trifluoroacetic acid; TEA for triethylamine; THF for tetrahydrofuran; TMSCl for trimethylsilyl chloride; $TMSCF_3$ for trimethyl(trifluoromethyl)-silane; TPP for triphenylphosphine; TPAP for tetra-n-propylammonium perruthenate; DMAP for 4-dimethylamino pyridine; TsOH for p-toluene sulfonic acid; MsOH for methanesulfonic acid; OMs for mesylate, OTs for tosylate; OTf for triflate; Boc for tert-butoxycarbonyl; Fmoc for N-fluorenylmethoxycarbonyl; Su for succinimide; Ph for phenyl; HBPyU for O-benzotriazol-1-yl-N,N,N',N',-bis(tetramethylene)uronium hexafluorophosphate; PyBOP for benzotriazol-1-yloxytripyrrolidinophosphonium hexafluorophosphate; HATU for N,N,N',N'-tetramethyl-O-(7-azabenzotriazol-1-yl)uranium hexafluorophosphate.

The following Examples are intended as an illustration of the various embodiments as defined in the appended claims. The compounds can be prepared by a variety of synthetic routes. All publications, patents, and patent applications cited herein are hereby incorporated by reference for all purposes.

Example 1

Example 1a

Parenteral Composition

To prepare a parenteral pharmaceutical composition suitable for administration by injection, 100 mg of a water-soluble salt of a compound described herein is dissolved in DMSO and then mixed with 10 mL of 0.9% sterile saline. The mixture is incorporated into a dosage unit form suitable for administration by injection.

Example 1b

Oral Composition

To prepare a pharmaceutical composition for oral delivery, 100 mg of a compound described herein is mixed with 750 mg of starch. The mixture is incorporated into an oral dosage unit for, such as a hard gelatin capsule, which is suitable for oral administration.

Example 1c

Sublingual (Hard Lozenge) Composition

To prepare a pharmaceutical composition for buccal delivery, such as a hard lozenge, mix 100 mg of a compound described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 1d

Inhalation Composition

To prepare a pharmaceutical composition for inhalation delivery, 20 mg of a compound described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 1e

Rectal Gel Composition

To prepare a pharmaceutical composition for rectal delivery, 100 mg of a compound described herein is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 1f

Topical Gel Composition

To prepare a pharmaceutical topical gel composition, 100 mg of a compound described herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 1g

Ophthalmic Solution Composition

To prepare a pharmaceutical ophthalmic solution composition, 100 mg of a compound described herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 2

2-p-Tolylbenzo[d]oxazole-4-carboxamide

Example 2A 2-p-Tolylbenzo[d]oxazole-4-carboxylic acid

To a suspension of 3-hydroxyanthranilic acid (0.153 g, 1 mmol) in toluene (10 mL) was added 4-methylbenzoylchloride (0.464 g, 3 mmol) followed by pyridine (0.275 g, 3.5 mmol) at room temperature. The resulting mixture was stirred at room temperature for 30 minutes then heated to 80C for 1 hr. After this time the reaction was cooled and poured into a mixture of ethyl acetate (50 mL) and 5% aqueous hydrochloric acid (20 mL). Subsequent separation of the layers, drying the organic over MgSO$_4$ and filtration afforded a solution. After removal of the solvent, the residue was dissolved in xylenes (20 mL) and the solution treated with p-TsOH (0.4 g, 2.1 mmol). The reaction mixture was then heated to reflux overnight. After this time the reaction was cooled and poured into water (100 mL), the organic layer separated then washed with water (100 mL). The organic was dried over MgSO$_4$, filtered and concentrated to a solid. Recrystallization of this solid from ethyl acetate gave a white solid product, 2-p-tolylbenzo[d]oxazole-4-carboxylic acid (0.15 g, 60% yield). MS (ESI) m/e 254 [M+H]$^+$.

Example 2B 2-p-Tolylbenzo[d]oxazole-4-carboxamide

Oxalyl chloride (0.04 g, 0.3 mmol) was slowly added to a solution of 2-p-tolylbenzo[d]oxazole-4-carboxylic acid (0.064 g, 0.25 mmol) in dichloromethane (10 mL) with stirring. The reaction mixture was warmed to 50° C. for 4 h and then cooled to 25° C. The solution was condensed in vacuum and then slowly added to 28% NH$_4$OH (10 mL) and a solids precipitated out immediately. The mixture was warmed to 50° C. and stirred for another 2 h. Water (20 mL) was added to the reaction mixture and the slurry was cooled to 25° C. The product was filtered and the cake was washed with water, dried to afford 0.44 g 2-p-tolylbenzo[d]oxazole-4-carboxamide solid (Yield: 69.8%). $^1$H-NMR (300 MHz, DMSO-d$_6$): 2.46 (s, 3H), 6.01 (s, 1H), 7.34-1.36 (d, J=5.7 Hz, 2H), 7.43-7.47 (t, J=6.0 Hz, 1H), 7.71-7.73 (d, J=6.0 Hz, 1H), 8.15-8.18 (m, 3H), 9.02 (s, 1H). MS (ESI) m/e 253 [M+H]$^+$.

Example 3

2-(4-((Methylamino)methyl)phenyl)benzo[d]oxazole-4-carboxamide

Example 3A 2-(4-(((benzyloxycarbonyl)(methyl)amino)methyl)phenyl)benzo[d]oxazole-4-carboxylic acid To a suspension of 3-hydroxyanthranilic acid (0.300 g, 1.96 mmol) in toluene (10 mL) is added benzyl 4-(chlorocarbonyl)benzyl(methyl)carbamate (1.811 g, 5.7 mmol) followed by pyridine (0.545 g, 6.92 mmol) at room temperature. The resulting mixture is stirred at room temperature for 30 minutes then heated to 80° C. for 1 hr. After this time the reaction is cooled and poured into a mixture of ethyl acetate (50 mL) and 5% aqueous hydrochloric acid (50 mL). Subsequent separation of the layers, drying the organic over MgSO$_4$ and filtration afford a solution. After removal of the solvent, the residue is dissolved in xylenes (20 mL) and the solution treated with p-TsOH (0.800 g, 4.20 mmol). The reaction mixture is then heated to reflux for 6 hrs. After this time the reaction is cooled and poured into water (50 mL), the organic layer is separated and then washed with water (3×50 mL). The organic is dried over MgSO$_4$, filtered and concentrated to a solid. Flash column chromatography on silica gel using ethyl acetate and hexanes as the eluents gives a solid product, 2-(4-(((benzyloxycarbonyl)(methyl)amino)methyl)phenyl)benzo[d]oxazole-4-carboxylic acid. MS (ESI) m/e 417 [M+H]$^+$.

Example 3B

Benzyl 4-(4-carbamoylbenzo[d]oxazol-2-yl)benzyl(methyl)carbamate

Oxalyl chloride (218 mg, 1.72 mmol) is slowly added to a solution of 2-(4-(((benzyloxycarbonyl)(methyl)-amino)methyl)phenyl)benzo[d]oxazole-4-carboxylic acid (0.65 g, 1.57 mmol) in dichloromethane (10 mL) with stirring. The reaction mixture is warmed to 50° C. for 4 h and then cooled to 25° C. The solution is condensed in vacuum and then slowly added to 28% NH$_4$OH (6 mL). The mixture is warmed to 50° C. and stirred for another 2 h. Water (50 mL) is added to the reaction mixture and the slurry is cooled to 25° C. The product is filtered and the cake is washed with water, dried to afford benzyl 4-(4-carbamoylbenzo[d]oxazol-2-yl)benzyl(methyl)carbamate solid. MS (ESI) m/e 416 [M+H]$^+$.

Example 3C 2-(4-((Methylamino)methyl)phenyl)benzo[d]oxazole-4-carboxamide

A solution of benzyl 4-(4-(chlorocarbonyl)benzo[d]oxazol-2-yl)benzyl(methyl)carbamate (0.500 g, 1.20 mmol) in a mixture solvents of EtOH and THF (1:1 volume, 40 mL) is hydrogenated at room temperature in the presence of hydrogen (50 psi) and palladium on carbon (10 wt %, 0.050 g) for 18 hours. After filtration and removal of the solvents, the residue is purified by silica gel chromatography using ethyl acetate and hexanes as the eluents. This affords 2-(4-((methylamino)methyl)phenyl)benzo[d]oxazole-4-carboxamide. MS (ESI) m/e 282 [M+H]$^+$.

Example 4

2-(2-Methylpyrrolidin-2-yl)benzo[d]oxazole-4-carboxamide

Example 4A 2-(1-(Benzyloxycarbonyl)-2-methylpyrrolidin-2-yl)benzo[d]oxazole-4-carboxylic acid 2-(1-(Benzyloxycarbonyl)-2-methylpyrrolidin-2-yl)benzo[d]oxazole-4-carboxylic acid is prepared from 3-hydroxyanthranilic acid and benzyl 2-(chlorocarbonyl)-2-methylpyrrolidine-1-carboxylate using the conditions described in Example 3A. MS (ESI) m/e 381 [M+H]$^+$.

Example 4B

Benzyl 2-(4-carbamoylbenzo[d]oxazol-2-yl)-2-methylpyrrolidine-1-carboxylate

Benzyl 2-(4-carbamoylbenzo[d]oxazol-2-yl)-2-methylpyrrolidine-1-carboxylate is prepared from 2-(1-(benzyloxycarbonyl)-2-methylpyrrolidin-2-yl)benzo[d]oxazole-4-carboxylic acid using the conditions described in Example 3B. MS (ESI) m/e 380 [M+H]$^+$.

Example 4C 2-(2-Methylpyrrolidin-2-yl)benzo[d]oxazole-4-carboxamide 2-(2-Methylpyrrolidin-2-yl)benzo[d]oxazole-4-carboxamide is prepared from benzyl 2-(4-carbamoylbenzo[d]oxazol-2-yl)-2-methylpyrrolidine-1-carboxylate using conditions described in Example 3C. MS (ESI) m/e 246 [M+H]+.

Example 5

2-(4-((Methylamino)methyl)phenyl)benzo[d]oxazole-7-carboxamide

Example 5A 2-(4-(((Benzyloxycarbonyl)(methyl)amino)methyl) phenyl)benzo[d]oxazole-7-carboxylic acid 2-(4-(((Benzyloxycarbonyl)(methyl)amino)methyl)phenyl)benzo[d]oxazole-7-carboxylic acid is prepared from 3-aminosalicylic acid and benzyl 4-(chlorocarbonyl)benzyl (methyl)carbamate using identical conditions described in Example 3A. MS (ESI) m/e 417 [M+H]+.

Example 5B

Benzyl 4-(7-carbamoylbenzo[d]oxazol-2-yl)benzyl (methyl)carbamate

Benzyl 4-(7-carbamoylbenzo[d]oxazol-2-yl)benzyl(methyl)carbamate is prepared from 2-(4-(((benzyloxycarbonyl) (methyl)amino)methyl)phenyl)benzo[d]oxazole-7-carboxylic acid using the same conditions described in Example 3B. MS (ESI) m/e 416 [M+H]+.

Example 5C 2-(4-((Methylamino)methyl)phenyl)benzo[d]oxazole-7-carboxamide 2-(4-((Methylamino)methyl)phenyl)benzo[d]oxazole-7-carboxamide is prepared from benzyl 4-(7-carbamoylbenzo [d]oxazol-2-yl)benzyl(methyl)carbamate using the same conditions described in Example 3C. MS (ESI) m/e 282 [M+H]+.

Example 6

2-(2-Methylpyrrolidin-2-yl)benzo[d]oxazole-7-carboxamide

Example 6A 2-(1-(Benzyloxycarbonyl)-2-methylpyrrolidin-2-yl) benzo[d]oxazole-7-carboxylic acid 2-(1-(Benzyloxycarbonyl)-2-methylpyrrolidin-2-yl) benzo[d]oxazole-7-carboxylic acid is prepared from 3-aminosalicylic acid and benzyl 2-(chlorocarbonyl)-2-methylpyrrolidine-1-carboxylate using identical conditions described in Example 3A. MS (ESI) m/e 381 [M+H]+.

Example 6B

Benzyl 2-(7-carbamoylbenzo[d]oxazol-2-yl)-2-methylpyrrolidine-1-carboxylate

Benzyl 2-(7-carbamoylbenzo[d]oxazol-2-yl)-2-methylpyrrolidine-1-carboxylate is prepared from 2-(1-(benzyloxycarbonyl)-2-methylpyrrolidin-2-yl)benzo[d]oxazole-7-carboxylic acid using the same conditions described in Example 3B. MS (ESI) m/e 380 [M+H]−.

Example 6C 2-(2-Methylpyrrolidin-2-yl)benzo[d]oxazole-7-carboxamide 2-(2-Methylpyrrolidin-2-yl)benzo[d]oxazole-7-carboxamide is prepared from benzyl 2-(7-carbamoylbenzo[d]oxazol-2-yl)-2-methylpyrrolidine-1-carboxylate using the same conditions described in the Example 3C. MS (ESI) m/e 246 [M+H]+.

Example 7

2-(Pyrrolidin-2-yl)benzo[d]oxazole-4-carboxamide

Following the experimental procedure as described in Examples 4A to 4C, and substituting benzyl 2-(4-carbamoylbenzo[d]oxazol-2-yl)-2-methylpyrrolidine-1-carboxylate with benzyl 2-(4-carbamoylbenzo[d]oxazol-2-yl)pyrrolidine-1-carboxylate, and the title compound 2-(pyrrolidin-2-yl)benzo[d]oxazole-4-caroxamide is made.

Example 8

2-(Pyrrolidin-2-yl)benzo[d]oxazole-7-carboxamide

Following the experimental procedure as described in Examples 6A to 6C, and substituting benzyl 2-(4-carbamoylbenzo[d]oxazol-2-yl)-2-methylpyrrolidine-1-carboxylate with benzyl 2-(4-carbamoylbenzo[d]oxazol-2-yl)pyrrolidine-1-carboxylate, the title compound 2-(pyrrolidin-2-yl) benzo[d]oxazole-7-caroxamide is made.

Example 9

2-(7-Azabicyclo[2.2.1]heptan-1-yl)benzo[d]oxazole-4-carboxamide

Following the experimental procedure as described in Examples 3A to 3C, and substituting benzyl 4-(chlorocarbonyl)benzyl(methyl)carbamate with benzyl 1-(chlorocarbonyl)-7-azabicyclo[2.2.1]heptanes-7-carboxylate, the title compound 2-(7-azabicyclo[2.2.1]heptan-1-yl)benzo[d]oxazole-4-carboxamide is made.

Example 10

2-(7-Azabicyclo[2.2.1]heptan-1-yl)benzo[d]oxazole-7-carboxamide

Following the similar experimental procedure as described in Examples 5A to 5C, and substituting benzyl 4-(chlorocarbonyl)benzyl(methyl)carbamate with benzyl 1-(chlorocarbonyl)-7-azabicyclo[2.2.1]heptanes-7-carboxylate, the title compound 2-(7-azabicyclo[2.2.1]heptan-1-yl)benzo[d]oxazole-7-carboxamide is made.

Example 11

2-(2-Methyl-7-azabicyclo[2.2.1]heptan-1-yl)benzo [d]oxazole-4-carboxamide

Following the experimental procedure as described in Examples 9 and substituting (benzyl 1-(chlorocarbonyl)-7-azabicyclo[2.2.1]heptanes-7-carboxylate with benzyl 1-(chlorocarbonyl)-2-methyl-7-azabicyclo[2.2.1]heptanes-7-carboxylate, the title compound 2-(2-methyl-7-azabicyclo [2.2.1]heptan-1-yl)benzo[d]oxazole-4-caroxamide is made

Example 12

2-(2-Methyl-7-azabicyclo[2.2.1]heptan-1-yl)benzo[d]oxazole-7-carboxamide

Following the experimental procedure as described in Examples 10 and substituting (benzyl 1-(chlorocarbonyl)-7-azabicyclo[2.2.1]heptanes-7-carboxylate with benzyl 1-(chlorocarbonyl)-2-methyl-7-azabicyclo[2.2.1]heptanes-7-carboxylate, the title compound 2-(2-methyl-7-azabicyclo[2.2.1]heptan-1-yl)benzo[d]oxazole-7-caroxamide is made.

Example 13

2-(2-Azabicyclo[2.1.1]hexan-1-yl)benzo[d]oxazole-4-carboxamide

Following the experimental procedure as described in Examples 3A to 3C, and substituting benzyl 4-(chlorocarbonyl)benzyl(methyl)carbamate with benzyl 1-(chlorocarbonyl)-2-azabicyclo[2.1.1]hexane-2-carboxylate, the title compound 2-(2-azabicyclo[2.1.1]hexan-1-yl)benzo[d]oxazole-4-carboxamide is made.

Example 14

2-(2-Azabicyclo[2.1.1]hexan-1-yl)benzo[d]oxazole-7-carboxamide

Following the experimental procedure as described in Examples 5A to 5C, and substituting benzyl 4-(chlorocarbonyl)benzyl(methyl)carbamate with benzyl 1-(chlorocarbonyl)-2-azabicyclo[2.1.1]hexane-2-carboxylate, the title compound 2-(2-azabicyclo[2.1.1]hexan-1-yl)benzo[d]oxazole-7-carboxamide is made.

Example 15

2-(6-Azabicyclo[3.2.1]octan-5-yl)benzo[d]oxazole-4-carboxamide

Following the experimental procedure as described in Examples 3A to 3C, and substituting benzyl 4-(chlorocarbonyl)benzyl(methyl)carbamate with benzyl 5-(chlorocarbonyl)-6-azabicyclo[3.2.1]octane-6-carboxylate, the title compound 2-(6-azabicyclo[3.2.1]octan-5-yl)benzo[d]oxazole-4-carboxamide is made.

Example 16

2-(6-Azabicyclo[3.2.1]octan-5-yl)benzo[d]oxazole-7-carboxamide

Following the experimental procedure as described in Examples 5A to 5C, and substituting benzyl 4-(chlorocarbonyl)benzyl(methyl)carbamate with benzyl 5-(chlorocarbonyl)-6-azabicyclo[3.2.1]octane-6-carboxylate, the title compound 2-(6-azabicyclo[3.2.1]octan-5-yl)benzo[d]oxazole-7-carboxamide is made.

Example 17

2-((1S,5R)-6-Azabicyclo[3.2.1]octan-5-yl)benzo[d]oxazole-4-carboxamide

Following the experimental procedure as described in Examples 3A to 3C, and substituting benzyl 4-(chlorocarbonyl)benzyl(methyl)carbamate with (1S,5R)-benzyl 5-(chlorocarbonyl)-6-azabicyclo[3.2.1]octane-6-carboxylate, the title compound 2-((1S,5R)-6-azabicyclo[3.2.1]octan-5-yl)benzo[d]oxazole-4-carboxamide is made.

Example 18

2-((1S,5R)-6-Azabicyclo[3.2.1]octan-5-yl)benzo[d]oxazole-7-carboxamide

Following the experimental procedure as described in Examples 5A to 5C, and substituting benzyl 4-(chlorocarbonyl)benzyl(methyl)carbamate with (1S,5R)-benzyl 5-(chlorocarbonyl)-6-azabicyclo[3.2.1]octane-6-carboxylate, the title compound 2-((1S,5R)-6-azabicyclo[3.2.1]octan-5-yl)benzo[d]oxazole-7-carboxamide is made.

Example 19

2-((1R,5S)-6-Azabicyclo[3.2.1]octan-5-yl)benzo[d]oxazole-4-carboxamide

Following the experimental procedure as described in Examples 3A to 3C, and substituting benzyl 4-(chlorocarbonyl)benzyl(methyl)carbamate with (1R,5S)-benzyl 5-(chlorocarbonyl)-6-azabicyclo[3.2.1]octane-6-carboxylate, the title compound 2-((1R,5S)-6-azabicyclo[3.2.1]octan-5-yl)benzo[d]oxazole-4-carboxamide is made.

Example 20

2-((1R,5S)-6-Azabicyclo[3.2.1]octan-5-yl)benzo[d]oxazole-7-carboxamide

Following the experimental procedure as described in Examples 5A to 5C, and substituting benzyl 4-(chlorocarbonyl)benzyl(methyl)carbamate with (1R,5S)-benzyl 5-(chlorocarbonyl)-6-azabicyclo[3.2.1]octane-6-carboxylate, the title compound 2-((1R,5S)-6-azabicyclo[3.2.1]octan-5-yl)benzo[d]oxazole-7-carboxamide is made.

Example 21

2-(2-Benzyl-2-azabicyclo[2.2.2]octan-1-yl)benzo[d]oxazole-4-carboxamide

Following the experimental procedure as described in Examples 2A to 2B, and substituting 4-methylbenzoylchloride with 2-benzyl-2-azabicyclo[2.2.2]octane-4-carbonyl chloride, the title compound 2-(2-benzyl-2-azabicyclo[2.2.2]octan-1-yl)-benzo[d]oxazole-4-carboxamide is made.

Example 22

2-(2-Benzyl-2-azabicyclo[2.2.2]octan-1-yl)benzo[d]oxazole-7-carboxamide

Following the experimental procedure as described in Examples 2A to 2B, and substituting 4-methylbenzoylchloride with 2-benzyl-2-azabicyclo[2.2.2]octane-4-carbonyl chloride and 3-hydroxyanthranilic acid with 3-aminosalicylic acid, the title compound 2-(2-benzyl-2-azabicyclo[2.2.2]octan-1-yl)benzo[d]oxazole-7-carboxamide is made.

Example 23

2-(2-Azabicyclo[2.2.2]octan-1-yl)benzo[d]oxazole-4-carboxamide

Following the experimental procedure as described in Examples 3A to 3C, and substituting benzyl 4-(chlorocarbonyl)benzyl(methyl)carbamate with benzyl 1-(chlorocarbonyl)-2-azabicyclo[2.2.2]octane-2-carboxylate, the title compound 2-(2-azabicyclo[2.2.2]octan-1-yl)benzo[d]oxazole-4-carboxamide is made.

Example 24

2-(2-Azabicyclo[2.2.2]octan-1-yl)benzo[d]oxazole-7-carboxamide

Following the experimental procedure as described in Examples 5A to 5C, and substituting benzyl 4-(chlorocarbonyl)benzyl(methyl)carbamate with benzyl 1-(chlorocarbonyl)-2-azabicyclo[2.2.2]octane-2-carboxylate, the title compound 2-(2-azabicyclo[2.2.2]octan-1-yl)benzo[d]oxazole-7-carboxamide is made.

Example 25

2-(4-Azaspiro[2.4]heptan-5-yl)benzo[d]oxazole-4-carboxamide

Following the experimental procedure as described in Examples 3A to 3C, and substituting benzyl 4-(chlorocarbonyl)benzyl(methyl)carbamate with benzyl 5-(chlorocarbonyl)-4-azaspiro[2.4]heptane-4-carboxylate, the title compound 2-(4-azaspiro[2.4]heptan-5-yl)benzo[d]oxazole-4-carboxamide is made.

Example 26

2-(4-Azaspiro[2.4]heptan-5-yl)benzo[d]oxazole-7-carboxamide

Following the experimental procedure as described in Examples 5A to 5C, and substituting benzyl 4-(chlorocarbonyl)benzyl(methyl)carbamate with benzyl 5-(chlorocarbonyl)-4-azaspiro[2.4]heptane-4-carboxylate, the title compound 2-(4-azaspiro[2.4]heptan-5-yl)benzo[d]oxazole-7-carboxamide is made.

Example 27

2-((1R,4S)-2-Methyl-2-azabicyclo[2.2.1]heptan-1-yl)benzo[d]oxazole-4-carboxamide Following the experimental procedure as described in Examples 2A to 2B, and substituting 4-methylbenzoylchloride with (1R,4S)-2-methyl-2-azabicyclo[2.2.1]heptane-1-carbonyl chloride, the title compound 2-((1R,4S)-2-methyl-2-azabicyclo[2.2.1]heptan-1-yl)benzo[d]oxazole-4-carboxamide.

Example 28

2-((1R,4S)-2-Methyl-2-azabicyclo[2.2.1]heptan-1-yl)benzo[d]oxazole-7-carboxamide Following the experimental procedure as described in Examples 2A to 2B, and substituting 4-methylbenzoylchloride with (1R,4S)-2-methyl-2-azabicyclo[2.2.1]heptane-1-carbonyl chloride and 3-hydroxyanthranilic acid with 3-aminosalicylic acid, the title compound 2-((1R,4S)-2-methyl-2-azabicyclo[2.2.1]heptan-1-yl)benzo[d]oxazole-7-carboxamide.

Example 29

2-((1R,4S)-2-Ethyl-2-azabicyclo[2.2.1]heptan-1-yl)benzo[d]oxazole-4-carboxamide

The title compound, 2-((1R,4S)-2-ethyl-2-azabicyclo[2.2.1]heptan-1-yl)benzo[d]oxazole-4-carboxamide is prepared according to the procedure for Example 27, substituting (1R,4S)-2-ethyl-2-azabicyclo[2.2.1]heptane-1-carbonyl chloride for (1R,4S)-2-methyl-2-azabicyclo[2.2.1]heptane-1-carbonyl chloride.

Example 30

2-((1R,4S)-2-Ethyl-2-azabicyclo[2.2.1]heptan-1-yl)benzo[d]oxazole-7-carboxamide

The title compound, 2-((1R,4S)-2-ethyl-2-azabicyclo[2.2.1]heptan-1-yl)benzo[d]oxazole-7-carboxamide is prepared according to the procedure for Example 28, substituting (1R,4S)-2-ethyl-2-azabicyclo[2.2.1]heptane-1-carbonyl chloride for (1R,4S)-2-methyl-2-azabicyclo[2.2.1]heptane-1-carbonyl chloride.

Example 31

2-((1R,4S)-2-Cyclopropyl-2-azabicyclo[2.2.1]heptan-1-yl)benzo[d]oxazole-4-carboxamide The title compound, 2-((1R,4S)-2-cyclopropyl-2-azabicyclo[2.2.1]heptan-1-yl)benzo[d]oxazole-4-carboxamide is prepared according to the procedure for Example 27, substituting (1R,4S)-2-cyclopropyl-2-azabicyclo[2.2.1]heptane-1-carbonyl chloride for (1R,4S)-2-methyl-2-azabicyclo[2.2.1]heptane-1-carbonyl chloride.

Example 32

2-((1R,4S)-2-Cyclopropyl-2-azabicyclo[2.2.1]heptan-1-yl)benzo[d]oxazole-7-carboxamide The title compound, 2-((1R,4S)-2-cyclopropyl-2-azabicyclo[2.2.1]heptan-1-yl)benzo[d]oxazole-7-carboxamide is prepared according to the procedure for Example 28, substituting (1R,4S)-2-cyclopropyl-2-azabicyclo[2.2.1]heptane-1-carbonyl chloride for (1R,4S)-2-methyl-2-azabicyclo[2.2.1]heptane-1-carbonyl chloride.

Example 33

2-((1R,4S)-2-Cyclohexyl-2-azabicyclo[2.2.1]heptan-1-yl)benzo[d]oxazole-4-carboxamide The title compound, 2-((1R,4S)-2-cyclohexyl-2-azabicyclo[2.2.1]heptan-1-yl)benzo[d]oxazole-4-carboxamide is prepared according to the procedure for Example 27, substituting (1R,4S)-2-cyclohexyl-2-azabicyclo[2.2.1]heptane-1-carbonyl chloride for (1R,4S)-2-methyl-2-azabicyclo[2.2.1]hepta-1-carbonyl chloride.

Example 34

2-((1R,4S)-2-Cyclohexyl-2-azabicyclo[2.2.1]heptan-1-yl)benzo[d]oxazole-7-carboxamide The title compound, 2-((1R,4S)-2-cyclohexyl-2-azabicyclo[2.2.1]heptan-1-yl)benzo[d]oxazole-7-carboxamide is prepared according to the procedure for Example 28, substituting (1R,4S)-2-cyclohexyl-2-azabicyclo[2.2.1]heptane-1-carbonyl chloride for (1R,4S)-2-methyl-2-azabicyclo[2.2.1]heptane-1-carbonyl chloride.

Example 35

2-(2-Azabicyclo[2.2.1]heptan-1-yl)benzo[d]oxazole-4-carboxamide

Following the experimental procedure as described in Examples 3A to 3C, and substituting benzyl 4-(chlorocarbonyl)benzyl(methyl)carbamate with benzyl 1-(chlorocarbonyl)-2-azabicyclo[2.2.1]heptane-2-carboxylate, the title compound 2-(2-azabicyclo[2.2.1]heptan-1-yl)benzo[d]oxazole-4-carboxamide is made.

Example 36

2-(2-Azabicyclo[2.2.1]heptan-1-yl)benzo[d]oxazole-7-carboxamide

Following the experimental procedure as described in Examples 5A to 5C, and substituting benzyl 4-(chlorocarbonyl)benzyl(methyl)carbamate with benzyl 1-(chlorocarbonyl)-2-azabicyclo[2.2.1]heptane-2-carboxylate, the title compound 2-(2-azabicyclo[2.2.1]heptan-1-yl)benzo[d]oxazole-7-carboxamide is made.

Example 37

2-(7-Azabicyclo[2.2.1]heptan-1-yl)-5-chlorobenzo[d]oxazole-4-carboxamide

Following the experimental procedure as described in Examples 3A to 3C, and substituting benzyl 4-(chlorocarbonyl)benzyl(methyl)carbamate with benzyl 1-(chlorocarbonyl)-7-azabicyclo[2.2.1]heptane-7-carboxylate and replacing 3-hydroxyanthranilic acid with 2-amino-6-chloro-3-hydroxybenzamide, the title compound 2-(7-azabicyclo[2.2.1]heptan-1-yl)-5-chlorobenzo[d]oxazole-4-carboxamide is made.

Example 38

2-(7-Azabicyclo[2.2.1]heptan-1-yl)-5-chlorobenzo[d]oxazole-7-carboxamide

Following the experimental procedure as described in Examples 3A to 3C, and substituting benzyl 4-(chlorocarbonyl)benzyl(methyl)carbamate with benzyl 1-(chlorocarbonyl)-7-azabicyclo[2.2.1]heptane-7-carboxylate and replacing 3-hydroxyanthranilic acid with 3-amino-6-chloro-2-hydroxybenzamide, the title compound 2-(7-azabicyclo[2.2.1]heptan-1-yl)-5-chlorobenzo[d]oxazole-7-carboxamide is made.

Example 39

2-(2-Azabicyclo[2.2.1]heptan-1-yl)-5-chlorobenzo[d]oxazole-4-carboxamide

Following the experimental procedure as described in Examples 3A to 3C, and substituting benzyl 4-(chlorocarbonyl)benzyl(methyl)carbamate with benzyl 1-(chlorocarbonyl)-2-azabicyclo[2.2.1]heptane-2-carboxylate and replacing 3-hydroxyanthranilic acid with 2-amino-6-chloro-3-hydroxybenzamide, the title compound 2-(2-azabicyclo[2.2.1]heptan-1-yl)-5-chlorobenzo[d]oxazole-4-carboxamide is made.

Example 40

2-(2-Azabicyclo[2.2.1]heptan-1-yl)-5-chlorobenzo[d]oxazole-7-carboxamide

Following the experimental procedure as described in Examples 3A to 3C, and substituting benzyl 4-(chlorocarbonyl)benzyl(methyl)carbamate with benzyl 1-(chlorocarbonyl)-2-azabicyclo[2.2.1]heptane-2-carboxylate and replacing 3-hydroxyanthranilic acid with 3-amino-6-chloro-2-hydroxybenzamide, the title compound 2-(2-azabicyclo[2.2.1]heptan-1-yl)-5-chlorobenzo[d]oxazole-7-carboxamide is made.

Example 41

2-(1-Azabicyclo[2.2.1]heptan-4-yl)benzo[d]oxazole-4-carboxamide

Following the experimental procedure as described in Examples 2A to 2B, and substituting benzyl 4-methylbenzoylchlordie with 1-azabicyclo[2.2.1]heptane-4-carbonyl chloride, the title compound 2-(1-azabicyclo[2.2.1]heptan-4-yl)benzo[d]oxazole-4-carboxamide is made.

Example 42

2-(1-Azabicyclo[2.2.1]heptan-4-yl)benzo[d]oxazole-7-carboxamide

Following the experimental procedure as described in Examples 2A to 2B, and substituting benzyl 4-methylbenzoylchlordie with 1-azabicyclo[2.2.1]heptane-4-carbonyl chloride, and replacing 3-hydroxyanthranilic with 3-aminosalicylic acid, the title compound 2-(1-azabicyclo[2.2.1]heptan-4-yl)benzo[d]oxazole-7-carboxamide is made.

Example 43

2-(Quinuclidin-4-yl)benzo[d]oxazole-4-carboxamide

Following the experimental procedure as described in Examples 2A to 2B, and substituting benzyl 4-methylbenzoylchlordie with quinuclidine-4-carbonyl chloride, the title compound 2-(quinuclidin-4-yl)benzo[d]oxazole-4-carboxamide is made.

Example 44

2-(Quinuclidin-4-yl)benzo[d]oxazole-7-carboxamide

Following the experimental procedure as described in Examples 2A to 2B, and substituting benzyl 4-methylbenzoylchlordie with quinuclidine-4-carbonyl chloride, and replacing 3-hydroxyanthranilic with 3-aminosalicylic acid, the title compound 2-(quinuclidin-4-yl)benzo[d]oxazole-7-carboxamide is made.

Example 45

2-(1-Azabicyclo[3.3.1]nonan-5-yl)benzo[d]oxazole-4-carboxamide

Following the experimental procedure as described in Examples 2A to 2B, and substituting benzyl 4-methylbenzoylchlordie with 1-azabicyclo[3.3.1]nonane-5-carbonyl chloride, the title compound 2-(1-azabicyclo[3.3.1]nonan-5-yl)[d]oxazole-4-carboxamide is made.

Example 46

2-(1-Azabicyclo[3.3.1]nonan-5-yl)benzo[d]oxazole-7-carboxamide

Following the experimental procedure as described in Examples 2A to 2B, and substituting benzyl 4-methylbenzoylchlordie with 1-azabicyclo[3.3.1]nonane-5-carbonyl chloride, and replacing 3-hydroxyanthranilic with 3-aminosalicylic acid, the title compound 2-(1-azabicyclo[3.3.1]nonan-5-yl)benzo[d]oxazole-7-carboxamide is made.

Example 47

2-(Octahydro-1H-quinolizin-2-yl)benzo[d]oxazole-4-carboxamide

Following the experimental procedure as described in Examples 2A to 2B, and substituting benzyl 4-methylbenzoylchlordie with octahydro-1H-quinolizine-2-carbonyl chloride, the title compound 2-(octahydro-1H-quinolizin-2-yl)[d]oxazole-4-carboxamide is made.

Example 48

2-(Octahydro-1H-quinolizin-2-yl)benzo[d]oxazole-7-carboxamide

Following the experimental procedure as described in Examples 2A to 2B, and substituting benzyl 4-methylbenzoylchlordie with octahydro-1H-quinolizine-2-carbonyl chloride, and replacing 3-hydroxyanthranilic with 3-aminosalicylic acid, the title compound 2-(octahydro-1H-quinolizin-2-yl)benzo[d]oxazole-7-carboxamide is made.

Example 49

2-(Octahydro-1H-quinolizin-1-yl)benzo[d]oxazole-4-carboxamide

Following the experimental procedure as described in Examples 2A to 2B, and substituting benzyl 4-methylbenzoylchlordie with octahydro-1H-quinolizine-1-carbonyl chloride, the title compound 2-(octahydro-1H-quinolizin-1-yl)benzo[d]oxazole-4-carboxamide is made.

Example 50

2-(Octahydro-1H-quinolizin-1-yl)benzo[d]oxazole-7-carboxamide

Following the experimental procedure as described in Examples 2A to 2B, and substituting benzyl 4-methylbenzoylchlordie with octahydro-1H-quinolizine-1-carbonyl chloride, and replacing 3-hydroxyanthranilic with 3-aminosalicylic acid, the title compound 2-(octahydro-1H-quinolizin-1-yl)benzo[d]oxazole-7-carboxamide is made

Example 51

2-(Octahydro-1H-quinolizin-4-yl)benzo[d]oxazole-4-carboxamide

Following the experimental procedure as described in Examples 2A to 2B, and substituting benzyl 4-methylbenzoylchlordie with octahydro-1H-quinolizine-4-carbonyl chloride, the title compound 2-(octahydro-1H-quinolizin-4-yl)benzo[d]oxazole-4-carboxamide is made.

Example 52

2-(Octahydro-1H-quinolizin-1-yl)benzo[d]oxazole-7-carboxamide

Following the experimental procedure as described in Examples 2A to 2B, and substituting benzyl 4-methylbenzoylchlordie with octahydro-1H-quinolizine-4-carbonyl chloride, and replacing 3-hydroxyanthranilic with 3-aminosalicylic acid, the title compound 2-(octahydro-1H-quinolizin-4-yl)benzo[d]oxazole-7-carboxamide is made

Example 53

2-(Octahydro-1H-quinolizin-3-yl)benzo[d]oxazole-4-carboxamide

Following the experimental procedure as described in Examples 2A to 2B, and substituting benzyl 4-methylbenzoylchlordie with octahydro-1H-quinolizine-3-carbonyl chloride, the title compound 2-(octahydro-1H-quinolizin-3-yl)benzo[d]oxazole-4-carboxamide is made.

Example 54

2-(Octahydro-1H-quinolizin-3-yl)benzo[d]oxazole-7-carboxamide

Following the experimental procedure as described in Examples 2A to 2B, and substituting benzyl 4-methylbenzoylchlordie with octahydro-1H-quinolizine-3-carbonyl chloride, and replacing 3-hydroxyanthranilic with 3-aminosalicylic acid, the title compound 2-(octahydro-1H-quinolizin-3-yl)benzo[d]oxazole-7-carboxamide is made

Example 55

2-(Octahydrocyclopenta[c]pyrrol-1-yl)benzo[d]oxazole-4-carboxamide

Following the experimental procedure as described in Examples 3A to 3C, and substituting benzyl 4-(chlorocarbonyl)benzyl(methyl)carbamate with benzyl 1-(chlorocarbonyl)hexahydropenta[c]pyrrole-2 (1H)-carboxylate, the title compound 2-(octahydrocyclopenta[c]pyrrol-1-yl)benzo[d]oxazole-4-carboxamide is made.

Example 56

2-(Octahydrocyclopenta[c]pyrrol-1-yl)benzo[d]oxazole-7-carboxamide

Following the experimental procedure as described in Examples 5A to 5C, and substituting benzyl 4-(chlorocarbonyl)benzyl(methyl)carbamate with benzyl 1-(chlorocarbonyl)hexahydropenta[c]pyrrole-2 (1H)-carboxylate, the title compound 2-(octahydrocyclopenta[c]pyrrol-1-yl)benzo[d]oxazole-7-carboxamide is made.

The following compounds is made performing the experimental procedure as described in Examples 2A to 2B, or 3A to 3C or 5A to 5C with appropriate various carbonyl chorides or protected amino carbonyl chlorides.

Example 57

2-(2-Azabicyclo[2.2.1]heptan-4-yl)benzo[d]oxazole-4-carboxamide

Example 58

2-(2-Oxa-5-Azabicyclo[2.2.1]heptan-4-yl)benzo[d]oxazole-4-carboxamide

Example 59

2-(2-Azabicyclo[2.2.2]octan-4-yl)benzo[d]oxazole-4-carboxamide

Example 60

2-(2-Azabicyclo[3.2.0]heptan-1-yl)benzo[d]oxazole-4-carboxamide

Example 61

2-(3-Azabicyclo[3.2.0]heptan-1-yl)benzo[d]oxazole-4-carboxamide

Example 62

2-(2-Azabicyclo[3.2.0]heptan-4-yl)benzo[d]oxazole-4-carboxamide

Example 63

2-(2-Azabicyclo[3.2.0]heptan-3-yl)benzo[d]oxazole-4-carboxamide

Example 64

2-(5-Azaspiro[2.4]heptan-6-yl)benzo[d]oxazole-4-carboxamide

Example 65

2-(4-Azaspiro[2.4]heptan-6-yl)benzo[d]oxazole-4-carboxamide

Example 66

2-(6-Azaspiro[3.4]octan-7-yl)benzo[d]oxazole-4-carboxamide

Example 67

2-(5-Azaspiro[3.4]octan-6-yl)benzo[d]oxazole-4-carboxamide

Example 68

2-(5-Azaspiro[3.4]octan-7-yl)benzo[d]oxazole-4-carboxamide

Example 69

2-(6-Azaspiro[2.5]octan-5-yl)benzo[d]oxazole-4-carboxamide

Example 70

2-(4-Azaspiro[2.5]octan-5-yl)benzo[d]oxazole-4-carboxamide

Example 71

2-(5-Azaspiro[2.5]octan-7-yl)benzo[d]oxazole-4-carboxamide

Example 72

2-(4-Oxa-7-azaspiro[2.5]octan-6-yl)benzo[d]oxazole-4-carboxamide

Example 73

2-(4-Oxa-7-azaspiro[2.5]octan-5-yl)benzo[d]oxazole-4-carboxamide

Example 74

2-(4-Azaspiro[2.5]octan-7-yl)benzo[d]oxazole-4-carboxamide

Example 75

2-(5-Azaspiro[3.5]nonan-6-yl)benzo[d]oxazole-4-carboxamide

Example 76

2-(6-Azaspiro[3.5]nonan-8-yl)benzo[d]oxazole-4-carboxamide

Example 77

2-(7-Azaspiro[3.5]nonan-6-yl)benzo[d]oxazole-4-carboxamide

Example 78

2-(5-Azaspiro[3.5]nonan-8-yl)benzo[d]oxazole-4-carboxamide

Example 79

2-(8-Oxa-5-azaspiro[3.5]nonan-6-yl)benzo[d]oxazole-4-carboxamide

Example 80

2-(5-Oxa-5-azaspiro[3.5]nonan-6-yl)benzo[d]oxazole-4-carboxamide

Example 81

2-(2,3,4,6,7,9a-Hexahydro-1H-quinolizin-2-yl)benzo[d]oxazole-4-carboxamide

Example 82

2-(Decahydropyrido[1,2-a]azepin-4-yl)benzo[d]oxazole-4-carboxamide

Example 83

2-(2-Azabicyclo[2.2.1]heptan-4-yl)benzo[d]oxazole-7-carboxamide

Example 84

2-(2-Oxa-5-azabicyclo[2.2.1]heptan-4-yl)benzo[d]oxazole-7-carboxamide

Example 85

2-(2-Azabicyclo[2.2.2]octan-4-yl)benzo[d]oxazole-7-carboxamide

Example 86

2-(2-Azabicyclo[3.2.0]heptan-1-yl)benzo[d]oxazole-7-carboxamide

Example 87

2-(3-Azabicyclo[3.2.0]heptan-1-yl)benzo[d]oxazole-7-carboxamide

Example 88

2-(2-Azabicyclo[3.2.0]heptan-4-yl)benzo[d]oxazole-7-carboxamide

Example 89

2-(2-Azabicyclo[3.2.0]heptan-3-yl)benzo[d]oxazole-7-carboxamide

Example 90

2-(5-Azaspiro[2.4]heptan-6-yl)benzo[d]oxazole-7-carboxamide

Example 91

2-(4-Azaspiro[2.4]heptan-6-yl)benzo[d]oxazole-7-carboxamide

Example 92

2-(6-Azaspiro[3.4]octan-7-yl)benzo[d]oxazole-7-carboxamide

Example 93

2-(5-Azaspiro[3.4]octan-6-yl)benzo[d]oxazole-7-carboxamide

Example 94

2-(5-Azaspiro[3.4]octan-7-yl)benzo[d]oxazole-7-carboxamide

Example 95

2-(6-Azaspiro[2.5]octan-5-yl)benzo[d]oxazole-7-carboxamide

Example 96

2-(4-Azaspiro[2.5]octan-5-yl)benzo[d]oxazole-7-carboxamide

Example 97

2-(5-Azaspiro[2.5]octan-7-yl)benzo[d]oxazole-7-carboxamide

Example 98

2-(4-Oxa-7-azaspiro[2.5]octan-6-yl)benzo[d]oxazole-7-carboxamide

Example 99

2-(4-Oxa-7-azaspiro[2.5]octan-5-yl)benzo[d]oxazole-7-carboxamide

Example 100

2-(4-Azaspiro[2.5]octan-7-yl)benzo[d]oxazole-7-carboxamide

Example 101

2-(5-Azaspiro[3.5]nonan-6-yl)benzo[d]oxazole-7-carboxamide

Example 102

2-(6-Azaspiro[3.5]nonan-8-yl)benzo[d]oxazole-7-carboxamide

Example 103

2-(7-Azaspiro[3.5]nonan-6-yl)benzo[d]oxazole-7-carboxamide

Example 104

2-(5-Azaspiro[3.5]nonan-8-yl)benzo[d]oxazole-7-carboxamide

Example 105

2-(8-Oxa-5-azaspiro[3.5]nonan-6-yl)benzo[d]oxazole-7-carboxamide

Example 106

2-(5-Oxa-5-azaspiro[3.5]nonan-6-yl)benzo[d]oxazole-7-carboxamide

Example 107

2-(2,3,4,6,7,9a-Hexahydro-1H-quinolizin-2-yl)benzo[d]oxazole-7-carboxamide

Example 108

2-(Decahydropyrido[1,2-a]azepin-4-yl)benzo[d]oxazole-7-carboxamide

Example 109

2-(2-fluoro-4-(pyridine-2-yl)phenyl)benzo[d]oxazole-7-carboxamide

Example 109A

Methyl 4-bromo-2-fluorobenzoic acid 4-bromo-2-fluorobenzoic acid (30 g, 0.14 mol) was dissolved in methanol with a few drops of sulfuric acid. The reaction medium was refluxed for 20 hours. The cooled reaction mixture was evaporated and the residue partitioned between ethyl acetate and saturated aqueous sodium bicarbonate solution. The organic layer was separated and washed with brine, dried over sodium sulfate, filtered and evaporated to give methyl 4-bromo-2-fluorobenzoate (20.7 g, yield 64%) as a white solid. $^1$H-NMR (400 MHz, DMSO-d$_6$) δ (ppm); 3.85 (s, 3H), 7.55-7.58 (m, 1H), 7.70-7.73 (m, 1H), 7.79-7.83 (m, 1H); LC-MS (ESI) m/z: 233 (M+1)$^+$, 235 (M+3)$^+$

Example 109 B 2-(tributylstannyl)pyridine 2-bromopyridine (14.9 g, 93.1 mmol) in anhydrous THF (700 mL) was cooled to −78° C. under a stream of nitrogen gas, n-BuLi in hexane (54 mL) were added thereto and the mixture was stirred for 30 min. Tributyltin chloride (29 mL, 108 mmol) was added and the mixture was stirred, at −78° C. for 2 hours and afterwards at −20° C. for 3 hours. It was poured into an aqueous ammonium chloride solution and extracted with ethyl acetate. The organic phase was dried and the solvent was evaporated. The residue was purified by chromatography (petroleum ether/ethyl acetate=9/1) to give 2-(tributylstannyl)pyridine (12 g, yield 34%) as a yellow liquid, LC-MS (ESI) m/z: 370 (M+1)$^+$.

Example 109 C

Methyl 2-fluoro-4-(pyridine-2-yl)benzoate 2-(Tributylstannyl)pyridine (11.2 g, 30.4 mmol) was dissolved in toluene (240 mL), methyl 4-bromo-2-fluorobenzoate (7.4 g, 33.4 mmol) and tetrakis(triphenyl-phosphine) Pd (1.75 g) were added thereto. The mixture was poured into water, extraction was carried out with ethyl acetate, the organic phase was dried and the solvent was evaporated. The residue was purified by column chromatography (silica gel, petroleum ether:ethyl acetate 50:1 to 10:1) to give methyl 2-fluoro-4-(pyridin-2-yl)benzoate (2.5 g, yield 35%). $^1$H-NMR (400 MHz, CDCl$_3$) δ (ppm): 3.93 (s, 3H), 7.31-7.34 (m, 1H), 7.76-7.85 (m, 4H), 8.05 (t, J=7.6 Hz, 1H), 8.72-8.74 (m, 1H); LC-MS (ESI) m/z: 232 (M+1)$^+$.

Example 109 D 2-fluoro-4-(pyridin-2-yl)benzoic acid

A solution of methyl 2-fluoro-4-(pyridin-2-yl)benzoate (2.50 g, 11.0 mmol) in a mixture of THF (12 mL) and water was treated with lithium hydroxide monohydrate (0.9 g, 4 mmol) in water (12 mL). Methanol (8 mL) was added until a transparent solution formed. This solution was heated at 60° C. overnight, and the organic solvents were removed under vacuum. The residual aqueous solution was acidified with 2 N HCl to pH=2. Solvents were evaporated under reduced pressure to give 2-fluoro-4-(pyridin-2-yl)benzoic acid as a white solid. LC-MS (ESI) m/z: 218 (M+1)$^+$.

Example 109 E 2-fluoro-4-(pyridin-2-yl)benzoyl chloride

Thionyl chloride (20 ml) was added to 2-fluoro-4-(pyridine-2-yl)benzoic acid (1.91 g, 8.66 mmol) and the mixture was stirred at 70° C. overnight. The solvent was evaporated under reduced pressure and the residue was dried in vacuum to yield 2-fluoro-4-(pyridin-2-yl)benzoyl chloride.

Example 109 F

Methyl 3-(2-fluoro-4-(pyridin-2-yl)benzamido)-2-hydroxybenzoate

To a solution of methyl 3-amino-2-hydroxybenzoate (1.42 g, 8.50 mmol) and pyridine (1.0 mL, 8.5 mmol) in toluene (20 ml) was added 2-fluoro-4-(pyridine-2-yl)benzoyl chloride (2.0 g, 8.50 mmol) portion wise at 0° C. and then stirred at 70° C. for 4 h. The resulting mixture was extracted with ethyl acetate (4×100 mL). The organic phase was washed with water and saturated sodium bicarbonate, dried with anhydrous sodium sulfate and evaporated under reduced pressure to obtain methyl 3-(2-fluoro-4-(pyridin-2-yl)benzamido)-2-hydroxybenzoate as a yellow solid (1.40 g, yield 45%). LC-MS (ESI) m/z: 367 (M+1)$^+$.

Example 109 G

Methyl 2-(2-fluoro-4-(pyridin-2-yl)phenyl)benzo[d]oxazole-7-carboxylate

Methyl 3-(2-fluoro-4-(pyridin-2-yl)benzamido)-2-hydroxybenzoate (1.40 g, 3.8 mmol) and 4-methylbenzenesulfonic acid (1.82 g, 9.6 mmol) were added to toluene (50 mL) and the mixture was stirred at 118° C. for 2 days. The resulting mixture was extracted with ethyl acetate (100 mL×4) and concentrated. The crude product was purified by column chromatography (silica gel, petroleum ether/ethyl acetate=20/1 to 10/1). 500 mg of methyl 2-(2-fluoro-4-(pyridin-2-yl)phenyl)benzo[d]oxazole-7-carboxylate was obtained as a solid; yield 38%. LC-MS (ESI) m/z: 349 (M+1)$^+$.

Example 109 H 2-(2-Fluoro-4-(pyridin-2-yl)phenyl)benzo[d]oxazole-7-carboxamide Methyl 2-(2-fluoro-4-(pyridin-2-yl)phenyl)benzo[d]oxazole-7-carboxylate (500 mg, 1.40 mmol) was added to ammonia in methanol (30 ml) and the mixture was stirred at room temperature for 3 days. The solid was filtered, washed with methanol and ammonium hydroxide, dried in vacuum. 400 mg of 2-(2-fluoro-4-(pyridin-2-yl)phenyl)benzo[d]oxazole-7-carboxamide as a solid was obtained, yield 84%. $^1$H-NMR (400 MHz, DMSO-$d_6$) δ (ppm): 7.5-7.54 (m, 2H), 7.87-8.04 (m, 5H), 8.21-8.23 (m, 3H), 8.47 (s, 1H), 8.76 (s, 1H); LC-MS (ESI) m/z: 334 (M+1)$^+$.

Example 110

2-(2-fluoro-4-(piperidin-2-yl)phenyl)benzo[d]oxazole-7-carboxamide 2-(2-Fluoro-4-(pyridin-2-yl)phenyl)benzo[d]oxazole-7-carboxamide (380 mg, 1.1 mmol) and PtO$_2$ (190 mg) in methanol (20 ml) was hydrogenated under 25 atm of hydrogen at 45° C. for two days. The mixture was filtered. The solvent was removed in vacuum. The crude product was purified by prep-HPLC to give 2-(2-fluoro-4-(piperidin-2-yl)phenyl)benzo[d]oxazole-7-carboxamide (228 mg, yield 44%). $^1$H-NMR (400 MHz, CD$_3$OD) δ (ppm): 1.76-1.90 (m, 2H), 1.96-2.06 (m, 3H), 2.13-2.16 (m, 1H), 3.19-3.25 (m, 1H), 3.52-3.55 (d, J=12.4 Hz, 1H); 4.37-4.40 (d, J=11.2 Hz, 1H); 7.27-7.40 (m, 1H); 7.49-7.53 (m, 3H); 7.92-7.93 (m, 2H); 8.35-8.39 (t, J=7.2 Hz, 3H); LC-MS (ESI) m/z: 340 (M+1)$^+$.

Example 111

2-(2-fluoro-4-(1-propylpiperidin-2-yl)phenyl)benzo[d]oxazole-7-carboxamide

A solution of 2-(2-fluoro-4-(piperidin-2-yl)phenyl)benzo[d]oxazole-7-carboxamide (200 mg, 0.44 mmol), 10% Pd/C (100 mg) and propanal (10 ml, 4 mmol) in methanol (10 ml) was hydrogenated at room temperature for two days. The solution was filtered off and concentrated; the residue was purified by prep-HPLC to give 2-(2-fluoro-4-(1-propylpiperidin-2-yl)phenyl)benzo[d]oxazole-7-carboxamide (94 mg, yield 43%). $^1$H-NMR (400 MHz, CD$_3$OD) δ (ppm): 0.80 (s, 3H), 1.60-1.77 (m, 3H), 1.97-2.13 (m, 5H), 2.86 (s, 2H), 3.18 (s, 1H), 3.78-3.80 (m, 1H), 4.39-4.413 (m, 1H), 7.302-7.43 (m, 1H), 7.50-7.70 (m, 3H), 7.92-7.93 (m, 2H), 8.39 (s, 1H); LC-MS (ESI) m/z: 382 (M+1)$^+$.

Example 112

2-(2-fluoro-4-(pyrrolidin-2-yl)phenyl)benzo[d]oxazole-7-carboxamide

Example 112 A tert-butyl 2-oxopyrrolidine-1-carboxylate

To a solution of 2-pyrrolidinone (10.82 g, 127 mmol) in acetonitrile (400 mL) was added DMAP (1.53 g, 12.6 mmol) followed by a solution of 33.6 g of di-tert-butyldicarbonate (77.1 mmol) in 20 mL of acetonitrile. The colorless reaction mixture was stirred at room temperature for 1 h. The resulting dark yellow reaction mixture was concentrated by rotary evaporation in vacuo and the resulting oil was taken up in diethyl ether. The mixture was washed with an aqueous solution of 1N HCl and a saturated aqueous brine solution. The organic phase was dried over sodium sulfate, and concentrated by rotary evaporation in vacuo to afford a yellow oil. Purification by gradient column chromatography on triethylamine washed silica gel (5:1→3:1→1:1 petroleum ether: ethyl acetate) afforded tert-butyl 2-oxopyrrolidine-1-carboxylate as a pale yellow semi-solid (22.2 g, yield 94%). $^1$H-NMR (400 MHz, CDCl$_3$) δ (ppm): 3.61 (t, J=7.3 Hz, 2H), 2.36 (t, J=7.9 Hz, 2H), 1.86 (tt, J=7.9 Hz, 7.3 Hz, 2H), 1.38 (s, 9H); LC-MS (ESI) m/z: 208 (M+Na)$^+$.

Example 112 B tert-butyl 4-(4-bromo-3-fluorophenyl)-4-oxobutylcarbamate

To a solution of 1-bromo-2-fluoro-4-iodobenzene (26.3 g, 88.1 mol) in tetrahydrofuran (95 mL) was added isopropylmagnesium chloride (2.0 M solution in tetrahydrofuran, 44 mL) at 0° C. and the mixture stirred at 0° C. for 3 hours. This solution was cannulated into a solution of compound 2 (13.5 g, 73.1 mol) in tetrahydrofuran (120 mL) at −78° C. and the mixture stirred at −78° C. for 1 hour. The solution was warmed to ambient temperature and stirred for one hour before quenching with water. Hydrochloric acid (2N, 80 mL) was added and the mixture stirred at ambient temperature for 10 minutes. The mixture was concentrated and the residue partitioned between ethyl acetate and brine. The organic layer was washed with brine, dried over magnesium sulfate and filtered, then concentrated to afford the crude product which was recrystallized from hexane and dichloromethane to give tert-butyl 4-(4-bromo-3-fluorophenyl)-4-oxobutylcarbamate as a white solid (23 g, yield 91%). LC-MS (ESI) m/z: 360 (M+1)$^+$.

Example 112 C 5-(4-bromo-3-fluorophenyl)-3,4-dihydro-2H-pyrrole

A solution of tert-butyl 4-(4-bromo-3-fluorophenyl)-4-oxobutylcarbamate (23 g, 64.07 mmol) in formic acid (290 mL) was heated at 40° C. for 5 hours. The reaction mixture was cooled, concentrated and the residue was partitioned between ethyl acetate and aqueous sodium hydroxide. The organic phase was washed with water, dried over magnesium sulfate, filtered and concentrated. The residue was purified by flash chromatography on silica gel, using a gradient of 20-60% ethyl acetate in petroleum ether to give 5-(4-bromo-3-fluorophenyl)-3,4-dihydro-2H-pyrrole (12.7 g, yield 82%). LC-MS (ESI) m/z: 242 (M+1)$^+$.

Example 112 D 2-(4-bromo-3-fluorophenyl)pyrrolidine

To a solution of 5-(4-bromo-3-fluorophenyl)-3,4-dihydro-2H-pyrrole ((12.7 g, 52.7 mmol) in 360 mL methanol was added NaBH$_3$CN (6.6 g, 105 mmol) at 0° C. The resulting solution was adjusted to pH=6 with acetic acid. The reaction mixture was stirred at room temperature overnight. The reaction was quenched with 2 N HCl and the methanol was removed by evaporation. The residue was diluted with water, the aqueous phase adjusted to pH=10 with NaOH, extracted with ethyl acetate, dried by Na$_2$SO$_4$, concentrated and the residue was purified by chromatography on silica gel to give 2-(4-bromo-3-fluorophenyl)pyrrolidine as a yellow solid (12.5 g, yield 98%). LC-MS (ESI) m/z: 244 (M+1)$^+$.

Example 112 E benzyl 2-(4-bromo-3-fluorophenyl)pyrrolidine-1-carboxylate 2-(4-Bromo-3-fluorophenyl)pyrrolidine (12.5 g, 51.4 mmol) was dissolved in a mixture of dioxane (180 mL) and water (120 mL) and treated with potassium carbonate (28.4 g, 0.21 mol) and benzyl chloroformate (9.65 g, 56.5 mmol) at ambient temperature overnight. The mixture was partitioned between ethyl acetate and brine. The organic phase was concentrated and the residue was purified by flash chromatography on silica gel using a gradient of 5-20% ethyl acetate in petroleum ether to give benzyl 2-(4-bromo-3-fluorophenyl)pyrrolidine-1-carboxylate as a yellow solid (15.3 g, yield 82%). LC-MS (ESI) m/z: 378 (M+1)$^+$.

Example 112 F benzyl 2-(3-fluoro-4-(methoxycarbonyl)phenyl)pyrrolidine-1-carboxylate A mixture of benzyl 2-(4-bromo-3-fluorophenyl)pyrrolidine-1-carboxylate (15.3 g, 40.6 mmol), 1,1'-bis(diphenylphosphino)ferrocene palladium (II) dichloride (1.67 g, 2.0 mmol) and triethylamine (8.4 mL, 60.9 mmol) in methanol (180 mL) was stirred under 60 psi of carbon monoxide at 100° C. for 4 hour. After cooling to ambient temperature, the mixture was concentrated and the residue purified by flash chromatograph on silica gel using a gradient of 8-15% ethyl acetate in petroleum ether to give benzyl 2-(3-fluoro-4-(methoxycarbonyl)phenyl)pyrrolidine-1-carboxylate as colorless oil (8.71 g, yield 60%). LC-MS (ESI) m/z: 358 (M+1)$^+$.

Example 112 G 4-(1-(benzyloxycarbonyl)pyrrolidin-2-yl)-2-fluorobenzoic acid

To a solution of benzyl 2-(3-fluoro-4-(methoxycarbonyl)phenyl)pyrrolidine-1-carboxylate (8.7 g, 24.4 mmol) in tetrahydrofuran (90 mL) was added lithium hydroxide monohydrate (2.05 g, 48.8 mmol) in 90 mL of water (90 mL) and methanol (90 mL) was added until a transparent solution formed. This mixture was stirred at ambient temperature for 2 hours and acidified with 2N hydrochloric acid to pH=2. The mixture was concentrated to about 90 mL, diluted with water and left to stand at ambient temperature overnight. The solid was collected by filtration, washed with water and dried to give 4-(1-(benzyloxycarbonyl)pyrrolidin-2-yl)-2-fluorobenzoic acid (8.4 g, yield 98%). LC-MS (ESI) m/z: 344 (M+1)$^+$.

Example 112 H benzyl 2-(4-(chlorocarbonyl)-3-fluorophenyl)pyrrolidine-1-carboxylate To a stirred solution of 4-(1-(benzyloxycarbonyl)pyrrolidin-2-yl)-2-fluorobenzoic acid (8.4 g, 24.5 mmol) in anhydrous dichloromethane (300 mL) was added dropwise thionyl chloride (2.2 mL, 29.4 mmol) at 0° C. After the addition, the reaction mixture was stirred at room temperature overnight. The solvent was removed in vacuo to give benzyl 2-(4-(chlorocarbonyl)-3-fluorophenyl)pyrrolidine-1-carboxylate (8.87 g).

Example 112 I benzyl 2-(3-fluoro-4-(2-hydroxy-3-(methoxycarbonyl)phenylcarbamyl)phenyl)pyrrolidine-1-carboxylate To a stirred solution of methyl 3-amino-2-hydroxybenzoate (3.4 g, 20.4 mmol) and pyridine in anhydrous dichloromethane (35 mL) was added dropwise a solution of benzyl 2-(4-(chlorocarbonyl)-3-fluorophenyl)pyrrolidine-1-carboxylate (8.87 g, 24.5 mmol) in anhydrous dichloromethane (90 mL). After the addition, the mixture was stirred at room temperature overnight. The mixture was diluted with dichloromethane, washed with water, 1N HCl, brine, dried over anhydrous sodium sulfate, and concentrated, re-crystallized from ethyl acetate to give benzyl 2-(3-fluoro-4-(2-hydroxy-3-(methoxycarbonyl)phenylcarbamyl)phenyl)pyrrolidine-1-carboxylate as white solid (8.20 g, yield 68%). $^1$H-NMR (400 MHz, DMSO-d$_6$) δ (ppm): 1.77-1.87 (m, 3H), 2.33-2.37 (m, 1H), 3.55-3.58 (m, 1H), 3.64-3.70 (m, 1H), 3.83 (s, 3H), 4.86-5.07 (m, 3H), 6.65 (s, 1H), 6.92 (s, 1H), 7.19-7.39 (m, 6H), 7.48-7.51 (m, 1H), 7.82-7.84 (m, 1H), 8.25-8.30 (m, 1H), 9.86 (br s, 1H), 10.99 (br s, 1H); LC-MS (ESI) m/z: 493 (M+1)$^+$.

Example 112 J 2-(2-fluoro-4-(pyrrolidin-2-yl)phenyl)benzo[d]oxazole-7-carboxylic acid The mixture of polyphosphoric acid (4 g) and 2-(3-fluoro-4-(2-hydroxy-3-(methoxycarbonyl)phenylcarbamyl)phenyl)pyrrolidine-1-carboxylate (1.1 g, 2.23 mmol) was stirred at 180° C. for 0.5 h under nitrogen, and then cooled to 0° C. Water (50 mL) was added to the mixture and adjusted to pH=7 with sodium hydroxide at 0° C., the solution was extracted with ethyl acetate; the liquid layer was adjusted to pH=5, the water was evaporated under vacuum, the methanol was added, filtered, the solvent was dried over anhydrous sodium sulfate, evaporated to obtain 2-(2-fluoro-4-(pyrrolidin-2-yl)phenyl)benzo[d]oxazole-7-carboxylic acid (500 mg, yield 69%). LC-MS (ESI) m/z: 327 (M+1)$^+$.

Example 112 K methyl 2-(2-fluoro-4-(pyrrolidin-2-yl)phenyl)benzo[d]oxazole-7-carboxylate 2-(2-Fluoro-4-(pyrrolidin-2-yl)phenyl)benzo[d]oxazole-7-carboxylic acid (500 mg, 1.53 mmol) was dissolved in methanol (20 mL) at −5° C.-0° C., thionyl chloride (0.2 mL, 2.40 mmol) was added dropwise. The mixture was heated at 70° C. for 3 h., then evaporated and the residue was adjusted to pH=9 by NaHCO$_3$, and extracted with ethyl acetate. The organic layer was separated and washed with brine, dried over anhydrous sodium sulfate and evaporated to give methyl 2-(2-fluoro-4-(pyrrolidin-2-yl)phenyl)benzo[d]oxazole-7-carboxylate (200 mg, yield 38%) as white solid. LC-MS (ESI) m/z: 341 (M+1)$^+$.

Example 112 L 2-(2-fluoro-4-(pyrrolidin-2-yl)phenyl)benzo[d]oxazole-7-carboxamide Methyl 2-(2-fluoro-4-(pyrrolidin-2-yl)phenyl)benzo[d]oxazole-7-carboxylate (200 mg, 1.40 mmol) was added to ammonia in methanol (10 mL) and the mixture was stirred at room temperature for 3 days. The mixture was concentrated, and then purified by prep-HPLC to obtain 2-(2-fluoro-4-(pyrrolidin-2-yl)phenyl)benzo[d]oxazole-7-carboxamide as a white solid (34.6 mg, yield 18%). $^1$H-NMR (400 MHz, DMSO-$d_6$) δ (ppm): 1.50-1.55 (m, 1H), 1.74-1.79 (m, 2H), 2.18-2.23 (m, 1H), 2.95-3.02 (m, 2H), 4.19-4.23 (m, 1H), 7.42-7.51 (m, 3H), 7.74-7.80 (br s, 1H), 7.80-7.82 (d, J=6.8 Hz, 2H), 7.96-7.98 (dd, $J_1$=7.6 Hz, $J_2$=0.8 Hz, 1H), 8.22 (t, J=8.4 Hz, 1H); LC-MS (ESI) m/z: 326 (M+1)$^+$.

Example 113 methyl 2-amino-3-hydroxybenzoate

Example 113 A 3-hydroxy-2-nitrobenzoic acid

A mixture of 3-chloro-2-nitrobenzoic acid (40 g, 0.20 mol) and KOH (160 g, 2.86 mol) in water (200 mL) was heated to reflux for 16 hr. 6N aqueous hydrochloric acid was added to the mixture to pH=3, then extracted with ethyl acetate (500 mL×4). The combined organic layers were washed with brine, dried over anhydrous sodium sulfate, and concentrated to give 3-hydroxy-2-nitrobenzoic acid (55 g), LC-MS (ESI) m/z 184 [M+1]$^-$.

Example 113 B methyl 3-hydroxy-2-nitrobenzoate

A solution of 3-hydroxy-2-nitrobenzoic acid (51 g) and con.$H_2SO_4$ (5 mL) in anhydrous methanol (450 mL) was heated to reflux for 48 hr. The mixture was concentrated to remove methanol, and the residue was partitioned between water (500 mL) and ethyl acetate (800 mL). The organic layer was washed with brine (300 mL), dried over anhydrous sodium sulfate, and concentrated to give crude compound. The crude product was purified by chromatography (silica gel, petroleum ether/ethyl acetate=40:1 to 5:1) to give methyl 3-hydroxy-2-nitrobenzoate (28 g) $^1$H-NMR (400 MHz, CDCl$_3$) δ 3.8 (s, 3H), 7.32-7.34 (d, J=8.4 Hz, 1H), 7.39-7.41 (d, J=8.0 Hz, 1H), 7.48-7.52 (t, J=8.0 Hz, 1H), 11.37 (s, 1H); LC-MS (m/z) 198 [M+1]$^+$.

Example 113 C methyl 2-amino-3-hydroxybenzoate

A suspension of methyl 3-hydroxy-2-nitrobenzoate (14 g, 71 mmol) and 10% Pd/C (1.4 g) in ethyl acetate (300 mL) was purged in 1 atm hydrogen and stirred at 25° C. for 4 hr. The mixture was filtered, and the filtrate was concentrated to give methyl 2-amino-3-hydroxybenzoate (11.5 g, yield 97%) as a light yellow solid. $^1$H-NMR (400 MHz, CDCl$_3$-d) δ 3.88 (s, 1H), 5.84 (s, br 3H), 6.50-6.54 (t, J=8.0 Hz, 1H), 6.84-6.86 (d, J=7.2 Hz, 1H), 7.47-7.49 (d, J=7.6 Hz, 1H); LC-MS (ESI) m/z 168 [M+1]$^+$.

Example 114 methyl 3-amino-2-hydroxybenzoate

Example 114 A methyl 5-bromo-2-hydroxybenzoate

To a solution of methyl 2-hydroxybenzoate (152 g, 1.0 mol) in chloroform (500 mL) was added dropwise with stirring a solution of bromine (172 g, 1.08 mol) in chloroform (300 mL) at 10° C. After the addition, the solution was stirred at room temperature overnight. The mixture was diluted with dichloromethane (500 mL), washed with water (1 L×3), saturated sodium bicarbonate solution (500 mL), brine (500 mL), dried over anhydrous sodium sulfate and concentrated to give crude product. The crude product was re-crystallized from methanol to give methyl 5-bromo-2-hydroxybenzoate (192 g, yield 83%) as a white solid. $^1$H-NMR (400 MHz, CDCl$_3$) δ 3.96 (s, 3H), 6.89 (d, J=8.8 Hz, 1H), 7.52-7.55 (dd, J=8.8 Hz, J=2 Hz, 1H), 7.96 (d, J=2.8 Hz, 1H), 10.7 (s, 1H); LC-MS (ESI) m/z 233 [M+1]$^+$.

Example 114 B methyl 5-bromo-2-hydroxy-3-nitrobenzoate

To a mixture of methyl 5-bromo-2-hydroxybenzoate (150 g, 0.65 mol) in concentrated $H_2SO_4$ (320 mL) below 0° C. was added dropwise a mixture of concentrated HNO$_3$ (69.2 g, 0.71 mol) and concentrated $H_2SO_4$ (97 mL) with stirring below 5° C. After the addition, the mixture was stirred at this temperature for 3 hr. The reaction mixture was poured into crash ice and the precipitate was collected, washed with cold water, hot ethanol and dried to give methyl 5-bromo-2-hydroxy-3-nitrobenzoate (153 g, yield 85%). $^1$H-NMR (400 MHz, CDCl$_3$-d) δ 4.04 (s, 3H), 8.25 (d, J=2.4 Hz, 1H), 8.28 (d, J=2.4 Hz, 1H), 11.92 (s, 1H); LC-MS (ESI) m/z 278 [M+1]$^+$.

Example 114 C methyl 3-amino-2-hydroxybenzoate

A suspension of methyl 5-bromo-2-hydroxy-3-nitrobenzoate (38.4 g, 0.14 mol), sodium acetate (19.63 g, 0.24 mol) and 10% Pd/C (3.84 g) in ethyl acetate (500 mL) and water (30 mL) was stirred at 25° C. under 1 atm of hydrogen for 16 hr. The mixture was filtered and the filtrate was washed with water (500 mL×2), brine (300 mL), dried over anhydrous sodium sulfate and concentrated to give crude product. The crude product was washed with methanol at 0° C. to give methyl 3-amino-2-hydroxybenzoate (13.67 g, yield 59%) as a light yellow solid. $^1$H-NMR (400 MHz, CDCl$_3$-d) δ 3.88-3.94 (s, br, 2H), 3.91 (s, 3H), 6.70-6.74 (t, J=7.8 Hz, 1H), 6.88-6.90 (m, 1H), 7.24-7.26 (m, 1H), 10.91 (s, 1H); LC-MS (ESI) m/z 168 [M+1]$^-$.

Example 115 methyl 3-amino-5-fluoro-2-hydroxybenzoate

Example 115 A 5-fluoro-2-hydroxy-3-nitrobenzoic acid

To a mixture of 5-fluoro-2-hydroxybenzoic acid (3.08 g, 19.76 mmol) in concentrated $H_2SO_4$ (30 mL) below 0° C. was added dropwise a mixture of concentrated HNO$_3$ (2.11 g, 21.74 mmol) and concentrated $H_2SO_4$ (6 mL) with stirring below 5° C. After the addition, the mixture was stirred at this temperature for 2 hr. The reaction mixture was poured onto crash ice and the precipitate was collected, then the precipitate was dissolved in ethyl acetate (100 mL), washed with water (50 mL×2), brine (30 mL), dried over anhydrous sodium sulfate and concentrated to give 5-fluoro-2-hydroxy-3-nitrobenzoic acid (3.8 g) as a brown solid. LC-MS (ESI) m/z 202 [M+1]$^+$.

Example 115 B methyl 5-fluoro-2-hydroxy-3-nitrobenzoate

Thionyl chloride (5.88 g, 49.4 mmol) was added dropwise to anhydrous methanol (45 mL) at 5° C. The mixture was stirred at this temperature for 30 min. Then 5-fluoro-2-hydroxy-3-nitrobenzoic acid was added to the mixture and the resulting mixture was heated to reflux for 24 hr. Solvent was removed under reduced pressure. The residue was dissolved in ethyl acetate (100 mL), washed with water (100 mL×3), brine (50 mL), dried over anhydrous sodium sulfate and concentrated to give crude product. The crude product was purified by chromatography (silica gel, petroleum ether/ethyl acetate=100:1 to 5:1) to give methyl 5-fluoro-2-hydroxy-3-nitrobenzoate (3.4 g, yield 80% for two steps). $^1$H-NMR (400 MHz, CDCl$_3$-d) δ 4.04 (s, 3H), 7.88-7.90 (dd, J$_1$=7.6 Hz, J$_2$=3.2 Hz, 1H), 7.93-7.96 (dd, J$_1$=7.6 Hz, J$_2$=3.2 Hz, 1H), 11.74 (s, 1H); LC-MS (ESI) m/z 216 [M+1]$^+$.

Example 115 C methyl 3-amino-5-fluoro-2-hydroxybenzoate

A suspension of methyl 5-fluoro-2-hydroxy-3-nitrobenzoate (2.3 g, 10.7 mmol), acetic acid (2 mL) and 10% Pd/C (0.23 g) in ethyl acetate (50 mL) was stirred at 25° C. over 1 atm hydrogen for 4 hr. The mixture was filtered and the filtrate was concentrated to give crude product. The crude product was purified by chromatography (silica gel, petroleum ether/ethyl acetate=100:1 to 20:1) to give methyl 3-amino-5-fluoro-2-hydroxybenzoate (2.0 g, yield 100%) as a light yellow solid. $^1$H-NMR (400 MHz, CDCl$_3$-d) δ 3.95 (s, 3H), 3.98-4.13 (s, br, 2H), 6.60-6.63 (dd, J$_1$=9.4 Hz, J$_2$=2.4 Hz, 1H), 6.86-6.89 (dd, J$_1$=8.8 Hz, J$_2$=2.8 Hz, 1H), 10.70 (s, 1H); LC-MS (ESI) m/z 186 [M+1]$^+$.

Example 116

2-p-tolylbenzo[d]oxazole-4-carboxamide

Example 116 A 2 p-tolylbenzo[d]oxazole-4-carboxylic acid 4-methylbenzoic acid (0.408 g, 3 mmol) was dissolved in thionyl chloride (10 mL) and the mixture was stirred at reflux for 6 hr. The mixture was condensed under vacuum to yield 4-methylbenzoyl chloride. To a suspension of 3-hydroxyanthranilic acid (0.153 g, 1.0 mmol) in toluene (10 mL) was added 4-methylbenzoyl chloride (0.464 g, 3.0 mmol) followed by pyridine (0.275 g, 3.5 mmol) at room temperature. The resulting mixture was stirred at room temperature for 30 minutes then heated to 80° C. for 1 hr. The mixture was cooled and poured into a mixture of ethyl acetate (50 mL) and 5% aqueous hydrochloric acid (20 mL). Subsequent separation of the layers, drying the organic over anhydrous magnesium sulfate and filtration afforded a solution. After removal of the solvent, the residue was dissolved in toluene (20 mL) and the solution treated with 4-methylbenzenesulfonic acid (0.4 g, 2.1 mmol). The reaction mixture was then heated to reflux overnight. After this time the reaction was cooled and poured into water (100 mL), the organic layer was separated then washed with water (100 mL). The organic phase was dried over anhydrous magnesium sulfate, filtered and concentrated to get a solid. Re-crystallization of this solid from ethyl acetate gave 2 p-tolybenzo[d]oxazole-4-carboxylic acid as a white solid (0.15 g, 60% yield). LC-MS (ESI) m/z 254 [M+1]$^+$.

Example 116 B 2-p-tolylbenzo[d]oxazole-4-carboxamide

Oxalyl chloride (0.04 g, 0.3 mmol) was slowly added to a solution of 2-p-tolylbenzo[d]oxazole-4-carboxylic acid (0.064 g, 0.25 mmol) in dichloromethane (10 mL) with stirring. The reaction mixture was warmed to 50° C. for 4 hr and then cooled to 25° C. The solution was condensed in vacuum and then slowly added to 28% ammonia water (10 mL) and a solid precipitated out immediately. The mixture was warmed to 50° C. and stirred for another 2 hr. Water (20 mL) was added to the mixture and the slurry was cooled to 25° C. The product was filtered and the cake was washed with water, dried to afford 44 mg 2-p-tolylbenzo[d]oxazole-4-carboxamide as a solid (yield 69.8%). $^1$H-NMR (400 MHz, DMSO-d6) δ 2.46 (s, 3H), 6.01 (s, 1H), 7.34-7.36 (d, J=7.6 Hz, 2H), 7.43-7.47 (t, J=8.0 Hz, 1H), 7.71-7.73 (d, J=8.0 Hz, 1H), 8.15-8.18 (m, 3H), 9.02 (s, 1H); LC-MS (ESI) m/z 253 [M+1]$^+$.

Example 117

2-(4-((methylamino)methyl)phenyl)benzo[d]oxazole-4-carboxamide

Example 117 A methyl 4-(bromomethyl)benzoate

Methyl 4-methylbenzoate 3 (2.9 g, 19.3 mmol) was dissolved in tetrachloromethane (CCl$_4$, 20 mL) at room temperature. N-bromosuccinimide (NBS, 3.5 g, 19.0 mmol) and benzoyl peroxide (BPO, 0.26 g, 1.9 mmol) was added. The resulting mixture was stirred at reflux for 5 hr, then cooled to room temperature, washed with saturated sodium bicarbonate solution and brine, dried with anhydrous sodium sulfate and condensed under vacuum. The residue was purified by silica gel chromatography (petrol ether:ethyl acetate=50:1 to 10:1) to get a white solid of methyl 4-(bromomethyl)benzoate (4.3 g, 97%), LC-MS (ESI) m/z 230 [M+1]$^+$.

Example 117 B methyl 4-((methylamino)methyl)benzoate

Methyl 4-(bromomethyl)benzoate was dissolved in methylamine ethanol solution and the mixture was stirred at reflux for 3 hr. The mixture was condensed under vacuum and poured into ethyl acetate and filtered. The cake was dried to get methyl 4-((methylamino)methyl)benzoate (2.5 g, 74.4%), LC-MS (ESI) m/e 180 [M+1]$^-$.

Example 117 C methyl 4-(((benzyloxycarbonyl)(methyl)amino)methyl)benzoate

Methyl 4-((methylamino)methyl)benzoate was dissolved in the mixed solution of THF (12 mL) and water (12 mL), then benzyl carbonochloridate (2.57 g, 15.0 mmol) was dropped into it. To the mixture sodium bicarbonate (1.7 g, 20.5 mmol) was added and the mixture was stirred at room temperature overnight. The mixture was poured into ethyl acetate (50 mL×3) and the organic layer was washed with saturated sodium bicarbonate solution, dried with anhydrous sodium sulfate and condensed to get methyl 4-(((benzyloxycarbonyl)(methyl)amino)methyl)benzoate (2.3 g, 53.5%), LC-MS (ESI) m/z 314 [M+1]$^+$.

Example 117 D 4-(((benzyloxycarbonyl)(methyl)amino)methyl)benzoic acid

The methyl 4-(((benzyloxycarbonyl)(methyl)amino)methyl)benzoate was dissolved in methanol, then LiOH (0.35 g, 14.7 mmol) was added. The resulting mixture was maintained at room temperature for 2 days. The mixture was adjusted to pH=1~2 with 2N aqueous hydrochloric acid then extracted with ethyl acetate (50 mL×3). The combined organic layer was washed with brine, dried over anhydrous sodium sulfate and condensed under vacuum. The residue was purified by silica gel chromatography (petrol ether:ethyl acetate=10:1) to yield a white solid of 4-(((benzyloxycarbonyl)(methyl)amino)methyl)benzoic acid (1.25 g, 56.8%), LC-MS (ESI) m/z 300 [M+1]$^+$.

Example 117 E 2-(4-(((benzyloxycarbonyl)(methyl)amino)methyl)phenyl)benzo[d]oxazole-4-carboxylic acid 4-(((benzyloxycarbonyl)(methyl)amino)methyl)benzoic acid 7 (1.25 g, 4.18 mmol) was dissolved in thionyl chloride (10 mL) and the mixture was stirred at reflux overnight. The mixture was condensed under vacuum and used at next step without treatment. To a suspension of 3-amino-2-hydroxybenzoic acid (0.153 g, 1 mmol) in toluene (10 mL) was added benzyl 4-(chlorocarbonyl)benzyl(methyl)carbamate (0.636 g, 2 mmol) followed by pyridine (0.275 g, 3.5 mmol) at room temperature. The resulting mixture was stirred at room temperature for 30 minutes then heated to 80° C. for 1 hr. After this time the reaction was cooled and poured into a mixture of ethyl acetate (50 mL) and 5% aqueous hydrochloric acid (20 mL). Subsequent separation of the layers, drying the organic over anhydrous magnesium sulfate and filtration afforded a solution. After removal of the solvent, the residue was dissolved in toluene (20 mL) and the solution treated with 4-methylbenzenesulfonic acid (0.4 g, 2.1 mmol). The reaction mixture was then heated to reflux overnight. After this time the reaction was cooled and poured into water (100 mL), the organic layer separated then washed with water (100 mL), dried over anhydrous magnesium sulfate, filtered and concentrated to a solid. Pure2-(4-(((benzyloxycarbonyl)(methyl)amino)methyl)phenyl)benzo[d]oxazole-4-carboxylic acid was obtained after re-crystallization from ethyl acetate as a solid (0.060 g, 47.4% yield). LC-MS (ESI) m/z 417 [M+1]$^+$.

Example 117 F benzyl 4-(4-carbamoylbenzo[d]oxazol-2-yl)benzyl(methyl)carbamate 2-(4-(((Benzyloxycarbonyl)(methyl)amino)methyl)phenyl)benzo[d]oxazole-4-carboxylic acid, (0.060 g, 0.14 mmol) in dimethyl formamide (10 mL) was added HOBT (0.025 g, 0.165 mmol), EDCI (0.035 g, 0.18 mmol), DIPEA (0.058 g, 0.45 mmol) and ammonium chloride (0.008 g, 0.15 mmol). The reaction mixture was stirred at room temperature for 20 hr, cooled and poured into water (10 mL). The pH was adjusted to 3 with 1N aqueous hydrochloric acid. The solution was extracted with dichloromethane (70 mL×3). The solution was washed with brine, dried, condensed in vacuum and separated by silica gel chromatography (ethyl acetate:methanol=1:0 to 10:1) to afford benzyl 4-(4-carbamoylbenzo[d]oxazol-2-yl)benzyl(methyl)carbamate 0.045 g solid (yield: 75.2%); LC-MS (ESI) m/z 416 [M+1]$^+$.

Example 117 G 2-(4-((methylamino)methyl)phenyl)benzo[d]oxazole-4-carboxamide

Benzyl 4-(4-carbamoylbenzo[d]oxazol-2-yl)benzyl(methyl)carbamate (0.050 g, 0.12 mmol) was dissolved in THF (10 mL) and 10% Pd/C (5.0 mg) was added, Hydrogen was purged into the mixture, and the mixture was maintained at room temperature for 6 hr, then the Pd/C was filtered off and the filtrate was condensed to get 2-(4-((methylamino)methyl)phenyl)benzo[d]oxazole-4-carboxamide (0.0212 g, 69.6% yield). $^1$H-NMR (400 MHz, DMSO-d6) δ 2.59 (s, 3H), 4.24-4.26 (t, J=5.0 Hz, 1H), 7.56-7.60 (t, J=8.0 Hz, 1H), 7.80-7.82 (d, J=8.0 Hz, 2H), 8.00-8.07 (m, 3H), 8.38-8.40 (d, J=8.0 Hz, 2H), 8.49 (s, 1H), 9.39 (s, 2H); LC-MS (ESI) m/z 282 [M+1]$^+$.

Example 118

2-(3-aminophenyl)benzo[d]oxazole-4-carboxamide

Example 118 A 3-hydroxy-2-(3-nitrobenzeneamido)benzoic acid

Thionyl chloride (25 mL) was added to 3-nitrobenzoic acid (3 g, 18 mmol) and the mixture was stirred at reflux for 6 hr. Thionyl chloride was evaporated under reduced pressure and the residues was dried to obtain 3-nitrobenzoyl chloride as a yellow solid. 3-Hydroxyanthranilic acid (0.92 g, 6.0 mmol) and pyridine (1.45 mL, 18.0 mmol) were added to toluene (30 mL) and the mixture was stirred at room temperature for 30 min. Then 3-nitrobenzoyl chloride prepared above (3.34 g, 18 mmol) was added. The mixture was stirred at room temperature for 30 min and then at 80° C. for 2 hr. The solvents was evaporated under reduced pressure and the residue was washed with 5% aqueous hydrochloric acid (100 mL×3), filtered, the solid was washed with water (100 mL×3), dried in vacuum at 50° C. to obtain 3-hydroxy-2-(3-nitrobenzeneamido)benzoic acid as a yellow solid (1.8 g, yield 100%). LC-MS (ESI) m/z 303 [M+1]$^+$.

Example 118 B 2-(3-nitrophenyl)benzo[d]oxazole-4-carboxylic acid

3-Hydroxy-2-(3-nitrobenzeneamido)benzoic acid (1.8 g, 6.0 mmol) and 4-methylbenzenesulfonic acid (2 g, 12.0 mmol) were added to toluene (36 mL) and the mixture was stirred under reflux for 10 hr. The solvents was evaporated under reduced pressure and the residue was washed with water (100 mL×3), filtered, the solid was dried in vacuum at 50° C. to obtain 2-(3-nitrophenyl)benzo[d]oxazole-4-carboxylic acid as a yellow solid (1.42 g, yield 83%). LC-MS (ESI) m/z 285 [M+1]$^+$.

Example 118 C 2-(3-nitrophenyl)benzo[d]oxazole-4-carboxamide

To a solution of 2-(3-nitrophenyl)benzo[d]oxazole-4-carboxylic acid (1.42 g, 5 mmol) in DMF (70 mL) was added HOBt (0.75 g, 5.5 mmol), NH$_4$Cl (0.27 g, 5.0 mmol), DIPEA (1.94 g, 15.0 mmol) and EDCI (1.15 g, 6.0 mmol). The mixture was stirred at 30° C. for 17 hr. To the resulting mixture, water (10 mL) was added and 1N aqueous hydrochloric acid to pH=3, then filtered, the filtrate was washed with saturated sodium bicarbonate solution (100 mL×2), brine (100 mL×2) and dried in vacuum to get a crude product. The crude product was re-crystallized in THF to obtain 2-(3-nitrophenyl)benzo[d]oxazole-4-carboxamide as a yellow solid (700 mg, yield 49%); LC-MS (ESI) m/z 284 [M+1]$^-$.

Example 118 D 2-(3-aminophenyl)benzo[d]oxazole-4-carboxamide

To a mixture of 2-(3-nitrophenyl)benzo[d]oxazole-4-carboxamide (700 mg, 2.47 mmol) in methanol (30 mL) was added Raney Ni (2 g). The mixture was purged with hydrogen and stirred at room temperature for 5 hr. Then the mixture was filtered and washed with methanol; the filtrate was evaporated under reduced pressure and purified by silica gel chromatography to obtain 2-(3-aminophenyl)benzo[d]oxazole-4-carboxamide as a yellow solid (265 mg, yield 42%). $^1$H-NMR (400 MHz, DMSO-d6) δ 5.57 (s, 2H), 6.83-6.86 (dd, $J_1$=8 Hz, $J_2$=2 Hz, 1H), 7.25-7.29 (t, J=8 Hz, 1H), 7.42-7.44 (d, J=8 Hz, 1H), 7.51-7.56 (m, 2H), 7.96-8.00 (t, J=8 Hz, 2H), 8.07 (s, 1H), 8.47 (s, 1H); LC-MS (ESI) m/z 254 [M+1]$^+$.

Example 119

2-(3-acetamidophenyl)benzo[d]oxazole-4-carboxamide

To a solution of 2-(3-aminophenyl)benzo[d]oxazole-4-carboxamide (100 mg, 0.39 mmol) in dichloromethane (5 mL) was added pyridine (34 mg, 0.43 mmol), then acetyl chloride (32 mg, 0.41 mmol) was added at 0° C. stirred at room temperature for 4 hr. The solvent was evaporated under reduced pressure and re-crystallized in methanol to obtain a white solid of 2-(3-acetamidophenyl)benzo[d]oxazole-4-carboxamide (45 mg, yield 38%). $^1$H-NMR (400 MHz, DMSO-d6) δ 2.09 (s, 3H), 7.53-7.58 (m, 2H), 7.84-7.86 (d, J=8 Hz, 1H), 7.97-8.07 (m, 4H), 8.44 (s, 1H), 8.57 (s, 1H), 10.29 (s, 1H); LC-MS (ESI) m/z 296 [M+1]$^+$.

Example 120

2-(3-(2-(dimethylamino)acetamido)phenyl)benzo[d]oxazole-4-carboxamide

To a solution of 2-(3-aminophenyl)benzo[d]oxazole-4-carboxamide (60 mg, 0.23 mmol) in DMF (3 mL) was added HOBT (35 mg, 0.26 mmol), dimethylglycine (24 mg, 0.23 mmol), DIPEA (91 mg, 0.7 mmol) and EDCI (54 mg, 0.29 mmol). The mixture was stirred at 30° C. for 18 hr. The reaction mixture was purified by pre-HPLC to obtain 2-(3-(2-(dimethylamino)acetamido)phenyl)benzo[d]oxazole-4-carboxamide (30 mg, yield 37%). $^1$H-NMR (400 MHz, DMSO-d6) δ 2.29 (s, 6H), 3.12 (s, 2H), 7.54-7.58 (m, 2H), 7.95-8.06 (m, 5H), 8.46 (s, 1H), 8.69 (s, 1H), 10.11 (s, 1H); LC-MS (ESI) m/z 339 [M+1]$^-$.

Example 121

2-(4-aminophenyl)benzo[d]oxazole-4-carboxamide

Example 121 A 3-hydroxy-2-(4-nitrobenzamido)benzoic acid

Thionyl chloride (25 mL) was added to 3-nitrobenzoic acid (3 g, 18.0 mmol) and the mixture was stirred at reflux for 6 hr. Thionyl chloride was evaporated under reduced pressure to give a residue which was dried in vacuum to obtain a yellow solid of 4-nitrobenzoyl chloride. 3-Hydroxyanthranilic acid (0.92 g, 6.0 mmol) and pyridine (1.45 mL, 18.0 mmol) were added to toluene (30 mL) and the mixture was stirred at room temperature for 30 min. 4-nitrobenzoyl chloride (3.34 g, 18.0 mmol) was then added. The mixture was stirred at room temperature for 30 min and then at 80° C. for 2 hr. Evaporated the solvents under reduced pressure and the residue was washed with 5% aqueous hydrochloric acid (100 mL×3), filtered, and washed with water (100 mL×3), dried in vacuum at 50° C. to obtain 3-hydroxy-2-(4-nitrobenzamido)benzoic acid (1.8 g, yield 100%) as a yellow solid. MS (ESI) m/z 303 [M+1]$^+$.

Example 121 B 2-(4-nitrophenyl)benzo[d]oxazole-4-carboxylic acid

3-Hydroxy-2-(4-nitrobenzamido)benzoic acid (1.8 g, 6.0 mmol) and 4-methylbenzenesulfonic acid (2 g, 12.0 mmol) were added to toluene (36 mL) and the mixture was stirred at reflux for 17 hr. The solvent was evaporated under reduced pressure and the residue was washed with water (100 mL×3), filtered and dried under reduced pressure at 50° C. to obtain a yellow solid of 2-(4-nitrophenyl)benzo[d]oxazole-4-carboxylic acid (1.42 g, yield 83%). LC-MS (ESI) m/z 285 [M+1]$^+$.

Example 121 C 2-(4-nitrophenyl)benzo[d]oxazole-4-carboxamide

To a solution of 2-(4-nitrophenyl)benzo[d]oxazole-4-carboxylic acid (1.42 g, 5 mmol) in DMF (70 mL) was added HOBt (0.75 g, 5.5 mmol), NH$_4$Cl (0.27 g, 5.0 mmol), DIPEA (1.94 g, 15.0 mmol) and EDCI (1.15 g, 6.0 mmol). The mixture was stirred at 30° C. for 18 hr. The resulting mixture was purged in water (10 mL) and aqueous hydrochloric acid (1 N) to pH=3, then filtered, and the filtrate was washed with saturated sodium bicarbonate solution (100 mL×2) and brine (100 mL×2), and dried in vacuum to obtain the crude product. Re-crystallization in THF obtained 2-(4-nitrophenyl)benzo[d]oxazole-4-carboxamide as a yellow solid (800 mg, yield 56%). LC-MS (ESI) m/e 284 [M+1]$^+$.

Example 121 D 2-(4-aminophenyl)benzo[d]oxazole-4-carboxamide

To a mixture of 2-(4-nitrophenyl)benzo[d]oxazole-4-carboxamide (800 mg, 2.83 mmol) in methanol (30 mL) was added Raney Ni (2 g), the mixture was purged into hydrogen and stirred at room temperature for 5 hr. The mixture was filtered, washed with methanol, the filtrate was evaporated under reduced pressure to obtain a solid, purified by silica gel chromatography to give 2-(4-aminophenyl)benzo[d]oxazole- 4-carboxamide as a yellow solid (450 mg, yield 63%). $^{1}$H-NMR (400 MHz, DMSO-d6) δ 6.16 (s, 2H), 6.69-6.72 (d, J=9.2 Hz, 2H), 7.38-7.42 (t, J=8 Hz, 1H), 7.85-7.96 (m, 5H), 8.54 (s, 1H); LC-MS (ESI) m/z 254 [M+1]$^{+}$.

Example 122

2-(4-acetamidophenyl)benzo[d]oxazole-4-carboxamide

To a solution of 2-(4-aminophenyl)benzo[d]oxazole-4-carboxamide (150 mg, 0.59 mmol) in dichloromethane (5 mL) was added pyridine (51 mg, 0.65 mmol) and acetyl chloride (49 mg, 0.62 mmol) at 0° C., and the mixture was stirred at room temperature for 4 hr, then the solvent was evaporated under reduced pressure and the residue was re-crystallized in methanol to obtain 2-(4-acetamidophenyl) benzo[d]oxazole-4-carboxamide as a white solid (155 mg, yield 89%). $^{1}$H-NMR (400 MHz, DMSO-d6) δ 2.10 (s, 3H), 7.49-7.53 (t, J=8 Hz, 1H), 7.83-7.85 (d, J=8 Hz, 2H), 7.95-7.99 (m, 3H), 8.23-8.26 (d, J=8 Hz, 2H), 8.48 (s, 1H), 10.36 (s, 1H); LC-MS (ESI) m/z 296 [M+1]$^{+}$.

Example 123

2-(4-fluorophenyl)benzo[d]oxazole-4-carboxamide

Example 123 A 2-(4-fluorophenyl)benzo[d]oxazole-4-carboxylic acid

To a suspension of 3-hydroxyanthranilic acid (0.153 g, 1.0 mmol) in toluene (10 mL) was added 4-fluorobenzoyl chloride (0.475 g, 3.0 mmol) followed by pyridine (0.275 g, 3.5 mmol) at room temperature. The resulting mixture was stirred at room temperature for 30 minutes then heated to 80° C. for 1 hr. After this time the reaction was cooled and poured into a mixture of ethyl acetate (50 mL) and 5% aqueous hydrochloric acid (20 mL). Subsequent separation of the layers, drying the organic over MgSO$_{4}$ and filtration afforded a solution. After removal of the solvent, the residue was dissolved in toluene (20 mL) and the solution treated with 4-methylbenzenesulfonic acid (0.4 g, 2.1 mmol). The reaction mixture was then heated to reflux overnight. After this time the reaction was cooled and poured into water (100 mL), the organic layer was separated, washed with water (100 mL), dried over anhydrous magnesium sulfate and concentrated to give a solid. Re-crystallization of this solid from acetate gave 2-(4-fluorophenyl)benzo[d]oxazole-4-carboxylic acid as a white solid product (0.064 g, yield 24.9%). LC-MS (ESI) m/z 258 [M+1]$^{+}$.

Example 123 B 2-(4-fluorophenyl)benzo[d]oxazole-4-carboxamide 2-(4-fluorophenyl)benzo[d]oxazole-4-carboxylic acid (0.064 g, 0.25 mmol) in dimethyl formamide (10 mL) was added HOBT (0.043 g, 0.28 mmol), EDCI (0.058 g, 0.3 mmol), DIPEA (0.097 g, 0.75 mmol) and ammonium chloride (0.0133 g, 0.25 mmol). The reaction mixture was stirred at room temperature for 20 hr, cooled and poured into water (10 mL). The solution was acidified to pH=3 with 1N aqueous hydrochloric acid. Then the solution was extracted with dichloromethane (70 mL×3). The organic layer was washed with brine, dried over anhydrous sodium sulfate, condensed in vacuum and separated by silica gel chromatography (ethyl acetate:methanol=1:0 to 10:1) to afford 0.005 g 2-(4-fluorophenyl)benzo[d]oxazole-4-carboxamide as a solid (yield: 7.8%). $^{1}$H-NMR (400 MHz, DMSO-d6) δ 7.37-7.40 (m, 1H), 7.46-7.56 (m, 3H), 7.97-8.05 (m, 3H), 8.38 (s, 2H); LC-MS (ESI) m/z 257 [M+1]$^{+}$.

Example 124

2-(4-chlorophenyl)benzo[d]oxazole-4-carboxamide

Example 124 A 2-(4-chlorophenyl)benzo[d]oxazole-4-carboxylic acid

To a suspension of 3-hydroxyanthranilic acid (0.153 g, 1.0 mmol) in toluene (10 mL) was added 4-chlorobenzoyl chloride (0.525 g, 3.0 mmol) followed by pyridine (0.275 g, 3.5 mmol) at room temperature. The resulting mixture was stirred at room temperature for 30 minutes then heated to 80° C. for 1 hr. After this time the reaction was cooled and poured into a mixture of ethyl acetate (50 mL) and 5% aqueous hydrochloric acid (20 mL). Subsequent separation of the layers, drying the organic over anhydrous magnesium sulfate and filtration afforded a solution. After removal of the solvent, the residue was dissolved in toluene (20 mL) and the solution treated with 4-methylbenzenesulfonic acid (0.4 g, 2.1 mmol). The reaction mixture was then heated to reflux overnight. After this time the reaction was cooled and poured into water (100 mL), the organic layer separated then washed with water (100 mL). The organic was dried over anhydrous magnesium sulfate, filtered and concentrated to a solid. Re-crystallization of this solid from acetate gave 2-(4-chlorophenyl)benzo[d]oxazole-4-carboxylic acid as a white solid product (0.068 g, 24.9% yield). MS (ESI) m/z 274 [M+1]$^{+}$.

Example 124 B 2-(4-chlorophenyl)benzo[d]oxazole-4-carboxamide 2-(4-chlorophenyl)benzo[d]oxazole-4-carboxylic acid 4 (0.137 g, 0.5 mmol) in dimethyl formamide (10 mL) was added was added HOBT (0.085 g, 0.55 mmol), EDCI (0.115 g, 0.6 mmol), DIPEA (0.194 g, 1.5 mmol) and ammonium chloride (0.0265 g, 0.5 mmol). The reaction mixture was stirred at room temperature for 20 hr, cooled and poured into water (10 mL). The solution was acidified to pH=3 with 1N aqueous hydrochloric acid. Then the solution was extracted with dichloromethane (70 mL×3). The organic layer was washed with brine, dried over anhydrous sodium sulfate, condensed in vacuum and separated by silica gel chromatography (ethyl acetate:methanol=1:0 to 10:1) to afford 10 mg 2-(4-chlorophenyl)benzo[d]oxazole-4-carboxamide (yield: 14.8%). $^{1}$H-NMR (400 MHz, DMSO-d6) δ 7.54-7.58 (t, J=8.0 Hz, 1H), 7.70-7.72 (d, J=8.0 Hz, 2H), 7.96-8.02 (m, 3H), 8.31-8.33 (d, J=8.0 Hz, 2H), 8.44 (s, 1H); LC-MS (ESI) m/z 273 [M+1]$^{+}$.

Example 125

2-(4-bromophenyl)benzo[d]oxazole-4-carboxamide

Example 125 A 2-(4-bromophenyl)benzo[d]oxazole-4-carboxylic acid

To a suspension of 3-hydroxyanthranilic acid (0.153 g, 1.0 mmol) in toluene (10 mL) was added 4-bromobenzoyl chloride (0.603 g, 3.0 mmol) followed by pyridine (0.275 g, 3.5 mmol) at room temperature. The resulting mixture was stirred at room temperature for 30 minutes then heated to 80° C. for 1 hr. After this time the reaction was cooled and poured into a mixture of ethyl acetate (50 mL) and 5% aqueous hydrochloric acid (20 mL). Subsequent separation of the layers, drying the organic over anhydrous magnesium sulfate and filtration afforded a solution. After removal of the solvent, the residue was dissolved in toluene (20 mL) and the solution treated with 4-methylbenzenesulfonic acid (0.4 g, 2.1 mmol). The reaction mixture was then heated to reflux overnight. After this time the reaction was cooled and poured into water (100 mL), the organic layer was separated, washed with water (100 mL), dried over anhydrous magnesium sulfate, filtered and concentrated to a solid. Re-crystallization of this solid from acetate gave 2-(4-bromophenyl)benzo[d]oxazole-4-carboxylic acid as a white solid (0.075 g, yield 24%). LC-MS (ESI) m/z 320 [M+1]$^+$.

Example 125 B 2-(4-bromophenyl)benzo[d]oxazole-4-carboxamide 2-(4-bromophenyl)benzo[d]oxazole-4-carboxylic acid (0.075 g, 0.24 mmol) in dimethyl formamide (10 mL) was added HOBT (0.0425 g, 0.28 mmol), EDCI (0.0575 g, 0.3 mmol), DIPEA (0.097 g, 0.75 mmol) and ammonium chloride (0.0133 g, 0.25 mmol). The reaction mixture was stirred at room temperature for 20 hr, cooled and poured into water (10 mL). The solution was acidified to pH=3 with 1N aqueous hydrochloric acid. Then the solution was extracted with dichloromethane (70 mL×3). The organic layer was washed with brine, dried over anhydrous sodium sulfate, condensed in vacuum and separated by silica gel chromatography (ethyl acetate:methanol=1:0 to 10:1) to afford 2-(4-bromophenyl) benzo[d]oxazole-4-carboxamide as a solid (0.003 g, yield 4.15%). LC-MS (ESI) m/z 319 [M+1]$^+$.

Example 126

2-(pyridin-4-yl)benzo[d]oxazole-4-carboxamide

Example 126 A 3-hydroxy-2-(isonicotinamido)benzoic acid

Thionyl chloride (10 mL) was added to isonicotinic acid (370 mg, 3 mmol) and the mixture was stirred at reflux for 6 hr. Thionyl chloride was evaporated under reduced pressure and the residues was dried in vacuum to get isonicotinoyl chloride. 3-Hydroxyanthranilic acid (153 mg, 1.0 mmol) and pyridine (240 mg, 3.0 mmol) were added to toluene (10 mL) and the mixture was stirred at room temperature for 30 min. Then isonicotinoyl chloride (420 mg, 3.0 mmol) was added. The mixture was stirred at room temperature for 30 min and then at 80° C. for 2 hr. The resulting mixture was extracted with ethyl acetate (100 mL×4) and concentrated. The crude product was purified by column chromatography (silica gel, PE: ethyl acetate 20:1 to 5:1) to obtain 3-hydroxy-2-(isonicotinamido)benzoic acid as a solid (200 mg, yield 77%). LC-MS (ESI) m/z 259 [M+1]$^-$.

Example 126 B 2-oxo-2-(2-(pyridin-4-yl)benzo[d]oxazol-4-yl)acetic acid

3-Hydroxy-2-(isonicotinamido)benzoic acid (200 mg, 0.77 mmol) and 4-methylbenzenesulfonic acid monohydrate (400 mg, 2.0 mmol) were added to toluene (10 mL) and the mixture was stirred at reflux for 10 hr. The resulting mixture was extracted with ethyl acetate (100 mL×4) and concentrated to obtain 2-oxo-2-(2-(pyridin-4-yl)benzo[d]oxazol-4-yl)acetic acid as a solid (120 mg, yield 64%). LC-MS (ESI) m/z 241 [M+1]$^+$.

Example 126 C 2-(pyridin-4-yl)benzo[d]oxazole-4-carboxamide

To a solution of 2-oxo-2-(2-(pyridin-4-yl)benzo[d]oxazol-4-yl)acetic acid (120 mg, 0.5 mmol) in DMF (15 mL) was added HOBt (148 mg, 1.1 mmol), NH$_4$Cl (54 mg, 1.0 mmol), DIPEA (387 mg, 3.0 mmol) and EDCI (211 mg, 1.1 mmol). The mixture was stirred at 25° C. for 10 hr., water (10 mL) and 1N aqueous hydrochloric acid was added to the mixture until pH=3, then extracted with ethyl acetate (100 mL×4). The organic phase was washed with saturated sodium bicarbonate solution and brine, concentrated and dried in vacuum. The crude product was purified by preparative HPLC to obtain 2-(pyridin-4-yl)benzo[d]oxazole-4-carboxamide as a solid (17 mg, yield 14%). $^1$H-NMR (400 MHz, DMSO-d6) δ 7.60-7.64 (t, J=8 Hz, 1H), 8.01-8.03 (d, J=8 Hz, 1H), 8.06-8.08 (d, J=8 Hz, 2H), 8.23-8.24 (d, J=8 Hz, 2H), 8.41 (s, 1H), 8.87 (d, 2H); LC-MS (ESI) m/z 240 [M+1]$^+$.

Example 127

2-(pyridin-3-yl)benzo[d]oxazole-4-carboxamide

Example 127 A 3-hydroxy-2-(nicotinamido)benzoic acid

Thionyl chloride (10 mL) was added to nicotinic acid (370 mg, 3 mmol) and the mixture was stirred at reflux for 6 hr. Thionyl chloride was evaporated under reduced pressure and the residues was dried in vacuum to obtain nicotinoyl chloride. 3-Hydroxyanthranilic acid (153 mg, 1.0 mmol) and pyridine (240 mg, 3.0 mmol) were added to toluene (10 mL) and the mixture was stirred at room temperature for 30 min. Then nicotinoyl chloride (420 mg, 3.0 mmol) was added. The mixture was stirred at room temperature for 30 min and then at 80° C. for 2 hr. The resulting mixture was extracted with ethyl acetate (100 mL×4) and concentrated. The crude product was purified by column chromatography (silica gel, petroleum ether:ethyl acetate 20: to 5:1) to get 3-hydroxy-2-(nicotinamido)benzoic acid as a solid (210 mg, yield 81%). LC-MS (ESI) m/z 259 [M+1]$^+$.

Example 127 B 2-oxo-2-(2-(pyridin-3-yl)benzo[d]oxazol-4-yl)acetic acid

3-Hydroxy-2-(nicotinamido)benzoic acid (210 mg, 0.81 mmol) and 4-methylbenzenesulfonic acid (400 mg, 2.0 mmol) were added to toluene (10 mL) and the mixture was stirred at reflux for 10 hr. The resulting mixture was extracted with ethyl acetate (100 mL×4) and concentrated to obtain 2-oxo-2-(2-(pyridin-3-yl)benzo[d]oxazol-4-yl)acetic acid as a solid (135 mg, yield 69%). LC-MS (ESI) m/z 241 [M+1]$^+$.

Example 127 C 2-(pyridin-3-yl)benzo[d]oxazole-4-carboxamide

To a solution of 2-oxo-2-(2-(pyridin-3-yl)benzo[d]oxazol-4-yl)acetic acid (135 mg, 0.56 mmol) in DMF (15 mL) was added HOBt (148 mg, 1.1 mmol), NH₄Cl (54 mg, 1.0 mmol), DIPEA (387 mg, 3.0 mmol) and EDCI (211 mg, 1.1 mmol). The mixture was stirred at 25° C. for 10 hr. To the resulting mixture, water (10 mL) and 1N aqueous hydrochloric acid was added to pH=3, then extracted with ethyl acetate (100 mL×4). The organic phase was washed with saturated sodium bicarbonate solution and brine, concentrated, and dried in vacuum. The crude product was purified by preparative HPLC to obtain 2-(pyridin-3-yl)benzo[d]oxazole-4-carboxamide as a solid (25 mg, yield 18%). $^1$H-NMR (400 MHz, DMSO-d6) δ 7.52-7.56 (t, J=8 Hz, 1H), 7.88-7.95 (m, 3H), 8.03-8.05 (d, J=8 Hz, 1H), 8.21-8.22 (d, J=4 Hz, 2H), 8.86 (d, J=4 Hz, 2H); LC-MS (ESI) m/z 240 [M+1]⁺.

Example 128

2-(4-((methylamino)methyl)phenyl)benzo[d]oxazole-7-carboxamide

Example 128 A methyl 2-p-tolylbenzo[d]oxazole-7-carboxylate

Methyl 3-amino-2-hydroxybenzoate (4.4 g, 26 mmol) and 4-methylbenzoic acid (3.6 g, 26.0 mmol) were added to the polyphosphoric acid (20 g). The mixture was heated at 180° C. for 2 hr, and then cooled, poured into water, extracted with ethyl acetate, washed with saturated sodium bicarbonate solution, brine, dried over anhydrous sodium sulfate and condensed to obtain methyl 2-p-tolylbenzo[d]oxazole-7-carboxylate as a white solid (2.1 g, yield 30%). LC-MS (ESI) m/z 268 [M+1]⁺.

Example 128 B methyl 2-(4-(bromomethyl)phenyl)benzo[d]oxazole-7-carboxylate

To a mixture of methyl 2-p-tolylbenzo[d]oxazole-7-carboxylate (1 g, 3.74 mmol) in CCl₄ (7 mL) was added NBS (665 mg, 3.74 mmol) and BPO (52 mg, 0.37 mmol), heated to reflux for 24 hr, then the solvent was evaporated, and purified by silica gel chromatography (petroleum ether:ethyl acetate=100:1-50:1) to obtain methyl 2-(4-(bromomethyl)phenyl)benzo[d]oxazole-7-carboxylate as a white solid (1.0 g, yield 77%). LC-MS (ESI) m/z 346 [M+1]⁺.

Example 128 C methyl 2-(4-((methylamino)methyl)phenyl)benzo[d]oxazole-7-carboxylate To the solution of methyl 2-(4-(bromomethyl)phenyl)benzo[d]oxazole-7-carboxylate (500 mg, 1.4 mmol in methanol (10 mL), was added methylamine solution (4 mL), and the resulting mixture was stirred at room temperature for 1 hr, then heated to 30° C. for 30 min. Then the solvent was evaporated and purified by pre-HPLC to obtain methyl 2-(4-((methylamino)methyl)phenyl)benzo[d]oxazole-7-carboxylate (as TFA salt, 90 mg, yield 42%). LC-MS (ESI) m/z 297 [M+1]⁺.

Example 128 D 2-(4-((methylamino)methyl)phenyl)benzo[d]oxazole-7-carboxamide

Methyl 2-(4-((methylamino)methyl)phenyl)benzo[d]oxazole-7-carboxylate (25 mg, 0.06 mmol) in ammonium water (2 mL) was stirred at 30° C. for 17 hr, then the solvents were evaporated and purified by pre-HPLC to obtain 2-(4-((methylamino)methyl)phenyl)benzo[d]oxazole-7-carboxamide as a white solid (25 mg, yield 33%). $^1$H-NMR (400 MHz, MeOH-d4) δ 2.07 (s, 1H), 2.30 (s, 3H), 3.78 (s, 2H), 7.45-7.49 (t, J=8 Hz, 1H), 7.57-7.59 (d, J=8 Hz, 2H), 7.79-7.81 (d, J=8 Hz, 1H), 7.86-7.95 (m, 3H), 8.24-8.26 (d, J=8 Hz, 2H); LC-MS (ESI) m/z 282 [M+1]⁺.

Example 129

5-fluoro-2-(4-((methylamino)methyl)phenyl)benzo[d]oxazole-7-carboxamide

Example 129 A methyl 5-fluoro-2-p-tolylbenzo[d]oxazole-7-carboxylate

Methyl 3-amino-5-fluoro-2-hydroxybenzoate (340 mg, 1.8 mmol) and p-telic acid (280 mg, 2.1 mmol) were added to the polyphosphoric acid (2 g). The mixture was heated to 180° C. for 2 hr, cooled, poured into water, and filtered; the cake was washed with water, dried in vacuum at 50° C. to obtain a mixture of 5-fluoro-2-p-tolylbenzo[d]oxazole-7-carboxylic acid and methyl 5-fluoro-2-p-tolylbenzo[d]oxazole-7-carboxylate. This mixture (0.92 g) was added to thionyl chloride (30 mL) and stirred at reflux for 2 hr. The solvents were evaporated under reduced pressure, the residue was diluted with methanol (10 mL) and stirred at room temperature for 10 min; the solvents were evaporated and the residue was dissolved in ethyl acetate, washed with water, dried over anhydrous sodium sulfate, filtered and removed the solvents to obtain methyl 5-fluoro-2-p-tolylbenzo[d]oxazole-7-carboxylate as a yellow solid (420 mg, yield 80%). LC-MS (ESI) m/z 286 [M+1]⁻.

Example 129 B methyl 2-(4-(bromomethyl)phenyl)-5-fluorobenzo[d]oxazole-7-carboxylate To methyl 5-fluoro-2-p-tolylbenzo[d]oxazole-7-carboxylate (420 mg, 1.47 mmol) in CCl₄ (5 mL) was added NBS (262 mg, 1.47 mmol) and BPO (69 mg, 0.735 mmol), the resulting mixture was heated to reflux for 24 hr; then the solvent was evaporated and the residue was purified by silica gel chromatography (petroleum ether:ethyl acetate=100:1-50:1) to obtain methyl 2-(4-(bromomethyl)phenyl)-5-fluorobenzo[d]oxazole-7-carboxylate as a white solid (350 mg, yield 65%). LC-MS (ESI) m/z 264 [M+1]⁺.

Example 129 C methyl 5-fluoro-2-(4-((methylamino)methyl)phenyl)benzo[d]oxazole-7-carboxylate To the solution of methyl 2-(4-(bromomethyl)phenyl)-5-fluorobenzo[d]oxazole-7-carboxylate (350 mg, 0.96 mmol) in methanol (20 mL), methylamine (6 mL) was added, the mixture was stirred at room temperature for 1 hr, then heated to 30° C. for 30 min; the solvents were evaporated and the residue was purified by pre-HPLC to obtain methyl 5-fluoro-2-(4-((methylamino)methyl)phenyl)benzo[d]oxazole-7-carboxylate as a white solid (25 mg, yield 8%). LC-MS (ESI) m/z 315 [M+1]⁺.

Example 129 D 5-fluoro-2-(4-((methylamino)methyl)phenyl)benzo[d]oxazole-7-carboxamide Methyl 5-fluoro-2-(4-((methylamino)methyl)phenyl)benzo[d]oxazole-7-carboxylate (25 mg, 0.06 mmol) in ammonium water (2 mL) was stirred at 30° C. for 17 hr and the solvents were evaporated; the residue was purified by pre-HPLC to obtain 5-fluoro-2-(4-((methylamino)methyl)phenyl)benzo[d]oxazole-7-carboxamide as a white solid (4 mg, yield 22%). $^1$H-NMR (400 MHz, MeOD-d4) δ 2.07 (s, 1H), 2.41 (s, 3H), 3.85 (s, 2H), 7.52-7.55 (m, 2H), 7.57-7.61 (m, 2H), 8.25-8.27 (d, J=7.6 Hz, 2H); LC-MS (ESI) m/z 300 [M+1]$^+$.

Example 130

2-(4-((dimethylamino)methyl)phenyl)benzo[d]oxazole-7-carboxamide

Example 130 A methyl 2-(4-((dimethylamino)methyl)phenyl)benzo[d]oxazole-7-carboxylate To the solution of methyl 2-(4-(bromomethyl)phenyl)benzo[d]oxazole-7-carboxylate (150 mg, 0.72 mmol) in methanol (2 mL), was added dimethylamine solution (0.5 mL, 2.88 mmol), the resulting mixture was stirred at room temperature for 17 hr, then the solvents were evaporated and methyl 2-(4-((dimethylamino)methyl)phenyl)benzo[d]oxazole-7-carboxylate. LC-MS (ESI) m/z 311 [M+1]$^+$.

Example 130 B 2-(4-((dimethylamino)methyl)phenyl)benzo[d]oxazole-7-carboxamide Methyl 2-(4-((dimethylamino)methyl)phenyl)benzo[d]oxazole-7-carboxylate in ammonium water (10 mL) was stirred at 30° C. for 17 hr, then the solvents were evaporated and purified by pre-HPLC to obtain 2-(4-((dimethylamino)methyl)phenyl)benzo[d]oxazole-7-carboxamide as a white solid (10 mg). $^1$H-NMR (400 MHz, DMSO-d6) δ 2.18 (s, 6H), 3.5 (s, 2H), 7.47-7.49 (t, J=8 Hz, 1H), 7.54-7.56 (d, J=8.4 Hz, 2H), 7.79-7.81 (d, J=8 Hz, 1H), 7.86-7.90 (d, J=14.4 Hz, 2H), 7.94-7.96 (d, J=8 Hz, 1H), 8.24-8.26 (d, J=8 Hz, 2H); LC-MS (ESI) m/z 296 [M+1]$^+$.

Example 131

2-(4-(piperazin-1-ylmethyl)phenyl)benzo[d]oxazole-7-carboxamide

Example 131 A 2-(Octahydro-1H-quinolizin-3-yl)benzo[d]oxazole-7-carboxamide

To the mixture of methyl 2-(4-(bromomethyl)phenyl)benzo[d]oxazole-7-carboxylate (250 mg, 0.72 mmol) in methanol (2 mL), was added piperazine (186 mg, 2.16 mmol), and the resulting mixture was stirred at room temperature for 17 hr, then the solvents were evaporated to give methyl 2-(4-(piperazin-1-ylmethyl)phenyl)benzo[d]oxazole-7-carboxylate LC-MS (ESI) m/z 352 [M+1]$^+$.

Example 131 B 2-(4-(piperazin-1-ylmethyl)phenyl)benzo[d]oxazole-7-carboxamide Methyl 2-(4-(piperazin-1-ylmethyl)phenyl)benzo[d]oxazole-7-carboxylate in ammonium water (10 mL) was stirred at 30° C. for 17 hr, cooled, and filtered; then the cake was washed with water, dried under reduced pressure to obtain 2-(4-(piperazin-1-ylmethyl)phenyl)benzo[d]oxazole-7-carboxamide as a white solid (80 mg, yield 33% for two steps). $^1$H NMR (400 MHz, DMSO-d6) δ 2.32 (s, 4H), 2.69-2.72 (t, J=4 Hz, 4H), 3.53 (s, 2H), 3.98 (s, 1H), 7.45-7.49 (t, J=8 Hz, 1H), 7.54-7.56 (d, J=8 Hz, 2H), 7.79-7.80 (d, J=7.2 Hz, 1H), 7.86-7.89 (d, J=10.4 Hz, 2H), 7.93-7.95 (d, J=8 Hz, 1H), 8.23-8.25 (d, J=8 Hz, 2H); LC-MS (ESI) m/z 337 [M+1]$^+$.

Example 132

2-(3-((methylamino)methyl)phenyl)benzo[d]oxazole-7-carboxamide

Example 132 A methyl 2-hydroxy-3-(3-methylbenzamido)benzoate

Thionyl chloride (30 mL) was added to 1 (4.5 g, 33 mmol) and the mixture was stirred at reflux overnight. Thionyl chloride was evaporated under reduced pressure and the residue was dried in vacuum to obtain 3-methylbenzoyl chloride (3.59 g). Methyl-3-amino-2-hydroxybenzoate (3.34 g, 20.0 mmol) and pyridine (2 mL) were added to toluene (10 mL) and the mixture was stirred at room temperature for 30 min. Then 3-methylbenzoyl chloride (1.54 g, 10 mmol) was added. The mixture was stirred at room temperature for 30 min and then at 80° C. for 2 hr. The resulting mixture was extracted with ethyl acetate (100 mL×4) and concentrated. The crude product was purified by column chromatography (silica gel, petroleum ether:ethyl acetate 20:1 to 5:1) to obtain methyl 2-hydroxy-3-(3-methylbenzamido)benzoate as a solid (1.8 g, yield 63%). LC-MS (ESI) m/z 287 [M+1]$^+$.

Example 132 B methyl 2-m-tolylbenzo[d]oxazole-7-carboxylate

Methyl 2-hydroxy-3-(3-methylbenzamido)benzoate (1.8 mg, 6.29 mmol) and 4-methylbenzenesulfonic acid (1.61 g, 9.4 mmol) were added to toluene (10 mL) and the mixture was stirred at reflux for 10 hr. The resulting mixture was extracted with ethyl acetate (100 mL×4) and concentrated to obtain methyl 2-m-tolylbenzo[d]oxazole-7-carboxylate as a solid (120 mg, yield 64%). LC-MS (ESI) m/z 269 [M+1]$^-$.

Example 132 C methyl 2-(3-(bromomethyl)phenyl)benzo[d]oxazole-7-carboxylate

Methyl 2-m-tolylbenzo[d]oxazole-7-carboxylate (500 mg, 1.87 mmol), 1-bromopyrrolidine-2,5-dione (367 mg, 2.06 mmol) and benzoperoxoic acid (25.81 mg, 0.187 mmol) were added to toluene (30 mL) and the mixture was stirred at reflux overnight. The resulting mixture was evaporated, extracted with ethyl acetate (100 mL×4) and concentrated to obtain methyl 2-(3-(bromomethyl)phenyl)benzo[d]oxazole-7-carboxylate as a solid (194 mg, yield 30%). LC-MS (ESI) m/z 347 [M+1]$^+$.

Example 132 D methyl 2-(3-((methylamino)methyl)phenyl)benzo[d]oxazole-7-carboxylate Methyl 2-(3-(bromomethyl)phenyl)benzo[d]oxazole-7-carboxylate (70 mg, 0.2 mmol) and dimethylamine (50 mg, 1.6 mmol) were added to ethanol (30 mL) and the mixture was stirred at room temperature for 1 hr. The resulting mixture was evaporated under reduced pressure to obtain methyl 2-(3-((methylamino)methyl)phenyl)benzo[d]oxazole-7-carboxylate (80 mg, yield 76%). LC-MS (ESI) m/z 297 [M+1]$^+$.

Example 132 E 2-(3-((methylamino)methyl)phenyl)benzo[d]oxazole-7-carboxamide

Methyl 2-(3-((methylamino)methyl)phenyl)benzo[d]oxazole-7-carboxylate (80 mg, 0.27 mmol) and ammonium water (75.7 mg, 2.16 mmol) were added to ethanol (30 mL) and the mixture was stirred at 30° C. for 1 hr. The resulting mixture was evaporated under reduced pressure and purified with Pre-HPLC to obtain 2-(3-((methylamino)methyl)phenyl)benzo[d]oxazole-7-carboxamide (16 mg, yield 21%). $^1$H-NMR (400 MHz, DMSO-d6) δ 2.62 (s, 3H), 4.29 (s, 2H), 7.48-7.52 (t, J=8 Hz, 1H), 7.70-7.74 (m, 1H), 7.81-7.83 (d, J=8 Hz, 1H), 7.90-7.98 (m, 3H), 8.34-8.43 (m, 2H), 9.06 (s, 2H); LC-MS (ESI) m/z 282 [M+1]$^+$.

Example 133

2-(3-((dimethylamino)methyl)phenyl)benzo[d]oxazole-7-carboxamide

Example 133 A methyl 2-(3-((dimethylamino)methyl)phenyl)benzo[d]oxazole-7-carboxylate Methyl 2-(3-(bromomethyl)phenyl)benzo[d]oxazole-7-carboxylate (70 mg, 0.2 mmol) and dimethylamine (72 mg, 1.6 mmol) were added to ethanol (30 mL) and the mixture was stirred at room temperature for 1 hr. The resulting mixture was evaporated under reduced pressure to obtain methyl 2-(3-((dimethylamino)methyl)phenyl)benzo[d]oxazole-7-carboxylate (74 mg, yield 86%). LC-MS (ESI) m/z 310 [M+1]$^+$.

Example 133 B 2-(3-((dimethylamino)methyl)phenyl)benzo[d]oxazole-7-carboxamide

Methyl 2-(3-((dimethylamino)methyl)phenyl)benzo[d]oxazole-7-carboxylate (66 mg, 0.18 mmol) and ammonium water (50.4 mg, 1.44 mmol) were added to ethanol (30 mL) and the mixture was stirred at 30° C. for 1 hr. The resulting mixture was evaporated under reduced pressure and purified with Pre-HPLC to obtain 2-(3-((dimethylamino)methyl)phenyl)benzo[d]oxazole-7-carboxamide (12 mg, yield 22%). $^1$H-NMR (400 MHz, DMSO-d6) δ 2.88 (s, 5H), 4.36 (s, 2H), 7.02 (s, 1H), 7.37-7.41 (t, J=8 Hz, 1H), 7.54-7.61 (m, 2H), 7.84-7.86 (d, J=8 Hz, 1H), 7.97-7.99 (d, J=8 Hz, 1H), 8.28-8.29 (d, J=4 Hz, 1H), 8.50 (s, 1H); LC-MS (ESI) m/z 296 [M+1]$^+$.

Example 134

2-(3-(pyrrolidin-1-ylmethyl)phenyl)benzo[d]oxazole-7-carboxamide

Example 134 A methyl 2-(3-(pyrrolidin-1ylmethyl)phenyl)benzo[d]oxazole-7-carboxylate Methyl 2-(3-(bromomethyl)phenyl)benzo[d]oxazole-7-carboxylate (70 mg, 0.2 mmol) and pyrrolidine (56.8 mg, 0.8 mmol) were added to ethanol (30 mL) and the mixture was stirred at room temperature for 1 hr. The resulting mixture was evaporated under reduced pressure to obtain methyl 2-(3-(pyrrolidin-1ylmethyl)phenyl)benzo[d]oxazole-7-carboxylate (81 mg, yield 88%). LC-MS (ESI) m/z 337 [M+1]$^+$.

Example 134 B 2-(3-(pyrrolidin-1-ylmethyl)phenyl)benzo[d]oxazole-7-carboxamide

Methyl 2-(3-(pyrrolidin-1-ylmethyl)phenyl)benzo[d]oxazole-7-carboxylate (56 mg, 0.18 mmol) and ammonium water (50.4 mg, 1.44 mmol) were added to ethanol (30 mL) and the mixture was stirred at 30° C. for 1 hr. The resulting mixture was evaporated under reduced pressure and purified with Pre-HPLC to obtain 2-(3-(pyrrolidin-1-ylmethyl)phenyl)benzo[d]oxazole-7-carboxamide (14 mg, yield 22%). $^1$H-NMR (400 MHz, DMSO-d6) δ 1.92 (s, 4H), 3.19 (s, 4H), 4.42 (s, 2H), 7.49 (s, 1H), 7.70-7.94 (m, 6H), 8.35-8.43 (d, J=32 Hz, 2H); LC-MS (ESI) m/z 322 [M+1]$^+$.

Example 135

2-(3-(piperazin-1-ylmethyl)phenyl)benzo[d]oxazole-7-carboxamide

Example 135 A methyl 2-(3-(piperazin-1-ylmethyl)phenyl)benzo[d]oxazole-7-carboxylate Methyl 2-(3-(bromomethyl)phenyl)benzo[d]oxazole-7-carboxylate (70 mg, 0.2 mmol) and piperazine (68.8 mg, 0.8 mmol) were added to ethanol (30 mL) and the mixture was stirred at room temperature for 1 hr. The resulting mixture was evaporated under reduced pressure to obtain methyl 2-(3-(piperazin-1-ylmethyl)phenyl)benzo[d]oxazole-7-carboxylate (79 mg, yield 91%). LC-MS (ESI) m/z 354 [M+1]$^+$.

Example 135 B 2-(3-(piperazin-1-ylmethyl)phenyl)benzo[d]oxazole-7-carboxamide

Methyl 2-(3-(piperazin-1-ylmethyl)phenyl)benzo[d]oxazole-7-carboxylate (79 mg, 0.23 mmol) and ammonium water (64.4 mg, 1.84 mmol) were added to ethanol (30 mL) and the mixture was stirred at 30° C. for 1 hr. The resulting mixture was evaporated under reduced pressure and purified with Pre-HPLC to obtain 2-(3-(piperazin-1-ylmethyl)phenyl)benzo[d]oxazole-7-carboxamide (12 mg, yield 13%). $^1$H-NMR (400 MHz, DMSO-d6) δ 2.91 (s, 4H), 3.21 (s, 4H), 4.20 (s, 2H), 7.48-7.52 (t, J=8 Hz, 1H), 7.67 (s, 2H), 7.81-7.97 (m, 4H), 8.31 (s, 2H); LC-MS (ESI) m/z 337 [M+1]$^+$.

Example 136

2-(3-((2-(dimethylamino)ethylamino)methyl)phenyl)benzo[d]oxazole-7-carboxamide

Example 136 A methyl 2-(3-((2-(dimethylamino)ethylamino)methyl)phenyl)benzo[d]oxazole-7-carboxylate Methyl 2-(3-(bromomethyl)phenyl)benzo[d]oxazole-7-carboxylate (70 mg, 0.2 mmol) and N,N-dimethylethane-1,2-diamine (140.8 mg, 1.6 mmol) were added to ethanol (30 mL) and the mixture was stirred at room temperature for 1 hr and evaporated under reduced pressure to obtain methyl 2-(3-((2-(dimethylamino)ethylamino)methyl)phenyl)benzo[d]oxazole-7-carboxylate (100 mg, yield 85%). LC-MS (ESI) m/z 354 [M+1]$^+$.

Example 136 B 2-(3-((2-(dimethylamino)ethylamino)methyl)phenyl)benzo[d]oxazole-7-carboxamide Methyl 2-(3-((2-(dimethylamino)ethylamino)methyl)phenyl)benzo[d]oxazole-7-carboxylate (100 mg, 0.28 mmol) and ammonium water (58.8 mg, 1.68 mmol) were added to ethanol (30 mL) and the mixture was stirred at 30° C. for 1 hr. Evaporation under reduced pressure and purification with pre-HPLC gave 2-(3-((2-(dimethylamino)ethylamino)methyl)phenyl)benzo[d]oxazole-7-carboxamide (10.0 mg, yield 11%). $^1$H-NMR (400 MHz, DMSO-d6) δ 2.85 (s, 6H), 3.37-3.42 (d, J=20 Hz, 4H), 4.36 (s, 2H), 7.48-7.52 (t, J=8 Hz, 1H), 7.71-7.97 (m, 6H), 8.35-8.37 (d, J=8 Hz, 1H), 8.43 (s, 1H); LC-MS (ESI) m/z 339 [M+1]$^+$.

Example 137

2-(pyridin-4-yl)benzo[d]oxazole-7-carboxamide

Example 137 A methyl 2-hydroxy-3-(isonicotinamido)benzoate

Thionyl chloride (10 mL) was added to isonicotinic acid (370 mg, 3 mmol) and the mixture was stirred at reflux for 6 hr. Thionyl chloride was evaporated under reduced pressure and the residues was dried in vacuum to give isonicotinoyl chloride. Methyl 2-amino-3-hydroxybenzoate (167 mg, 1.0 mmol) and pyridine (240 mg, 3.0 mmol) were added to toluene (10 mL) and the mixture was stirred at room temperature for 30 min. isonicotinoyl chloride (420 mg, 3.0 mmol) was added and the mixture was stirred at room temperature for 30 min then at 80° C. for 2 hr. The resulting mixture was extracted with ethyl acetate (100 mL×4) and concentrated. The crude product was purified by column chromatography (silica gel, petroleum ether:ethyl acetate 20: to 5:1) to obtain methyl 2-hydroxy-3-(isonicotinamido)benzoate as a solid (210 mg, yield 77%). LC-MS (ESI) m/z 273 [M+1]$^+$.

Example 137 B methyl 2-(pyridin-4-yl)benzo[d]oxazole-7-carboxylate

To a solution of toluene (10 ml) was added methyl 2-hydroxy-3-(isocicotinamido)benzoate (210 mg, 0.77 mmol) and 4-methylbenzenesulfonic acid (400 mg, 2 mmol) and the mixture was stirred at reflux for 10 hr. The resulting mixture was extracted with ethyl acetate (100 mL×4) and concentrated to yield methyl 2-(pyridin-4-yl)benzo[d]oxazole-7-carboxylate as a solid (130 mg, yield 66%). LC-MS (ESI) m/z 255 [M+1]$^-$.

Example 137 C 2-(pyridin-4-yl)benzo[d]oxazole-7-carboxamide

Methyl 2-(pyridin-4-yl)benzo[d]oxazole-7-carboxylate (130 mg, 0.51 mmol) in ammonium water (15 mL) was stirred at 25° C. overnight. The solvent was removed under reduced pressure. The crude product was purified by pre-HPLC to obtain 2-(pyridin-4-yl)benzo[d]oxazole-7-carboxamide as a solid (41 mg, yield 33%). $^1$H-NMR (400 MHz, DMSO-d6) δ 7.56-7.60 (t, J=8 Hz, 3H), 7.66-7.69 (q, 3H), 7.99-8.05 (q, 3H), 8.45 (s, 1H), 8.65-8.67 (d, J=8 Hz, 1H), 8.83-8.84 (d, J=4 Hz, 1H), 9.47 (s, 1H); LC-MS (ESI) m/z 240 [M+1]$^+$.

Example 138

2-(pyridin-3-yl)benzo[d]oxazole-7-carboxamide

Example 138 A methyl 2-hydroxy-3-(nicotinamido)benzoate

Thionyl chloride (10 mL) was added to nicotinic acid (370 mg, 3.0 mmol) and the mixture was stirred under reflux for 6 hr. Thionyl chloride was evaporated under reduced pressure and the residues was dried in vacuum to yield nicotinoyl chloride. Methyl 2-amino-3-hydroxybenzoate (167 mg, 1.0 mmol) and pyridine (240 mg, 3.0 mmol) were added to toluene (10 mL) and the mixture was stirred at room temperature for 30 min. Then nicotinoyl chloride (420 mg, 3.0 mmol) was added. The mixture was stirred at room temperature for 30 min then at 80° C. for 2 hr. The resulting mixture was extracted with ethyl acetate (100 mL×4) and concentrated. The crude product was purified by column chromatography (silica gel, petroleum ether:ethyl acetate 20: to 5:1) to obtain methyl 2-hydroxy-3-(nicotinamido)benzoate as a solid (215 mg, yield 79%). LC-MS (ESI) m/z 273 [M+1]$^+$.

Example 138 B methyl 2-(pyridin-3-yl)benzo[d]oxazole-7-carboxylate

Methyl 2-hydroxy-3-(nicotinamido)benzoate (215 mg, 0.79 mmol) and 4-methylbenzenesulfonic acid (400 mg, 2.0 mmol) were added to toluene (10 mL) and the mixture was stirred at reflux for 10 hr. The resulting mixture was extracted with ethyl acetate (100 mL×4) and concentrated to obtain methyl 2-(pyridin-3-yl)benzo[d]oxazole-7-carboxylate as a solid (135 mg, yield 67%); LC-MS (ESI) m/z 255 [M+1]$^+$.

Example 138 C 2-(pyridin-3-yl)benzo[d]oxazole-7-carboxamide

Methyl 2-(pyridin-3-yl)benzo[d]oxazole-7-carboxylate (135 mg, 0.53 mmol) in ammonium water (15 mL) was stirred at 25° C. overnight. The solvent was removed under reduced pressure. The crude product was purified by pre-HPLC to obtain 2-(pyridin-3-yl)benzo[d]oxazole-7-carboxamide a solid (39 mg, yield 31%). $^1$H-NMR (400 MHz, DMSO-d6) δ 7.50-7.54 (t, J=8 Hz, 1H), 7.65-7.69 (q, 1H), 7.65-7.69 (q, 1H), 7.85-7.87 (d, J=8 Hz, 1H), 7.91-7.93 (d, J=8 Hz, 2H), 7.99-8.01 (d, J=8 Hz, 1H), 8.64-8.66 (d, J=8 Hz, 1H), 8.81-8.82 (d, J=4 Hz, 1H), 9.46-9.47 (s, J=4 Hz, 1H); LC-MS (ESI) m/z 240 [M+1]$^+$.

Example 139

2-(1H-indol-2-yl)benzo[d]oxazole-7-carboxamide

Example 139 A methyl 2-hydroxy-3-(1H-indole-2-carboxamido)benzoate

To a solution of 1H-indole-2-carboxylic acid (965 mg, 1.2 mmol) in DMF (15 mL) was added HOBt (740 mg, 1.1 mmol), DIPEA (1.98 g, 3.0 mmol) and EDCI (1.05 g, 1.1 mmol). The mixture was stirred at room temperature for 30 min. Then methyl 3-amino-2-hydroxybenzoate (835 mg, 1 mmol) was added. The mixture was stirred at room temperature for 10 hr. To the resulting mixture, water (10 mL) and aqueous hydrochloric acid (1 N) were added to pH=3, then extracted with ethyl acetate (100 mL×4). The organic phase was washed with saturated sodium bicarbonate solution and brine, dried by anhydrous sodium sulfate and concentrated to yield the crude product. The crude product was purified by column chromatography (silica gel, petroleum ether:ethyl acetate 20:1) to obtain methyl 2-hydroxy-3-(1H-indole-2-carboxamido)benzoate as a solid (530 mg, yield 26%). LC-MS (ESI) m/z 296 [M+1]$^-$.

Example 139 B methyl 2-(1H-indol-2-yl)benzo[d]oxazole-7-carboxylate

Methyl 2-hydroxy-3-(1H-indole-2-carboxamido)benzoate (170 mg, 0.5 mmol) and 4-methylbenzenesulfonic acid monohydrate (400 mg, 4.0 mmol) were added to xylene (10 mL) and the mixture was stirred at reflux for 10 hr. The resulting mixture was extracted with dichloromethane (100 mL×4) and concentrated. Then the crude product was purified by column chromatography (silica gel, petroleum ether:ethyl acetate 20:1) to obtain methyl 2-(1H-indol-2-yl)benzo[d]oxazole-7-carboxylate as a solid (70 mg, yield 43%). LC-MS (ESI) m/z 293 [M+1]$^+$.

Example 139 C 2-(1H-indol-2-yl)benzo[d]oxazole-7-carboxamide

Methyl 2-(1H-indol-2-yl)benzo[d]oxazole-7-carboxylate (70 mg, 0.24 mmol) in ammonium water (10 mL) was stirred at 35° C. overnight. Then the suspension was filtered, and the solid was purified by column chromatography (silica gel, petroleum ether:ethyl acetate 1:1) to obtain 2-(1H-indol-2-yl)benzo[d]oxazole-7-carboxamide as a solid (32 mg, yield 51%). $^1$H-NMR (400 MHz, DMSO-d6) δ 6.54 (s, 1H), 7.11-7.13 (t, J=8 Hz, 1H), 7.26-7.30 (t, J=8 Hz, 1H), 7.48-7.54 (dd, J$_1$=16 Hz, J$_2$=8 Hz, 2H), 7.70-7.72 (d, J=8 Hz, 1H), 7.84-7.86 (d, 1H), 7.88 (brs, 1H), 7.93-7.95 (d, J=8 Hz, 1H), 8.01 (brs, 1H), 12.47 (brs, 1H); LC-MS (ESI) m/z 278 [M+1]$^+$.

Example 140

2-phenylbenzo[d]oxazole-4-carboxamide

Example 140 A 2-phenylbenzo[d]oxazole-4-carboxylic acid

Benzoic acid (122 mg, 1.0 mmol) and 3-hydroxyanthranilic acid (153 mg, 1.0 mmol) were added to PPA (1 g), the mixture was stirred at 180° C. for 2 hr. After cooled to room temperature, water (50 mL) was added and filtered; the cake was washed with water and dried in vacuum to obtain 2-phenylbenzo[d]oxazole-4-carboxylic acid. LC-MS (ESI) m/z 240 [M+1]$^+$.

Example 140 B 2-phenylbenzo[d]oxazole-4-carboxamide

To a solution of 2-phenylbenzo[d]oxazole-4-carboxylic acid in DMF (15 mL) was added HOBt (148 mg, 1.1 mmol), NH$_4$Cl (54 mg, 1.0 mmol), DIPEA (387 mg, 3.0 mmol) and EDCI (211 mg, 1.1 mmol). The mixture was stirred at 25° C. for 10 hr. Then water (10 mL) was added and aqueous hydrochloric acid (1 N) to pH=3 and extracted with ethyl acetate (100 mL×4). The organic phase was washed with saturated sodium bicarbonate solution and brine, concentrated and dried in vacuum. The crude product was purified by pre-HPLC to obtain 2-phenylbenzo[d]oxazole-4-carboxamide as a white solid (40 mg). $^1$H-NMR (400 MHz, DMSO-d6) δ 7.47-7.56 (m, 1H), 7.63-7.68 (m, 3H), 7.93-8.01 (m, 3H), 8.28-8.30 (d, J=8 Hz, 2H), 8.47 (s, 1H); LC-MS (ESI) m/z 239 [M+1]$^+$.

Example 141

2-phenylbenzo[d]oxazole-7-carboxamide

Example 141 A 2-phenylbenzo[d]oxazole-7-carboxylic acid

Benzoic acid (122 mg, 1 mmol) and methyl 2-amino-3-hydroxybenzoate (167 mg, 1.0 mmol) were added to PPA (1 g), the mixture was stirred at 180° C. for 2 hr. After cooled to room temperature, water (50 mL) was added and filtered; the solid residue was washed with water and dried in vacuum to give 2-phenylbenzo[d]oxazole-7-carboxylic acid. LC-MS (ESI) m/z 240 [M+1]$^+$.

Example 141 B 2-phenylbenzo[d]oxazole-7-carboxamide

To a solution of 2-phenylbenzo[d]oxazole-7-carboxylic acid in DMF (15 mL) was added HOBt (148 mg, 1.1 mmol), NH$_4$Cl (54 mg, 1.0 mmol), DIPEA (387 mg, 3.0 mmol) and EDCI (211 mg, 1.1 mmol). The mixture was stirred at 25° C. for 10 hr. To the resulting mixture, water (10 mL) and aqueous hydrochloric acid (1 N) was added to pH=3, then extracted with ethyl acetate (100 mL×4). The organic phase was washed with saturated sodium bicarbonate solution and brine, concentrated and dried in vacuum. The crude product was purified by pre-HPLC to obtain 2-phenylbenzo[d]oxazole-7-carboxamide as a white solid (40 mg, yield 16% for 2 steps). $^1$H-NMR (400 MHz, DMSO-d6) δ 7.48-7.52 (t, J=8 Hz, 1H), 7.62-7.68 (m, 3H), 7.81-7.83 (dd, J$_1$=8 Hz, J$_2$=1 Hz, 1H), 7.88-7.92 (d, J=8 Hz, 2H), 7.96-7.99 (dd, J$_1$=8 Hz, J$_2$=1 Hz, 1H), 8.30-8.33 (dd, J$_1$=8 Hz, J$_2$=2 Hz, 2H); LC-MS (ESI) m/z 239 [M+1]$^+$.

Example 142

2-(4-methoxyphenylbenzo[d]oxazole-4-carboxamide

Example 142 A methyl 3-hydroxy-2-(4-methoxybenzamido)benzoate

Thionyl chloride (10 mL) was added to 4-methoxybenzoic acid (306 mg, 2.0 mmol) and the mixture was stirred at reflux for 3 hr. Thionyl chloride was evaporated under reduced pressure and the residues was dried in vacuum to obtain 4-methoxybenzoyl chloride (320 mg). 3-Hydroxyanthranilic acid (167 mg, 1.0 mmol) and pyridine (158 mg, 2.0 mmol) were added to dichlormethane (10 mL) and the mixture was stirred at room temperature for 30 min. Then 2 (320 mg, 2.0 mmol) was added. The mixture was stirred at room temperature overnight and concentrated. The residue was purified by column chromatography (silica gel, petroleum ether:ethyl acetate=20:1 to 10:1) to yield methyl 3-hydroxy-2-(4-methoxybenzamido)benzoate as a solid (178 mg, yield 59%). LC-MS (ESI) m/z 302 [M+1]$^+$.

Example 142 B methyl 2-(4-methoxyphenylbenzo[d]oxazole-4-carboxylate

Methyl 3-hydroxy-2-(4-methoxybenzamido)benzoate (178 mg, 0.66 mmol) and 4-methylbenzenesulfonic acid monohydrate (400 mg, 2.0 mmol) were added to toluene (20 mL) and the mixture was stirred at reflux for 24 hr. The resulting mixture was extracted with ethyl acetate (100 mL×4) and concentrated. The crude product was purified by column chromatography (silica gel, petroleum ether:ethyl acetate 20:1 to 10:1) to obtain methyl 2-(4-methoxyphenyl-benzo[d]oxazole-4-carboxylate (M+1)$^+$, Example 142 C 2-(4-methoxyphenylbenzo[d]oxazole-4-carboxamide Methyl 2-(4-methoxyphenylbenzo[d]oxazole-4-carboxylate (68 mg, 0.24 mmol) in ammonium water (10 mL) was stirred at 30° C. overnight, then filtered, and the cake was washed with water, dried in vacuum to obtain 2-(4-methoxyphenylbenzo[d]oxazole-4-carboxamide (29 mg, yield 45%). $^1$H-NMR (400 MHz, DMSO-d6) δ 3.88 (s, 3H), 7.17-7.19 (d, J=8 Hz, 1H), 7.49 (dd, 1H), 7.94-7.97 (m, 3H), 8.25-8.26 (d, J=8 Hz, 2H), 8.49 (brs, 1H); LC-MS (ESI) m/z 269 [M+1]$^-$.

Example 143

2-(4-methoxyphenylbenzo[d]oxazole-7-carboxamide

Example 143 A methyl 2-(4-methoxyphenylbenzo[d]oxazole-7-carboxylate

4-Methoxybenzoic acid (152 mg, 1.0 mmol) and methyl 2-amino-3-hydroxybenzoate (167 mg, 1.0 mmol) were added to PPA (1 g), the mixture was stirred at 180° C. for 2 hr. After cooled to room temperature, water (50 mL) was added and filtered and the cake was washed with water and dried in vacuum to give methyl 2-(4-methoxyphenylbenzo[d]oxazole-7-carboxylate. LC-MS (ESI) m/z 240 [M+1]$^+$.

Example 143 B 2-(Octahydro-1H-quinolizin-3-yl)benzo[d]oxazole-7-carboxamide

To a solution of methyl 2-(4-methoxyphenylbenzo[d]oxazole-7-carboxylate in DMF (15 mL) was added HOBt (148 mg, 1.1 mmol), NH$_4$Cl (54 mg, 1.0 mmol), DIPEA (387 mg, 3.0 mmol) and EDCI (211 mg, 1.1 mmol). The mixture was stirred at 25° C. for 10 hr. To the resulting mixture, water (10 mL) and aqueous hydrochloric acid (1 N) were added to pH=3, then extracted with ethyl acetate (100 mL×4). The organic phase was washed with saturated sodium bicarbonate solution and brine, concentrated, and dried in vacuum. The crude product was purified by pre-HPLC to obtain 2-(4-methoxyphenylbenzo[d]oxazole-7-carboxamide as a white solid (8 mg, yield 3% for 2 steps). $^1$H-NMR (400 MHz, CDCl$_3$-d) δ 3.93 (s, 3H), 6.16 (s, 1H), 7.06-7.08 (d, J=8 Hz, 3H), 7.47 (s, 1H), 7.90-8.18 (m, 4H); LC-MS (ESI) m/z 269 [M+1]$^+$.

Example 144

2-(4-((dimethylamino)methyl)phenyl)benzo[d]oxazole-4-carboxamide

Example 144 A 2-p-tolylbenzo[d]oxazole-4-carboxylic acid

4-Methylbenzoic acid (275 g, 2 mmol) and methyl 2-amino-3-hydroxybenzoate (334 mg, 2 mmol) were added to the polyphosphoric acid (2.0 g). The mixture was heated at 180° C. for 2 h, allowed to cool, poured into water, and filtered; the cake was washed with water, dried under reduced pressure at 50° C. to obtain a mixture of methyl 2-p-tolyl-benzo[d]oxazole-4-carboxylate and 2-p-tolylbenzo[d]oxazole-4-carboxylic acid powders. The mixture were added to thionyl chloride (10 ml) and the mixture was stirred under reflux for 2 h. Evaporated the solvents under reduced pressure and the residue was added to methanol (20 ml), stirred at room temperature for 10 min. Then evaporated the solvents, the residue was dissolved in ethyl acetate, washed with water, the organic layer was dried with sodium sulfate, removed the solvents to obtain 2-p-tolylbenzo[d]oxazole-4-carboxylic acid (500 mg) as a yellow solid. Yield: 93%. LC-MS (ESI) m/z: 268 (M+1)$^+$.

Example 144 B methyl 2-(4-(bromomethyl)phenyl)benzo[d]oxazole-4-carboxylate 2-p-Tolylbenzo[d]oxazole-4-carboxylic acid (500 mg, 1.86 mmol), 1-bromopyrrolidine-2,5-dione (391.6 mg, 2.2 mmol) and benzoperoxide (27.6 mg, 0.2 mmol) were added to carbon tetrachloride (30 ml) and the mixture was stirred under reflux overnight. The resulting mixture was evaporated under reduced pressure and purified by column chromatography (silica gel, petroleum ether/ethyl acetate=100:1 to 20:1). 276.8 mg of methyl 2-(4-(bromomethyl)phenyl)benzo[d]oxazole-4-carboxylate as a solid was obtained, yield 40%. LC-MS (ESI) m/z: 347 (M+1)$^+$, 349 M+3)$^+$.

Example 144 C methyl 2-(4-((dimethylamino)methyl)phenyl)benzo[d]oxazole-4-carboxylate Methyl 2-(4-(bromomethyl)phenyl)benzo[d]oxazole-4-carboxylate (100 mg, 0.29 mmol) and dimethylamine (26 mg, 0.58 mmol) were added into ethanol (30 ml) and the mixture was stirred at 30° C. for 12 h. The resulting mixture was evaporated under reduced pressure. 60 mg of methyl 2-(4-((dimethylamino)methyl)phenyl)benzo[d]oxazole-4-carboxylate solid was obtained, yield: 44.5%. LC-MS (ESI) m/z: 311 (M+1)$^+$.

Example 144 D 2-(4-((dimethylamino)methyl)phenyl)benzo[d]oxazole-4-carboxamide Methyl 2-(4-((dimethylamino)methyl)phenyl)benzo[d]oxazole-4-carboxylate (40 mg, 0.13 mmol) and ammonia water (17.2 mg, 0.52 mmol) were added and the mixture was stirred at 30° C. for 1 h. The resulting mixture was evaporated under reduced pressure and purified by pre-HPLC. 2-(4-((dimethylamino)methyl)phenyl)benzo[d]oxazole-4-carboxamide (16 mg) was obtained, yield 41%. LC-MS (ESI) m/z: 296 (M+1)$^+$. $^1$H-NMR (400 MHz, DMSO-d6): δ 2.94 (s, 6H), 4.46 (s, 2H), 7.57-7.58 (m, 1H), 7.75-7.77 (m, 2H), 7.93 (brs, 1H), 8.09 (brs, 1H), 8.43-8.44 (m, 2H).

Example 145

2-(4-((dimethylamino)methyl)phenyl)-5-fluorobenzo[d]oxazole-7-carboxamide

Example 145 A methyl 5-fluoro-2-p-Tolylbenzo[d]oxazole-7-carboxylic acid

Following the experimental procedure as described in Examples 144A, and substituting methyl 2-amino-3-hydroxybenzoate with methyl 3-amino-5-fluoro-2-hydroxybenzoate, methyl 5-fluoro-2-p-tolylbenzo[d]oxazole-7-carboxylic acid (Yield: 79%. LC-MS (ESI) m/z: 285 (M+1)$^+$) was made.

Example 145 B methyl 2-(4-(bromomethyl)phenyl)-5-fluorobenzo[d]oxazole-7-carboxylate Following the experimental procedure as described in Example 144 B, and methyl 2-p-tolylbenzo[d]oxazole-4-carboxylic acid with methyl 5-fluoro-2-p-tolylbenzo[d]oxazole-7-carboxylic acid, methyl 2-(4-(bromomethyl)phenyl)-5-fluorobenzo[d]oxazole-7-carboxylate (yield: 70%. LC-MS (ESI) m/z: 365 (M+1)$^+$, 367 (M+3)$^+$) was made.

Example 145 C methyl 2-(4-((dimethylamino)methyl)phenyl)-5-fluorobenzo[d]oxazole-7-carboxylate Following the experimental procedure as described in Example 144 C, and replacing methyl 2-(4-(bromomethyl)phenyl)benzo[d]oxazole-4-carboxylate with methyl 2-(4-(bromomethyl)phenyl)-5-fluorobenzo[d]oxazole-7-carboxylate, methyl 2-(4-((dimethylamino)methyl)phenyl)-5-fluorobenzo[d]oxazole-7-carboxylate (yield: 70%. LC-MS (ESI) m/z: 365 (M+1)$^+$) was made.

Example 145 D 2-(4-((dimethylamino)methyl)phenyl)-5-fluorobenzo[d]oxazole-7-carboxamide Following the experimental procedure as described in Example 144 D, and replacing methyl 2-(4-((dimethylamino)methyl)phenyl)benzo[d]oxazole-4-carboxylate with methyl 2-(4-((dimethylamino)methyl)phenyl)-5-fluorobenzo[d]oxazole-7-carboxylate, methyl 2-(4-((dimethylamino)methyl)phenyl)-5-fluorobenzo[d]oxazole-7-carboxylate was made. Yield 4.3%. LC-MS (ESI) m/z: 314 (M+1)$^+$. $^1$H-NMR (400 MHz, MeOH-d3): δ 2.17 (s, 6H), 3.49 (s, 2H), 7.57-7.59 (d, J=8 Hz, 2H), 7.63-7.69 (m, 2H), 8.31-8.33 (m, 2H).

Example 146

2-(4-((methoxyamino)methyl)phenyl)benzo[d]oxazole-7-carboxamide

Example 146 A methyl 2-p-tolylbenzo[d]oxazole-7-carboxylic acid

Following the experimental procedure as described in Examples 144A, and substituting methyl 2-amino-3-hydroxybenzoate with methyl 3-amino-2-hydroxybenzoate, methyl-2-p-tolylbenzo[d]oxazole-7-carboxylic acid (Yield: 74%. LC-MS (ESI) m/z: 268 (M+1)$^+$) was made.

Example 146 B methyl 2-(4-(bromomethyl)phenyl)benzo[d]oxazole-7-carboxylate

Following the experimental procedure as described in Example 144 B, and methyl 2-p-tolylbenzo[d]oxazole-4-carboxylic acid with methyl 2-p-tolylbenzo[d]oxazole-7-carboxylic acid, methyl 2-(4-(bromomethyl)phenyl)benzo[d]oxazole-7-carboxylate (yield: 77%. LC-MS (ESI) m/z: 346 (M+1)$^+$, 348 (M+3)$^+$) was made.

Example 146 C methyl 2-(4-((methoxyamino)methyl)phenyl)benzo[d]oxazole-7-carboxylate Following the experimental procedure as described in Example 144 C, and replacing methyl 2-(4-(bromomethyl)

phenyl)benzo[d]oxazole-4-carboxylate with methyl 2-(4-(bromomethyl)phenyl)benzo[d]oxazole-7-carboxylate and substituting dimethylamine with methoxyamine, methyl 2-(4-((methoxyamino)methyl)phenyl)benzo[d]oxazole-7-carboxylate (Yield: 65%. LC-MS (ESI) m/z: 313 (M+1)$^+$) was made.

Example 146 D 2-(4-((methoxyamino)methyl)phenyl)benzo[d]oxazole-7-carboxamide

Following the experimental procedure as described in Example 144 D, and replacing methyl 2-(4-((dimethylamino)methyl)phenyl)benzo[d]oxazole-4-carboxylate with methyl 2-(4-((methoxyamino)methyl)phenyl)benzo[d]oxazole-7-carboxylate, 2-(4-((methoxyamino)methyl)phenyl)benzo[d]oxazole-7-carboxamide was made. Yield: 22%. LC-MS (ESI) m/z: 298 (M+1)$^+$ $^1$H-NMR (400 MHz, DMSO-d6): δ 3.37 (s, 3H), 4.02-4.03 (d, J=5.6 Hz, 2H), 7.09-7.12 (t, J=6 Hz, 1H), 7.47-7.51 (t, J=8 Hz, 1H), 7.60-7.62 (d, J=8.4 Hz, 2H), 7.80-7.82 (d, J=7.2 Hz, 1H), 7.87-7.91 (d, J=14.4 Hz, 2H), 7.95-7.97 (d, J=8 Hz, 1H), 8.25-8.27 (d, J=8 Hz, 2H).

Example 147

2-(4-((methoxy(methyl)amino)methyl)phenyl)benzo[d]oxazole-7-carboxamide

Example 147 A methyl 2-(4-((methoxy(methyl)amino)methyl)phenyl)benzo[d]oxazole-7-carboxylate Following the experimental procedure as described in Example 144 C, and replacing methyl 2-(4-(bromomethyl)phenyl)benzo[d]oxazole-4-carboxylate with methyl 2-(4-(bromomethyl)phenyl)benzo[d]oxazole-7-carboxylate and substituting dimethylamine with methoxy(methyl)amine, methyl 2-(4-((methoxy(methyl)amino)methyl)phenyl)benzo[d]oxazole-7-carboxylate (Yield: 65%. LC-MS (ESI) m/z: 327 (M+1)$^+$) was made.

Example 147 B 2-(4-((methoxy(methyl)amino)methyl)phenyl)benzo[d]oxazole-7-carboxamide Following the experimental procedure as described in Example 144 D, and replacing methyl 2-(4-((dimethylamino)methyl)phenyl)benzo[d]oxazole-4-carboxylate with methyl 2-(4-((methoxy(methyl)amino)methyl)phenyl)benzo[d]oxazole-7-carboxylate, 2-(4-((methoxy(methyl)amino)methyl)phenyl)benzo[d]oxazole-7-carboxamide was made. Yield: 24%. LC-MS (ESI) m/z: 312 (M+1)$^+$. $^1$H-NMR (400 MHz, DMSO-d6): δ 2.60 (s, 3H), 3.30 (s, 3H), 3.86 (s, 2H), 7.47-7.51 (t, J=7.8 Hz, 1H), 7.59-7.61 (d, J=8.4 Hz, 2H), 7.80-7.82 (dd, J1=8 Hz, J2=1 Hz, 1H), 7.88-7.91 (d, J=13.6 Hz, 2H), 7.95-7.97 (dd, J1=8 Hz, J2=1 Hz, 1H), 8.26-8.28 (d, J=8 Hz, 2H).

Example 148

5-fluoro-2-(4-((methoxyamino)methyl)phenyl)benzo[d]oxazole-7-carboxamide

Example 148 A methyl 5-fluoro-2-(4-((methoxyamino)methyl)phenyl)benzo[d]oxazole-7-carboxylate Following the experimental procedure as described in Example 144 C, and replacing methyl 2-(4-(bromomethyl)phenyl)benzo[d]oxazole-4-carboxylate with methyl 2-(4-(bromomethyl)phenyl)-5-fluorobenzo[d]oxazole-7-carboxylate and substituting dimethylamine with methoxyamine, methyl 5-fluoro-2-(4-((methoxyamino)methyl)phenyl)benzo[d]oxazole-7-carboxylate (Yield: 87%. LC-MS (ESI) m/z: 331 (M+1)$^+$) was made.

Example 148 B 5-fluoro-2-(4-((methoxyamino)methyl)phenyl)benzo[d]oxazole-7-carboxamide Following the experimental procedure as described in Example 144 D, and replacing methyl 2-(4-((dimethylamino)methyl)phenyl)benzo[d]oxazole-4-carboxylate with methyl 5-fluoro-2-(4-((methoxyamino)methyl)phenyl)benzo[d]oxazole-7-carboxylate, 5-fluoro-2-(4-((methoxyamino)methyl)phenyl)benzo[d]oxazole-7-carboxamide was made. Yield 34%. LC-MS (ESI) m/z: 316 (M+1)$^+$. $^1$H-NMR (400 MHz, DMSO-d6): δ 3.37 (s, 3H), 4.02-4.03 (d, J=5.6 Hz, 2H), 7.09-7.12 (t, J=5.8 Hz, 1H), 7.58-7.63 (m, 3H), 7.87-7.90 (dd, J$_1$=8 Hz, J$_2$=2.4 Hz, 1H), 8.00 (s, 2H), 8.23-8.26 (d, J=8.4 Hz, 2H).

Example 149

5-fluoro-2-(4-((methoxy(methyl)amino)methyl)phenyl)benzo[d]oxazole-7-carboxamide Example 149 A methyl 5-fluoro-2-(4-((methoxy(methyl)amino)methyl)phenyl)benzo[d]oxazole-7-carboxylate Following the experimental procedure as described in Example 144 C, and replacing methyl 2-(4-(bromomethyl)phenyl)benzo[d]oxazole-4-carboxylate with methyl 2-(4-(bromomethyl)phenyl)-5-fluorobenzo[d]oxazole-7-carboxylate and substituting dimethylamine with methoxy(methyl)amine, methyl 5-fluoro-2-(4-((methoxy(methyl)amino)methyl)phenyl)benzo[d]oxazole-7-carboxylate (Yield: 84%. LC-MS (ESI) m/z: 345 (M+1)$^+$) was made.

Example 149 B 5-fluoro-2-(4-((methoxy(methyl)amino)methyl)phenyl)benzo[d]oxazole-7-carboxamide Following the experimental procedure as described in Example 144 D, and replacing methyl 2-(4-((dimethylamino)methyl)phenyl)benzo[d]oxazole-4-carboxylate with methyl 5-fluoro-2-(4-((methoxy(methyl)amino)methyl)phenyl)benzo[d]oxazole-7-carboxylate, 5-fluoro-2-(4-((methoxy(methyl)amino)methyl)phenyl)benzo[d]oxazole-7-carboxamide was made. Yield: 53%. LC-MS (ESI) m/z: 330 (M+1).

¹H-NMR (400 MHz, DMSO-d6) δ 2.60 (s, 3H), 3.29 (s, 3H), 3.87 (s, 2H), 7.59-7.62 (m, 3H), 7.88-7.90 (dd, $J_1$=8.4 Hz, $J_2$=2.8 Hz, 1H), 8.00 (s, 2H), 8.25-8.27 (d, J=8.4 Hz, 2H).

Example 150

2-(pyrrolidin-2-yl)benzo[d]oxazole-7-carboxamide

Example 150 A 1-(benzyloxycarbonyl)pyrrolidine-2-carboxylic acid

To the solution of pyrrolidine-2-carboxylic acid (1.15 g, 10 mmol) of water (20 ml) was added sodium hydrate (1.6 g, 40 mmol). Then benzyloxycarbonyl chloride (2.02 g, 12 mmol) was added drop wise at 0° C. The mixture was stirred at 0° C. for 2 h. The resulting mixture was treated with 5N hydrochloric acid to pH=6 and extracted with ethyl acetate, the solvent was removed under reduced pressure and dried in vacuum. 2.0 g of 1-(benzyloxycarbonyl)pyrrolidine-2-carboxylic acid.

Example 150 B benzyl 2-(chlorocarbonyl)pyrrolidine-1-carboxylate

To a stirred solution of compound 2.0 g of 1-(benzyloxycarbonyl)pyrrolidine-2-carboxylic acid (1.0 g, 4.01 mmol) in anhydrous dichloromethane (10 mL) was added dropwise thionyl chloride (0.573 g, 4.81 mmol) at 0° C. After the addition, the solution was stirred at room temperature overnight. Solvent was removed in vacuum to give benzyl 2-(chlorocarbonyl)pyrrolidine-1-carboxylate.

Example 150 C benzyl 2-(2-hydroxy-3-(methoxycarbonyl)phenylcarbamoyl)pyrrolidine-1-carboxylate To a stirred solution of ethyl 3-amino-2-hydroxybenzoate (0.601 g, 3.6 mmol) and pyridine (0.633 g, 8 mmol) in anhydrous dichloromethane (20 mL) was added dropwise a solution of benzyl 2-(chlorocarbonyl)pyrrolidine-1-carboxylate (1.12 g, 4 mmol) in anhydrous dichloromethane (5 mL). After the addition, the mixture was stirred at room temperature overnight. The mixture was diluted with dichloromethane, washed with water (30 mL×3), 1N hydrochloric acid (30 mL×3), brine (30 mL), dried over anhydrous sodium sulfate, and concentrated to give benzyl 2-(2-hydroxy-3-(methoxycarbonyl)phenylcarbamoyl)pyrrolidine-1-carboxylate (1.43 g). LC-MS (ESI) m/z: 399 (M+1)⁺.

Example 150 D methyl 2-(1-(benzyloxycarbonyl)pyrrolidin-2-yl)benzo[d]oxazole-7-carboxylate A mixture of benzyl 2-(2-hydroxy-3-(methoxycarbonyl)phenylcarbamoyl)pyrrolidine-1-carboxylate (400 mg, 1 mmol) in phosphoryl trichloride (5 mL) was heated to reflux for 40 mins. The mixture was cooled to room temperature and poured into water (100 mL) carefully with vigorous stirring, then extracted with ethyl acetate (50 mL×3). The combined organic layers were dried over anhydrous sodium sulfate, and concentrated to give crude product. The crude product was purified by chromatography (silica gel, petroleum ether/ethyl acetate=30:1 to 8:1) to give methyl 2-(1-(benzyloxycarbonyl) pyrrolidin-2-yl)benzo[d]oxazole-7-carboxylate (170 mg, yield 45%). LC-MS (ESI) m/z: 381 (M+1).

Example 150 E benzyl 2-(7-carbamoylbenzo[d]oxazol-2-yl)pyrrolidine-1-carboxylate To a stirred solution of methyl 2-(1-(benzyloxycarbonyl) pyrrolidin-2-yl)benzo[d]oxazole-7-carboxylate (150 mg, 0.394 mmol) in methanol (8 mL) was added ammonia water (6 mL) at 0° C. After the addition, the mixture was allowed to stir at room temperature overnight. Methanol was removed in vacuum. The residue was diluted with water (100 mL), extracted with ethyl acetate (50 mL×3). The combined organic layers washed with brine, dried over anhydrous sodium sulfate, and concentrated to give crude product. The crude product was purified by chromatography (silica gel, petroleum ether/ethyl acetate=20:1 to 1:1) to give benzyl 2-(7-carbamoylbenzo[d]oxazol-2-yl)pyrrolidine-1-carboxylate (68 mg, yield 42%). LC-MS (ESI) m/z: 366 (M+1)⁺.

Example 150 F 2-(pyrrolidin-2-yl)benzo[d]oxazole-7-carboxamide

A mixture of benzyl 2-(7-carbamoylbenzo[d]oxazol-2-yl) pyrrolidine-1-carboxylate (68 mg, 0.19 mmol), 10% Pd/C (20 mg) in methanol (30 ml) was stirred at room temperature over 1 atm hydrogen for 2 hr. Then the mixture solution was filtered and the filtrate was evaporated under reduced pressure. The residue was purified by pre-HPLC to give 6 mg of 2-(pyrrolidin-2-yl)benzo[d]oxazole-7-carboxamide. Yield 13%. LC-MS (ESI) m/z: 232 (M+1)⁺. ¹H-NMR (400 MHz, CDCl₃): δ 1.24 (brs, 1H), 1.97 (m, 2H), 2.21 (m, 1H), 2.35 (m, 1H), 3.12 (m, 1H), 3.22 (m, 1H), 4.58 (m, 1H), 5.99 (brs, 1H), 7.03 (brs, 1H), 7.43-7.47 (t, J=8 Hz, 1H), 7.85-7.87 (d, J=8 Hz 1H), 8.08-8.09 (d, J=7.6 Hz, 1H).

Example 151

2-(piperidin-4-yl)benzo[d]oxazole-7-carboxamide

Example 151 A & B

A: benzyl-4-(2-hydroxy-3-(methoxycarbonyl)phenylcarbamoyl)piperidine-1-carboxylate B: 1-benzyl 4-(2-(1-(benzyloxycarbonyl)piperidine-4-carboxamido)-6-(methoxycarbonyl)phenyl)piperidine-1,4-dicarboxylate To the solution of piperidine-4-carboxylic acid (1.3 g, 10 mmol) of water (20 ml) was added sodium hydroxide (1.6 g, 40 mmol). Then benzyloxycarbonyl chloride (2.02 g, 12 mmol) was added dropwise at 0° C. The mixture was stirred at 0° C. for 2 h. The resulting mixture was treated with 5N hydrochloric acid to pH=6 and extracted with ethyl acetate, the solvent was removed under reduced pressure and dried in vacuum. 2.2 g of crude 1-(benzyloxycarbonyl)piperidine-4-carboxylic acid was obtained. To a stirred solution of crude 1-(benzyloxycarbonyl)piperidine-4-carboxylic acid (1.05 g, 4 mmol) in anhydrous dichloromethane (10 mL) was added dropwise thionyl chloride (0.573 g, 4.81 mmol) at 0° C. After the addition, the solution was stirred at room temperature overnight. Solvent was removed in vacuum to give crude benzyl-4-(chlorocarbonyl)piperidine-1-carboxylate. To a stirred solution of ethyl 3-amino-2-hydroxybenzoate (0.501 g, 3.0 mmol) and triethylamine (0.455 g, 4.5 mmol) in anhydrous dichloromethane (20 mL) was added dropwise a solution of crude benzyl-4-(chlorocarbonyl)piperidine-1-carboxylate (1.014 g, 3.6 mmol) in anhydrous dichloromethane (5 mL) at 0° C. After the addition, the mixture was stirred at room temperature overnight. The mixture was diluted with dichloromethane, washed with water (30 mL×3), brine (30 mL), dried over anhydrous sodium sulfate, and concentrated to give crude product. The crude product was purified by chromatography (silica gel, petroleum ether/ethyl acetate=30:1 to 5:1) to give benzyl-4-(2-hydroxy-3-(methoxycarbonyl)phenylcarbamoyl)piperidine-1-carboxylate (0.25 g, yield 20%; LC-MS (ESI) m/z: 413 (M+1)$^+$) and 1-benzyl 4-(2-(1-(benzyloxycarbonyl)piperidine-4-carboxamido)-6-(methoxycarbonyl)phenyl)piperidine-1,4-dicarboxylate (1.0 g, yield 51%; LC-MS (ESI) m/z: 658 (M+1)$^+$).

Example 151 C methyl 2-(1-(benzyloxycarbonyl)piperidin-4-yl)benzo[d]oxazole-7-carboxylate A mixture of benzyl-4-(2-hydroxy-3-(methoxycarbonyl)phenylcarbamoyl)piperidine-1-carboxylate (400 mg, 0.61 mmol) in propionic acid (5 mL) was heated to reflux for 4 days. The mixture was diluted with water (50 mL), neutralized with sodium bicarbonate, and then extracted with ethyl acetate (50 mL×3). The combined organic layers were washed with brine, dried over anhydrous sodium sulfate, and concentrated to give crude product. The crude product was purified by pre-HPLC to afford methyl 2-(1-(benzyloxycarbonyl)piperidin-4-yl)benzo[d]oxazole-7-carboxylate (102 mg) as a yellow oil. LC-MS (ESI) m/z: 395 (M+1)$^+$.

Example 151 D benzyl 4-(7-carbamoylbenzo[d]oxazol-2-yl)piperidine-1-carboxylate

Methyl 2-(1-(benzyloxycarbonyl)piperidin-4-yl)benzo[d]oxazole-7-carboxylate (102 mg, 0.26 mmol) was added to a mixture of methanol (5 mL) and ammonia water (10 mL) and the mixture was stirred at room temperature for overnight. Then the solid was filtered. 98 mg of solid of benzyl 4-(7-carbamoylbenzo[d]oxazol-2-yl)piperidine-1-carboxylate was obtained. LC-MS (ESI) m/z: 380 (M+1)$^+$.

Example 151 E 2-(piperidin-4-yl)benzo[d]oxazole-7-carboxamide

A mixture of benzyl 4-(7-carbamoylbenzo[d]oxazol-2-yl)piperidine-1-carboxylate (98 mg, 0.26 mmol), 10% Pd/C (20 mg) in methanol (30 ml) was stirred at room temperature over 1 atm hydrogen for 2 hr. The mixture was filtered, and evaporated under reduced pressure. The residue was purified by pre-HPLC. 21 mg of 2-(piperidin-4-yl)benzo[d]oxazole-7-carboxamide as a solid was obtained, yield 33%. LCMS (ESI) m/z: 246 (M+1)$^+$. $^1$H-NMR (400 MHz, DMSO-d6): δ 1.24 (brs, 1H), 1.71-1.74 (m, 2H), 2.03-2.06 (d, J=12 Hz, 2H), 2.64 (t, 2H), 3.01-3.04 (t, 2H), 3.14 (t, 1H), 7.41 (t, J=7.2 Hz, 1H), 7.72 (d, J=7.2 Hz, 1H), 7.72 (brs, 1H), 7.78 (brs, 1H), 7.85 (d, J=7.2 Hz, 1H).

Example 152

2-(azetidin-3-yl)benzo[d]oxazole-7-carboxamide

Example 152 A 1-(benzyloxycarbonyl)azetidine-3-carboxylic acid

To the solution of azetidine-3-carboxylic acid (1 g, 10 mmol) of tetrahydrofuran/water (50 ml:50 ml) was added NaHCO$_3$ (2.05 g, 25 mmol). Then benzyloxycarbonyl chloride (2.02 g, 12 mmol) was added dropwise at 0° C. The mixture was stirred at room temperature overnight. The solvent was removed under reduced pressure and adjusted to pH=2, extracted with ethyl acetate. The residue was dried in vacuum. 2.4 g of crude 1-(benzyloxycarbonyl)azetidine-3-carboxylic acid was obtained.

Example 152 B benzyl 3-(2-hydroxy-3-(methoxycarbonyl)phenylcarbamoyl)azetidine-1-carboxylate To a solution of 1-(benzyloxycarbonyl)azetidine-3-carboxylic acid (2.4 g) in dichloride methane (15 ml) was added 1-hydroxybenzotriazole (1.48 mg, 11 mmol), diisopropylethylamine (4 g, 30 mmol) and 1-ethly-3-(3-dimethylaminopropyl)carbodiimide hydrochloric (2 g, 11 mmol). The mixture was stirred at room temperature for 30 min. Then ethyl 3-amino-2-hydroxybenzoate (700 mg, 4 mmol) was added. The mixture was stirred at room temperature for 2 h. To the resulting mixture, water (10 ml) was added and hydrochloride acid (1N) to pH=3, then extracted with ethyl acetate (100 ml×4). The organic phase was washed with sodium bicarbonate (saturated) and brine and concentrated, dried with sodium sulfate. The crude was purified by column chromatography (silica gel, petroleum ether/ethyl acetate=20:1). 820 mg of benzyl 3-(2-hydroxy-3-(methoxycarbonyl)phenylcarbamoyl)azetidine-1-carboxylate was obtained. Yield 52%. LC-MS (ESI) m/z: 385 (M+1)$^+$.

Example 152 C methyl 2-(1-(benzyloxycarbonyl)azetidin-3-yl)benzo[d]oxazole-7-carboxylate A mixture of benzyl 3-(2-hydroxy-3-(methoxycarbonyl)phenylcarbamoyl)azetidine-1-carboxylate (820 mg, 2.13 mmol) in propionic acid (20 ml) was stirred at reflux for 2 days. Then the mixture was adjusted pH=7 by sodium bicarbonate. The mixture was extracted with ethyl acetate. The extraction was washed with sodium bicarbonate, brine, dried with sodium sulfate. The residue was removed in vacuum. The crude was purified by chromatography (silica gel, petroleum ether/ethyl acetate=5:1). 280 mg of methyl 2-(1-(benzyloxycarbonyl)azetidin-3-yl)benzo[d]oxazole-7-carboxylate as a solid was obtained, yield 39%. LC-MS (ESI) m/z: 367 (M+1)$^+$.

Example 152 D benzyl 3-(7-carbamoylbenzo[d]oxazol-2-yl)azetidine-1-carboxylate

Methyl 2-(1-(benzyloxycarbonyl)azetidin-3-yl)benzo[d]oxazole-7-carboxylate (280 mg, 0.76 mmol) was added to ammonia water (10 ml) and the mixture was stirred at 35° C.

for overnight. Then the solid was filtered. 160 mg of benzyl 3-(7-carbamoylbenzo[d]oxazol-2-yl)azetidine-1-carboxylate was obtained, yield 60%. LC-MS (ESI) m/z: 352 (M+1)+. (M+1)+,

Example 152 E 2-(azetidin-3-yl)benzo[d]oxazole-7-carboxamide

A mixture of benzyl 3-(7-carbamoylbenzo[d]oxazol-2-yl) azetidine-1-carboxylate (160 mg, 0.45 mmol), 10% Pd/C (20 mg) of methanol (30 ml) was stirred at room temperature for 2 h. Then the mixture was filtered and evaporated under reduced pressure. The residue was purified by pre-HPLC. 6 mg of 2-(azetidin-3-yl)benzo[d]oxazole-7-carboxamide was obtained. LC-MS (ESI) m/z: 218 (M+1)+. $^1$H-NMR (400 MHz, CDCl$_3$): δ 1.84 (brs, 1H), 3.39 (t, 3H), 4.11 (t, 3H), 4.21 (m, 1H), 6.12 (brs, 1H), 6.96 (brs, 1H), 7.39 (t, J=8 Hz, 1H), 7.81 (d, J=8 Hz, 1H), 8.01 (d, J=8 Hz, 1H).

Example 153

2-(piperidin-3-yl)benzo[d]oxazole-7-carboxamide

Example 153 A 1-(benzyloxycarbonyl)piperidine-3-carboxylic acid

To the solution of piperidine-3-carboxylic acid (1.3 g, 10 mmol) in water (20 mL) was added sodium hydroxide (1.6 g, 40 mmol). Then benzyloxycarbonyl chloride (2.02 g, 12 mmol) was added dropwise at 0° C. The mixture was stirred at 0° C. for 2 h. The resulting mixture was treated with 5N hydrochloric acid to pH=6 and extracted with ethyl acetate, the solvent was removed under reduced pressure and dried in vacuum. 2.2 g of solid of 1-(benzyloxycarbonyl)piperidine-3-carboxylic acid was obtained. LC-MS (ESI) m/z: 264 (M+1)+.

Example 153 B benzyl-3-(chlorocarbonyl)piperidine-1-carboxylate

To a stirred solution of 1-(benzyloxycarbonyl)piperidine-3-carboxylic acid (1.05 g, 4 mmol) in anhydrous dichloromethane (10 mL), thionyl chloride (0.573 g, 4.81 mmol) was added drop wise at 0° C. After the addition, the solution was stirred at room temperature overnight. Solvent was removed in vacuum to give benzyl-3-(chlorocarbonyl)piperidine-1-carboxylate.

Example 153 C benzyl-3-(2-hydroxy-3-(methoxycarbonyl)phenylcarbamoyl)piperidine-1-carboxylate Benzyl-3-(chlorocarbonyl)piperidine-1-carboxylate (0.85 g, 3 mmol) and methyl 3-amino-2-hydroxybenzoate (0.6 g, 3.6 mmol) were added in anhydrous dichloromethane (20 mL) and the mixture was stirred at room temperature overnight. The mixture was extracted with dichloromethane (100 mL×4) and the organic phase was dried with anhydrous sodium sulfate and evaporated under reduced pressure. 1.2 g of benzyl-3-(2-hydroxy-3-(methoxycarbonyl)phenylcarbamoyl)piperidine-1-carboxylate was obtained, yield: 97%. LC-MS (ESI) m/z: 413 (M+1)+.

Example 153 D methyl 2-(1-(benzyloxycarbonyl)piperidin-3-yl)benzo[d]oxazole-7-carboxylate A mixture of benzyl-3-(2-hydroxy-3-(methoxycarbonyl) phenylcarbamoyl)piperidine-1-carboxylate (210 mg, 0.5 mmol) in propionic acid (20 mL) was heated to reflux for 4 days. The mixture was diluted with water (50 mL), neutralized with sodium bicarbonate, and then extracted with ethyl acetate (50 mL×3). The combined organic layers were dried over anhydrous sodium sulfate and concentrated. 180 mg of methyl 2-(1-(benzyloxycarbonyl)piperidin-3-yl)benzo[d] oxazole-7-carboxylate was obtained. Yield: 91%. LC-MS (ESI) m/z: 395 (M+1)+.

Example 153 E benzyl 3-(7-carbamoylbenzo[d]oxazol-2-yl)piperidine-1-carboxylate Methyl 2-(1-(benzyloxycarbonyl)piperidin-3-yl)benzo[d] oxazole-7-carboxylate (180 mg, 0.46 mmol) was added to ammonia in methanol (20 mL) and the mixture was stirred at room temperature for 2 days. Then the mixture was evaporated under reduced pressure and extracted with ethyl acetate (100 mL×4), the organic phase was dried with anhydrous sodium sulfate and evaporated under reduced pressure. 100 mg of benzyl 3-(7-carbamoylbenzo[d]oxazol-2-yl)piperidine-1-carboxylate was obtained. Yield: 57%. LC-MS (ESI) m/z: 380 (M+1)+.

Example 153 F 2-(piperidin-3-yl)benzo[d]oxazole-7-carboxamide

A mixture of benzyl 3-(7-carbamoylbenzo[d]oxazol-2-yl) piperidine-1-carboxylate (100 mg, 0.26 mmol), 10% Pd/C (20 mg) in methanol (30 mL) was stirred at room temperature over 1 atm hydrogen for 2 hr. The mixture was evaporated under reduced pressure and purified by pre-HPLC to give 16 mg of 2-(piperidin-3-yl)benzo[d]oxazole-7-carboxamide as a solid. Yield 25%. $^1$H-NMR (400 MHz, DMSO-d6): δ 1.50-1.53 (m, 1H), 1.65-1.67 (m, 1H), 1.81-1.84 (m, 1H), 2.16-2.19 (m, 1H), 2.50-2.54 (m, 1H), 2.81-2.90 (m, 2H), 3.07-3.12 (m, 1H), 3.28-3.31 (m, 1H), 7.39-7.43 (t, J=8.0 Hz, 1H), 7.72-7.78 (m, 3H), 7.83-7.85 (m, 1H). LC-MS (ESI) m/z: 246 (M+1)+.

Example 154

2-(2-methylpyrrolidin-2-yl)benzo[d]oxazole-7-carboxamide

Example 154 A 1-(benzyloxycarbonyl)-2-methylpyrrolidine-2-carboxylic acid

To the solution of 1-benzyl 2-methyl 2-methylpyrrolidine-1,2-dicarboxylate (3.1 g, 10.8 mmol) in the mixture of Methanol (20 mL) and water (20 mL) was added lithium hydroxide monohydrate (0.9 g, 21.6 mmol). The mixture was stirred at 30° C. for 3 h. The resulting mixture was treated with 5N hydrochloric acid to pH=2 and filtrated, washed with water, dried in vacuum at 45° C. 1.9 g of 1-(benzyloxycarbonyl)-2- methylpyrrolidine-2-carboxylic acid was obtained. Yield: 67%. LC-MS (ESI) m/z: 264 (M+1)$^+$.

Example 154 B benzyl 2-(chlorocarbonyl)-2-methylpyrrolidine-1-carboxylate

To a stirred solution of 1-(benzyloxycarbonyl)-2-methylpyrrolidine-2-carboxylic acid (1.0 g, 3.8 mmol) in anhydrous dichloromethane (10 mL) thionyl chloride (0.54 g, 4.56 mmol) was added drop wise at 0° C. After the addition, the solution was stirred at room temperature overnight. Solvent was removed in vacuum to give benzyl 2-(chlorocarbonyl)-2-methylpyrrolidine-1-carboxylate.

Example 154 C benzyl 2-(2-hydroxy-3-(methoxycarbonyl)phenylcarbamoyl)-2-methylpyrrolidine-1-carboxylate To a stirred solution of methyl 3-amino-2-hydroxybenzoate (0.576 g, 3.45 mmol) and pyridine (0.546 g, 6.9 mmol) in anhydrous dichloromethane (20 mL) was added drop wise a solution of benzyl 2-(chlorocarbonyl)-2-methylpyrrolidine-1-carboxylate (1.07 g, 3.8 mmol) in anhydrous dichloromethane (5 mL). After the addition, the mixture was stirred at room temperature overnight. Removed the solvents and purified by silica gel chromatography (petroleum ether/ethyl acetate=100:1 to 25:1) to obtain a yellow oil of benzyl 2-(2-hydroxy-3-(methoxycarbonyl)phenylcarbamoyl)-2-methylpyrrolidine-1-carboxylate (1 g, yield 66%). $^1$H-NMR (400 MHz, DMSO-d6): δ 1.53-1.58 (m, 3H), 1.88-1.91 (m, 3H), 1.28 (brs, 1H), 3.53-3.65 (m, 2H), 3.92 (s, 3H), 5.02-5.15 (m, 2H), 6.92-6.96 (m, 1H), 7.16-7.34 (m, 5H), 7.55-7.57 (d, J=7.8 Hz, 1H), 7.88-8.12 (m, 1H), 8.72-8.89 (d, 1H), 10.82 (s, 1H); LC-MS (ESI) m/z: 413 (M+1)$^+$.

Example 154 D methyl 2-(1-(benzyloxycarbonyl)-2-methylpyrrolidin-2-yl)benzo[d]oxazole-7-carboxylate A mixture of benzyl 2-(2-hydroxy-3-(methoxycarbonyl)phenylcarbamoyl)-2-methylpyrrolidine-1-carboxylate (550 mg, 1.33 mmol) in anhydrous toluene (10 mL) was added anhydrous pyridine (0.583 mL, 7.3 mmol), then thionyl chloride (0.39 mL, 7.3 mmol) was added, the mixture was heated to 110° C. for 6 h. The mixture was cooled to room temperature and poured into ice water (100 mL) carefully with vigorous stirring, then extracted with ethyl acetate (50 mL×3). The organic phase was washed with saturated sodium bicarbonate solution and brine, dried over anhydrous sodium sulfate, and concentrated to give crude product. The crude product was purified by chromatography (silica gel, petroleum ether/ethyl acetate=30:1 to 8:1) to give methyl 2-(1-(benzyloxycarbonyl)-2-methylpyrrolidin-2-yl)benzo[d]oxazole-7-carboxylate (164 mg, yield 32%). $^1$H-NMR (400 MHz, CDCl$_3$): δ 1.63 (s, 3H) 2.02-2.05 (m, 2H), 2.14-2.16 (m, 1H), 2.40-2.44 (m, 1H), 3.73-3.77 (m, 1H), 3.87-3.90 (m, 1H), 3.94 (s, 3H), 4.71-4.73 (d, J=9.6 Hz, 1H), 5.06-5.09 (m, 2H), 6.79-6.81 (d, J=6 Hz, 1H), 6.89-6.92 (m, 1H), 7.02-7.04 (m, 1H), 7.33-7.37 (m, 3H), 7.80-7.95 (m, 2H); LC-MS (ESI) m/z: 395 (M+1)$^+$.

Example 154 E benzyl 2-(7-carbamoylbenzo[d]oxazol-2-yl)-2-methylpyrrolidine-1-carboxylate Methyl 2-(1-(benzyloxycarbonyl)-2-methylpyrrolidin-2-yl)benzo[d]oxazole-7-(150 mg, 0.42 mmol) was added to ammonia in methanol (10 mL) and the mixture was stirred at room temperature for 2 days. Evaporated the solvents to obtain benzyl 2-(7-carbamoylbenzo[d]oxazol-2-yl)-2-methylpyrrolidine-1-carboxylate as white oil (144 mg, Y: 90%). LC-MS (ESI) m/z: 380 (M+1)$^+$.

Example 154 F 2-(2-methylpyrrolidin-2-yl)benzo[d]oxazole-7-carboxamide

A mixture of benzyl 2-(7-carbamoylbenzo[d]oxazol-2-yl)-2-methylpyrrolidine-1-carboxylate (144 mg, 0.37 mmol), 10% Pd/C (20 mg) in methanol (10 mL) was stirred at room temperature over 1 atm hydrogen for 3 h. Then the mixture was filtered and the filtrate was evaporated under reduced pressure. The residue was purified by flash chromatography. 40 mg of yellow oil of 2-(2-methylpyrrolidin-2-yl)benzo[d]oxazole-7-carboxamide was obtained, yield 43%. $^1$H-NMR (400 MHz, DMSO-d6): δ 1.58 (s, 3H), 1.76-1.87 (m, 3H), 2.47-2.49 (m, 1H), 2.86-2.91 (m, 1H), 2.97-3.02 (m, 1H), 7.41-7.44 (t, J=6.4 Hz, 1H), 7.69 (s, 1H), 7.74-7.76 (d, J=5.6 Hz, 1H), 7.82 (s, 1H), 8.85-8.87 (d, J=6.4 Hz, 1H). LC-MS (ESI) m/z: 246 (M+1)$^+$.

Example 155

2-(4-(pyridin-2-yl)phenyl)benzo[d]oxazole-7-carboxamide

Example 155 A 4-(pyridin-2-yl)benzoic acid

To a solution of 4-boronobenzoic acid (1.66 g, 10 mmol) and 2-bromopyridine (1.72 g, 11 mmol) in acetonitrile (40 mL) and water (40 mL), potassium carbonate (5.5 g, 40 mmol), bis(triphenylphosphine)palladium(II) chloride (400 mg, 0.37 mmol) were added. The mixture was degassed and purged withed nitrogen. The mixture was stirred under reflux for 24 h. Then the hot suspension was filtered and concentrated to half of the original volume and washed with dichloromethane. The aquatic phase was adjusted to pH=4 with hydrochloric acid (1 M) and filtrated, washed with water. The residue was dried in vacuum to obtain 1.81 g of white solid of 4-(pyridin-2-yl)benzoic acid. Yield: 91%. LC-MS (ESI) m/z: 200 (M+1)$^+$.

Example 155 B methyl 2-hydroxy-3-(4-(pyridin-2-yl)benzamido)benzoate

Thionyl chloride (10 mL) was added to 4-(pyridin-2-yl) benzoic acid (1.8 g, 9 mmol) and the mixture was stirred under reflux overnight. The solvent was evaporated under reduced pressure and the residue was dried in vacuum to give crude 4-(pyridin-2-yl)benzoyl chloride. To a solution of methyl 3-amino-2-hydroxybenzoate (1 g, 6 mmol) and pyridine (480 mg, 6 mmol) in toluene (50 mL) were added the crude 4-(pyridin-2-yl)benzoyl chloride (1.3 g, 6 mmol) portion wise at 0° C. and then stirred at 70° C. for 4 h. The resulting mixture was extracted with ethyl acetate (100 mL×4), the organic phase was washed with water and saturated sodium bicarbonate, dried with anhydrous sodium sulfate and evaporated under reduced pressure to obtain yellow solid of methyl 2-hydroxy-3-(4-(pyridin-2-yl)benzamido)benzoate (1.6 g, yield 76%). LC-MS (ESI) m/z: 349 (M+1)$^+$. (M+1)$^+$.

Example 155 C methyl 2-(4-(pyridin-2-yl)phenyl)benzo[d]oxazole-7-carboxylate

Methyl 2-hydroxy-3-(4-(pyridin-2-yl)benzamido)benzoate (1.04 g, 3 mmol) and 4-methylbenzenesulfonic acid monohydrate (1.2 g, 6 mmol) were added to toluene (20 mL) and the mixture was stirred under reflux for 2 days. The resulting mixture was extracted with ethyl acetate (100 mL×4) and concentrated. The crude product was purified by column chromatography (silica gel, petroleum ether:ethyl acetate 20:1 to 10:1). 170 mg of solid of methyl 2-(4-(pyridin-2-yl)phenyl)benzo[d]oxazole-7-carboxylate was obtained. Yield: 17%. LC-MS (ESI) m/z: 331 (M+1)$^+$.

Example 155 D 2-(4-(pyridin-2-yl)phenyl)benzo[d]oxazole-7-carboxamide

Methyl 2-(4-(pyridin-2-yl)phenyl)benzo[d]oxazole-7-carboxylate (170 mg, 0.5 mmol) was added to ammonia in methanol (30 mL) and the mixture was stirred at room temperature for 3 days. Then the solid was filtered, washed with methanol, dried in vacuum. 110 mg of solid of 2-(4-(pyridin-2-yl)phenyl)benzo[d]oxazole-7-carboxamide was obtained. Yield: 69%. $^1$H-NMR (400 MHz, DMSO-d6) δ 7.43-7.45 (m, 1H), 7.50-7.53 (t, J=7.6 Hz, 1H), 7.83-7.85 (m, 1H), 7.89 (brs, 1H), 7.95-8.01 (m, 3H); 8.12-8.14 (d, J=8.0 Hz, 1H); 8.36-8.44 (q, 3H); 8.74-8.75 (m, 1H); LC-MS (ESI) m/z: 316 (M+1)$^+$.

Example 156

2-(4-(piperidin-2-yl)phenyl)benzo[d]oxazole-7-carboxamide 2-(4-(Pyridin-2-yl)phenyl)benzo[d]oxazole-7-carboxamide (100 mg, 0.3 mmol) and platinum (IV) oxide monohydrate (55 mg) in methanol (20 mL) was purged with 20 atm of hydrogen at 50° C. for 24 h. Then the mixture was filtered and adjusted to pH=9. The solvent was removed in vacuum. The crude was purified by pre-HPLC. 7 mg of 2-(4-(piperidin-2-yl)phenyl)benzo[d]oxazole-7-carboxamide was obtained. Yield: 7%. $^1$H-NMR (400 MHz, DMSO-d6) δ 1.23 (s, 1H), 1.56-1.70 (m, 4H), 1.87 (brs, 2H), 2.88-2.91 (m, 1H), 4.02-4.04 (m, 1H); 7.48-7.52 (m, 1H); 7.72-7.74 (m, 2H); 7.82-7.98 (m, 4H); 8.30-8.32 (d, J=7.2 Hz, 2H); LC-MS (m/z) 316 (M+1)$^+$.

Example 157

2-(4-(pyridin-3-yl)phenyl)benzo[d]oxazole-7-carboxamide

Example 157 A 4-(pyridin-3-yl)benzoic acid

To a solution of 4-boronobenzoic acid (1.66 g, 10 mmol) and 3-bromopyridine (1.72 g, 11 mmol) in acetonitrile (40 mL) and water (40 mL), potassium carbonate (5.5 g, 40 mmol), bis(triphenylphosphine)palladium(II) chloride (400 mg, 0.37 mmol) were added. The mixture was degassed and purged withed nitrogen. The mixture was stirred under reflux for 24 h. Then the hot suspension was filtered and concentrated to half of the original volume and washed with dichloromethane. The aquatic phase was adjusted to pH=3 with hydrochloric acid (1 M) and filtrated, washed with water. The residue was dried in vacuum to obtain 1.7 g of white solid of 4-(pyridin-3-yl)benzoic acid. Yield: 85%. LC-MS (ESI) m/z: 200 (M+1)$^+$.

Example 157 B methyl 2-hydroxy-3-(4-(pyridin-3-yl)benzamido)benzoate 4-bromo-2-fluorobenzoic acid (30 g, 0.14 mol) of was dissolved in methanol with a few drops of sulfuric acid. The reaction medium was refluxed for 20 hours. The cooled reaction mixture was evaporated and the residue partitioned between ethyl acetate and saturated aqueous sodium bicarbonate solution. The organic layer was separated and washed with brine, dried over sodium sulfate, filtered and evaporated to give methyl 4-bromo-2-fluorobenzoate (20.7 g, yield 64%) as a white solid. $^1$H-NMR (400 MHz, DMSO-d$_6$) δ (ppm); 3.85 (s, 3H), 7.55-7.58 (m, 1H), 7.70-7.73 (m, 1H), 7.79-7.83 (m, 1H); LC-MS (ESI) m/z: 233 (M+1)$^+$, 235 (M+3)$^+$ Example 157 C methyl 2-(4-(pyridin-3-yl)phenyl)benzo[d]oxazole-7-carboxylate Methyl 2-hydroxy-3-(4-(pyridin-3-yl)benzamido)benzoate (1.04 g, 3 mmol) and 4-methylbenzenesulfonic acid (1.2 g, 6 mmol) were added to toluene (20 mL) and the mixture was stirred under reflux for 2 days. The resulting mixture was extracted with ethyl acetate (100 mL×4) and concentrated. The crude product was purified by column chromatography (silica gel, petroleum ether/ethyl acetate 20:1 to 10:1). 150 mg of methyl 2-(4-(pyridin-3-yl)phenyl)benzo[d]oxazole-7-carboxylate as a solid was obtained, yield: 15%. 1H-NMR (400 MHz, DMSO-d6) δ 4.02 (s, 3H), 7.55-7.59 (m, 1H), 7.97-7.99 (m, 1H), 8.04-8.06 (d, J=8.0 Hz, 2H), 8.13-8.15 (m, 1H), 8.21-8.24 (m, 1H), 8.33-8.35 (d, J=8.2 Hz, 2H), 8.65-8.66 (m, 1H), 9.03-9.04 (d, J=2.0 Hz, 1H); LC-MS (ESI) m/z: 331 (M+1)$^+$.

Example 157 D 2-(4-(pyridin-3-yl)phenyl)benzo[d]oxazole-7-carboxamide

Methyl 2-(4-(pyridin-3-yl)phenyl)benzo[d]oxazole-7-carboxylate (150 mg, 0.45 mmol) was added to ammonia in methanol (30 mL) and the mixture was stirred at room temperature for 3 days. Then the solid was filtered, washed with methanol, dried in vacuum. 120 mg of 2-(4-(pyridin-3-yl)phenyl)benzo[d]oxazole-7-carboxamide was obtained. Yield: 84%. 1H-NMR (400 MHz, DMSO-d6) δ 7.52-7.58 (m, 2H), 7.83-8.05 (m, 6H), 8.21-8.23 (m, 1H), 8.42-8.44 (d, J=8 Hz, 2H), 8.64-8.66 (m, 1H); 9.03-9.04 (m, 1H); LC-MS (ESI) m/z: 316 (M+1)$^+$.

Example 158

2-(4-(piperidin-3-yl)phenyl)benzo[d]oxazole-7-carboxamide 2-(4-(Pyridin-3-yl)phenyl)benzo[d]oxazole-7-carboxamide (100 mg, 0.35 mmol) and platinum (IV) oxide monohydrate (55 mg) in methanol (20 mL) was purged with 20 atm of hydrogen at 50° C. for 24 h. Then the mixture was filtered and adjusted to pH=9. The solvent was removed in vacuum. The crude was purified by pre-HPLC. 11 mg of 2-(4-(piperidin-3-yl)phenyl)benzo[d]oxazole-7-carboxamide was obtained, yield: 11%. $^1$H-NMR (400 MHz, DMSO-d$_6$) δ 1.45 (s, 3H), 1.74-1.77 (m, 2H), 1.89-1.96 (m, 2H), 2.87-2.90 (m, 1H), 3.06-3.09 (m, 2H), 7.85-7.90 (brs, 2H), 7.94-7.96 (d, J=8.0 Hz, 2H), 8.26-8.28 (d, J=8.2 Hz, 2H); LC-MS (ESI) m/z: 316 (M+1)$^+$.

Example 159

2-(4-(pyridin-4-yl)phenyl)benzo[d]oxazole-7-carboxamide

Example 159 A

4-(pyridin-4-yl)benzoic acid

To a solution of 4-boronobenzoic acid (1.66 g, 10 mmol) and 4-bromopyridine (1.72 g, 11 mmol) in acetonitrile (40 mL) and water (40 mL), potassium carbonate (5.5 g, 40 mmol), Bis(triphenylphosphine)palladium(II) chloride (400 mg, 0.37 mmol) was added. The mixture was degassed and purged withed nitrogen. The mixture was stirred at 100° C. for 24 h. Then the hot suspension was filtered and concentrated to half of the original volume and washed with dichloromethane. The aquatic phase was adjusted to pH=3 with hydrochloric acid (1 M) and filtrated, washed with water. The residue was dried in vacuum to obtain 1.8 g of white solid of 4-(pyridin-4-yl)benzoic acid. Yield: 90%. LC-MS (ESI) m/z: 200 (M+1)$^+$.

Example 159 B methyl 2-hydroxy-3-(4-(pyridin-4-yl)benzamido)benzoate

Thionyl chloride (10 mL) was added to 4-(pyridin-4-yl)benzoic acid (1.6 g, 8 mmol) and the mixture was stirred under reflux overnight. The solvent was evaporated under reduced pressure and the residue was dried in vacuum giving 4-(pyridin-3-yl)benzoyl chloride. To a solution of methyl 3-amino-2-hydroxybenzoate (1 g, 6 mmol) and pyridine (480 mg, 6 mmol) in toluene (50 mL) was added 4-(pyridin-3-yl)benzoyl chloride (1.3 g, 6 mmol) portion wise at 0° C. and then stirred at 70° C. for 4 h. The resulting mixture was extracted with ethyl acetate (100 mL×4), the organic phase was washed with water and saturated sodium bicarbonate, dried with anhydrous sodium sulfate and evaporated under reduced pressure to obtain methyl 2-hydroxy-3-(4-(pyridin-4-yl)benzamido)benzoate as yellow solid (1.5 g, yield 71%). $^1$H-NMR (400 MHz, CDCl$_3$) δ 4.00 (s, 3H), 6.97-7.01 (t, J=8.2 Hz, 1H), 7.57-7.63 (m, 3H), 7.78-7.80 (d, J=8.0 Hz, 2H), 8.05-8.07 (d, J=8.8 Hz, 2H), 8.67-8.78 (m, 4H), 11.44 (s, 1H); LC-MS (ESI) m/z: 349 (M+1)$^+$.

Example 159 C methyl 2-(4-(pyridin-4-yl)phenyl)benzo[d]oxazole-7-carboxylate

A mixture of methyl 2-hydroxy-3-(4-(pyridin-4-yl)benzamido)benzoate (1.04 g, 3 mmol) in propionic acid (50 mL) was stirred at reflux for 3 days. Then the mixture was adjusted to pH=7 by sodium bicarbonate. The mixture was extracted with ethyl acetate. The organic phase was washed with saturated sodium bicarbonate, brine, dried with anhydrous sodium sulfate. The solvent was removed under reduced pressure. The crude products was purified by chromatography (petroleum ether/ethyl acetate=20:1 to 5:1). 160 mg of methyl 2-(4-(pyridin-4-yl)phenyl)benzo[d]oxazole-7-carboxylate as a solid was obtained. Yield: 16%. LC-MS (ESI) m/z: 331 (M+1)$^+$.

Example 159 D

2-(4-(pyridin-4-yl)phenyl)benzo[d]oxazole-7-carboxamide

Methyl 2-(4-(pyridin-4-yl)phenyl)benzo[d]oxazole-7-carboxylate (160 mg, 0.5 mmol) was added to ammonia in methanol (30 mL) and the mixture was stirred at room temperature for 3 days. Then the solid was filtered, washed with methanol, dried in vacuum. 140 mg of solid of 2-(4-(pyridin-4-yl)phenyl)benzo[d]oxazole-7-carboxamide was obtained, yield: 90%. $^1$H-NMR (400 MHz, DMSO-d6) δ 7.50-7.54 (t, J=8 Hz, 1H), 7.83-7.86 (m, 2H), 7.89-7.96 (brs, 2H), 7.99-8.01 (d, J=7.6 Hz, 2H), 8.08-8.10 (d, J=8.4 Hz, 2H); 8.44-8.46 (d, J=8.4 Hz, 2H); 8.71-8.72 (d, J=4.4 Hz, 2H); LC-MS (ESI) m/z: 316 (M+1)$^+$.

Example 160

2-(4-(piperidin-4-yl)phenyl)benzo[d]oxazole-7-carboxamide 2-(4-(Pyridin-4-yl)phenyl)benzo[d]oxazole-7-carboxamide (135 mg, 0.43 mmol) and platinum (IV) oxide monohydrate (70 mg) in methanol (20 mL) was purged with 20 atm of hydrogen at 50° C. for 24 h. Then the mixture was filtered and adjusted to pH=9. The solvent was removed in vacuum. The crude was purified by chromatography (dichloromethane:methanol=8:1) to give the solid. The solid was acidified by hydrochloride acid. 4.6 mg of 2-(4-(piperidin-4-yl)phenyl)benzo[d]oxazole-7-carboxamide was obtained. Yield: 3%. $^1$H-NMR (400 MHz, CD$_3$OD-d$_4$) δ 1.89 (m, 2H), 2.03 (m, 2H), 2.95 (m, 1H), 3.09-3.12 (m, 2H), 3.43-3.46 (m, 2H), 7.40-7.46 (m, 3H), 7.81 (t, J=8.4 Hz, 2H), 8.21 (d, J=8.0 Hz, 2H). LC-MS (ESI) m/z: 316 (M+1)$^+$.

Example 161

2-(3-(pyridin-2-yl)phenyl)benzo[d]oxazole-7-carboxamide

Example 161 A

3-(pyridin-2-yl)benzoic acid

To a solution of 3-boronobenzoic acid (1.66 g, 10 mmol) and 2-bromopyridine (1.72 g, 11 mmol) in acetonitrile (40 mL) and water (40 mL), potassium carbonate (5.5 g, 40 mmol), Bis(triphenylphosphine)palladium(II)chloride (400 mg, 0.37 mmol) was added. The mixture was degassed and purged withed nitrogen. The mixture was stirred at 100° C. for 24 h. Then the hot suspension was filtered and concentrated to half of the original volume and washed with dichloromethane. The aquatic phase was adjusted to pH=3 with hydrochloric acid (1 M) and filtrated, washed with water. The residue was dried in vacuum to obtain 1.69 g of white solid of 3-(pyridin-2-yl)benzoic acid. Yield: 85%. LC-MS (ESI) m/z: 200 (M+1)$^+$.

Example 161 B methyl 2-hydroxy-3-(3-(pyridin-2-yl)benzamido)benzoate

Thionyl chloride (10 mL) was added to 3-(pyridin-2-yl) benzoic acid (1.69 g, 8.5 mmol) and the mixture was stirred under reflux overnight. The solvent was evaporated under reduced pressure and the residue was dried in vacuum to give 3-(pyridin-2-yl)benzoyl chloride. 1.66 g of crude product was obtained. To a solution of methyl 3-amino-2-hydroxybenzoate (0.84 g, 5 mmol) and pyridine (790 mg, 10 mmol) in toluene (50 mL) were added crude 3-(pyridin-2-yl)benzoyl chloride (1.6 g, 7.37 mmol) portion-wise at 0° C. and then stirred at 70° C. for 4 h. The resulting mixture was extracted with ethyl acetate (100 mL×4), the organic phase was washed with water and saturated sodium bicarbonate, dried with anhydrous sodium sulfate and evaporated under reduced pressure to obtain yellow solid of methyl 2-hydroxy-3-(3-(pyridin-2-yl)benzamido)benzoate (1.48 g, yield 85%). LC-MS (ESI) m/z: 349 (M+1)$^+$.

Example 161 C methyl 2-(3-(pyridin-2-yl)phenyl)benzo[d]oxazole-7-carboxylate

Methyl 2-hydroxy-3-(3-(pyridin-2-yl)benzamido)benzoate (1.4 g, 4 mmol) and 4-methylbenzenesulfonic acid (1.9 g, 10 mmol) were added to toluene (30 mL) and the mixture was stirred under reflux for 2 days. The resulting mixture was extracted with ethyl acetate (100 mL×4) and concentrated. The crude product was purified by column chromatography (silica gel, petroleum ether/ethyl acetate=20:1 to 10:1). 264 mg of methyl 2-(3-(pyridin-2-yl)phenyl)benzo[d]oxazole-7-carboxylate as a solid was obtained, yield: 20%. LC-MS (ESI) m/z: 331 (M+1)$^+$.

Example 161 D 2-(3-(pyridin-2-yl)phenyl)benzo[d]oxazole-7-carboxamide

Methyl 2-(3-(pyridin-2-yl)phenyl)benzo[d]oxazole-7-carboxylate (150 mg, 0.43 mmol) was added to ammonia in methanol (30 mL) and the mixture was stirred at room temperature for 3 days. Then the solid was filtered, washed with methanol, dried in vacuum. 100 mg of 2-(3-(pyridin-2-yl) phenyl)benzo[d]oxazole-7-carboxamide was obtained, yield: 74%. $^1$H-NMR (400 MHz, DMSO-d6) δ 7.44-7.47 (t, J=5.2 Hz, 1H), 7.50-7.54 (t, J=8.0 Hz, 1H), 7.76-7.88 (m, 3H), 7.96-8.01 (m, 3H), 8.12-8.14 (d, J=7.6 Hz, 1H); 8.35-8.39 (t, J=8.0 Hz, 2H); 8.76-8.77 (d, J=2.8 Hz, 1H); 9.01 (s, 1H); LC-MS (ESI) m/z: 316 (M+1)$^+$.

Example 162

2-(3-(piperidin-2-yl)phenyl)benzo[d]oxazole-7-carboxamide 2-(3-(Pyridin-2-yl)phenyl)benzo[d]oxazole-7-carboxamide (90 mg, 0.28 mmol) and platinum (IV) oxide monohydrate (45 mg) in methanol (20 mL) was purged with 20 atm of hydrogen at 50° C. for 24 h. Then the mixture was filtered and adjusted to pH=9. The solvent was removed in vacuum. The crude was purified by chromatography (petroleum ether/ethyl acetate=1:1). 30 mg of 2-(3-(piperidin-2-yl)phenyl)benzo[d] oxazole-7-carboxamide was obtained, yield: 33%. $^1$H-NMR (400 MHz, DMSO-d6) δ 1.35-1.38 (m, 1H), 1.45-1.47 (m, 2H), 1.58-1.60 (m, 1H), 1.75-1.82 (m, 2H); 2.68-2.69 (m, 1H); 3.08-3.10 (d, J=9.6 Hz, 1H); 3.66-3.69 (m, 1H); 7.48-7.50 (t, J=6.0 Hz, 1H), 7.55-7.58 (d, J=6.4 Hz, 1H), 7.63-7.64 (d, J=5.6 Hz, 1H); 7.79-7.81 (m, 1H); 7.86 (brs, 1H); 7.94 (brs, 1H); 7.95-7.97 (m, 1H); 8.16-8.18 (m, 1H); 8.302 (s, 1H); LC-MS (ESI) m/z: 322 (M+1)$^+$.

Example 163

2-(3-(pyridin-3-yl)phenyl)benzo[d]oxazole-7-carboxamide

Example 163 A 3-(pyridin-3-yl)benzoic acid

To a solution of 3-boronobenzoic acid (1.5 g, 9 mmol) and 3-bromopyridine (1.5 g, 9.9 mmol) in acetonitrile (40 mL) and water (40 mL), potassium carbonate (5.5 g, 40 mmol), Bis(triphenylphosphine)palladium(II) chloride (400 mg, 0.37 mmol) was added. The mixture was stirred under reflux overnight. Then the hot suspension was filtered and concentrated to half of the original volume and washed with dichloromethane. The aquatic phase was adjusted to pH=3 with hydrochloric acid (1 M) and filtrated, washed with water. The residue was dried in vacuum to obtain 1.5 g of 3-(pyridin-3-yl)benzoic acid. Yield: 83%. LC-MS (ESI) m/z: 200 (M+1)$^+$.

Example 163 B methyl 2-hydroxy-3-(3-(pyridin-3-yl)benzamido)benzoate

Thionyl chloride (10 mL) was added to 3-(pyridin-3-yl) benzoic acid (1.5 g, 7.5 mmol) and the mixture was stirred under reflux overnight. The solvent was evaporated under reduced pressure and the residue was dried in vacuum giving 1.5 g crude 3-(pyridin-3-yl)benzoyl chloride. To a solution of methyl 3-amino-2-hydroxybenzoate (950 mg, 5.8 mmol) and pyridine (480 mg, 6 mmol) in toluene (50 mL) was added 3-(pyridin-3-yl)benzoyl chloride (1.5 g, 7 mmol) portion-wise at 0° C. and then stirred at 70° C. for 4 h. The resulting mixture was extracted with ethyl acetate (100 mL×4), the organic phase was washed with water and saturated sodium bicarbonate, dried with anhydrous sodium sulfate and evaporated under reduced pressure to obtain methyl 2-hydroxy-3-(3-(pyridin-3-yl)benzamido)benzoate as a yellow solid (1.8 g, yield 85%). LC-MS (ESI) m/z: 349 (M+1)$^+$.

Example 163 C methyl 2-(3-(pyridin-3-yl)phenyl)benzo[d]oxazole-7-carboxylate

Methyl 2-hydroxy-3-(3-(pyridin-3-yl)benzamido)benzoate (0.9 g, 2.5 mmol) and 4-methylbenzenesulfonic acid monohydrate (1 g, 5 mmol) were added to toluene (20 mL) and the mixture was stirred under reflux for 2 days. The resulting mixture was extracted with ethyl acetate (100 mL×4) and concentrated. The crude product was purified by column chromatography (silica gel, petroleum ether/ethyl acetate=20:1 to 10:1). 130 mg of methyl 2-(3-(pyridin-3-yl) phenyl)benzo[d]oxazole-7-carboxylate as a solid was obtained. Yield: 15%. LC-MS (ESI) m/z: 331 (M+1)$^+$.

Example 163 D 2-(3-(pyridin-3-yl)phenyl)benzo[d]oxazole-7-carboxamide

Methyl 2-(3-(pyridin-3-yl)phenyl)benzo[d]oxazole-7-carboxylate (130 mg, 0.24 mmol) was added to ammonia in methanol (30 mL) and the mixture was stirred at room temperature for 3 days. Then the solid was filtered, washed with methanol, dried in vacuum. 110 mg of 2-(3-(pyridin-3-yl) phenyl)benzo[d]oxazole-7-carboxamide was obtained. Yield: 88%. $^1$H-NMR (400 MHz, DMSO-d6) 7.53 (t, 1H), 7.81 (t, 1H), 7.85-7-87 (m, 3H), 7.91 (brs, 1H), 7.98 (brs, 1H), 8.01 (d, J=6.4 Hz, 1H), 8.09 (d, J=6.4 Hz, 1H), 8.41 (d, 1H), 8.66 (s, 1H), 8.72 (d, 1H). LC-MS (ESI) m/z: 316 (M+1)$^+$.

Example 164

2-(3-(piperidin-3-yl)phenyl)benzo[d]oxazole-7-carboxamide

A solution of 2-(3-(Pyridin-3-yl)phenyl)benzo[d]oxazole-7-carboxamide (110 mg, 0.35 mmol) and platinum (IV) oxide monohydrate (55 mg) in methanol (20 mL) was purged with 20 atm of hydrogen at 50° C. for 24 h. Then the mixture was filtered and adjusted to pH=9. The solvent was removed in vacuum. The crude was purified by chromatography (dichlormethane/methanol=9:1) to give the solid. The solid was acidified by hydrochloride acid and wash with ethyl acetate. The solvent was removed in vacuum. 11 mg of 2-(3-(piperidin-3-yl)phenyl)benzo[d]oxazole-7-carboxamide was obtained, yield: 10%. $^1$H-NMR (400 MHz, CD$_3$OD) δ 1.93-1.97 (m, 2H), 2.12-2.14 (m, 2H), 3.07-3.27 (m, 3H), 3.51 (t, 2H), 7.53 (t, 1H); 7.60-7.63 (m, 2H), 7.91 (d, J=6.4 Hz, 1H); 7.94 (d, J=6.4 Hz, 1H); 8.26-8.29 (d, J=3.2 Hz, 1H). LC-MS (ESI) m/z: 321 (M+1)$^+$.

Example 165

2-(3-(pyridin-4-yl)phenyl)benzo[d]oxazole-7-carboxamide

Example 165 A 3-(pyridin-4-yl)benzoic acid

To a solution of 3-boronobenzoic acid (1.5 g, 9 mmol) and 4-bromopyridine (1.5 g, 9.9 mmol) in acetonitrile (40 mL) and water (40 mL), potassium carbonate (5.5 g, 40 mmol), Bis(triphenylphosphine)palladium(II) chloride (400 mg, 0.37 mmol) was added. The mixture was stirred under reflux overnight. Then the hot suspension was filtered and concentrated to half of the original volume and washed with dichloromethane. The aquatic phase was adjusted to pH=3 with hydrochloric acid (1 M) and filtrated, washed with water. The residue was dried in vacuum to obtain 1.5 g 3-(pyridin-4-yl) benzoic acid. Yield: 83%. LC-MS (ESI) m/z: 200 (M+1)$^+$.

Example 165 B methyl 2-hydroxy-3-(3-(pyridin-4-yl)benzamido)benzoate

Thionyl chloride (10 mL) was added to 3-(pyridin-4-yl) benzoic acid (1.5 g, 7.5 mmol) and the mixture was stirred under reflux overnight. The solvent was evaporated under reduced pressure and the residue was dried in vacuum giving 1.5 g of crude 3-(pyridin-4-yl)benzoyl chloride. To a solution of methyl 3-amino-2-hydroxybenzoate (950 g, 5.8 mmol) and pyridine (480 mg, 6 mmol) in toluene (50 mL) was added crude 3-(pyridin-4-yl)benzoyl chloride (1.5 g, 7 mmol) portion wise at 0° C. and then stirred at 70° C. for 4 h. The resulting mixture was extracted with ethyl acetate (100 mL×4), the organic phase was washed with water and saturated sodium bicarbonate, dried with anhydrous sodium sulfate and evaporated under reduced pressure to obtain methyl 2-hydroxy-3-(3-(pyridin-4-yl)benzamido)benzoate as a yellow solid (1.8 g, yield 85%). LC-MS (ESI) m/z: 349 (M+1)$^+$.

Example 165 C methyl 2-(3-(pyridin-4-yl)phenyl)benzo[d]oxazole-7-carboxylate

A mixture of methyl 2-hydroxy-3-(3-(pyridin-4-yl)benzamido)benzoate (0.9 g, 5 mmol) of propionic acid (50 mL) was stirred at reflux for 3 days. Then the mixture was adjusted to pH=7 by sodium bicarbonate. The mixture was extracted with ethyl acetate. The organic phase was washed with saturated sodium bicarbonate, brine, dried with anhydrous sodium sulfate. The solvent was removed under reduced pressure. The crude products was purified by chromatography (petroleum ether/ethyl acetate=5:1). 240 mg of methyl 2-(3-(pyridin-4-yl)phenyl)benzo[d]oxazole-7-carboxylate as a solid was obtained. Yield 28%. LC-MS (ESI) m/z: 331 (M+1)$^+$.

Example 165 D 2-(3-(pyridin-4-yl)phenyl)benzo[d]oxazole-7-carboxamide

Methyl 2-(3-(pyridin-4-yl)phenyl)benzo[d]oxazole-7-carboxylate (130 mg, 0.24 mmol) was added to ammonia in methanol (30 mL) and the mixture was stirred at room temperature for 3 days. Then the solid was filtered, washed with methanol, dried in vacuum. 110 mg 2-(3-(pyridin-4-yl)phenyl)benzo[d]oxazole-7-carboxamide was obtained, yield: 88%. 1HNMR (400 MHz, DMSO-d6): δ7.52-7.54 (t, J=6.0 Hz, 1H), 7.56-7.59 (m, 1H), 7.77-7.80 (t, J=6.0 Hz, 1H), 7.86-7.88 (dd, J=6.4 Hz, 0.8 Hz, 1H), 7.92 (brs, 1H), 7.98 (brs, 1H), 8.00-8.03 (m, 2H), 8.22-8.24 (m, 1H), 8.36-8.38 (d, J=6.4 Hz, 1H), 8.61 (s, 1H), 8.65-8.67 (m, 1H), 9.03-9.04 (d, J=1.6 Hz, 1H). LC-MS (ESI) m/z: 316 (M+1)+.

Example 166

2-(3-(piperidin-4-yl)phenyl)benzo[d]oxazole-7-carboxamide 2-(3-(Pyridin-4-yl)phenyl)benzo[d]oxazole-7-carboxamide (110 mg, 0.35 mmol) and platinum (IV) oxide monohydrate in methanol was purged with 20 atm of hydrogen at 50° C. for 24 h. Then the mixture was filtered and adjusted to pH=9. The solvent was removed in vacuum. The crude was purified by chromatography (dichloromethane:methanol=9:

1) to give the solid. The solid was acidified by hydrochloride acid. 24 mg 2-(3-(piperidin-4-yl)phenyl)benzo[d]oxazole-7-carboxamide was obtained, yield: 21%. $^1$HNMR (400 MHz, DMSO-d6): δ 1.96 (m, 5H), 3.03 (m, 4H), 7.51 (m, 2H), 7.62 (t, 1H), 7.81 (d, J=6.4 Hz, 1H), 7.83 (brs, 1H), 7.94 (brs, 1H), 7.97 (d, J=6.4 Hz, 1H), 8.14 (s, 1H), 8.19 (d, J=6.4 Hz, 1H), 8.85 (brs, 1H), 9.02 (brs, 1H). LC-MS (ESI) m/z: 322 (M+1)$^+$.

Example 167

2-((1-(2-dimethylamino)acetyl)piperidin-3-yl)benzo[d]oxazole-7-carboxamide

Example 167 A benzyl-3-(2-hydroxy-3-(methoxycarbonyl)phenylcarbamoyl)piperidine-1-carboxylate Benzyl 3-(chlorocarbonyl)piperidine-1-carboxylate (500 mg, 3 mmol) and methyl 3-amino-2-hydroxybenzoate (1.014 g, 3.6 mmol) were added in anhydrous dichloromethane (20 mL) and the mixture was stirred at room temperature overnight. The mixture was extracted with dichloromethane (100 mL×4) and the organic phase was dried with anhydrous sodium sulfate and evaporated under reduced pressure. 1.2 g benzyl-3-(2-hydroxy-3-(methoxycarbonyl)phenylcarbamoyl)piperidine-1-carboxylate was obtained. Yield: 97%. LC-MS (ESI) m/z: 413 (M+1)$^+$.

Example 167 B methyl 2-(1-(benzyloxycarbonyl)piperidin-3-yl)benzo[d]oxazole-7-carboxylate A mixture of benzyl-3-(2-hydroxy-3-(methoxycarbonyl)phenylcarbamoyl)piperidine-1-carboxylate (400 mg, 0.98 mmol) in propionic acid (20 mL) was heated to reflux for 4 days. The mixture was diluted with water (50 mL), neutralized with sodium bicarbonate, and then extracted with ethyl acetate (50 mL×3). The combined organic layers were dried over anhydrous sodium sulfate and concentrated. 360 mg of methyl 2-(1-(benzyloxycarbonyl)piperidin-3-yl)benzo[d]oxazole-7-carboxylate was obtained. Yield: 89%. LC-MS (ESI) m/z: 395 (M+1)$^+$.

Example 167 C benzyl 3-(7-carbamoylbenzo[d]oxazol-2-yl)piperidine-1-carboxylate

Methyl 2-(1-(benzyloxycarbonyl)piperidin-3-yl)benzo[d]oxazole-7-carboxylate (360 mg, 0.92 mmol) was added to a solution of ammonia in methanol (10 mL) and the mixture was stirred at room temperature overnight. Then the mixture was evaporated under reduced pressure and extracted with ethyl acetate (100 mL×4), the organic phase was dried with anhydrous sodium sulfate and evaporated under reduced pressure. 200 mg benzyl 3-(7-carbamoylbenzo[d]oxazol-2-yl)piperidine-1-carboxylate was obtained. Yield: 26%. LC-MS (ESI) m/z: 380 (M+1)$^+$.

Example 167 D 2-(piperidin-3-yl)benzo[d]oxazole-7-carboxamide

A mixture of benzyl 3-(7-carbamoylbenzo[d]oxazol-2-yl)piperidine-1-carboxylate (200 mg, 0.27 mmol), 10% Pd/C (40 mg) in methanol (30 ml) was stirred at room temperature over 1 atm hydrogen for 2 hr. Then the mixture was filtered and evaporated, 160 mg of 2-(piperidin-3-yl)benzo[d]oxazole-7-carboxamide as a solid was obtained. Yield 24%. LC-MS (ESI) m/z: 246 (M+1)$^+$.

Example 167 E 2-(1-(2-dimethylamino)acetyl)piperidin-3-yl)benzo[d]oxazole-7-carboxamide A mixture of 2-(piperidin-3-yl)benzo[d]oxazole-7-carboxamide (160 mg, 1.2 mmol), 1-ethyl-3-(3-dimethylaminopropyl)carbodiimide hydrochloride (82.4 mg, 0.61 mmol), 1-hydroxybenzotriazole (82 mg, 0.61 mmol), triethyl amine (117 mg, 0.61 mmol), 2-(dimethylamino)acetic acid (83 mg, 0.61 mmol) were added in 50 ml dichloride methane and stirred at room temperature over night. The mixture was evaporated under reduced pressure and purified by pre-HPLC. 13 mg 2-(1-(2-dimethylamino)acetyl)piperidin-3-yl)benzo[d]oxazole-7-carboxamide was obtained. Yield 7%. $^1$H-NMR (400 MHz, CD$_3$OD): δ 1.52-1.65 (m, 1H), 1.77-1.85 (m, 1H), 2.15-2.31 (m, 8H), 2.20-2.28 (m, 2H), 3.31-3.39 (m, 2H), 3.75-3.90 (m, 2H), 4.42-4.36 (m, 1H), 7.44-7.47 (m, 1H), 7.81-7.88 (m, 2H). LC-MS (ESI) m/z: 331 (M+1)$^+$.

Example 168

2-(3-(4-isobutyrylpiperazine-1-carbonyl)phenyl)benzo[d]oxazole-7-carboxamide

Example 168 A methyl 3-(4-isobutyrylpiperazine-1-carbonyl)benzoate

To a solution of 3-(methoxycarbonyl)benzoic acid (0.9 g, 5 mmol) in dichloromethane (20 mL), 1-hydroxybenzotriazole (0.75 g, 5.5 mmol), 1-ethyl-3-(3-dimethylaminopropyl)carbodiimide hydrochloride (1.06 g, 5.5 mmol) and triethyl amine (2 mL) was added. The mixture was stirred at room temperature for 30 min, then 2-methyl-1-(piperazin-1-yl)propan-1-one (1.0 g, 5 mmol) was added and the mixture was stirred at room temperature for 16 h. The resulting mixture was added water (50 mL) and extracted with dichloromethane (100 mL×3). The organic phase was washed with sodium bicarbonate and brine and concentrated. The crude product was purified by column chromatography (silica gel, petroleum ether/ethyl acetate 20:1 to 2:1) to give 1.25 g of methyl 3-(4-isobutyrylpiperazine-1-carbonyl)benzoate as an oil. Yield 94%. $^1$H-NMR (400 MHz, CDCl$_3$) 1.14-1.15 (d, J=6.4 Hz, 6H), 2.81 (brs, 1H), 3.44-3.80 (m, 8H), 3.94 (s, 3H), 7.52-7.55 (t, J=7.6 Hz, 1H), 7.62-7.64 (d, J=8.0 Hz, 1H), 8.08-8.14 (m, 2H); LC-MS (ESI) m/z: 319 (M+1)$^+$.

Example 168 B 3-(4-isobutyrylpiperazine-1-carbonyl)benzoic acid

To a solution of methyl 3-(4-isobutyrylpiperazine-1-carbonyl)benzoate (1.25 g, 3.9 mmol) in water (10 mL) and tetrahydrofuran (10 mL) at 0° C., lithium hydroxide monohydrate (250 mg, 6 mmol) was added. The mixture was stirred at that temperature for 2 h. The resulting mixture was neutralized to pH=5 with hydrochloric acid, and extracted with ethyl acetate (100 mL×4) and concentrated to obtain a white solid of 3-(4-isobutyrylpiperazine-1-carbonyl)benzoic acid (1.1 g, yield 76%). LC-MS (ESI) m/z: 305 (M+1)$^+$.

Example 168 C methyl 2-hydroxy-3-(3-(4-isobutyrylpiperazine-1-carbonylbenzamido)benzoate 3-(4-isobutyrylpiperazine-1-carbonyl)benzoic acid (610 mg, 2 mmol) was added thionyl chloride (10 mL), the mixture was added at room temperature for 48 h. Then the solvent was removed under reduced pressure. The crude 3-(4-isobutyrylpiperazine-1-carbonyl)benzoyl chloride was dried in vacuum. Methyl 2-amino-3-hydroxybenzoate (167 mg, 1.0 mmol) and triethyl amine (300 mg, 3.0 mmol) were added to toluene (10 mL) and the mixture was stirred at room temperature for 30 min. and 3-(4-isobutyrylpiperazine-1-carbonyl)benzoyl chloride was added and the mixture was stirred at room temperature for 30 min then at 80° C. for 4 hr. The resulting mixture was extracted with ethyl acetate (100 mL×4) and concentrated. The crude product was purified by column chromatography (silica gel, petroleum ether:ethyl acetate 20:1 to 1:1) to obtain methyl 2-hydroxy-3-(4-isobutyrylpiperazine-1-carbonylbenzamido)benzoate as a solid (180 mg, yield 40%). LC-MS (ESI) m/z: 454 (M+1)$^+$.

Example 168 D methyl 2-(3-(4-isobutyrylpiperazine-1-carbonyl)phenyl)benzo[d]oxazole-7-carboxylate Methyl 2-hydroxy-3-(3-(4-isobutyrylpiperazine-1-carbonylbenzamido)benzoate (180 mg, 0.4 mmol) and 4-methylbenzenesulfonic acid monohydrate (200 mg, 1 mmol) were added to toluene (10 mL) and the mixture was stirred at reflux for 18 hr. The resulting mixture was extracted with ethyl acetate (100 mL×4) and concentrated to yield methyl 2-(3-(4-isobutyrylpiperazine-1-carbonyl)phenyl)benzo[d]oxazole-7-carboxylate as a solid (150 mg, yield 86%). LC-MS (ESI) m/z: 436 (M+1)$^+$.

Example 168 E 2-(3-(4-isobutyrylpiperazine-1-carbonyl)phenyl)benzo[d]oxazole-7-carboxamide Methyl 2-(3-(4-isobutyrylpiperazine-1-carbonyl)phenyl)benzo[d]oxazole-7-carboxylate (150 mg, 0.34 mmol) was added to ammonium in methanol (10 mL) in a sealing tube and stirred at 25° C. for 3 days. The solvent was removed under reduced pressure. The crude product was purified by pre-HPLC to obtain 2-(3-(4-isobutyrylpiperazine-1-carbonyl)phenyl)benzo[d]oxazole-7-carboxamide as a white solid (20 mg, yield 14%). $^1$H-NMR (400 MHz, CD$_3$OD) δ: 1.12-1.13 (d, J=6 Hz, 6H), 2.97 (brs, 1H), 3.55-3.85 (m, 8H), 7.50-7.54 (t, J=8.0 Hz, 1H), 7.71-7.75 (m, 2H), 7.91-7.95 (m, 2H), 8.41-8.45 (m, 2H); LC-MS (ESI) m/z: 421 (M+1)$^+$.

Example 169

2-(3-(4-(cyclopropanecarbonyl)piperazine-1-carbonyl)phenyl)benzo[d]oxazole-7-carboxamide

Example 169 A methyl 3-(4-(cyclopropanecarbonyl)piperazine-1-carbonyl)benzoate To a solution of 3-(methoxycarbonyl)benzoic acid (0.9 g, 5 mmol) in dichloromethane (20 mL), 1-hydroxybenzotriazole (0.75 g, 5.5 mmol), 1-ethyl-3-(3-dimethylaminopropyl)carbodiimide hydrochloride (1.06 g, 5.5 mmol) and triethyl amine (2 mL) were added. The mixture was stirred at room temperature for 30 min, and then cyclopropyl(piperazin-1-yl)methanone (1.0 g, 5 mmol) was added and the mixture was stirred at room temperature for 16 h. The resulting mixture was added water (50 mL) and extracted with dichloromethane (100 mL×3), the organic phase was washed with sodium bicarbonate, brine and concentrated. The crude product was purified by column chromatography (silica gel, petroleum ether/ethyl acetate 20:1 to 2:1), 0.95 g of methyl 3-(4-(cyclopropanecarbonyl)piperazine-1-carbonyl)benzoate as an oil was obtained, Yield 60%. $^1$H-NMR (400 MHz, CDCl$_3$) 0.80-0.82 (m, 2H), 1.00-1.04 (m, 2H), 1.24-1.27 (m, 1H), 3.25-3.78 (m, 8H), 3.94 (s, 3H), 7.52-7.55 (t, J=7.6 Hz, 1H), 7.63-7.65 (d, J=7.6 Hz, 1H), 8.09-8.14 (m, 2H); LC-MS (ESI) m/z: 317 (M+1)$^+$.

Example 169 B 3-(4-(cyclopropanecarbonyl)piperazine-1-carbonyl)benzoyl chloride To a solution of methyl 3-(4-(cyclopropanecarbonyl)piperazine-1-carbonyl)benzoate (0.95 g, 3 mmol) in water (10 mL) and tetrahydrofuran (10 mL) at 0° C., lithium hydroxide monohydrate (250 mg, 6 mmol) was added. The mixture was stirred at that temperature for 2 h. The resulting mixture was neutralized to pH=5 with hydrochloric acid, and extracted with ethyl acetate (100 mL×4) and concentrated to obtain a white solid of 3-(4-(cyclopropanecarbonyl)piperazine-1-carbonyl)benzoic acid (0.76 g, yield 83%). LC-MS (ESI) m/z: 303 (M+1)$^+$. 3-(4-(cyclopropanecarbonyl)piperazine-1-carbonyl)benzoic acid (610 mg, 2 mmol) was added to thionyl chloride (10 mL), and the mixture was added at room temperature for 48 h. Then the solvent was removed under reduced pressure, dried in vacuum to give 3-(4-(cyclopropanecarbonyl)piperazine-1-carbonyl)benzoyl chloride.

Example 169 C methyl 3-(3-(4-(cyclopropanecarbonyl)piperazine-1-carbonyl)benzamido)-2-hydroxybenzoate Methyl 2-amino-3-hydroxybenzoate (167 mg, 1.0 mmol) and triethyl amine (300 mg, 3.0 mmol) were added to toluene (10 mL) and the mixture was stirred at room temperature for 30 min. 3-(4-(Cyclopropanecarbonyl)piperazine-1-carbonyl)benzoyl chloride was added to the reaction mixture and the mixture was stirred at room temperature for 30 min then at 80° C. for 4 hr. The resulting mixture was extracted with ethyl acetate (100 mL×4) and concentrated. The crude product was purified by column chromatography (silica gel, petroleum ether:ethyl acetate 20:1 to 1:1) to obtain methyl 3-(3-(4-(cyclopropanecarbonyl)piperazine-1-carbonyl)benzamido)-2-hydroxybenzoate as a solid (160 mg, yield 35%). LC-MS (ESI) m/z: 452 (M+1)$^+$.

Example 169 D methyl 2-(3-(4-(cyclopropanecarbonyl)piperazine-1-carbonyl)phenyl)benzo[d]oxazole-7-carboxylate Methyl 3-(3-(4-(cyclopropanecarbonyl)piperazine-1-carbonyl)benzamido)-2-hydroxybenzoate (160 mg, 0.35 mmol) and 4-methylbenzenesulfonic acid monohydrate (200 mg, 1 mmol) were added to toluene (10 mL) and the mixture was stirred at reflux for 16 hr. The resulting mixture was extracted with ethyl acetate (100 mL×4) and concentrated to yield methyl 2-(3-(4-(cyclopropanecarbonyl)piperazine-1-carbonyl)phenyl)benzo[d]oxazole-7-carboxylate as a solid (130 mg, yield: 85%). LC-MS (ESI) m/z: 434 (M+1)$^+$.

Example 169 E 2-(3-(4-(cyclopropanecarbonyl)piperazine-1-carbonyl)phenyl)benzo[d]oxazole-7-carboxamide Methyl 2-(3-(4-(cyclopropanecarbonyl)piperazine-1-carbonyl)phenyl)benzo[d]oxazole-7-carboxylate (130 mg, 0.33 mmol) was added to ammonium in methanol (10 mL) in a sealing tube and stirred at 25° C. for 3 days. The solvent was removed under reduced pressure. The crude product was purified by pre-HPLC to obtain 2-(3-(4-(cyclopropanecarbonyl)piperazine-1-carbonyl)phenyl)benzo[d]oxazole-7-carboxamide (30 mg, yield 22%). $^1$H-NMR (400 MHz, CD$_3$OD) δ: 0.85-0.92 (m, 4H), 1.29 (m, 1H), 3.20-3.99 (m, 8H), 7.52-7.56 (t, J=8.0 Hz, 1H), 7.74-7.75 (m, 2H), 7.92-7.97 (m, 2H), 8.43-8.47 (m, 2H); LC-MS (ESI) m/z: 419 (M+1)$^+$.

Example 170

2-(4-(Piperidin-3-yl)phenyl)benzo[d]oxazole-7-carboxamide

Example 170 A methyl 2-hydroxy-3-(4-(pyridine-3-yl)enzamido)benzoate

To a solution of 4-boronobenzoic acid (4.15 g, 25 mmol) and 3-bromopyridine (4.3 g, 27.5 mmol) in acetonitrile (60 mL) and water (60 mL), potassium carbonate (13.8 g, 100 mmol), bis(triphenylphosphine)palladium(II) chloride (1.75 g, 2.5 mmol) was added. The mixture was degassed and purged withed nitrogen. The mixture was stirred under reflux for 24 hours. Then the hot suspension was filtered and concentrated to half of the original volume and washed with dichloromethane. The aquatic phase was adjusted to pH=3 with hydrochloric acid (1 M) and filtrated, washed with water. The residue was dried in vacuum to obtain 4 g of white solid of 4-(pyridin-3-yl)benzoic acid. (Yield: 80%. LC-MS (ESI) m/z: 200 (M+1)$^+$). Thionyl chloride (10 ml) was added to 4-(pyridin-3-yl)benzoic acid (4 g, 20 mmol) and the mixture was stirred at 70° C. overnight. The solvent was evaporated under reduced pressure and the residue was dried in vacuum. 4.5 g of crude 4-(pyridin-3-yl)benzoyl chloride was obtained. To a solution of methyl 3-amino-2-hydroxybenzoate (2.9 g, 17 mmol) and pyridine (4 g, 52 mmol) in toluene (50 ml) were added 4-(pyridin-3-yl)benzoyl chloride (4.5 g, 20.4 mmol) portion-wise at 0° C. and then stirred at 70° C. for 4 h. The resulting mixture was extracted with ethyl acetate (100 mL×4), the organic phase was washed with water and saturated sodium bicarbonate, dried with anhydrous sodium sulfate and evaporated under reduced pressure to obtain methyl 2-hydroxy-3-(4-(pyridine-3-yl)enzamido)benzoate as a yellow solid (5 g, yield 85%). LC-MS (ESI) m/z: 349 (M+1)$^+$.

Example 170 B methyl 2-(4-(pyridin-3-yl)phenyl)benzo[d]oxazole-7-carboxylate

A mixture of methyl 2-hydroxy-3-(4-(pyridine-3-yl)enzamido)benzoate (2.8 g, 8 mmol) in propionic acid (100 ml) was stirred at reflux for 3 days. Then the mixture was adjusted to pH=7 by sodium bicarbonate. The mixture was extracted with ethyl acetate. The organic phase was washed with saturated sodium bicarbonate, brine, dried with anhydrous sodium sulfate. The solvent was removed under reduced pressure. The crude products was purified by chromatography (petroleum ether/ethyl acetate 5:1). 600 mg of methyl 2-(4-(pyridin-3-yl)phenyl)benzo[d]oxazole-7-carboxylate was obtained. Yield 23%. LC-MS (ESI) m/z: 331 (M+1)$^+$.

Example 170 C 2-(4-(pyridin-3-yl)phenyl)benzo[d]oxazole-7-carboxamide

Methyl 2-(4-(pyridin-3-yl)phenyl)benzo[d]oxazole-7-carboxylate (600 mg, 1.81 mmol) was added to ammonia in methanol (30 ml) and the mixture was stirred at room temperature for 3 days. Then the solid was filtered, washed with methanol, dried in vacuum. 550 mg 2-(4-(pyridin-3-yl)phenyl)benzo[d]oxazole-7-carboxamide was obtained, yield: 96%. LC-MS (ESI) m/z: 316 (M+1)$^+$.

Example 170 D 2-(4-(piperidin-3-yl)phenyl)benzo[d]oxazole-7-carboxamide 2-(4-(Pyridin-3-yl)phenyl)benzo[d]oxazole-7-carboxamide (550 mg, 1.66 mmol) and platinum (IV) oxide (110 mg) in methanol (100 ml) was hydrogenated under 20 atm of hydrogen at 50° C. for 24 h. Then the mixture was filtered and adjusted pH=9. The solvent was removed in vacuum. The crude was purified by chromatography (dichlormethane:methanol=9:1) to give the solid. The solid was acidified by hydrochloride acid and wash with ethyl acetate. The solvent was removed in vacuum. 260 mg of 2-(4-(piperidin-3-yl)phenyl)benzo[d]oxazole-7-carboxamide was obtained. Yield: 47%. LC-MS (ESI) m/z: 322 (M+1)$^+$.

Example 170 E 2-(4-(1-(2-(dimethylamino)acetyl)piperidin-3-yl)phenyl)benzo[d]oxazole-7-carboxamide To a solution of 2-(dimethylamino)acetic acid (648 mg, 2.02 mmol), 1-ethyl-3-(3-dimethylaminopropyl)carbodiimide hydrochloride (186 mg, 0.97 mmol), 1-hydroxybenzotriazole (131 mg, 0.97 mmol) in N,N'-dimethylformamide (50 ml) was added diisopropylethylamine (280 mg). The mixture was stirred at room temperature for 0.5 h. 2-(4-(Piperidin-3-yl)phenyl)benzo[d]oxazole-7-carboxamide (260 mg, 0.81 mmol) was added to the reaction mixture at 0° C. Then the mixture was stirred at room temperature for 4 h. Then ethyl acetate and water was added to the mixture and extracted. The organic phase was washed with water (50 mL×3), brine (50 mL), dried over anhydrous sodium sulfate, and concentrated to give crude product which was purified by chromatography (silica gel, dichloromethane/methanol=10:1) to give 2-(4-(1-(2-(dimethylamino)acetyl)piperidin-3-yl)phenyl)benzo[d]oxazole-7-carboxamide (50 mg, Yield: 15%). $^1$H-NMR (400 MHz, DMSO-d6) δ: 1.41-1.58 (m, 1H), 1.76-1.84 (m, 2H), 1.96-1.98 (m, 1H), 2.10 (s, 6H), 2.54-2.88 (m, 2H), 2.93-3.09 (m, 2H), 3.14-3.26 (m, 2H), 4.11 (t, J=12 Hz, 1H), 4.44 (t, J=9.2 Hz, 1H), 7.48 (t, J=8.0 Hz, 1H), 7.54-7.57 (dd, J$_1$=8.0 Hz, J$_2$=2.4 Hz, 2H), 7.81 (d, J=8.0 Hz, 1H), 7.87 (brs, 1H), 7.90 (brs, 1H), 7.95 (d, J=7.6 Hz, 1H), 8.24-8.26 (dd, J$_1$=8.0 Hz, J$_2$=5.6 Hz, 2H); LC-MS (ESI) m/z: 407 (M+1)$^+$.

Example 171

2-(1-azabicyclo[3.2.1]octan-5-yl)benzo[d]oxazole-7-carboxamide

Example 171 A 3-(ethoxycarbonyl)piperidinium hydrochloride

To a solution of piperidine-3-carboxylic acid (10.7 g, 83 mmol) in ethanol (40 mL) was added thionyl chloride (22.5 mL) at 0° C. dropwise, the reaction mixture was refluxed overnight. Then the mixture was evaporated at reduced pressure to give 3-(ethoxycarbonyl)piperidinium hydrochloride. (13 g, Y: 100%). LC-MS (ESI) (m/z): 158 (M+1)$^+$.

Example 171 B ethyl 1-(2-chloroethyl)piperidine-3-carboxylate

A solution of 3-(ethoxycarbonyl)piperidinium hydrochloride (10 g, 65 mmol) in acetone was treated with 1-bromo-2-chloroethane (14.7 g, 0.1 mol) and anhydrous potassium carbonate (13.8 g, 0.1 mol) and the mixture stirred at room temperature for 24 h, the mixture was concentrated and the reside was treated with water and extracted with ether. The extracts were combined and concentrated and the crude was purified by chromatography (silica gel, ethyl acetate:petroleum ether 1:5) to give ethyl 1-(2-chloroethyl)piperidine-3-carboxylate. (3.73 g, Y: 26%). $^1$HNMR (400 MHz, CDCl$_3$); δ: 1.25 (t, J=7 Hz, 3H), 1.40-3.10 (m, 11H), 3.58 (t, J=7 Hz, 2H), 4.15 (q, 2H). LC-MS (ESI) (m/z): 220 (M+1)$^+$.

Example 171 C ethyl 1-azabicyclo[3.2.1]octane-5-carboxylate

Ethyl 1-(2-chloroethyl)piperidine-3-carboxylate (3.73 g, 17 mmol) in tetrahydrofuran (30 mL) was cooled to −65° C. under nitrogen; lithium diisopropylamine (17 mL, 2 M in tetrahydrofuran) was added slowly to the solution at −65° C. in 25 min. The mixture was allowed to warm up to room temperature and stirred overnight. The reaction was quenched with potassium carbonate and extracted with ether. The combined organic layer were dried over anhydrous magnesium sulfate, filtered and concentrated. The resulting orange oil was co-evaporated with dichloromethane three times. The extracts were combined and concentrated to give the ethyl 1-azabicyclo[3.2.1]octane-5-carboxylate (1.9 g, yield 61%). $^1$H-NMR (400 MHz, CD$_3$OD) δ: 1.33 (t, 3H), 1.90-2.25 (m, 5H), 2.32-2.47 (m, 1H), 3.20-3.38 (m, 3H), 3.40-3.53 (m, 1H), 3.57-3.80 (m, 2H), 4.20 (q, 2H). LC-MS (ESI) (m/z): 184 (M+1)$^+$.

Example 171 D 5-carboxy-1-azoniabicyclo[3.2.1]octane

A solution of ethyl 1-azabicyclo[3.2.1]octane-5-carboxylate (1.83 g, 10 mmol) in the mixture of tetrahydrofuran (10 mL) and water (10 mL) was treated with lithium hydroxide monohydrate (500 mg, 12 mmol) in water; methanol was added until a transparent solution formed. The solution was heated to 60° C. and stirred overnight. Then the solution was cooled, and acidified with 2N hydrochloric acid to pH=2 and evaporated under reduced pressure, then 8 mL water was added and subsequently concentrated under reduced pressure twice. To the obtained solid residue, 2~3 mL absolute ethanol were added, the resulting mixture was refluxed, then cooled and left in an ice bath for 3 h and filtered, the filtrate was evaporated to dried in vacuum to give 5-carboxy-1-azoniabicyclo[3.2.1]octane (1.5 g, yield 97%). LC-MS (ESI) (m/z): 156 (M+1)$^+$.

Example 171 E 5-(chlorocarbonyl)1-azoniabicyclo[3.2.1]octane

Thionyl chloride (50 ml) was added to 5-carboxy-1-azoniabicyclo[3.2.1]octane ((1.0 g, 5.2 mmol) and the mixture was stirred at 70° C. overnight. The solvent was evaporated under reduced pressure and the residue was dried in vacuum. 1.0 g of 5-(chlorocarbonyl)1-azoniabicyclo[3.2.1]octane was obtained.

Example 171 F methyl 3-(1-azabicyclo[3.2.1]octane-5-carboxamido)-2-hydroxybenzoate A solution of 3-hydroxyanthranilic acid (530 mg, 3.16 mmol) and pyridine (1.26 ml, 15.8 mmol) in toluene (80 mL) and acetonitrile (150 mL) was treated with 5-(chlorocarbonyl)1-azoniabicyclo[3.2.1]octane (800 mg, 3.8 mmol), then stirred at room temperature overnight. The solution was concentrated under vacuum, the crude product was purified by column chromatography, 500 mg of solid of methyl 3-(1-azabicyclo[3.2.1]octane-5-carboxamido)-2-hydroxybenzoate was obtained. Yield: 52%. LC-MS (ESI) (m/z): 305 (M+1)$^+$.

Example 171 G methyl 2-(1-azabicyclo[3.2.1]octan-5-yl)benzo[d]oxazole-7-carboxylate A solution of methyl 3-(1-azabicyclo[3.2.1]octane-5-carboxamido)-2-hydroxybenzoate (500 mg, 1.64 mmol) in proponic acid 10 ml) was heated to reflux for 2 days. The resulting solution was concentrated under vacuum, the crude product was purified by column chromatography (silica gel, petroleum ether/ethyl acetate 20:1 to 2:1), 100 mg methyl 2-(1-azabicyclo[3.2.1]octan-5-yl)benzo[d]oxazole-7-carboxylate was obtained. Yield: 21%. LC-MS (ESI) (m/z): 287 (M+1)$^+$.

Example 171 H 2-(1-azabicyclo[3.2.1]octan-5-yl)benzo[d]oxazole-7-carboxamide

Methyl 2-(1-azabicyclo[3.2.1]octan-5-yl)benzo[d]oxazole-7-carboxylate (80 mg, 0.28 mmol) was added to ammonia in methanol (15 ml) and the mixture was stirred at room temperature for 3 days. Then the solid was filtered, washed with methanol, the residue solution was concentrated under vacuum. Then the residue was purified by flash column chromatography to give 2-(1-azabicyclo[3.2.1]octan-5-yl)benzo[d]oxazole-7-carboxamide (20.6 mg, yield: 27%) $^1$H-NMR (400 MHz, CD$_3$OD) δ: 1.18 (s, 1H), 1.63-1.67 (m, 1H), 1.82 (s, 1H), 1.94-1.98 (m, 1H), 2.10-2.15 (m, 2H), 2.23-2.28 (m, 1H), 2.38-2.44 (m, 1H), 2.91-2.93 (m, 2H), 3.12-3.18 (m, 1H), 3.20-3.30 (m, 1H), 7.34-7.37 (t, J=8 Hz, 1H), 7.72-7.77 (m, 2H), LC-MS (m/z): 272 (M+1)$^+$.

Example 172

2-(4-(2-(methylamino)ethyl)phenyl)benzo[d]oxazole-7-carboxamide

Example 172 A methyl 4-(2-nitrovinyl)benzoate

To a solution of methyl 4-formylbenzoate (34 g, 207 mmol) in nitromethane (500 mL) was added ammonium acetate (24 g, 311 mmol) and then the mixture was stirred at 120° C. for 1 h. Evaporated the solvent and diluted with ethyl acetate, the mixture was hydrolyzed and extracted. The organic layers were dried over anhydrous sodium sulfate and concentrated in vacuo to obtain methyl 4-(2-nitrovinyl)benzoate as a yellow solid (26.6 g, yield 62%). $^1$H-NMR (400 MHz, DMSO-d6) δ (ppm): 3.87 (s, 3H), 7.09-8.04 (m, 4H), 8.17-8.21 (d, J=14 Hz, 1H), 8.30-8.34 (d, J=14 Hz, 1H). LC-MS (ESI) m/z: 208 (M+1)$^+$.

Example 172 B methyl 4-(2-(hydroxyimino)ethyl)benzoate

A mixture of methyl 4-(2-nitrovinyl)benzoate (18.6 g, 90 mmol), paraformaldehyde (3.2 g, 108 mmol) and 10% Pd/C (0.9 g) in the mixture of methanol (220 mL) and tetrahydrofuran (220 mL) was stirred at room temperature over 1 atm of hydrogen for 3 h. Then the mixture was filtered and evaporated, purified by column chromatography (silica gel, petroleum ether/ethyl acetate 15:1 to 8:1) to obtain methyl 4-(2-(hydroxyimino)ethyl)benzoate (3.6 g, yield 21%) as yellow solid. $^1$H-NMR (400 MHz, DMSO-d6) δ (ppm): 3.55-3.56 (d, J=6.0 Hz, 0.5H), 3.69-3.71 (d, J=5.2 Hz, 1.5H), 3.84 (s, 3H), 6.84-6.87 (t, J=5.6 Hz, 0.75H), 7.45-7.47 (t, J=6.2 Hz, 0.25H), 7.37-7.41 (m, 2H), 7.90-7.91 (m, 2H), 10.68 (s, 0.25H), 11.14 (s, 0.75H); LC-MS (ESI) m/z: 194 (M+1)$^+$.

Example 172 C 2-(4-(methoxycarbonyl)phenyl)ethanaminium chloride

A mixture of methyl 4-(2-(hydroxyimino)ethyl)benzoate (3.4 g, 17.6 mmol) and Raney Ni (0.34 g) in the mixture of ethanol (34 mL) and tetrahydrofuran (34 mL) was stirred at room temperature over 1 atm hydrogen overnight. Then the mixture was filtered and evaporated the solvent, and then concentrated hydrochloric acid (3 mL) was added. The solid was washed by ethyl acetate and dried under reduced pressure to obtain a white solid of 2-(4-(methoxycarbonyl)phenyl) ethanaminium chloride (3 g, yield 79%). $^1$H-NMR (400 MHz, DMSO-d6) δ (ppm): 2.91-2.95 (m, 2H), 3.07 (m, 2H), 3.84 (s, 3H), 7.40-7.42 (d, J=8.4 Hz, 2H), 7.86 (s, 3H), 7.91-7.93 (d, J=7.6 Hz, 2H); LC-MS (ESI) m/z: 294 (M+1)$^+$.

Example 172 D methyl 4-(2-(benzyloxycarbonylamino)ethyl)benzoate 2-(4-(Methoxycarbonyl)phenyl)ethanaminium chloride (3 g, 13.9 mmol) was dissolved in the mixed solution of tetrahydrofuran (30 mL) and water (30 mL), and then benzyl chloroformate (2.37 g, 13.9 mmol) was dropped into it. To the mixture, sodium bicarbonate (2.9 g, 34.7 mmol) was added and the mixture was stirred at room temperature for 1.5 h. Then the mixture was poured into ethyl acetate (50 mL×3) and the organic layer was washed with saturated sodium bicarbonate solution, dried with anhydrous sodium sulfate and condensed to get methyl 4-(2-(benzyloxycarbonylamino) ethyl)benzoate (3.3 g, yield 77%). LC-MS (ESI) m/z: 314 (M+1)$^+$.

Example 172 E 4-(2-((benzyloxycarbonyl)(methyl)amino)ethyl)benzoic acid

Methyl 4-(2-(benzyloxycarbonylamino)ethyl)benzoate ((3.2 g, 10.2 mmol) was added to tetrahydrofuran (34 mL) and reacted with methyl iodide (3.8 mL, 61.2 mmol), then sodium hydride (2.0 g, 51 mmol) was added batch-wise and the reaction mixture was stirred for 3 h at room temperature, and then water (1 mL) was added. The mixture was stirred at room temperature for 1 h, adjusted to pH=3 with 1N hydrochloric acid and the mixture was extracted by ethyl acetate (50 mL×3), washed by water and evaporated the solvent. The residue was purified by column chromatography (silica gel, petroleum ether/ethyl acetate 10:1 to 2:1, acetic acid was added) to obtain 4-(2-((benzyloxycarbonyl)(methyl)amino) ethyl)benzoic acid (2.3 g, yield 72%) as yellow oil. $^1$H-NMR (400 MHz, DMSO-d6) δ (ppm): 2.79-2.85 (m, 5H), 3.49 (m, 2H), 4.95-5.04 (t, J=19 Hz, 2H), 7.24-7.37 (m, 7H), 7.83-7.86 (m, 2H), 12.8 (s, 1H); LC-MS (ESI) m/z: 314 (M+1)$^+$.

Example 172 F methyl 3-(4-(2-((benzyloxycarbonyl)(methyl)amino) ethyl)benzamido)-2-hydroxybenzoate To a stirred solution of 4-(2-((benzyloxycarbonyl)(methyl) amino)ethyl)benzoic acid (2.0 g, 6.38 mmol) in anhydrous dichloromethane (30 mL) was added dropwise thionyl chloride (1.52 g, 12.76 mmol) at 0° C. After the addition, the solution was stirred at room temperature overnight. Solvent was removed in vacuum to give benzyl 4-(chlorocarbonyl) phenethyl(methyl)carbamate. To a stirred solution of methyl 3-amino-2-hydroxybenzoate (0.71 g, 4.25 mmol) and pyridine (0.19 mL, 10.2 mmol) in anhydrous toluene (20 mL) was added dropwise a solution of benzyl 4-(chlorocarbonyl)phenethyl(methyl)carbamate (1.7 g, 5.1 mmol) in anhydrous toluene (5 mL). After the addition, the mixture was stirred at room temperature 30 min, then 80° C. for 1 h. The mixture was diluted with toluene, washed with water (30 mL×3), 1N hydrochloric acid (30 mL×3), brine (30 mL), dried over anhydrous sodium sulfate, and concentrated. The residue was purified by column chromatography ((silica gel, petroleum ether/ethyl acetate 15:1 to 4:1), to obtain methyl 3-(4-(2-((benzyloxycarbonyl)(methyl)amino)ethyl)benzamido)-2-hydroxybenzoate (1.9 g, yield 97%) as yellow oil. $^1$H-NMR (400 MHz, DMSO-d6) δ (ppm): 2.82-2.87 (m, 5H), 3.49-3.53 (t, J=7 Hz, 2H), 3.94 (s, 1H), 4.98-5.06 (d, J=32 Hz, 2H), 6.98-7.02 (t, J=8 Hz, 1H), 7.26-7.39 (m, 7H), 7.66-7.68 (d, J=7.6 Hz, 1H), 7.89-7.91 (m, 2H), 7.94-7.96 (d, J=8 Hz, 1H), 9.61 (s, 1H), 10.92 (s, 1H); LC-MS (ESI) m/z: 463 (M+1)$^+$.

Example 172 G methyl 2-(4-(2-((benzyloxycarbonyl)(methyl)amino) ethyl)phenyl)benzo[d]oxazole-7-carboxylate A mixture of methyl 3-(4-(2-((benzyloxycarbonyl)(methyl)amino)ethyl)benzamido)-2-hydroxybenzoate (800 mg, 1.73 mmol) in anhydrous toluene (10 mL) was added anhydrous pyridine (0.76 mL, 9.5 mmol), then thionyl chloride (0.7 ml, 9.5 mmol) was added. The mixture was heated to 110° C. for 2 h. The mixture was cooled to room temperature and poured into ice water (100 mL) carefully with vigorous stirring, then extracted with ethyl acetate (50 mL×3). The organic phase was washed with saturated sodium bicarbonate solution and brine, dried over anhydrous sodium sulfate, and concentrated to give crude product. The crude product was purified by prep-HPLC to give methyl 2-(4-(2-((benzyloxycarbonyl)(methyl)amino)ethyl)phenyl)benzo[d]oxazole-7-carboxylate 200 mg, yield 22%). LC-MS (ESI) m/z: 445 $(M+1)^+$.

Example 172 H benzyl 4-(7-carbamoylbenzo[d]oxazol-2-yl)phenethyl(methyl)carbamate

Methyl 2-(4-(2-((benzyloxycarbonyl)(methyl)amino)ethyl)phenyl)benzo[d]oxazole-7-carboxylate (150 mg, 0.34 mmol) was added to ammonia in methanol (5 ml) and the mixture was stirred at room temperature for 2 days. Evaporate the solvent to obtain benzyl 4-(7-carbamoylbenzo[d]oxazol-2-yl)phenethyl(methyl)carbamate as a white solid (140 mg, yield 96%). $^1$H-NMR (400 MHz, DMSO-d6) δ (ppm): 2.84-2.91 (m, 5H), 3.52-3.56 (t, J=7 Hz, 2H), 4.96-5.05 (d, J=36 Hz, 2H), 7.28-7.42 (m, 6H), 7.47-7.51 (t, J=7.8 Hz, 2H), 7.80-7.82 (d, J=7.6 Hz, 1H), 7.85-7.87 (d, J=8 Hz, 2H), 7.94-7.96 (d, J=8 Hz, 1H), 8.18-8.2 (m, 2H); LC-MS (ESI) m/z: 430 $(M+1)^+$.

Example 172 I

2-(4-(2-(methylamino)ethyl)phenyl)benzo[d]oxazole-7-carboxamide

A mixture of benzyl 4-(7-carbamoylbenzo[d]oxazol-2-yl)phenethyl(methyl)carbamate (110 mg, 0.26 mmol), 10% Pd/C (20 mg) in methanol (20 ml) was stirred at room temperature over 1 atm hydrogen for 3 h. Then the mixture solution was filtered and the filtrate was evaporated under reduced pressure. The residue was purified by prep-HPLC to give 2-(4-(2-(methylamino)ethyl)phenyl)benzo[d]oxazole-7-carboxamide (20 mg, yield 26%). $^1$H-NMR (400 MHz, CD$_3$OD) δ (ppm): 2.45 (s, 3H), 2.91-2.94 (m, 4H), 7.47-7.52 (m, 3 H), 7.88-7.92 (t, J=7.2 Hz, 2H), 8.26-8.28 (d, J=8.4 Hz, 2H). LC-MS (ESI) m/z: 296 $(M+1)^+$.

Example 173

2-(4-(2-(dimethylamino)ethyl)phenyl)benzo[d]oxazole-7-carboxamide

A mixture of benzyl 4-(7-carbamoylbenzo[d]oxazol-2-yl)phenethyl(methyl)carbamate (30 mg, 0.069 mmol), paraformaldehyde (4 mg, 0.14 mmol), and 10% Pd/C (10 mg) in methanol (10 ml) was stirred at room temperature over 1 atm of hydrogen for 4 h. Then the mixture solution was filtered and the filtrate was evaporated under reduced pressure. The residue was purified by prep-HPLC to obtain 2-(4-(2-(dimethylamino)ethyl)phenyl)benzo[d]oxazole-7-carboxamide (10 mg, yield 48%). $^1$H-NMR (400 MHz, CD$_3$OD) δ (ppm): 2.34 (s, 6H), 2.62-2.66 (m, 2H), 2.89-2.93 (m, 2H), 7.46-7.52 (m, 3 H), 7.88-7.91 (m, 2H), 8.224-8.26 (d, J=8.4 Hz, 2H). LC-MS (ESI) m/z: 310 $(M+1)^+$.

Example 174

2-(1-propylpiperidin-3-yl)benzo[d]oxazole-7-carboxamide

A mixture of 2-(piperidin-3-yl)benzo[d]oxazole-7-carboxamide (25 mg, 0.1 mmol), propionaldehyde (9 mg, 0.156 mmol) and 10% Pd/C (10 mg) in methanol (5 ml) was stirred at room temperature over 1 atm hydrogen for 3 h. Then the mixture solution was filtered and the filtrate was evaporated under reduced pressure. The residue was purified by prep-HPLC to obtain 2-(1-propylpiperidin-3-yl)benzo[d]oxazole-7-carboxamide (15 mg, yield 41%). $^1$H-NMR (400 MHz, CDCl$_3$) δ (ppm): 0.88-0.93 (t, J=7.2 Hz, 3H), 1.51-1.61 (m, 2H), 1.72-1.91 (m, 4H), 2.07-2.13 (m, 1H), 2.24-2.27 (m, 1H), 2.38-2.43 (t, J=8 Hz, 2H), 2.91-2.94 (d, J=11.2 Hz, 1H), 3.29-3.35 (m, 2H), 6.26 (s, 1H), 7.0 (s, 1H), 7.41-7.45 (t, J=7.6 Hz, 1H), 7.85-7.87 (d, J=7.6 Hz, 1H), 8.06-8.08 (d, J=8 Hz, 1H). LC-MS (ESI) m/z: 288 $(M+1)^+$.

Example 175

2-(1-propylpiperidin-4-yl)benzo[d]oxazole-7-carboxamide

Example 175 A benzyl 4-(2-hydroxy-3-(methoxycarbonyl)phenylcarbamoyl)piperidine-1-carboxylate To a stirred solution of 1-(benzyloxycarbonyl)piperidine-4-carboxylic acid (2.6 g, 10 mmol) in anhydrous dichloromethane (10 mL) was added dropwise thionyl chloride (10 mL) at 0° C. After the addition, the solution was stirred at room temperature overnight, and then the solvent was removed in vacuum to give benzyl 4-(chlorocarbonyl)piperidine-1-carboxylate. Then it was added to a solution of ethyl 3-amino-2-hydroxybenzoate (1.34 g, 8 mmol) and triethylamine (3 g, 30 mmol) in anhydrous dichloromethane (20 mL) at 0° C. After the addition, the mixture was stirred at room temperature overnight. The mixture was diluted with dichloromethane, washed with water (30 mL×3), brine (30 mL), dried over anhydrous sodium sulfate, and concentrated to give a crude product. The crude product was purified by chromatography (silica gel, petroleum ether/ethyl acetate=20:1 to 2:1) to give benzyl 4-(2-hydroxy-3-(methoxycarbonyl)phenylcarbamoyl)piperidine-1-carboxylate (2.63 g, yield 80%). $^1$H-NMR (400 MHz, CDCl$_3$) δ (ppm): 1.46-1.56 (m, 2H), 1.79-1.82 (d, J=11.6 Hz, 2H), 2.75-2.87 (m, 3H), 3.92 (s, 3H), 4.04-4.07 (d, J=11.2 Hz, 2H), 5.08 (s, 2H), 6.90-6.94 (t, J=8 Hz, 1H), 7.30-7.40 (m, 5H), 7.54-7.56 (m, 1H), 8.09-8.11 (d, J=7.2 Hz, 1H), 9.34 (s, 1H), 10.99 (brs, 1H); LC-MS (ESI) m/z: 413 $(M+1)^+$.

Example 175 B methyl 2-(1-(benzyloxycarbonyl)piperidin-4-yl)benzo[d]oxazole-7-carboxylate

A mixture of benzyl 4-(2-hydroxy-3-(methoxycarbonyl)phenylcarbamoyl)piperidine-1-carboxylate (2.63 g, 6.4 mmol) in propionic acid (10 mL) was heated to reflux for 4 days. The mixture was diluted with water (50 mL), neutralized with sodium bicarbonate, and then extracted with ethyl acetate (50 mL×3). The combined organic layers were washed with brine, dried over anhydrous sodium sulfate, and concentrated to give crude product. The crude product was purified by prep-HPLC to afford methyl 2-(1-(benzyloxycarbonyl)piperidin-4-yl)benzo[d]oxazole-7-carboxylate (560 mg, yield 22%). $^1$H-NMR (400 MHz, CDCl$_3$) δ (ppm): 1.94-1.98 (m, 2H), 2.20-2.23 (m, 2H), 3.07-3.09 (m, 2H), 3.21-3.24 (m, 1H), 4.00 (s, 3H), 4.23 (brs, 2H), 5.16 (s, 2H), 7.32-7.40 (m, 6H), 7.87-7.89 (dd, J$_1$=7.6 Hz, J$_2$=0.8 Hz, 1H), 7.95-7.97 (dd, J$_1$=8.0 Hz, J$_2$=0.8 Hz, 1H); LC-MS (ESI) m/z: 395 (M+1)$^+$.

Example 175 C benzyl 4-(7-carbamoylbenzo[d]oxazol-2-yl)piperidine-1-carboxylate Methyl 2-(1-(benzyloxycarbonyl)piperidin-4-yl)benzo[d]oxazole-7-carboxylate (560 mg, 1.4 mmol) was added to a solution of ammonium in methanol (10 mL) in a sealing tube and the mixture was stirred at room temperature for 2 days. The resulting mixture was evaporated and the crude product was purified by prep-HPLC to give benzyl 4-(7-carbamoyl-benzo[d]oxazol-2-yl)piperidine-1-carboxylate (200 mg, yield 37%). $^1$H-NMR (400 MHz, CDCl$_3$) δ (ppm): 1.94-1.98 (m, 2H), 2.18-2.22 (m, 2H), 3.06-3.12 (m, 2H), 3.20-3.23 (m, 1H), 4.26 (brs, 2H), 5.16 (s, 2H), 6.30 (s, 1H), 6.92 (s, 1H), 7.32-7.38 (m, 5H), 7.42-7.46 (t, J=8.0 Hz, 1H), 7.84-7.87 (dd, J$_1$=8.0 Hz, J$_2$=1.2 Hz, 1H), 8.06-8.08 (dd, J$_1$=8.0 Hz, J$_2$=1.2 Hz, 1H); LC-MS (ESI) m/z: 380 (M+1)$^+$.

Example 175 D 2-(1-propylpiperidin-4-yl)benzo[d]oxazole-7-carboxamide

A mixture of benzyl 4-(7-carbamoylbenzo[d]oxazol-2-yl)piperidine-1-carboxylate (200 mg, 0.53 mmol), propionaldehyde (40 mg, 0.7 mmol) and 10% Pd/C (20 mg) in methanol (20 mL) was stirred at room temperature over 1 atm hydrogen for 4 hr. The mixture was filtered, and evaporated under reduced pressure. The residue was purified by prep-HPLC to give 2-(1-propylpiperidin-4-yl)benzo[d]oxazole-7-carboxamide (71 mg, yield 46%). $^1$H-NMR (400 MHz, DMSO-d6) δ (ppm): 0.84-0.88 (t, J=7.2 Hz, 1H), 1.43-1.48 (m, 2H), 1.83-1.89 (m, 2H), 2.04-2.12 (m, 2H), 2.24-2.28 (m, 2H), 2.88-2.91 (m, 2H), 2.89-3.02 (m, 1H), 7.39-7.73 (t, J=7.6 Hz, 1H), 7.72-7.77 (m, 3H), 7.84-7.85 (d, J=6.8 Hz, 1H); LCMS (ESI) m/z: 288 (M+1)$^+$.

Example 176

2-(2-fluoro-4-(pyridin-4-yl)phenyl)benzo[d]oxazole-7-carboxamide

Example 176 A methyl 3-(2-fluoro-4-(pyridin-4-yl)benzamido)-2-hydroxybenzoate To a solution of 4-bromo-2-fluorobenzoic acid (4.34 g, 20 mmol) and pyridine-4-ylboronic acid (2.45 g, 20 mmol) in acetonitrile (40 mL) and water (40 mL), potassium carbonate (5.52 g, 40 mmol), bis(triphenylphosphine)palladium(II) chloride (1.08 g, 0.05 mmol) was added. The mixture was degassed and purged withed nitrogen. The mixture was stirred at 100° C. for 24 h. Then the hot suspension was filtered and concentrated to half of the original volume and washed with dichloromethane. The aquatic phase was adjusted to pH 3 with hydrochloric acid (1 M) and filtrated, washed with water. The residue was dried in vacuum to obtain 2-fluoro-4-(pyridine-4-yl)benzoic acid as a white solid (3.15 g, yield 72%. LC-MS (ESI) m/z: 218 (M+1)$^+$.) Thionyl chloride (20 mL) was added to 2-fluoro-4-(pyridine-4-yl)benzoic acid (3.15 g, 14.53 mmol) and the mixture was stirred at 70° C. overnight. The solvent was evaporated under reduced pressure and the residue was dried in vacuum giving 2-fluoro-4-(pyridine-4-yl)benzoyl chloride. To a solution of methyl 3-amino-2-hydroxybenzoate (2.42 g, 14.5 mmol) and pyridine (1.2 mL, 14.5 mmol) in toluene (20 mL) was added 2-fluoro-4-(pyridine-4-yl)benzoyl chloride (3.41 g, 14.5 mmol) portion-wise at 0° C. and then stirred at 70° C. for 4 h. The resulting mixture was extracted with ethyl acetate (100 mL×4), the organic phase was washed with water and saturated sodium bicarbonate, dried with anhydrous sodium sulfate and evaporated under reduced pressure to obtain methyl 3-(2-fluoro-4-(pyridin-4-yl)benzamido)-2-hydroxybenzoate as a yellow solid (3.5 g, yield 65%). LC-MS (ESI) m/z: 367 (M+1)$^+$.

Example 176 B methyl 2-(2-fluoro-4-(pyridin-4-yl)phenyl)benzo[d]oxazole-7-carboxylate Methyl 3-(2-fluoro-4-(pyridin-4-yl)benzamido)-2-hydroxybenzoate (2.50 g, 6.83 mmol) and 4-methylbenzenesulfonic acid (3.25 g, 17 mmol) were added to toluene (50 mL) and the mixture was stirred at 118° C. for 2 days. The resulting mixture was extracted with ethyl acetate (100 mL×4) and concentrated. The crude product was purified by column chromatography (silica gel, petroleum ether/ethyl acetate=20:1 to 10:1) to obtain methyl 2-(2-fluoro-4-(pyridin-4-yl)phenyl)benzo[d]oxazole-7-carboxylate as white solid (500 mg, yield 21%). LC-MS (ESI) m/z: 349 (M+1)$^+$.

Example 176 C 2-(2-fluoro-4-(pyridin-4-yl)phenyl)benzo[d]oxazole-7-carboxamide Methyl 2-(2-fluoro-4-(pyridin-4-yl)phenyl)benzo[d]oxazole-7-carboxylate (500 mg, 1.43 mmol) was added to ammonia in methanol (30 mL) and the mixture was stirred at room temperature for 3 days. Then the solid was filtered, washed with methanol and dried in vacuum to obtain 2-(2-fluoro-4-(pyridin-4-yl)phenyl)benzo[d]oxazole-7-carboxamide as white solid (300 mg, yield 62%). $^1$H-NMR (400 MHz, DMSO-d6) δ (ppm): 7.52-7.56 (t, J=7.6 Hz, 1H), 7.85-7.89 (m, 5H), 7.95-7.97 (d, J=8.4 Hz, 1H), 8.03-8.05 (m, 2H), 8.45-8.49 (t, J=7.6 Hz, 1H); 8.72-8.73 (d, J=4.4 Hz, 2H); LC-MS (ESI) m/z: 334 (M+1)$^+$.

Example 177

2-(2-fluoro-4-(piperidin-4-yl)phenyl)benzo[d]oxazole-7-carboxamide 2-(2-Fluoro-4-(pyridin-4-yl)phenyl)benzo[d]oxazole-7-carboxamide (300 mg, 0.9 mmol) and platinum (IV) oxide (150 mg) in methanol (20 mL) was purged with hydrogen (2.5 MPa) at 45° C. for two days. Then the mixture was filtered and the filtrate was concentrated. The crude was purified by prep-HPLC to obtain 2-(2-fluoro-4-(piperidin-4-yl)phenyl)benzo[d]oxazole-7-carboxamide (100 mg, yield 32%). $^1$H-NMR (400 MHz, CD$_3$OD) δ (ppm): 1.93-2.03 (m, 2H), 2.15-2.18 (m, 2H), 2.94-3.20 (m, 3H), 3.52-3.55 (m, 2H), 7.32-7.37 (m, 2H), 7.51-7.55 (t, J=7.6 Hz, 1H), 7.93-7.95 (t, J=7.6 Hz, 2H), 8.29-8.33 (t, J=7.6 Hz, 1H); LC-MS (ESI) m/z: 340 (M+1)$^+$.

Example 178

2-(2-fluoro-4-(1-propylpiperidin-4-yl)phenyl)benzo[d]oxazole-7-carboxamide

A solution of 2-(2-fluoro-4-(piperidin-4-yl)phenyl)benzo[d]oxazole-7-carboxamide (70 mg, 0.2 mmol), 10% Pd/C (30 mg) and propanal (5 mL, 2 mmol) in methanol (10 mL) was purged with hydrogen at room temperature for 2 days. The resulting solution was filtered and the filtrate was concentrated, the residue was purified by prep-HPLC to obtain 2-(2-fluoro-4-(1-propylpiperidin-4-yl)phenyl)benzo[d]oxazole-7-carboxamide (7.4 mg, yield 10%). $^1$H-NMR (400 MHz, CD$_3$OD) δ (ppm): 1.03-1.08 (m, 3H), 1.80-1.86 (m, 2H), 2.01-2.04 (m, 2H), 2.20-2.24 (m, 2H), 3.07-3.18 (m, 5H), 3.72-3.75 (m, 2H), 7.32-7.37 (m, 2H), 7.52-7.56 (t, J=7.6 Hz, 1H), 7.94-7.97 (t, J=7.6 Hz, 2H), 8.30-8.34 (t, J=7.6 Hz, 1H); LC-MS (ESI) m/z: 382 (M+1)$^+$.

Example 179

2-(1-pentylpiperidin-4-yl)benzo[d]oxazol-7-carboxamide

A mixture of compound benzyl 4-(7-carbamoylbenzo[d]oxazol-2-yl)piperidine-1-carboxylate (400 mg, 1.1 mmol), Pd/C (10% wt, 40 mg), pentanal (114 mg, 1.6 mmol) in anhydrous methanol (15 mL) was purged with hydrogen at room temperature for 12 hr. The mixture was filtered and the filtrate was concentrated to give the crude product. The crude product was purified by pre-HPLC to give the compound 2-(1-pentylpiperidin-4-yl)benzo[d]oxazol-7-carboxamide (44 mg, yield 14%). $^1$H-NMR (400 MHz, CDCl$_3$) δ (ppm): 0.91-0.97 (m, 3H), 1.25-1.37 (m, 4H), 1.50-1.57 (m, 2H), 2.03-2.21 (m, 6H), 2.36-2.40 (m, 2H), 3.00-3.06 (m, 3H), 6.11 (s, 1H); 6.99 (s, 1H), 7.85-7.87 (t, 1H), 7.87-8.06 (m, 1H), 8.08 (dd, 1H); LC-MS (ESI) m/z: 316 (M+1)$^+$.

Example 180

2-(1-butylpiperidin-4-yl)benzo[d]oxazol-7-carboxamide

A mixture of benzyl 4-(7-carbamoylbenzo[d]oxazol-2-yl)piperidine-1-carboxylate (400 mg, 1.06 mmol), Pd/C (10% wt, 40 mg), butyraldehyde (96 mg, 1.58 mmol) in anhydrous methanol (15 mL) was purged with hydrogen at room temperature for 12 hr. The mixture was filtered and the filtrate was concentrated to give crude product. The crude product was purified by prep-HPLC to give 2-(1-butylpiperidin-4-yl)benzo[d]oxazol-7-carboxamide (44 mg, yield 13%). $^1$H-NMR (400 MHz, CDCl$_3$) δ (ppm): 0.94 (t, 3H), 1.30-1.48 (m, 2H), 1.48-1.55 (m, 2H), 2.03-2.11 (m, 6H), 2.36-2.41 (m, 2H), 3.00-3.06 (m, 3H), 6.20 (s, 1H); 6.99 (s, 1H), 7.42-7.46 (t, 1H), 7.85-7.87 (m, 1H), 8.07 (dd, 1H); LC-MS (ESI) m/z: 302 (M+1)$^+$.

Example 181

2-(4-(1-propylpiperidin-3-yl)phenyl)benzo[d]oxazole-7-carboxamide

A mixture of 2-(4-(piperidin-3-yl)phenyl)benzo[d]oxazole-7-carboxamide (80 mg, 0.25 mmol) and propionaldehyde (72 mg, 1.25 mmol) in methanol (10 mL) was stirred at room temperature for 40 min. Then the mixture was cooled to 0° C. Sodium borohydride (45 mg, 0.75 mmol) was added. After the addition, the mixture was stirred at this temperature for 2 hr. Methanol was removed under reduced pressure. The residue was washed with ethyl acetate/methanol (10/1) and filtered. The filtrate was concentrated to give the crude product. The crude product was purified by pre-HPLC to give 2-(4-(1-propylpiperidin-3-yl)phenyl)benzo[d]oxazole-7-carboxamide as a light yellow solid (18 mg, yield 23%). $^1$H-NMR (400 MHz, CD$_3$OD) δ (ppm): 0.94 (t, 3H), 1.58-1.64 (m, 3H), 1.81-2.01 (m, 3H), 2.11-2.20 (m, 2H), 2.43 (m, 2H), 2.97 (m, 1H), 3.08 (t, 2H), 7.50-7.54 (m, 3H), 7.91-7.94 (m, 2H), 8.29 (d, 1H); LC-MS (ESI) m/z: 364 (M+1)$^+$.

Example 182

2-(4-(1-propylpiperidin-4-yl)phenyl)benzo[d]oxazole-7-carboxamide

A solution of 2-(4-(piperidin-4-yl)phenyl)benzo[d]oxazole-7-carboxamide (200 mg, 0.62 mmol), 10% Pd/C (50 mg) and propanal (0.8 mL, 1.86 mmol) in methanol (20 mL) was purged with hydrogen at room temperature overnight. The solution was filtered and the filtrate was concentrated, the residue was purified by prep-HPLC to give 2-(4-(1-propylpiperidin-4-yl)phenyl)benzo[d]oxazole-7-carboxamide (53 mg, yield 23%). $^1$H-NMR (400 MHz, CD$_3$OD) δ (ppm): 1.01 (s, 3H), 1.79 (s, 2H), 2.03-2.09 (m, 4H), 3.31-3.34 (m, 2H), 3.67 (s, 2H), 7.30-7.41 (m, 3H), 7.83 (s, 2H), 8.16 (s, 2H); LC-MS (ESI) m/z: 364 (M+1)$^+$.

Example 183

2-(4-(1-(2-(dimethylamoino)acetyl)piperidin-4-yl)phenyl)benzo[d]oxazole-7-carboxamide 2-(Dimethylamino)acetic acid (128 mg, 1.2 mmol) was dissolved in N,N-Dimethylformamide (10 mL), then the solution was added N,N-Diisopropylethylamine (0.5 mL, 2.5 mmol), 1-Ethyl-3-(3-dimethyllaminopropyl)carbodiimide hydrochloride (240 mg, 1.2 mmol), N-Hydroxybenzotriazole (168 mg, 1.2 mmol) and stirred at room temperature for 1 hour. To the resulting solution 2-(4-(piperidin-4-yl)phenyl)benzo[d]oxazole-7-carboxamide (200 mg, 0.62 mmol) was added and then stirred at room temperature overnight. The solution was extracted with ethyl acetate and water, washed with brine and dried with anhydrous sodium sulfate. The organic phase was concentrated, and the residue was purified by prep-HPLC to give 2-(4-(1-(2-(dimethylamoino)acetyl)piperidin-4-yl)phenyl)benzo[d]oxazole-7-carboxamide (46 mg, yield 18%) $^1$H-NMR (400 MHz, CD$_3$OD) δ (ppm): 1.66-1.79 (m, 2H), 1.95-1.97 (m, 2H), 2.83-2.89 (m, 1H), 2.98 (s, 6H), 3.24-3.31 (m, 2H), 3.79-3.83 (d, J=13.2 Hz, 1H), 4.26-4.39 (m, 2H), 4.67-4.70 (d, J=13.6 Hz, 1H), 7.45-7.51 (m, 3H), 7.86-7.90 (m, 2H), 8.22-8.24 (d, J=8.4 Hz, 2H); LC-MS (ESI) m/z: 407 (M+1)$^+$.

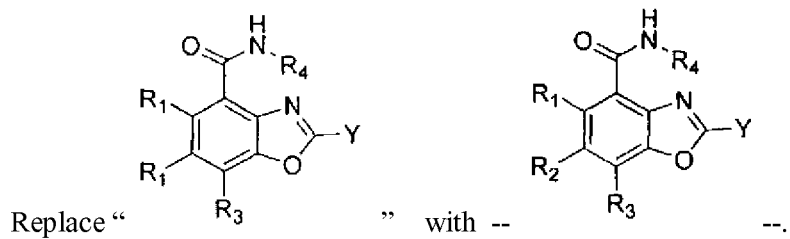

What is claimed is:

1. A compound of Formula (I) or Formula (II):

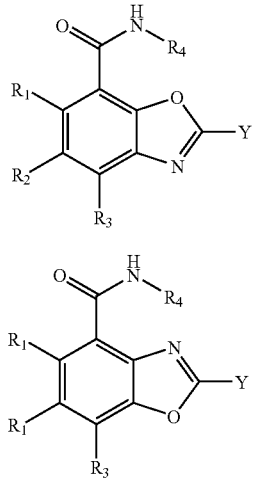

Formula (I)

Formula (II)

wherein:

Y is selected from the group consisting of
a) an aryl group optionally substituted with 1, 2, or 3 $R_5$; wherein each $R_5$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkyl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl, wherein when Y is phenyl, the phenyl is substituted with at least one substituent selected independently from the group consisting of alkoxyalkyl, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, and $(NR_AR_B)$alkyl;
b) a heteroaryl group optionally substituted with 1, 2, or 3 $R_5$; wherein each $R_5$ is as previously defined;
c) a L-T group where L is selected from the group consisting of alkenylene, alkylene, alkynylene, cycloalkylene and spiroheterocycle and T is selected from the group consisting of heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, and $NR_AR_B$;
d) a non-aromatic 4, 5, 6, 7, 8, 9, 10, 11, or 12-membered monocyclic or bicyclic heterocycle ring having 1 or 2 nitrogen atoms and, optionally, one sulfur or oxygen atom, wherein the heterocycle is optionally substituted with 1, 2, or 3 $R_6$; wherein each $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkyl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl and wherein when the heterocycle is bicyclic, the optional substituent(s) are attached to either one or both of the cyclic rings;

$R_1$, $R_2$, and $R_3$, are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkyl, nitro, $NR_CR_D$, and $(NR_CR_D)$carbonyl;

each $R_A$, $R_B$, $R_C$, and $R_D$ is independently selected from the group consisting of hydrogen, alkyl, cycloalkyl, and alkylcarbonyl;

$R_4$, is selected from the group consisting of hydrogen, alkyl, cycloalkyl, alkoxyalkyl, haloalkyl, hydroxyalkyl, and $(NR_AR_B)$alkyl; or stereoisomers, and salts thereof.

2. The compound of claim 1, wherein:

$R_1$, $R_2$, and $R_3$, are each independently selected from the group consisting of hydrogen, halogen, alkenyl, alkoxy, alkoxycarbonyl, alkyl, cycloalkyl, alkynyl, cyano, haloalkoxy, haloalkyl, hydroxyl, hydroxyalkyl, nitro, $NR_CR_D$, and $(NR_CR_D)$carbonyl;

$R_C$, and $R_D$ are each independently selected from the group consisting of hydrogen, alkyl, cycloalkyl, and alkylcarbonyl;

$R_4$, is selected from the group consisting of hydrogen, alkyl, cycloalkyl, alkoxyalkyl, haloalkyl, hydroxyalkyl, and $(NR_AR_B)$alkyl;

Y is selected from the group consisting of:
a) an aryl group optionally substituted with 1, 2, or 3 $R_5$; wherein each $R_5$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkyl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl, wherein when Y is phenyl, the phenyl is substituted with at least one substituent selected independently from the group consisting of alkoxyalkyl, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, and $(NR_AR_B)$alkyl;
b) a heteroaryl group optionally substituted with 1, 2, or 3 $R_5$; wherein each $R_5$ is as previously defined;
c) a L-T group where L is selected from the group consisting of alkenylene, alkylene, alkynylene, cycloalkylene and spiroheterocycle and T is selected from the group consisting of heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, and $NR_AR_B$;
d) a non-aromatic 4, 5, 6, 7, 8, 9, 10, 11, or 12-membered monocyclic or bicyclic heterocycle ring having 1 or 2 nitrogen atoms and, optionally, one sulfur or oxygen atom; selected from the group consisting of

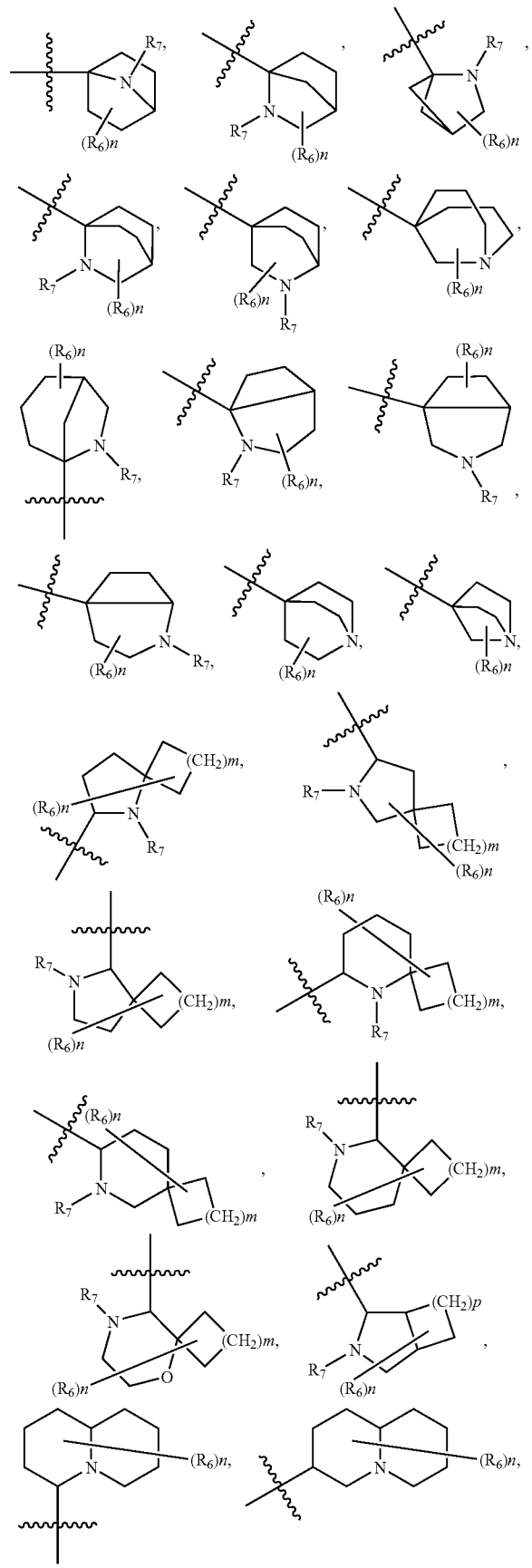

-continued

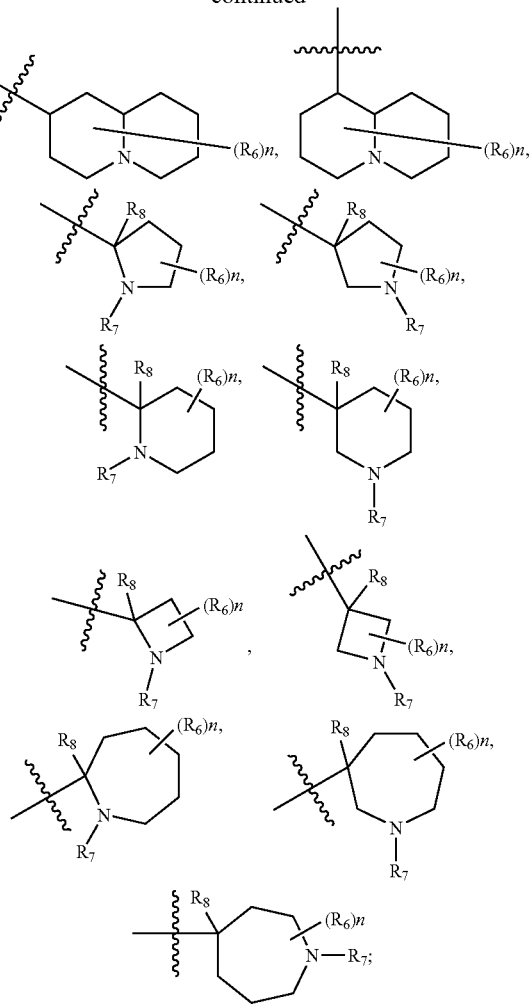

wherein
n is 0, 1, 2 or 3;
m is 0, 1, 2 or 3;
p is 0, 1, 2 or 3;
each $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl;
$R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl;
$R_8$ is selected from the group consisting of hydrogen, alkyl, alkynyl, alkenyl, alkoxyalkyl, cycloalkyl, haloalkyl, and hydroxyl-$C_2$-$C_6$ alkyl; and
$R_A$, and $R_B$ are independently selected from the group consisting of hydrogen, alkyl, cycloalkyl, and alkylcarbonyl.

3. The compound of claim 1, wherein:

$R_1$, $R_2$, $R_3$, and $R_4$ are hydrogen;

Y is selected from the group consisting of a) an aryl group optionally substituted with 1, 2, or 3 substituents $R_5$; wherein each $R_5$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkyl, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl, wherein when Y is phenyl, the phenyl is substituted with at least one substituent selected independently from the group consisting of alkoxyalkyl, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, and $(NR_AR_B)$alkyl;

b) a heteroaryl group optionally substituted with 1, 2, or 3 $R_5$; wherein each $R_5$ is as previously defined;

c) a L-T group where L is selected from the group consisting of alkenylene, alkylene, alkynylene, cycloalkylene and spiroheterocycle and T is selected from the group consisting of heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, and $NR_AR_B$;

d) a non-aromatic 4, 5, 6, 7, 8, 9, 10, 11, or 12-membered monocyclic or bicyclic heterocycle ring having 1 or 2 nitrogen atoms and, optionally, one sulfur or oxygen atom; selected from the group consisting of:

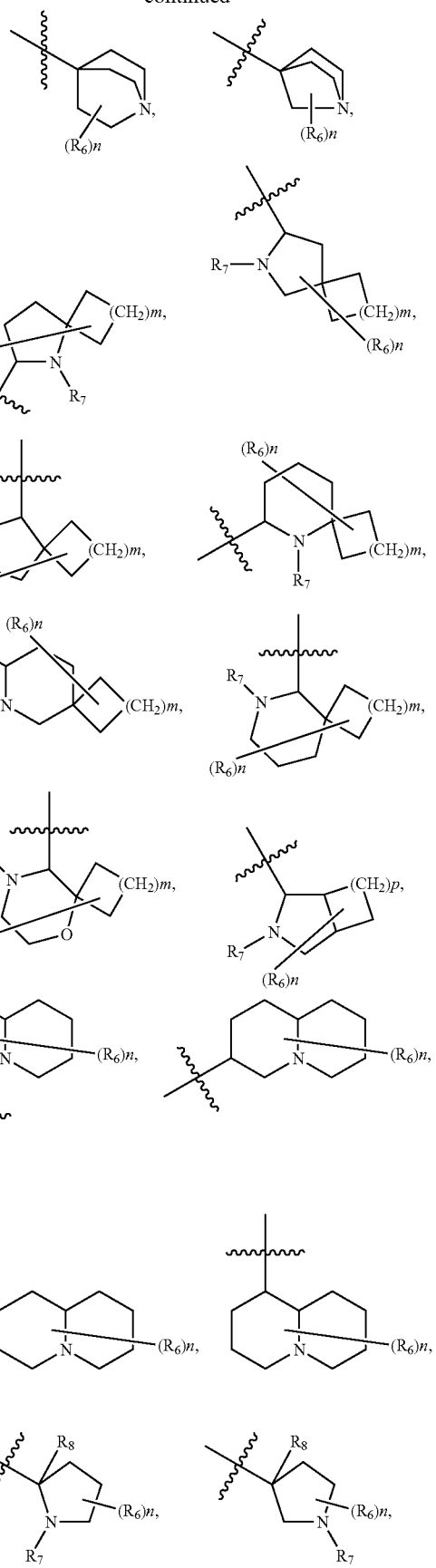

-continued

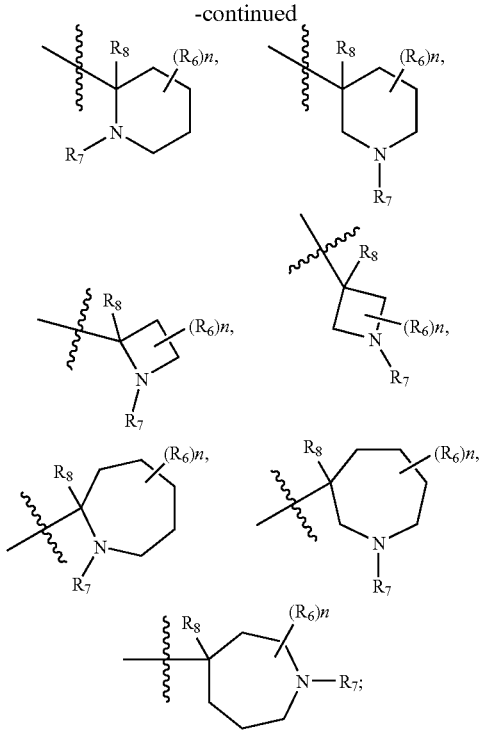

wherein
n is 0, 1, 2 or 3;
m is 0, 1, 2 or 3;
p is 0, 1, 2 or 3;
each $R_6$ is selected independently from the group consisting of alkenyl, alkoxy, alkoxyalkyl, alkoxycarbonyl, alkoxycarbonylalkyl, alkyl, alkynyl, aryl, arylalkyl, cycloalkyl, cycloalkylalkyl, cyano, haloalkoxy, haloalkyl, halogen, hydroxyl, hydroxyalkyl, nitro, oxo, heteroaryl, heteroarylalkoxy, heteroaryloxy, heteroarylthio, heteroarylalkylthio, heterocycle, heterocycloalkoxy, heterocycloalkylthio, heterocyclooxy, heterocyclothio, $NR_AR_B$, $(NR_AR_B)$alkyl, $(NR_AR_B)$carbonyl, $(NR_AR_B)$carbonylalkyl, and $(NR_AR_B)$sulfonyl;
$R_7$ is selected from the group consisting of hydrogen, alkenyl, alkoxy, alkoxyalkyl, alkoxycarbonyl, alkoxycarbonylalkyl, alkyl, alkynyl, aryl, arylalkyl, cycloalkyl, cycloalkylalkyl, haloalkyl, hydroxyalkyl, oxo, heteroaryl, heterocycle, heterocycloalkyl, $(NR_AR_B)$alkyl, $(NR_AR_B)$carbonyl, $(NR_AR_B)$carbonylalkyl, and $(NR_AR_B)$sulfonyl;
$R_8$ is selected from the group consisting of hydrogen, alkyl, alkynyl, alkenyl, alkoxyalkyl, cycloalkyl, haloalkyl, hydroxyl-$C_2$-$C_6$ alkyl; and
$R_A$, and $R_B$ are each independently selected from the group consisting of hydrogen, alkyl, cycloalkyl, and alkylcarbonyl.

4. The compound of claim 3, wherein:
n is 0;
$R_7$ is hydrogen; and
$R_8$ is hydrogen.

5. The compound of claim 3, wherein:
n is 0;
$R_7$ is hydrogen; and
$R_8$ is methyl.

6. The compound of claim 2, wherein Y is selected from the group consisting of

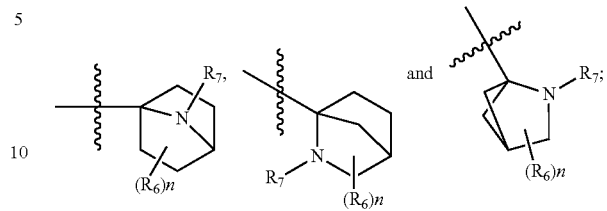

$R_1$, $R_2$, $R_3$, and $R_4$ are hydrogen;
n is 0; and
$R_7$ is selected from the group consisting of hydrogen, alkoxyalkyl, alkyl, aryl, arylalkyl, cycloalkyl, haloalkyl, $(NR_AR_B)$alkyl, and $(NR_AR_B)$sulfonyl; and
$R_A$, and $R_B$ are each independently selected from the group consisting of hydrogen, alkyl, and cycloalkyl.

7. The compound of claim 2, wherein Y is selected from the group consisting of

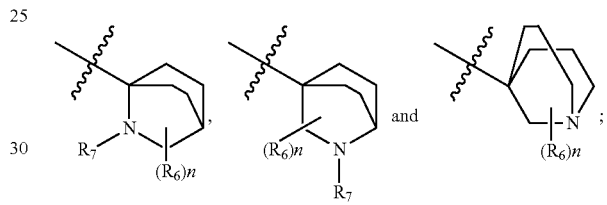

$R_1$, $R_2$, $R_3$, and $R_4$ are hydrogen;
n is 0;
$R_7$ is selected from the group consisting of hydrogen, alkoxyalkyl, alkyl, aryl, arylalkyl, cycloalkyl, haloalkyl, $(NR_AR_B)$alkyl, and $(NR_AR_B)$sulfonyl; and
$R_A$, and $R_B$ are each independently selected from the group consisting of hydrogen, alkyl, and cycloalkyl.

8. The compound of claim 2, wherein Y is selected from the group consisting of

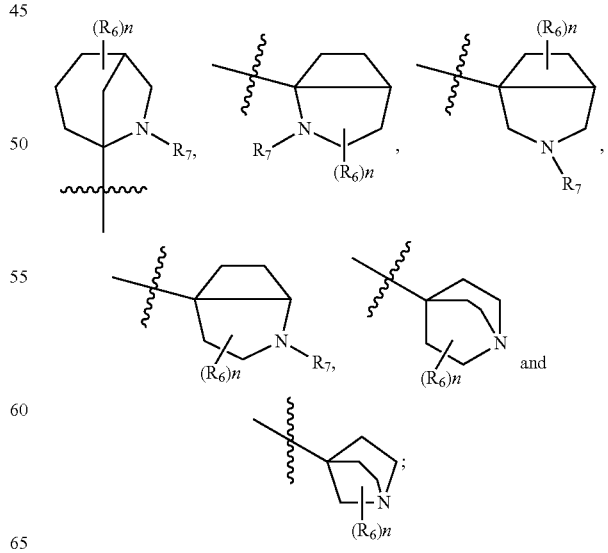

$R_1$, $R_2$, $R_3$, and $R_4$ are hydrogen;

n is 0;

$R_7$ is selected from the group consisting of hydrogen, alkoxyalkyl, alkyl, aryl, arylalkyl, cycloalkyl, haloalkyl, $(NR_AR_B)$alkyl, and $(NR_AR_B)$sulfonyl; and $R_A$, and $R_B$ are each independently selected from the group consisting of hydrogen, alkyl, and cycloalkyl.

9. The compound of claim 2, wherein Y is selected from the group consisting of

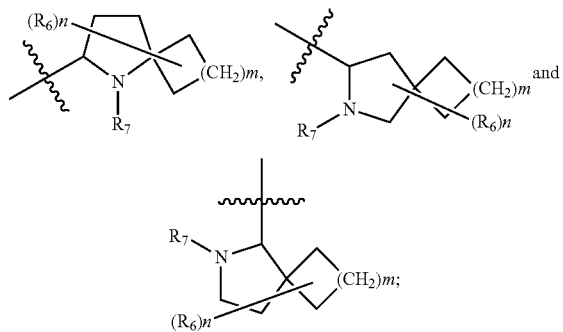

$R_1$, $R_2$, $R_3$, and $R_4$ are hydrogen;

m is 0, 1, 2, or 3;

n is 0;

$R_7$ is selected from the group consisting of hydrogen, alkoxyalkyl, alkyl, aryl, arylalkyl, cycloalkyl, haloalkyl, $(NR_AR_B)$alkyl, and $(NR_AR_B)$sulfonyl; and $R_A$, and $R_B$ are each independently selected from the group consisting of hydrogen, alkyl, and cycloalkyl.

10. The compound of claim 2, wherein Y is selected from the group consisting of

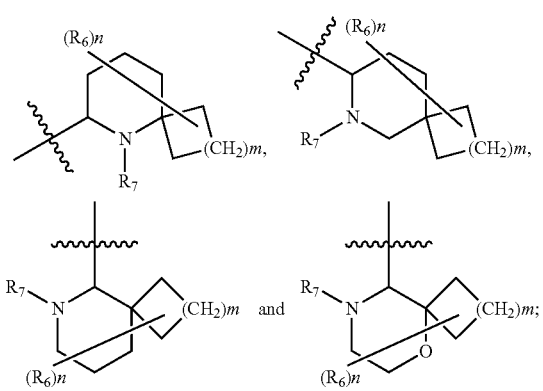

$R_1$, $R_2$, $R_3$, and $R_4$ are hydrogen;

m is 0, 1, 2, or 3;

n is 0;

$R_7$ is selected from the group consisting of hydrogen, alkoxyalkyl, alkyl, aryl, arylalkyl, cycloalkyl, haloalkyl, $(NR_AR_B)$alkyl, and $(NR_AR_B)$sulfonyl; and $R_A$, and $R_B$ are each independently selected from the group consisting of hydrogen, alkyl, and cycloalkyl.

11. The compound of claim 3, wherein Y is

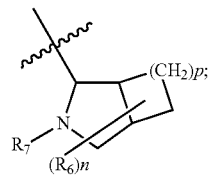

$R_1$, $R_2$, $R_3$, and $R_4$ are hydrogen;

n is 0;

p is 0, 1, 2, or 3;

$R_7$ is selected from the group consisting of hydrogen, alkoxyalkyl, alkyl, aryl, arylalkyl, cycloalkyl, haloalkyl, $(NR_AR_B)$alkyl, and $(NR_AR_B)$sulfonyl; and $R_A$, and $R_B$ are each independently selected from the group consisting of hydrogen, alkyl and cycloalkyl.

12. The compound of claim 3, wherein Y is selected from the group consisting of

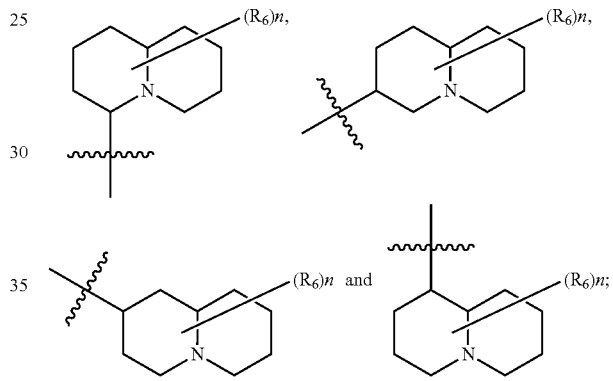

$R_1$, $R_2$, $R_3$, and $R_4$ are hydrogen; and n is 0.

13. The compound of claim 3, wherein Y is selected from the group consisting of

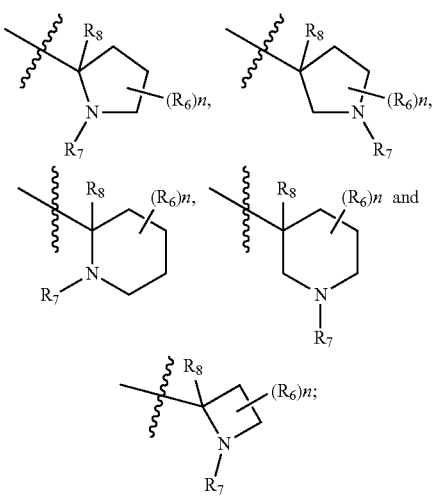

R$_1$, R$_2$, R$_3$, and R$_4$ are hydrogen;
n is 0;
R$_7$ is selected from the group consisting of hydrogen, alkoxyalkyl, alkyl, aryl, arylalkyl, cycloalkyl, haloalkyl, (NR$_A$R$_B$)alkyl, and (NR$_A$R$_B$)sulfonyl;
R$_8$ is methyl or hydrogen; and
R$_A$, and R$_B$ are each independently selected from the group consisting of hydrogen, alkyl, and cycloalkyl.

14. The compound of claim 3, wherein Y is selected from the group consisting of

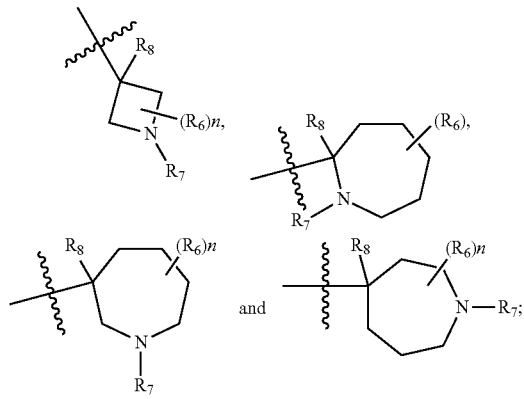

R$_1$, R$_2$, R$_3$, and R$_4$ are hydrogen;
n is 0;
R$_7$ is selected from the group consisting of hydrogen, alkoxyalkyl, alkyl, aryl, arylalkyl, cycloalkyl, haloalkyl, (NR$_A$R$_B$)alkyl, and (NR$_A$R$_B$)sulfonyl;
R$_8$ is methyl or hydrogen; and
R$_A$, and R$_B$ are each independently selected from the group consisting of hydrogen, alkyl, and cycloalkyl.

15. The compound of claim 2, wherein Y is phenyl substituted with (NR$_A$R$_B$)alkyl.

16. The compound of claim 2, wherein Y is phenyl substituted with substituted or unsubstituted heterocycle.

17. The compound of claim 2, wherein Y is the heteroaryl group optionally substituted with 1, 2, or 3 R$_5$.

18. The compound of claim 17, wherein the heteroaryl group is a pyridinyl group.

19. The compound of claim 2, wherein Y is the L-T group.

20. A compound selected from the group consisting of:
2-(4-((Methylamino)methyl)phenyl)benzo[d]oxazole-4-carboxamide;
2-(2-Methylpyrrolidin-2-yl)benzo[d]oxazole-4-carboxamide;
2-(4-((Methylamino)methyl)phenyl)benzo[d]oxazole-7-carboxamide;
2-(2-Methylpyrrolidin-2-yl)benzo[d]oxazole-7-carboxamide;
2-(Pyrrolidin-2-yl)benzo[d]oxazole-4-carboxamide;
2-(Pyrrolidin-2-yl)benzo[d]oxazole-7-carboxamide;
2-(7-Azabicyclo[2.2.1]heptan-1-yl)benzo[d]oxazole-4-carboxamide;
2-(7-Azabicyclo[2.2.1]heptan-1-yl)benzo[d]oxazole-7-carboxamide;
2-(2-Methyl-7-azabicyclo[2.2.1]heptan-1-yl)benzo[d]oxazole-4-carboxamide;
2-(2-Methyl-7-azabicyclo[2.2.1]heptan-1-yl)benzo[d]oxazole-7-carboxamide;
2-(2-Azabicyclo[2.1.1]hexan-1-yl)benzo[d]oxazole-4-carboxamide;
2-(2-Azabicyclo[2.1.1]hexan-1-yl)benzo[d]oxazole-7-carboxamide;
2-(6-Azabicyclo[3.2.1]octan-5-yl)benzo[d]oxazole-4-carboxamide;
2-(6-Azabicyclo[3.2.1]octan-5-yl)benzo[d]oxazole-7-carboxamide;
2-((1S,5R)-6-Azabicyclo[3.2.1]octan-5-yl)benzo[d]oxazole-4-carboxamide;
2-((1S,5R)-6-Azabicyclo[3.2.1]octan-5-yl)benzo[d]oxazole-7-carboxamide;
2-((1R,5S)-6-Azabicyclo[3.2.1]octan-5-yl)benzo[d]oxazole-4-carboxamide;
2-((1R,5S)-6-Azabicyclo[3.2.1]octan-5-yl)benzo[d]oxazole-7-carboxamide;
2-(2-Benzyl-2-azabicyclo[2.2.2]octan-1-yl)benzo[d]oxazole-4-carboxamide;
2-(2-Benzyl-2-azabicyclo[2.2.2]octan-1-yl)benzo[d]oxazole-7-carboxamide;
2-(2-Azabicyclo[2.2.2]octan-1-yl)benzo[d]oxazole-4-carboxamide;
2-(2-Azabicyclo[2.2.2]octan-1-yl)benzo[d]oxazole-7-carboxamide;
2-(4-Azaspiro[2.4]heptan-5-yl)benzo[d]oxazole-4-carboxamide;
2-(4-Azaspiro[2.4]heptan-5-yl)benzo[d]oxazole-7-carboxamide;
2-((1R,4S)-2-Methyl-2-azabicyclo[2.2.1]heptan-1-yl)benzo[d]oxazole-4-carboxamide;
2-((1R,4S)-2-Methyl-2-azabicyclo[2.2.1]heptan-1-yl)benzo[d]oxazole-7-carboxamide;
2-((1R,4S)-2-Ethyl-2-azabicyclo[2.2.1]heptan-1-yl)benzo[d]oxazole-4-carboxamide;
2-((1R,4S)-2-Ethyl-2-azabicyclo[2.2.1]heptan-1-yl)benzo[d]oxazole-7-carboxamide;
2-((1R,4S)-2-Cyclopropyl-2-azabicyclo[2.2.1]heptan-1-yl)benzo[d]oxazole-4-carboxamide;
2-((1R,4S)-2-Cyclopropyl-2-azabicyclo[2.2.1]heptan-1-yl)benzo[d]oxazole-7-carboxamide;
2-(2-Azabicyclo[2.2.1]heptan-1-yl)benzo[d]oxazole-4-carboxamide;
2-(2-Azabicyclo[2.2.1]heptan-1-yl)benzo[d]oxazole-7-carboxamide;
2-(7-Azabicyclo[2.2.1]heptan-1-yl)-5-chlorobenzo[d]oxazole-4-carboxamide;
2-(7-Azabicyclo[2.2.1]heptan-1-yl)-5-chlorobenzo[d]oxazole-7-carboxamide;
2-(2-Azabicyclo[2.2.1]heptan-1-yl)-5-chlorobenzo[d]oxazole-4-carboxamide;
2-(2-Azabicyclo[2.2.1]heptan-1-yl)-5-chlorobenzo[d]oxazole-7-carboxamide;
2-(1-Azabicyclo[2.2.1]heptan-4-yl)benzo[d]oxazole-4-carboxamide;
2-(1-Azabicyclo[2.2.1]heptan-4-yl)benzo[d]oxazole-7-carboxamide;
2-(Quinuclidin-4-yl)benzo[d]oxazole-4-carboxamide;
2-(Quinuclidin-4-yl)benzo[d]oxazole-7-carboxamide;
2-(1-Azabicyclo[3.3.1]nonan-5-yl)benzo[d]oxazole-4-carboxamide;
2-(1-Azabicyclo[3.3.1]nonan-5-yl)benzo[d]oxazole-7-carboxamide;
2-(Octahydro-1H-quinolizin-2-yl)benzo[d]oxazole-4-carboxamide;
2-(Octahydro-1H-quinolizin-2-yl)benzo[d]oxazole-7-carboxamide;
2-(Octahydro-1H-quinolizin-1-yl)benzo[d]oxazole-4-carboxamide;

2-(Octahydro-1H-quinolizin-1-yl)benzo[d]oxazole-7-carboxamide;
2-(Octahydro-1H-quinolizin-4-yl)benzo[d]oxazole-4-carboxamide;
2-(Octahydro-1H-quinolizin-4-yl)benzo[d]oxazole-7-carboxamide;
2-(Octahydro-1H-quinolizin-3-yl)benzo[d]oxazole-4-carboxamide;
2-(Octahydro-1H-quinolizin-3-yl)benzo[d]oxazole-7-carboxamide;
2-(Octahydrocyclopenta[c]pyrrol-1-yl)benzo[d]oxazole-4-carboxamide;
2-(Octahydrocyclopenta[c]pyrrol-1-yl)benzo[d]oxazole-7-carboxamide;
2-(2-Azabicyclo[2.2.1]heptan-4-yl)benzo[d]oxazole-4-carboxamide;
2-(2-Azabicyclo[2.2.1]heptan-4-yl)benzo[d]oxazole-7-carboxamide;
2-(2-Oxa-5-Azabicyclo[2.2.1]heptan-4-yl)benzo[d]oxazole-4-carboxamide;
2-(2-Oxa-5-Azabicyclo[2.2.1]heptan-4-yl)benzo[d]oxazole-7-carboxamide;
2-(2-Azabicyclo[2.2.2]octan-4-yl)benzo[d]oxazole-4-carboxamide;
2-(2-Azabicyclo[2.2.2]octan-4-yl)benzo[d]oxazole-7-carboxamide;
2-(3-Azabicyclo[3.2.0]heptan-1-yl)benzo[d]oxazole-4-carboxamide;
2-(3-Azabicyclo[3.2.0]heptan-1-yl)benzo[d]oxazole-7-carboxamide;
2-(2-Azabicyclo[3.2.0]heptan-1-yl)benzo[d]oxazole-4-carboxamide;
2-(2-Azabicyclo[3.2.0]heptan-1-yl)benzo[d]oxazole-7-carboxamide;
2-(2-Azabicyclo[3.2.0]heptan-4-yl)benzo[d]oxazole-4-carboxamide;
2-(2-Azabicyclo[3.2.0]heptan-4-yl)benzo[d]oxazole-7-carboxamide;
2-(2-Azabicyclo[3.2.0]heptan-3-yl)benzo[d]oxazole-4-carboxamide;
2-(2-Azabicyclo[3.2.0]heptan-3-yl)benzo[d]oxazole-7-carboxamide;
2-(5-Azaspiro[2.4]heptan-6-yl)benzo[d]oxazole-4-carboxamide;
2-(5-Azaspiro[2.4]heptan-6-yl)benzo[d]oxazole-7-carboxamide;
2-(4-Azaspiro[2.4]heptan-6-yl)benzo[d]oxazole-4-carboxamide;
2-(4-Azaspiro[2.4]heptan-6-yl)benzo[d]oxazole-7-carboxamide;
2-(6-Azaspiro[3.4]octan-7-yl)benzo[d]oxazole-4-carboxamide;
2-(6-Azaspiro[3.4]octan-7-yl)benzo[d]oxazole-7-carboxamide;
2-(5-Azaspiro[3.4]octan-6-yl)benzo[d]oxazole-4-carboxamide;
2-(5-Azaspiro[3.4]octan-6-yl)benzo[d]oxazole-7-carboxamide;
2-(5-Azaspiro[3.4]octan-7-yl)benzo[d]oxazole-4-carboxamide;
2-(5-Azaspiro[3.4]octan-7-yl)benzo[d]oxazole-7-carboxamide;
2-(6-Azaspiro[2.5]octan-5-yl)benzo[d]oxazole-4-carboxamide;
2-(6-Azaspiro[2.5]octan-5-yl)benzo[d]oxazole-7-carboxamide;
2-(4-Azaspiro[2.5]octan-5-yl)benzo[d]oxazole-4-carboxamide;
2-(4-Azaspiro[2.5]octan-5-yl)benzo[d]oxazole-7-carboxamide;
2-(5-Azaspiro[2.5]octan-7-yl)benzo[d]oxazole-4-carboxamide;
2-(5-Azaspiro[2.5]octan-7-yl)benzo[d]oxazole-7-carboxamide;
2-(4-Oxa-7-azaspiro[2.5]octan-5-yl)benzo[d]oxazole-4-carboxamide;
2-(4-Oxa-7-azaspiro[2.5]octan-5-yl)benzo[d]oxazole-7-carboxamide;
2-(4-Azaspiro[2.5]octan-7-yl)benzo[d]oxazole-4-carboxamide;
2-(4-Azaspiro[2.5]octan-7-yl)benzo[d]oxazole-7-carboxamide;
2-(5-Azaspiro[3.5]nonan-6-yl)benzo[d]oxazole-4-carboxamide;
2-(5-Azaspiro[3.5]nonan-6-yl)benzo[d]oxazole-7-carboxamide;
2-(6-Azaspiro[3.5]nonan-8-yl)benzo[d]oxazole-4-carboxamide;
2-(6-Azaspiro[3.5]nonan-8-yl)benzo[d]oxazole-7-carboxamide;
2-(7-Azaspiro[3.5]nonan-6-yl)benzo[d]oxazole-4-carboxamide;
2-(7-Azaspiro[3.5]nonan-6-yl)benzo[d]oxazole-7-carboxamide;
2-(5-Azaspiro[3.5]nonan-8-yl)benzo[d]oxazole-4-carboxamide;
2-(5-Azaspiro[3.5]nonan-8-yl)benzo[d]oxazole-7-carboxamide;
2-(8-Oxa-5-azaspiro[3.5]nonan-6-yl)benzo[d]oxazole-4-carboxamide;
2-(8-Oxa-5-azaspiro[3.5]nonan-6-yl)benzo[d]oxazole-7-carboxamide;
2-(5-Oxa-5-azaspiro[3.5]nonan-6-yl)benzo[d]oxazole-4-carboxamide;
2-(5-Oxa-5-azaspiro[3.5]nonan-6-yl)benzo[d]oxazole-7-carboxamide;
2-(2,3,4,6,7,9a-Hexahydro-1H-quinolizin-2-yl)benzo[d]oxazole-4-carboxamide;
2-(2,3,4,6,7,9a-Hexahydro-1H-quinolizin-2-yl)benzo[d]oxazole-7-carboxamide;
2-(Decahydropyrido[1,2-a]azepin-4-yl)benzo[d]oxazole-4-carboxamide;
2-(Decahydropyrido[1,2-a]azepin-4-yl)benzo[d]oxazole-7-carboxamide;
2-(2-fluoro-4-(pyridine-2-yl)phenyl)benzo[d]oxazole-7-carboxamide;
2-(2-fluoro-4-(piperidin-2-yl)phenyl)benzo[d]oxazole-7-carboxamide;
2-(2-fluoro-4-(1-propylpiperidin-2-yl)phenyl)benzo[d]oxazole-7-carboxamide;
2-(2-fluoro-4-(pyrrolidin-2-yl)phenyl)benzo[d]oxazole-7-carboxamide;
2-(4-((methylamino)methyl)phenyl)benzo[d]oxazole-4-carboxamide;
2-(pyridin-4-yl)benzo[d]oxazole-4-carboxamide;
2-(pyridin-3-yl)benzo[d]oxazole-4-carboxamide;
2-(4-((methylamino)methyl)phenyl)benzo[d]oxazole-7-carboxamide;
5-fluoro-2-(4-((methylamino)methyl)phenyl)benzo[d]oxazole-7-carboxamide;
2-(4-((dimethylamino)methyl)phenyl)benzo[d]oxazole-7-carboxamide;

2-(4-(piperazin-1-ylmethyl)phenyl)benzo[d]oxazole-7-carboxamide;
2-(3-((methylamino)methyl)phenyl)benzo[d]oxazole-7-carboxamide;
2-(3-((dimethylamino)methyl)phenyl)benzo[d]oxazole-7-carboxamide;
2-(3-(pyrrolidin-1-ylmethyl)phenyl)benzo[d]oxazole-7-carboxamide;
2-(3-(piperazin-1-ylmethyl)phenyl)benzo[d]oxazole-7-carboxamide;
2-(3-((2-(dimethylamino)ethylamino)methyl)phenyl)benzo[d]oxazole-7-carboxamide;
2-(pyridin-4-yl)benzo[d]oxazole-7-carboxamide;
2-(pyridin-3-yl)benzo[d]oxazole-7-carboxamide;
2-(1H-indol-2-yl)benzo[d]oxazole-7-carboxamide;
2-(4-methoxyphenylbenzo[d]oxazole-4-carboxamide;
2-(4-methoxyphenylbenzo[d]oxazole-7-carboxamide;
2-(4-((dimethylamino)methyl)phenyl)benzo[d]oxazole-4-carboxamide;
2-(4-((dimethylamino)methyl)phenyl)-5-fluorobenzo[d]oxazole-7-carboxamide;
2-(4-((methoxyamino)methyl)phenyl)benzo[d]oxazole-7-carboxamide;
2-(4-((methoxy(methyl)amino)methyl)phenyl)benzo[d]oxazole-7-carboxamide;
5-fluoro-2-(4-((methoxyamino)methyl)phenyl)benzo[d]oxazole-7-carboxamide;
5-fluoro-2-(4-((methoxy(methyl)amino)methyl)phenyl)benzo[d]oxazole-7-carboxamide;
2-(pyrrolidin-2-yl)benzo[d]oxazole-7-carboxamide;
2-(piperidin-4-yl)benzo[d]oxazole-7-carboxamide;
2-(azetidin-3-yl)benzo[d]oxazole-7-carboxamide;
2-(piperidin-3-yl)benzo[d]oxazole-7-carboxamide;
2-(2-methylpyrrolidin-2-yl)benzo[d]oxazole-7-carboxamide;
2-(4-(pyridin-2-yl)phenyl)benzo[d]oxazole-7-carboxamide;
2-(4-(piperidin-2-yl)phenyl)benzo[d]oxazole-7-carboxamide;
2-(4-(pyridin-3-yl)phenyl)benzo[d]oxazole-7-carboxamide;
2-(4-(piperidin-3-yl)phenyl)benzo[d]oxazole-7-carboxamide;
2-(4-(pyridin-4-yl)phenyl)benzo[d]oxazole-7-carboxamide;
2-(4-(piperidin-4-yl)phenyl)benzo[d]oxazole-7-carboxamide;
2-(3-(pyridin-2-yl)phenyl)benzo[d]oxazole-7-carboxamide;
2-(3-(piperidin-2-yl)phenyl)benzo[d]oxazole-7-carboxamide;
2-(3-(pyridin-3-yl)phenyl)benzo[d]oxazole-7-carboxamide;
2-(3-(piperidin-3-yl)phenyl)benzo[d]oxazole-7-carboxamide;
2-(3-(pyridin-4-yl)phenyl)benzo[d]oxazole-7-carboxamide;
2-(3-(piperidin-4-yl)phenyl)benzo[d]oxazole-7-carboxamide;
2-((1-(2-dimethylamino)acetyl)piperidin-3-yl)benzo[d]oxazole-7-carboxamide;
2-(3-(4-isobutyrylpiperazine-1-carbonyl)phenyl)benzo[d]oxazole-7-carboxamide;
2-(3-(4-(cyclopropanecarbonyl)piperazine-1-carbonyl)phenyl)benzo[d]oxazole-7-carboxamide;
2-(4-(Piperidin-3-yl)phenyl)benzo[d]oxazole-7-carboxamide;
2-(1-azabicyclo[3.2.1]octan-5-yl)benzo[d]oxazole-7-carboxamide;
2-(4-(2-(methylamino)ethyl)phenyl)benzo[d]oxazole-7-carboxamide;
2-(4-(2-(dimethylamino)ethyl)phenyl)benzo[d]oxazole-7-carboxamide;
2-(1-propylpiperidin-3-yl)benzo[d]oxazole-7-carboxamide;
2-(1-propylpiperidin-4-yl)benzo[d]oxazole-7-carboxamide;
2-(2-fluoro-4-(pyridin-4-yl)phenyl)benzo[d]oxazole-7-carboxamide;
2-(2-fluoro-4-(piperidin-4-yl)phenyl)benzo[d]oxazole-7-carboxamide;
2-(2-fluoro-4-(1-propylpiperidin-4-yl)phenyl)benzo[d]oxazole-7-carboxamide;
2-(1-pentylpiperidin-4-yl)benzo[d]oxazol-7-carboxamide;
2-(1-butylpiperidin-4-yl)benzo[d]oxazol-7-carboxamide;
2-(4-(1-propylpiperidin-3-yl)phenyl)benzo[d]oxazole-7-carboxamide;
2-(4-(1-propylpiperidin-4-yl)phenyl)benzo[d]oxazole-7-carboxamide; and
2-(4-(1-(2-(dimethylamino)acetyl)piperidin-4-yl)phenyl)benzo[d]oxazole-7-carboxamide.

21. A pharmaceutical composition comprising a compound, pharmaceutically acceptable salt, pharmaceutically acceptable solvate, or pharmaceutically acceptable prodrug thereof of claim 1 and a pharmaceutically acceptable carrier, excipient, binder or diluent.

22. A method of inhibiting poly(ADP-ribose)polymerase (PARP) in a subject in need of PARP inhibition comprising administering to the subject a therapeutically acceptable amount of a compound of claim 1.

23. A method of treating a disease ameliorated by the inhibition of PARP comprising administering to a subject in need of treatment a therapeutically-effective amount of a compound of claim 1.

24. The method of claim 23, wherein the disease is selected from the group consisting of: vascular disease; septic shock; ischaemic injury; reperfusion injury; neurotoxicity; haemorraghic shock; inflammatory diseases; multiple sclerosis; secondary effects of diabetes; and acute treatment of cytoxicity following cardiovascular surgery.

25. A method of treating a cancer deficient in Homologous Recombination (HR) dependent DNA double strand break (DSB) repair pathway, comprising administering to a subject in need of treatment a therapeutically-effective amount of a compound of claim 1.

* * * * *

UNITED STATES PATENT AND TRADEMARK OFFICE
CERTIFICATE OF CORRECTION

PATENT NO.         : 8,088,760 B2
APPLICATION NO.    : 12/355692
DATED              : January 3, 2012
INVENTOR(S)        : Chu et al.

It is certified that error appears in the above-identified patent and that said Letters Patent is hereby corrected as shown below:

On the title page in item (57) "Abstract," correct Formula (II) as follows:

Replace " 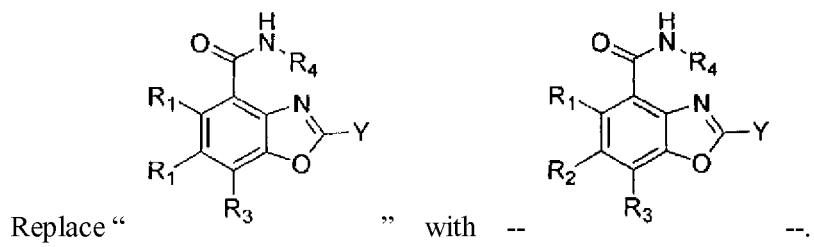 " with -- --.

In the "Summary of the Invention," column 2, lines 15-20, correct Formula (II) as follows:

Replace " 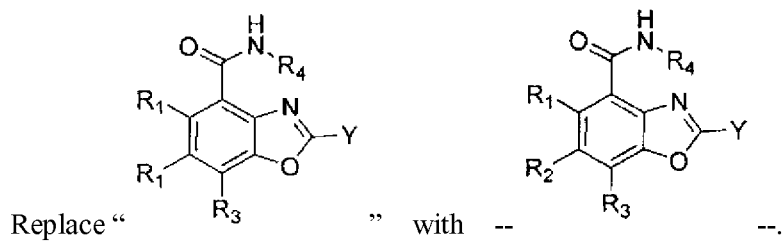 " with -- --.

In column 4, lines 5-10, correct Formula (II) as follows:

Replace " 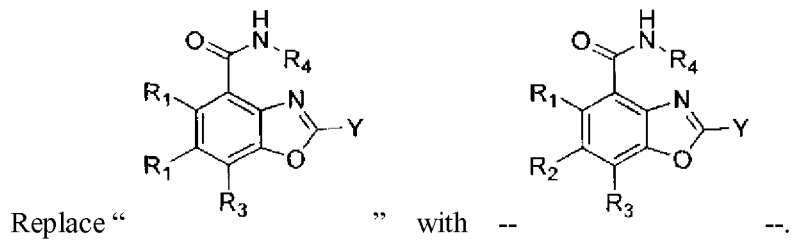 " with -- --.

Signed and Sealed this
Twelfth Day of June, 2012

David J. Kappos
*Director of the United States Patent and Trademark Office*

CERTIFICATE OF CORRECTION (continued)
U.S. Pat. No. 8,088,760 B2

In Claim 1, column 167, lines 15-20, correct Formula (II) as follows: